United States Patent
Ackermann et al.

(10) Patent No.: US 7,335,687 B2
(45) Date of Patent: Feb. 26, 2008

(54) 2,3-OXIDOSQUALENE-LANOSTEROL CYCLASE INHIBITORS

(75) Inventors: Jean Ackermann, Riehen (CH); Johannes Aebi, Basel (CH); Denise Blum, Basel (CH); Alexander Chucholowski, San Diego, CA (US); Henrietta Dehmlow, Grenzach-Wyhlen (DE); Hans-Peter Maerki, Basel (CH); Olivier Morand, Hegenheim (FR); Rene Trussardi, Birsfelden (CH); Elisabeth von der Mark, Bad Bellingen (DE); Sabine Wallbaum, Ostfildern (DE); Thomas Weller, Binningen (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 257 days.

(21) Appl. No.: 11/014,374

(22) Filed: Dec. 15, 2004

(65) Prior Publication Data

US 2005/0176766 A1    Aug. 11, 2005

Related U.S. Application Data

(62) Division of application No. 09/925,188, filed on Aug. 9, 2001, now Pat. No. 6,858,651.

(30) Foreign Application Priority Data

Aug. 16, 2000 (EP) .................................. 00117611
Jun. 19, 2001 (EP) .................................. 01113646

(51) Int. Cl.
*A61K 31/14* (2006.01)
*C07C 205/00* (2006.01)

(52) U.S. Cl. ..................................... 514/643; 568/306
(58) Field of Classification Search ................ 514/643; 568/306
See application file for complete search history.

(56) References Cited

U.S. PATENT DOCUMENTS

| 3,592,824 | A | 7/1971 | Schut |
| 5,455,273 | A | 10/1995 | Maier et al. |
| 6,034,275 | A | 3/2000 | Aebi et al. |
| 6,858,651 | B2 * | 2/2005 | Ackermann et al. ........ 514/643 |

FOREIGN PATENT DOCUMENTS

| EP | 636 367 | 2/1995 |
| EP | 0 778 264 | 6/1997 |
| FR | 1515629 | 1/1968 |
| WO | WO 02 20483 | 3/2002 |
| WO | WO 02 36584 | 5/2002 |

\* cited by examiner

*Primary Examiner*—Janet L. Andres
*Assistant Examiner*—Binta Robinson
(74) *Attorney, Agent, or Firm*—George W. Johnston; Patricia S. Rocha-Tramaloni

(57) ABSTRACT

The present invention relates to aminocyclohexanol derivatives useful for the treatment and/or prophylaxis of diseases which are associated with 2,3-oxidosqualene-lanosterol cyclase such as hypercholesterolemia, hyperlipemia, arteriosclerosis, vascular diseases, mycoses, gallstones, tumors and/or hyperproliferative disorders, and treatment and/or prophylaxis of impaired glucose tolerance and diabetes.

94 Claims, No Drawings

2,3-OXIDOSQUALENE-LANOSTEROL CYCLASE INHIBITORS

PRIORITY TO RELATED APPLICATIONS

This application is a Division of Ser. No. 09/925,188, filed Aug. 9, 2001 now U.S. Pat. No. 6,858,651.

FIELD OF THE INVENTION

The present invention is concerned with novel aminocyclohexanol derivatives, their manufacture and their use as 2,3-oxidosqualene-lanosterol cyclase inhibiting medicaments.

BACKGROUND OF THE INVENTION

Causal risk factors that directly promote the development of coronary and peripheral atherosclerosis include elevated low-density lipoprotein cholesterol (LDL-C), low high-density lipoprotein cholesterol (HDL-C), hypertension, cigarette smoking and diabetes mellitus. Other synergistic risk factors include elevated concentrations of triglyceride (TG)-rich lipoproteins, small, dense low-density lipoprotein particles, lipoprotein (a) (Lp(a)), and homocysteine. Predisposing risk factors modify the causal or conditional risk factors and thus affect atherogenesis indirectly. The predisposing risk factors are obesity, physical inactivity, family history of premature CVD, and male sex. The strong connection between coronary heart disease (CHD) and high LDL-C levels in plasma, and the therapeutic advantage of lowering elevated LDL-C levels are now well established (Gotto et al., Circulation 81, 1990, 1721-1733; Stein et al., Nutr. Metab. Cardiovasc. Dis. 2, 1992, 113-156; Illingworth, Med. Clin. North. Am. 84, 2000, 23-42). Cholesterol-rich, sometimes unstable, atherosclerotic plaques lead to the occlusion of blood vessels resulting in an ischemia or an infarct. Studies with respect to primary prophylaxis have shown that a lowering of plasma LDL-C levels in plasma reduces the frequency of non-fatal incidences of CHD, while the overall morbidity remains unchanged. The lowering of plasma LDL-C levels in patients with pre-established CHD (secondary intervention) reduces CHD mortality and morbidity; meta-analysis of different studies shows that this decrease is proportional to the reduction of the LDL-C (Ross et al., Arch. Intern. Med. 159, 1999, 1793-1802).

The clinical advantage of cholesterol lowering is greater for patients with pre-established CHD than for asymptomatic persons with hypercholesterolemia. According to current guidelines, cholesterol lowering treatment is recommended for patients who had survived a myocardial infarct or patients suffering from angina pectoris or another atherosclerotic disease, with a target LDL-C level of 100 mg/dl.

Preparations such as bile acid sequestrants, fibrates, nicotinic acid, probucol as well as statins, i.e. HMG-Co-A reductase inhibitors such as simvastatin and atorvastatin, are used for usual standard therapies. The best statins reduce plasma LDL-C effectively by at least 40%, and also plasma triglycerides, a synergistic risk factor, but less effectively. In contrast, fibrates reduce plasma triglycerides effectively, but not LDL-C. Combination of a statin and a fibrate proved to be very efficacious in lowering LDL-C and triglycerides (Ellen and McPherson, J. Cardiol. 81, 1998, 60B-65B), but safety of such a combination remains an issue (Shepherd, Eur. Heart J. 16, 1995, 5-13). A single drug with a mixed profile combining effective lowering of both LDL-C and triglycerides would provide additional clinical benefit to asymptomatic and symptomatic patients.

In humans, statins are well tolerated at standard dosage, but reductions in non-sterol intermediates in the cholesterol synthesis pathway, such as isoprenoids and coenzyme Q, may be associated with adverse clinical events at high doses (Davignon et al., Can. J. Cardiol. 8, 1992, 843-864; Pederson and Tobert, Drug Safety 14, 1996, 11-24).

This has stimulated the search for, and development of compounds that inhibit cholesterol biosynthesis, yet act distal to the synthesis of these important, non-sterol intermediates. 2,3-oxidosqualene:lanosterol cyclase (OSC), a microsomal enzyme, represents a unique target for a cholesterol-lowering drug (Morand et al., J. Lipid Res., 38, 1997, 373-390; Mark et al., J. Lipid Res. 37, 1996, 148-158). OSC is downstream of farnesyl-pyrophosphate, beyond the synthesis of isoprenoids and coenzyme Q. In hamsters, pharmacologically active doses of an OSC inhibitor showed no adverse side-effects, in contrast to a statin which reduced food-intake and body weight, and increased plasma bilirubin, liver weight and liver triglyceride content (Morand et al., J. Lipid Res., 38, 1997, 373-390). The compounds described in European Patent Application No. 636 367, which inhibit OSC and which lower the total cholesterol in plasma, belong to these substances.

OSC inhibition does not trigger the overexpression of HMGR because of an indirect, negative feed-back regulatory mechanism involving the production of 24(S),25-epoxycholesterol (Peffley et al., Biochem. Pharmacol. 56, 1998, 439-449; Nelson et al., J. Biol. Chem. 256, 1981, 1067-1068; Spencer et al., J. Biol. Chem. 260, 1985, 13391-13394; Panini et al., J. Lipid Res. 27, 1986, 1190-1204; Ness et al., Arch. Biochem. Biophys. 308, 1994, 420-425). This negative feed-back regulatory mechanism is fundamental to the concept of OSC inhibition because (i) it potentiates synergistically the primary inhibitory effect with an indirect down-regulation of HMGR, and (ii) it prevents the massive accumulation of the precursor monooxidosqualene in the liver. In addition, 24(S),25-epoxycholesterol was found to be one of the most potent agonists of the nuclear receptor LXR (Janowski et al., Proc. Natl. Acad. Sci. USA, 96, 1999, 266-271). Considering that 24(S),25-epoxycholesterol is a by-product of inhibition of OSC it is hypothesized that the OSC inhibitors could also indirectly activate LXR-dependent pathways such as (i) cholesterol-7alpha-hydroxylase to increase the consumption of cholesterol via the bile acid route, (ii) expression of ABC proteins with the potential to stimulate reverse cholesterol transport and increase plasma HDL-C levels (Venkateswaran et al., J. Biol. Chem. 275, 2000, 14700-14707; Costet et al., J. Biol. Chem. June 2000, in press; Ordovas, Nutr Rev 58, 2000, 76-79, Schmitz and Kaminsky, Front Biosci 6, 2001, D505-D514), and/or inhibit intestinal cholesterol absorption (Mangelsdorf, XIIth International Symposium on Atherosclerosis, Stockholm, June 2000). In addition, possible cross talks between fatty acid and cholesterol metabolism mediated by liver LXR have been hypothesized (Tobin et al., Mol. Endocrinol. 14, 2000, 741-752).

SUMMARY OF THE INVENTION

The compounds of the present invention inhibit 2,3-oxidosqualene-lanosterol cyclase (EC 5.4.99.) which is required for the biosynthesis of cholesterol, ergosterol and other sterols.

In particular, the invention relates to compounds of the formula (I)

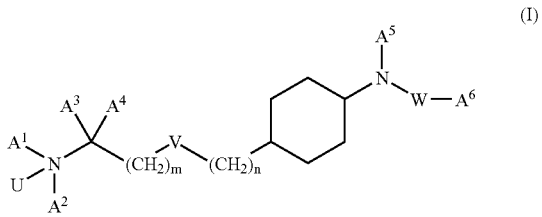

(I)

wherein

U is O or a lone pair,

V is O, S, —CH$_2$—, —CH=CH—, or —C≡C—,

W is CO, COO, CONR$^1$, CSO, CSNR$^1$, SO$_2$, or SO$_2$NR$^1$, m and n independently from each other are 0 to 7 and m+n is 0 to 7, with the proviso that m is not 0 if V is O or S, A$^1$ is H, lower-alkyl, hydroxy-lower-alkyl, or lower-alkenyl, A$^2$ is lower-alkyl, cycloalkyl, cycloalkyl-lower-alkyl, or lower-alkenyl, optionally substituted by R$^2$, A$^3$ and A$^4$ are hydrogen or lower-alkyl, or A$^1$ and A$^2$ or A$^1$ and A$^3$ are bonded to each other to form a ring and -A$^1$-A$^2$- or -A$^1$-A$^3$- are lower-alkylene or lower-alkenylene, optionally substituted by R$^2$, in which one —CH$_2$— group of -A$^1$-A$^2$- or -A$^1$-A$^3$- can optionally be replaced by NR$^3$, S, or O, or A$^3$ and A$^4$ are bonded to each other to form a ring together with the carbon atom to which they are attached and -A$^3$-A$^4$- is —(CH$_2$)$_{2-5}$— which can optionally be mono- or multiply-substituted by lower-alkyl, A$^5$ is H, lower-alkyl, lower-alkenyl, or aryl-lower-alkyl, A$^6$ is lower-alkyl, cycloalkyl, aryl, aryl-lower-alkyl, heteroaryl, heteroaryl-lower-alkyl, lower-alkoxy-carbonyl-lower-alkyl, R$^2$ is hydroxy, hydroxy-lower-alkyl, lower-alkoxy, lower-alkoxycarbonyl, N(R$^4$,R$^5$), or thio-lower-alkoxy, R$^1$, R$^3$, R$^4$ and R$^5$ independently from each other are hydrogen or lower-alkyl, and pharmaceutically acceptable salts and/or pharmaceutically acceptable esters thereof.

The present compounds of formula I inhibit OSC and therefore also inhibit the biosynthesis of cholesterol, ergosterol and other sterols, and reduce the plasma cholesterol levels. They can therefore be used in the therapy and prophylaxis of hypercholesterolemia, hyperlipemia, arteriosclerosis and vascular diseases in general. Furthermore, they can be used in the therapy and/or prevention of mycoses, parasite infections, gallstones, cholestatic liver disorders, tumors and hyperproliferative disorders, e.g. hyperproliferative skin and vascular disorders. In addition, it has unexpectedly been found that the compounds of the present invention can also be of therapeutical use to improve glucose tolerance in order to treat and/or prevent related diseases such as diabetes. The compounds of the present invention further exhibit improved pharmacological properties compared to known compounds.

DETAILED DESCRIPTION OF THE INVENTION

Unless otherwise indicated the following definitions are set forth to illustrate and define the meaning and scope of the various terms used to describe the invention herein.

In this specification the term "lower" is used to mean a group consisting of one to seven, preferably of one to four carbon atom(s).

The term "lone pair" refers to an unbound electron pair, in particular to the unbound electron pair of a nitrogen atom in e.g. an amine.

The term "halogen" refers to fluorine, chlorine, bromine and iodine, with chlorine and bromine being preferred.

The term "alkyl", alone or in combination with other groups, refers to a branched or straight-chain monovalent saturated aliphatic hydrocarbon radical of one to twenty carbon atoms, preferably one to sixteen carbon atoms. Alkyl groups can optionally be substituted e.g. with halogen, CN, NO$_2$, carboxy, and/or phenyl. Other, more preferred subsituents are hydroxy, lower-alkoxy, NH$_2$, N(lower-alkyl)$_2$, and/or lower-alkoxy-carbonyl.

The term "lower-alkyl", alone or in combination with other groups, refers to a branched or straight-chain monovalent alkyl radical of one to seven carbon atoms, preferably one to four carbon atoms. This term is further exemplified by such radicals as methyl, ethyl, n-propyl, isopropyl, n-butyl, s-butyl, t-butyl and the like. A lower-alkyl group may have a substitution pattern as described earlier in connection with the term "alkyl".

The term "cycloalkyl" refers to a monovalent carbocyclic radical of 3 to 10 carbon atom(s), preferably 3 to 6 carbon atoms. Cycloalkyl in which one or more —CH$_2$— group is replaced by O, S, NH or N(lower-alkyl) are referred to as "heterocycloalkyl".

The term "alkoxy" refers to the group R'—O—, wherein R' is an alkyl. The term "lower-alkoxy" refers to the group R'—O—, wherein R' is a lower-alkyl. The term "thio-alkoxy" refers to the group R'—S—, wherein R' is an alkyl. The term "thio-lower-alkoxy" refers to the group R'—S—, wherein R' is a lower-alkyl.

The term "alkenyl", alone or in combination with other groups, stands for a straight-chain or branched hydrocarbon residue comprising an olefinic bond and up to 20, preferably up to 16 carbon atoms. The term "lower-alkenyl" refers to a straight-chain or branched hydrocarbon residue comprising an olefinic bond and up to 7, preferably up to 4 carbon atoms, such as e.g. 2-propenyl. An alkenyl or lower-alkenyl group may have a substitution pattern as described earlier in connection with the term "alkyl".

The term "alkylene" refers to a straight chain or branched divalent saturated aliphatic hydrocarbon group of 1 to 20 carbon atoms, preferably 1 to 16 carbon atoms. The term "lower-alkylene" refers to a straight chain or branched divalent saturated aliphatic hydrocarbon group of 1 to 7, preferably 2 to 4 carbon atoms. An alkylene or lower-alkylene group may have a substitution pattern as described earlier in connection with the term "alkyl".

The term "alkenylene" refers to a straight chain or branched divalent hydrocarbon group comprising an olefinic bond and up to 20 carbon atoms, preferably up to 16 carbon atoms. The term "lower-alkenylene" refers to a straight chain or branched divalent hydrocarbon group comprising an olefinic bond and up to 7, preferably up to 4 C-atoms. An alkenylene or lower-alkenylene group may have a substitution pattern as described earlier in connection with the term "alkyl".

The term "aryl" relates to the phenyl or naphthyl group which can optionally be mono- or multiply-substituted by lower-alkyl, lower-alkyl-di-oxo, halogen, hydroxy, cyano, $CF_3$, $NH_2$, $N(lower-alkyl)_2$, aminocarbonyl, carboxy, nitro, lower-alkoxy, lower-alkylcarbonyl, lower-alkylcarbonyloxy, aryl, aryloxy, or lower-alkylcarbonyl-amino, preferably by lower-alkyl, lower-alkyl-di-oxo, halogen, hydroxy, cyano, $CF_3$, $NH_2$, $N(lower-alkyl)_2$, aminocarbonyl, carboxy, nitro, lower-alkoxy, lower-alkylcarbonyl, lower-alkylcarbonyloxy, aryl, or aryloxy. Preferred substituents are lower-alkyl, lower alkoxy, lower-alkyl-carbonyl, lower-alkoxycarbonyl, fluorine, chlorine, bromine, CN, $CF_3$, $NO_2$, $NH_2$, and/or $N(lower-alkyl)_2$. More preferred substituents are fluorine, chlorine, bromine and $CF_3$.

The term "heteroaryl" refers to an aromatic 5- or 6-membered ring which can contain 1, 2 or 3 atoms selected from nitrogen, oxygen and/or sulphur such as furyl, pyridyl, 1,2-, 1,3- and 1,4-diazinyl, thienyl, isoxazolyl, oxazolyl, imidazolyl, or pyrrolyl. The term "heteroaryl" further refers to bicyclic aromatic groups comprising two 5- or 6-membered rings, in which one or both rings can contain 1, 2 or 3 atoms selected from nitrogen, oxygen or sulphur such as e,g, indol or chinolin, or partially hydrogenated bicyclic aromatic groups such as e.g. indolinyl. A heteroaryl group may have a substitution pattern as described earlier in connection with the term "aryl".

The term "pharmaceutically acceptable salts" embraces salts of the compounds of formula (I) with inorganic or organic acids such as hydrochloric acid, hydrobromic acid, nitric acid, sulphuric acid, phosphoric acid, citric acid, formic acid, maleic acid, acetic acid, fumaric acid, succinic acid, tartaric acid, methanesulphonic acid, p-toluenesulphonic acid and the like, which are non toxic to living organisms. Preferred salts are formates, hydrochlorides and hydrobromides.

The term "pharmaceutically acceptable esters" embraces esters of the compounds of formula (I), in which hydroxy groups have been converted to the corresponding esters with inorganic or organic acids such as, nitric acid, sulphuric acid, phosphoric acid, citric acid, formic acid, maleic acid, acetic acid, succinic acid, tartaric acid, methanesulphonic acid, p-toluenesulphonic acid and the like, which are non toxic to living organisms.

In detail, the present invention relates to compounds of formula (I)

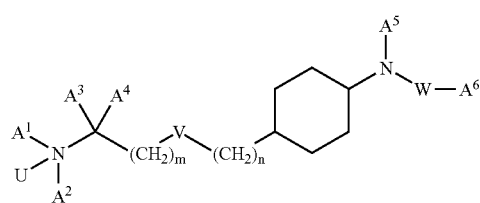

(I)

wherein

U is O or a lone pair,

V is O, S, $-CH_2-$, $-CH=CH-$, or $-C\equiv C-$,

W is CO, COO, $CONR^1$, CSO, $CSNR^1$, $SO_2$, or $SO_2NR^1$, m and n independently from each other are 0 to 7 and m+n is 0 to 7, with the proviso that m is not 0 if V is O or S, $A^1$ is H, lower-alkyl, hydroxy-lower-alkyl, or lower-alkenyl, $A^2$ is lower-alkyl, cycloalkyl, cycloalkyl-lower-alkyl, or lower-alkenyl, optionally substituted by $R^2$, $A^3$ and $A^4$ are hydrogen or lower-alkyl, or $A^1$ and $A^2$ or $A^1$ and $A^3$ are bonded to each other to form a ring and $-A^1-A^2-$ or $-A^1-A^3-$ are lower-alkylene or lower-alkenylene, optionally substituted by $R^2$, in which one $-CH_2-$ group of $-A^1-A^2-$ or $-A^1-A^3-$ can optionally be replaced by $NR^3$, S, or O, or $A^3$ and $A^4$ are bonded to each other to form a ring together with the carbon atom to which they are attached and $-A^3-A^4-$ is $-(CH_2)_{2-5}-$ which can optionally be mono- or multiply-substituted by lower-alkyl, $A^5$ is H, lower-alkyl, lower-alkenyl, or aryl-lower-alkyl, $A^6$ is lower-alkyl, cycloalkyl, aryl, aryl-lower-alkyl, heteroaryl, heteroaryl-lower-alkyl, lower-alkoxy-carbonyl-lower-alkyl, $R^2$ is hydroxy, hydroxy-lower-alkyl, lower-alkoxy, lower-alkoxycarbonyl, $N(R^4,R^5)$, or thio-lower-alkoxy, $R^1$, $R^3$, $R^4$ and $R^5$ independently from each other are hydrogen or lower-alkyl, and pharmaceutically acceptable salts and/or pharmaceutically acceptable esters thereof.

Compounds of formula (I) as defined above, wherein $A^3$ and $A^4$ are not bonded to each other to form a ring together with the carbon atom to which they are attached, are preferred. In such compounds, $A^1$ is H, lower-alkyl, hydroxy-lower-alkyl, or lower-alkenyl $A^2$ is lower-alkyl, cycloalkyl, cycloalkyl-lower-alkyl, or lower-alkenyl, optionally substituted by $R^2$, $A^3$ and $A^4$ are hydrogen or lower-alkyl, or $A^1$ and $A^2$ or $A^1$ and $A^3$ are bonded to each other to form a ring and $-A^1-A^2-$ or $-A^1-A^3-$ are lower-alkylene or lower-alkenylene, optionally substituted by $R^2$, in which one $-CH_2-$ group of $-A^1-A^2-$ or $-A^1-A^3-$ can optionally be replaced by $NR^3$, S, or O.

Preferred are compounds of formula (I) and/or pharmaceutically acceptable salts thereof. Another preferred embodiment relates to compounds of formula (I) wherein U is a lone pair and a further preferred embodiment relates to compounds of formula (I) wherein U is O.

A further preferred embodiment of the present invention relates to the trans-form of the compounds as defined above characterized by formula (Ia)

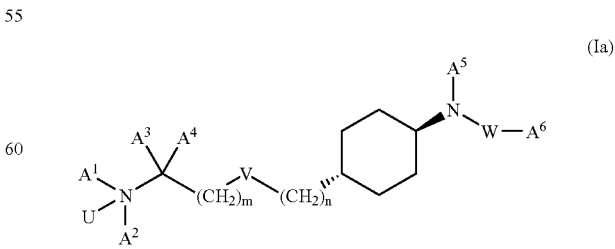

(Ia)

wherein U, V, W, m, n, $A^1$, $A^2$, $A^3$, $A^4$, $A^5$ and $A^6$ have the significances given above.

A particularly preferred embodiment of the present invention relates to the compounds of formula (Ib)

(Ib)

wherein

V is O, S, —$CH_2$—, —CH=CH—, or —C≡C—;

w is COO or SO2;

p is an integer from 0 to 7, with the proviso that p is not 0 when V is O or S;

A11 is H, lower-alkyl, or hydroxy-lower-alkyl and

A12 is lower-alkyl, hydroxy-lower alkyl, or lower-alkenyl, or

A11 and A12 bond together to form -$A^{11}$-$A^{12}$-, wherein -$A^{11}$-$A^{12}$- is lower-alkylene;

$A^{13}$ and $A^{14}$ are each hydrogen or bond together to form -$A^{13}$-$A^{14}$-, wherein -$A^{13}$-$A^{14}$- is —$(CH_2)_{2-5}$—;

A15 is lower-alkyl; and

A16 is halogen or trifluoromethyl.

Also preferred are pharmaceutically acceptable salts and esters of the compounds of formula (Ib).

Compounds in which V represents O are particularly preferred, as are compounds wherein V is —$CH_2$—. Compounds in which V represents —C=C— are also preferred. Further, compounds in which V represents —C≡C— also relate to a preferred embodiment of the present invention.

Of the compounds of the present invention, those in which W represents CO, COO, $CONR^1$, $CSNR^1$, $SO_2$ or $SO_2NR^1$ and $R^1$ is hydrogen are preferred, with those wherein W represents COO or $SO_2$ being particularly and individually preferred.

Compounds of the present invention in which n is 0 are preferred, as are those in which n is 1. Another preferred embodiment relates to compounds as defined above, wherein m is 1 to 6. In addition, compounds as defined above, wherein m is 0 and V is —C=C— or —C≡C—, are also preferred.

In compounds wherein $A^1$ represents lower-alkyl, such a lower-alkyl group can optionally be substituted by fluorine. Other preferred compounds of the present invention are those in which $A^1$ represents H, methyl, ethyl, isopropyl, 2-hydroxy-ethyl or 2-propenyl. Another group of preferred compounds of the present invention are those in which $A^2$ represents lower-alkyl, cycloalkyl-lower-alky, or lower-alkenyl, optionally substituted with $R^2$, wherein $R^2$ is hydroxy, methoxy, or ethoxycarbonyl, with those compounds wherein $A^2$ represents methyl, ethyl, 2-hydroxy-ethyl, 2-propenyl, propyl or isopropyl being especially preferred.

Compounds of formula (I), wherein $A^1$ and $A^2$ are bonded to each other to form a ring and -$A^1$-$A^2$- is lower-alkylene or lower-alkenylene, optionally substituted by $R^2$, in which one —$CH_2$— group of -$A^1$-$A^2$- can optionally be replaced by $NR^3$, S, or O, wherein $R^2$ and $R^3$ are as defined above are also preferred, with compounds as defined above, wherein $A^1$ and $A^2$ are bonded to each other to form a ring and -$A^1$-$A^2$- is lower-alkylene or lower-alkenylene, optionally substituted by $R^2$, in which one —$CH_2$— group of -$A^1$-$A^2$- can optionally be replaced by O, wherein $R^2$ is hydroxy or 2-hydroxyethyl being particularly preferred. In compounds wherein $A^1$ and $A^2$ are bonded to each other to form a ring, said ring is preferably a 4-, 5-, or 6-membered ring such as e.g. piperidinyl or pyrrolidinyl. Preferred compounds as defined above are those wherein $A^1$ and $A^2$ are bonded to each other to form a ring and -$A^1$-$A^2$- is —$(CH_2)_5$—. Such compounds consequently comprise a piperidinyl group.

A further preferred embodiment of the present invention relates to compounds of formula (I), wherein $A^3$ and/or $A^4$ represent hydrogen. Compounds of formula (I) as defined above, wherein $A^3$ and $A^4$ are bonded to each other to form a cyclopropyl-ring together with the carbon atom to which they are attached and -$A^3$-$A^4$- is —$(CH_2)_2$— represent another preferred embodiment of the present invention. The term —$(CH_2)_{2-5}$— denotes the groups —$(CH_2)_2$—, —$(CH_2)_3$—, —$(CH_2)_4$— and —$(CH_2)_5$—.

Compounds of formula (I), in which $A^5$ is H, lower-alkyl, lower-alkenyl, or benzyl optionally substituted with halogen are also preferred, with those wherein $A^5$ represents methyl or ethyl being especially preferred.

Compounds of formula (I), wherein $A^6$ is lower-alkyl, cycloalkyl, phenyl, naphthyl, phenyl-lower-alkyl, pyridyl, indolyl, indolinyl, thienyl, thienyl-methylene, furyl-methylene, benzodioxyl, chinolyl, isoxazolyl, or imidazolyl, optionally substituted by one or more substituents selected from the group consisting of lower-alkyl, lower-alkoxy, lower-alkylcarbonyl, lower-alkoxycarbonyl, fluorine, chlorine, bromine, CN, $CF_3$, $NO_2$, or $N(R^6,R^7)$, wherein $R^6$ and $R^7$ independently from each other are hydrogen or lower-alkyl are another preferred embodiment of the present invention, with those compounds wherein $A^6$ is phenyl optionally substituted by one or more substituents selected from the group consisting of fluorine, chlorine, bromine and $CF_3$, being more preferred, and with those compounds wherein $A^6$ is 4-chloro-phenyl, 4-bromo-phenyl or 4-trifluoromethyl-phenyl being particularly preferred.

Preferred compounds of general formula (I) are those selected from the group consisting of trans-{4-[6-(Allyl-methyl-amino)-hexyloxy]-cyclohexyl}-methyl-carbamic acid 4-nitro-phenyl ester, trans-{4-[6-(Allyl-methyl-amino)-hexyloxy]-cyclohexyl}-methyl-carbamic acid naphthalen-2-yl ester, trans-{4-[6-(Allyl-methyl-amino)-hexyloxy]-cyclohexyl}-methyl-carbamic acid pentafluorophenylmethyl ester, trans-{4-[6-(Allyl-methyl-amino)-hexyloxy]-cyclohexyl}-methyl-carbamic acid benzyl ester, trans-{4-[6-(Allyl-methyl-amino)-hexyloxy]-cyclohexyl}-methyl-carbamic acid phenyl ester, trans-{4-[6-(Allyl-methyl-amino)-hexyloxy]-cyclohexyl}-methyl-carbamic acid p-tolyl ester, trans-{4-[6-(Allyl-methyl-amino)-hexyloxy]-cyclohexyl}-methyl-carbamic acid 4-bromo-phenyl ester, trans-{4-[6-(Allyl-methyl-amino)-hexyloxy]-cyclohexyl}-methyl-carbamic acid 4-fluoro-phenyl ester, trans-{4-[6-(Allyl-methyl-amino)-hexyloxy]-cyclohexyl}-methyl-carbamic acid 4-chloro-phenyl ester, trans-{4-[6-(Allyl-methyl-amino)-hexyloxy]-cyclohexyl}-methyl-carbamic acid hexyl ester, trans-{4-[6-(Allyl-methyl-amino)-hexyloxy]-cyclohexyl}-methyl-carbamic acid 4-methoxy-phenyl ester, trans-{4-[6-(Allyl-methyl-amino)-hexyloxy]-cyclohexyl}-methyl-carbamic acid isobutyl ester, trans-{4-[6-(Allyl-methyl-amino)-hexyloxy]-cyclohexyl}-methyl-carbamic acid 4-trifluoromethyl-phenyl ester, trans-{4-[7-(Allyl-methyl-amino)-heptyloxy]-cyclohexyl}-methyl-carbamic acid 4-bromo-phenyl ester, trans-{4-[5-(Allyl-methyl-amino)-pentyloxy]-cyclohexyl}-methyl-carbamic acid 4-bromo-phenyl ester, trans-{4-[4-(Allyl-methyl-amino)-butoxy]-cyclohexyl}-methyl-carbamic acid 4-bromo-phenyl ester, trans-{4-[7-(Allyl-methyl-amino)-heptyloxy]-cyclohexyl}-methyl-carbamic acid 4-fluoro-phenyl ester, trans-{4-[5-(Allyl-methyl-amino)-pentyloxy]-cyclohexyl}-methyl-carbamic acid 4-fluoro-phenyl ester, trans-{4-[5-(Allyl-methyl-amino)-pentyloxy]-cyclohexyl}-methyl-carbamic acid 4-trifluoromethyl-phenyl ester, trans-{4-[4-(Allyl-methyl-amino)-butoxy]-cyclohexyl}-methyl-carbamic acid 4-trifluoromethyl-phenyl ester, {4-trans-[4-(Allyl-methyl-amino)-butoxy]-cyclohexyl}-methyl-carbamic acid 4-chloro-phenyl ester, {4-trans-[4-(Allyl-methyl-amino)-butoxy]-cyclohexyl}-methyl-carbamic acid isobutyl ester, {4-trans-[4-(Allyl-methyl-amino)-butoxy]-cyclohexyl}-methyl-carbamic acid phenyl ester, 4-({4-trans-[4-(Allyl-methyl-amino)-butoxy]-cyclohexyl}-methyl-carbamoyloxy)-benzoic acid methyl ester, {4-trans-[4-(Allyl-methyl-amino)-butoxy]-cyclohexyl}-methyl-carbamic acid 4-methoxy-phenyl ester, {4-trans-[4-(Allyl-methyl-amino)-butoxy]-cyclohexyl}-methyl-carbamic acid p-tolyl ester, trans-(4-{4-[Ethyl-(2-hydroxy-ethyl)-amino]-butoxy}-cyclohexyl)-methyl-carbamic acid 4-trifluoromethyl-phenyl ester, trans-[4-(4-Diethylamino-butoxy)-cyclohexyl]-methyl-carbamic acid 4-trifluoromethyl-phenyl ester, trans-[4-(4-Dimethylamino-butoxy)-cyclohexyl]-methyl-carbamic acid 4-trifluoromethyl-phenyl ester, trans-(4-{4-[Bis-(2-hydroxy-ethyl)-amino]-butoxy}-cyclohexyl)-methyl-carbamic acid 4-trifluoromethyl-phenyl ester, {4-trans-[3-(Allyl-methyl-amino)-propoxy]-cyclohexyl}-methyl-carbamic acid 4-fluoro-phenyl ester, {4-trans-[3-(Allyl-methyl-amino)-propoxy]-cyclohexyl}-methyl-carbamic acid 4-bromo-phenyl ester, trans{4-[6-(Allyl-methyl-amino)-hexyloxy]-cyclohexyl}-methyl-carbamic acid 2,4-difluoro-phenyl ester, {4-[trans-4-(Allyl-methyl-amino)-butoxy]-cyclohexyl}-methyl-carbamic acid 3,4-difluoro-phenyl ester,

[trans-4-(4-Dimethylamino-butoxy)-cyclohexyl]-methyl-carbamic acid 3,4-difluoro-phenyl ester, (trans-4-{4-[Ethyl-(2-hydroxy-ethyl)-amino]-butoxy}-cyclohexyl)-methyl-carbamic acid 3,4-difluoro-phenyl ester,

[trans-4-(4-Diethylamino-butoxy)-cyclohexyl]-methyl-carbamic acid 3,4-difluoro-phenyl ester, ethyl-[trans-4-(4-piperidin-1-yl-butoxy)-cyclohexyl]-carbamic acid 3,4-difluoro-phenyl ester,

[trans-4-(4-Azetidin-1-yl-butoxy)-cyclohexyl]-methyl-carbamic acid 3,4-difluoro-phenyl ester, Methyl-[trans-4-(4-morpholin-4-yl-butoxy)-cyclohexyl]-carbamic acid 3,4-difluoro-phenyl ester, Methyl-[trans-4-(4-pyrrolidin-1-yl-butoxy)-cyclohexyl]-carbamic acid 3,4-difluoro-phenyl ester, (4-{trans-4-[Ethyl-(2-methoxy-ethyl)-amino]-butoxy}-cyclohexyl)-methyl-carbamic acid 3,4-difluoro-phenyl ester, trans-5-Chloro-thiophene-2-sulfonic acid {4-[6-(allyl-methyl-amino)-hexyloxy]-cyclohexyl}-methyl-amide, trans-N-{4-[6-(Allyl-methyl-amino)-hexyloxy]-cyclohexyl}-4,N-dimethyl-benzenesulfonamide, trans-Naphthalene-2-sulfonic acid {4-[6-(allyl-methyl-amino)-hexyloxy]-cyclohexyl}-methyl-amide, trans-N-{4-[6-(Allyl-methyl-amino)-hexyloxy]-cyclohexyl}-N-methyl-methanesulfonamide, trans-Quinoline-8-sulfonic acid {4-[6-(allyl-methyl-amino)-hexyloxy]-cyclohexyl}-methyl-amide, trans-N-{4-[6-(Allyl-methyl-amino)-hexyloxy]-cyclohexyl}-N-methyl-C-phenyl-methanesulfonamide, trans-3,5-Dimethyl-isoxazole-4-sulfonic acid {4-[6-(allyl-methyl-amino)-hexyloxy]-cyclohexyl}-methyl-amide, trans-Naphthalene-1-sulfonic acid {4-[6-(allyl-methyl-amino)-hexyloxy]-cyclohexyl}-methyl-amide, trans-N-{4-[6-(Allyl-methyl-amino)-hexyloxy]-cyclohexyl}-4-methoxy-N-methyl-benzenesulfonamide, trans-N-{4-[6-(Allyl-methyl-amino)-hexyloxy]-cyclohexyl}-N-methyl-benzenesulfonamide, trans-N-{4-[6-(Allyl-methyl-amino)-hexyloxy]-cyclohexyl}-4-fluoro-N-methyl-benzenesulfonamide, trans-Thiophene-2-sulfonic acid {4-[6-(allyl-methyl-amino)-hexyloxy]-cyclohexyl}-methyl-amide, trans-N-{4-[6-(Allyl-methyl-amino)-hexyloxy]-cyclohexyl}-2-fluoro-N-methyl-benzenesulfonamide, trans-1-Methyl-1H-imidazole-4-sulfonic acid {4-[6-(allyl-methyl-amino)-hexyloxy]-cyclohexyl}-methyl-amide, trans-N-{4-[6-(Allyl-methyl-amino)-hexyloxy]-cyclohexyl}-4-tert-butyl-N-methyl-benzenesulfonamide, trans-N-{4-[6-(Allyl-methyl-amino)-hexyloxy]-cyclohexyl}-4-butoxy-N-methyl-benzenesulfonamide, trans-N-{4-[6-(Allyl-methyl-amino)-hexyloxy]-cyclohexyl}-4-chloro-N-methyl-benzenesulfonamide, trans-N-{4-[6-(Allyl-methyl-amino)-hexyloxy]-cyclohexyl}-N-methyl-4-trifluoromethyl-benzenesulfonamide, trans-N-{4-[6-(Allyl-methyl-amino)-hexyloxy]-cyclohexyl}-4-bromo-N-methyl-benzenesulfonamide, trans-N-{4-[6-(Allyl-methyl-amino)-hexyloxy]-cyclohexyl}-N-methyl-4-nitro-benzenesulfonamide, trans-4-Bromo-N-(4-{6-[(2-methoxy-ethyl)-methyl-amino]-hexyloxy}-cyclohexyl)-N-methyl-benzenesulfonamide, trans-N-(4-{6-[(2-Methoxy-ethyl)-methyl-amino]-hexyloxy}-cyclohexyl)-N-methyl-4-trifluoromethyl-benzenesulfonamide, trans-4-Bromo-N-methyl-N-[4-(6-morpholin-4-yl-hexyloxy)-cyclohexyl]-benzenesulfonamide, trans-N-[4-(6-Azetidin-1-yl-hexyloxy)-cyclohexyl]-4-bromo-N-methyl-benzenesulfonamide, trans-4-Bromo-N-{4-[6-(butyl-methyl-amino)-hexyloxy]-cyclohexyl}-N-methyl-benzenesulfonamide, trans-4-Bromo-N-methyl-N-[4-(6-piperidin-1-yl-hexyloxy)-cyclohexyl]-benzenesulfonamide, trans-4-Bromo-N-{4-[6-(3,6-dihydro-2H-pyridin-1-yl)-hexyloxy]-cyclohexyl}-N-methyl-benzenesulfonamide, trans-4-Bromo-N-(4-{6-[ethyl-(2-hydroxy-ethyl)-amino]-hexyloxy}-cyclohexyl)-N-methyl-benzenesulfonamide, trans-4-Bromo-N-{4-[6-(3-hydroxy-pyrrolidin-1-yl)-hexyloxy]-cyclohexyl}-N-methyl-benzenesulfonamide, trans-4-Bromo-N-methyl-N-{4-[6-(methyl-propyl-amino)-hexyloxy]-cyclohexyl}-benzenesulfonamide, trans-4-Bromo-N-[4-(6-diallylamino-hexyloxy)-cyclohexyl]-N-methyl-benzenesulfonamide, trans-4-Bromo-N-{4-[6-(4-hydroxymethyl-piperidin-1-yl)-hexyloxy]-cyclohexyl}-N-methyl-benzenesulfonamide, trans-4-Bromo-N-(4-{6-[(2-hydroxy-ethyl)-methyl-amino]-hexyloxy}-cyclohexyl)-N-methyl-benzenesulfonamide, trans-4-Bromo-N-methyl-N-{4-[6-(4-methyl-piperidin-1-yl)-hexyloxy]-cyclohexyl}-benzenesulfonamide, trans-4-Bromo-N-{4-[6-(4-hydroxy-piperidin-1-yl)-hexyloxy]-cyclohexyl}-N-methyl-benzenesulfonamide, trans-4-Bromo-N-{4-[6-(cyclopropylmethyl-methyl-amino)-hexyloxy]-cyclohexyl}-N-methyl-benzenesulfonamide, trans-[(6-{4-[(4-Bromo-benzenesulfonyl)-methyl-amino]-cyclohexyloxy}-hexyl)-methyl-amino]-acetic acid ethyl ester, trans-N-[4-(6-Allylamino-hexyloxy)-cyclohexyl]-4-bromo-N-methyl-benzenesulfonamide, trans-4-Bromo-N-{4-[6-(2-hydroxy-ethylamino)-hexyloxy]-cyclohexyl}-N-methyl-benzenesulfonamide, trans-4-Bromo-N-[4-(6-ethylamino-hexyloxy)-cyclohexyl]-N-methyl-benzenesulfonamide, trans-N-Methyl-N-[4-(6-morpholin-4-yl-hexyloxy)-cyclohexyl]-4-trifluoromethyl-benzenesulfonamide, trans-N-[4-(6-Azetidin-1-yl-hexyloxy)-cyclohexyl]-N-methyl-4-trifluoromethyl-benzenesulfonamide, trans-N-{4-[6-(Butyl-methyl-amino)-hexyloxy]-cyclohexyl}-N-methyl-4-trifluoromethyl-benzenesulfonamide, trans-N-Methyl-N-[4-(6-piperidin-1-yl-hexyloxy)-cyclohexyl]-4-trifluoromethyl-benzenesulfonamide, trans-N-{4-[6-(3,6-Dihydro-2H-pyridin-1-yl)-hexyloxy]-cyclohexyl}-N-methyl-4-trifluoromethyl-benzenesulfonamide, trans-N-(4-{6-[Ethyl-(2-hydroxy-ethyl)-amino]-hexyloxy}-cyclohexyl)-N-methyl-4-trifluoromethyl-benzenesulfonamide, trans-N-{4-[6-(3-Hydroxy-pyrrolidin-1-yl)-hexyloxy]-cyclohexyl}-N-methyl-4-trifluoromethyl-benzenesulfonamide, trans-N-Methyl-N-{4-[6-(methyl-propyl-amino)-hexyloxy]-cyclohexyl}-4-trifluoromethyl-benzenesulfonamide, trans-N-[4-(6-Diallylamino-hexyloxy)-cyclohexyl]-N-methyl-4-trifluoromethyl-benzenesulfonamide, trans-N-{4-[6-(4-Hydroxymethyl-piperidin-1-yl)-hexyloxy]-cyclohexyl}-N-methyl-4-trifluoromethyl-benzenesulfonamide, trans-N-(4-{6-[(2-Hydroxy-ethyl)-methyl-amino]-hexyloxy}-cyclohexyl)-N-methyl-4-trifluoromethyl-benzenesulfonamide, trans-N-{4-[6-(4-Hydroxy-piperidin-1-yl)-hexyloxy]-cyclohexyl}-N-methyl-4-trifluoromethyl-benzenesulfonamide, trans-N-{4-[6-(Cyclopropylmethyl-methyl-amino)-hexyloxy]-cyclohexyl}-N-methyl-4-trifluoromethyl-benzenesulfonamide, trans-[Methyl-(6{-4-[methyl-(4-trifluoromethyl-benzenesulfonyl)-amino]-cyclohexyloxy}-hexyl)-amino]-acetic acid ethyl ester, trans-[Methyl-(6-{4-[methyl-(4-trifluoromethyl-benzenesulfonyl)-amino]-cyclohexyloxy}-hexyl)-amino]-acetic acid, trans-N-[4-(6-Allylamino-hexyloxy)-cyclohexyl]-N-methyl-4-trifluoromethyl-benzenesulfonamide, N-{4-trans-[6-(Allyl-methyl-amino)-hexyloxy]-cyclohexyl}-3-chloro-N-methyl-benzenesulfonamide, N-{4-trans-[6-(Allyl-methyl-amino)-hexyloxy]-cyclohexyl}-2,4-difluoro-N-methyl-benzenesulfonamide, N-{4-trans-[6-(Allyl-methyl-amino)-hexyloxy]-cyclohexyl}-2-bromo-N-methyl-benzenesulfonamide, N-{4-trans-[6-(Allyl-methyl-amino)-hexyloxy]-cyclohexyl}-3-bromo-N-methyl-benzenesulfonamide, N-{4-trans-[6-(Allyl-methyl-amino)-hexyloxy]-cyclohexyl}-2,4-dichloro-N-methyl-benzenesulfonamide, N-{4-trans-[6-(Allyl-methyl-amino)-hexyloxy]-cyclohexyl}-3-fluoro-N-methyl-benzenesulfonamide, N-{4-trans-[6-(Allyl-methyl-amino)-hexyloxy]-cyclohexyl}-3,4-dichloro-N-methyl-benzenesulfonamide, N-{4-trans-[6-(Allyl-methyl-amino)-hexyloxy]-cyclohexyl}-2-chloro-N-methyl-benzenesulfonamide, N-{4-trans-[6-(Allyl-methyl-amino)-hexyloxy]-cyclohexyl}-3,4-difluoro-N-methyl-benzenesulfonamide, trans-N-[4-(3-Allylamino-propoxy)-cyclohexyl]-N-methyl-4-trifluoromethyl-benzenesulfonamide, trans-N-{4-[3-(Allyl-methyl-amino)-propoxy]-cyclohexyl}N-methyl-4-trifluoromethyl-benzenesulfonamide, trans-N-(4-{3-[Ethyl-(2-hydroxy-ethyl)-amino]-propoxy}-cyclohexyl) N-methyl-4-trifluoromethyl-benzenesulfonamide, trans-N-[4-(3-Diethylamino-propoxy)-cyclohexyl]-N-methyl-4-trifluoromethyl-benzenesulfonamide, trans-N-(4-{3-[(2-Hydroxy-ethyl)-methyl-amino]-propoxy}-cyclohexyl)-N-methyl-4-trifluoromethyl-benzenesulfonamide, trans-N-(4-{3-[Bis-(2-hydroxy-ethyl)-amino]-propoxy}-cyclohexyl) N-methyl-4-trifluoromethyl-benzenesulfonamide, trans-N-{4-[3-(Cyclopropylmethyl-methyl-amino)-propoxy]-cyclohexyl}-N-methyl-4-trifluoromethyl-benzenesulfonamide, trans-N-Methyl-N-[4-(3-pyrrolidin-1-yl-propoxy)-cyclohexyl]-4-trifluoromethyl-benzenesulfonamide, trans-N-[4-(3-Ethylamino-propoxy)-cyclohexyl]-N-methyl-4-trifluoromethyl-benzenesulfonamide, trans-N-Methyl-N-[4-(3-morpholin-4-yl-propoxy)-cyclohexyl]-4-trifluoromethyl-benzenesulfonamide, trans-N-{4-[3-(2-Hydroxy-ethylamino)-propoxy]-cyclohexyl}-N-methyl-4-trifluoromethyl-benzenesulfonamide, trans-N-(4-{3-[Ethyl-(2-methoxy-ethyl)-amino]-propoxy}-cyclohexyl)-N-methyl-4-trifluoromethyl-benzenesulfonamide, trans-N-{4-[3-(3,6-Dihydro-2H-pyridin-1-yl)-propoxy]-cyclohexyl}-N-methyl-4-trifluoromethyl-benzenesulfonamide, trans-N-Methyl-N-{4-[3-(methyl-propyl-amino)-propoxy]-cyclohexyl}-4-trifluoromethyl-benzenesulfonamide, trans-N-[4-(4-Allylamino-butoxy)-cyclohexyl]-N-methyl-4-trifluoromethyl-benzenesulfonamide, N-{4-trans-[4-(Allyl-methyl-amino)-butoxy]-cyclohexyl}-N-methyl-4-trifluoromethyl-benzenesulfonamide, trans-N-(4-{4-[Ethyl-(2-hydroxy-ethyl)-amino]-butoxy}-cyclohexyl)-N-methyl-4-trifluoromethyl-benzenesulfonamide, trans-N-[4-(4-Diethylamino-butoxy)-cyclohexyl]-N-methyl-4-trifluoromethyl-benzenesulfonamide, trans-N-[4-(4-Dimethylamino-butoxy)-cyclohexyl]-N-methyl-4-trifluoromethyl-benzenesulfonamide, trans-N-(4-{4-[(2-Methoxy-ethyl)-methyl-amino]-butoxy}-cyclohexyl)-N-methyl-4-trifluoromethyl-benzenesulfonamide, trans-N-(4-{4-[(2-Hydroxy-ethyl)-methyl-amino]-butoxy}-cyclohexyl)-N-methyl-4-trifluoromethyl-benzenesulfonamide, trans-N-(4-{4-[Bis-(2-hydroxy-ethyl)-amino]-butoxy}-cyclohexyl)-N-methyl-4-trifluoromethyl-benzenesulfonamide, trans-N-{4-[4-(Cyclopropylmethyl-methyl-amino)-butoxy]-cyclohexyl}-N-methyl-4-trifluoromethyl-benzenesulfonamide, trans-N-[4-(4-Ethylamino-butoxy)-cyclohexyl]-N-methyl-4-trifluoromethyl-benzenesulfonamide, trans-N-Methyl-N-[4-(4-morpholin-4-yl-butoxy)-cyclohexyl]-4-trifluoromethyl-benzenesulfonamide, trans-N-{4-[4-(2-Hydroxy-ethylamino)-butoxy]-cyclohexyl}-N-methyl-4-trifluoromethyl-benzenesulfonamide, trans-N-{4-[4-(3,6-Dihydro-2H-pyridin-1-yl)-butoxy]-cyclohexyl}-N-methyl-4-trifluoromethyl-benzenesulfonamide, trans-N-Methyl-N-{4-[4-(methyl-propyl-amino)-butoxy]-cyclohexyl}-4-trifluoromethyl-benzenesulfonamide, trans-N-(4-{4-[Ethyl-(2-methoxy-ethyl)-amino]-butoxy}-cyclohexyl)-N-methyl-4-trifluoromethyl-benzenesulfonamide, trans-N-(4-{3-[(2-Methoxy-ethyl)-methyl-amino]-propoxy}-cyclohexyl)-N-methyl-4-trifluoromethyl-benzenesulfonamide, N-{4-trans-[3-(Allyl-methyl-amino)-propoxy]-cyclohexyl}-4-chloro-N-methyl-benzenesulfonamide, N-{4-trans-[4-(Allyl-methyl-amino)-butoxy]-cyclohexyl}-4-chloro-N-methyl-benzenesulfonamide, N-{4-trans-[4-(Allyl-methyl-amino)-butoxy]-cyclohexyl}-4-bromo-N-methyl-benzenesulfonamide, N-{4-trans-[4-(Allyl-methyl-amino)-butoxy]-cyclohexyl}-N-methyl-C-phenyl-methanesulfonamide, N-{4-trans-[4-(Allyl-methyl-amino)-butoxy]-cyclohexyl}-4-fluoro-N-methyl-benzenesulfonamide, N-{4-trans-[4-(Allyl-methyl-amino)-butoxy]-cyclohexyl}-2-fluoro-N-methyl-benzenesulfonamide, N-{4-trans-[4-(Allyl-methyl-amino)-butoxy]-cyclohexyl}-N-methyl-benzenesulfonamide, 5-Chloro-thiophene-2-sulfonic acid {4-trans-[4-(allyl-methyl-amino)-butoxy]-cyclohexyl}-methyl-amide, trans-Pyridine-2-carboxylic acid {4-[6-(allyl-methyl-amino)-hexyloxy]-cyclohexyl}-methyl-amide, trans-1H-Indole-2-carboxylic acid {4-[6-(allyl-methyl-amino)-hexyloxy]-cyclohexyl}-methyl-amide, trans-N-{4-[6-(Allyl-methyl-amino)-hexyloxy]-cyclohexyl}-N-methyl-benzamide, trans-N-{4-[6-(Allyl-methyl-amino)-hexyloxy]-cyclohexyl}-4-chloro-N-methyl-benzamide, trans-N-{4-[6-(Allyl-methyl-amino)-hexyloxy]-cyclohexyl}-4-fluoro-N-methyl-benzamide, trans-N-{4-[6-(Allyl-methyl-amino)-hexyloxy]-cyclohexyl}-4-bromo-N-methyl-benzamide, trans-N-{4-[6-(Allyl-methyl-amino)-hexyloxy]-cyclohexyl}-N-methyl-4-trifluoromethyl-benzamide, trans-Thiophene-3-carboxylic acid {4-[6-(allyl-methyl-amino)-hexyloxy]-cyclohexyl}-methyl-amide, trans-5-Bromo-thiophene-2-carboxylic acid {4-[6-(allyl-methyl-amino)-hexyloxy]-cyclohexyl}-methyl-amide, trans-N-{4-[6-(Allyl-methyl-amino)-hexyloxy]-cyclohexyl}-N-methyl-2-thiophen-3-yl-acetamide, trans-N-{4-[6-(Allyl-methyl-amino)-hexyloxy]-cyclohexyl}-2-(2,4-difluoro-phenyl)-N-methyl-acetamide, trans-5-Fluoro-1H-indole-2-carboxylic acid {4-[6-(allyl-methyl-amino)-hexyloxy]-cyclohexyl}-methyl-amide, trans-N-{4-[6-(Allyl-methyl-amino)-hexyloxy]-cyclohexyl}-2-(4-fluoro-phenyl)-N-methyl-acetamide, trans-1H-Indole-5-carboxylic acid {4-[6-(allyl-methyl-amino)-hexyloxy]-cyclohexyl}-methyl-amide, trans-N-{4-[6-(Allyl-methyl-amino)-hexyloxy]-cyclohexyl}-3-chloro-N-methyl-benzamide, trans-N-{4-[6-(Allyl-methyl-amino)-hexyloxy]-cyclohexyl}-4-fluoro-3,N-dimethyl-benzamide, trans-N-{4-[6-(Allyl-methyl-amino)-hexyloxy]-cyclohexyl}-N-methyl-4-nitro-benzamide, trans-N-{4-[6-(Allyl-methyl-amino)-hexyloxy]-cyclohexyl}-4,N-dimethyl-benzamide, trans-N-{4-[6-(Allyl-methyl-amino)-hexyloxy]-cyclohexyl}-3-cyano-N-methyl-benzamide, trans-N-{4-[6-(Allyl-methyl-amino)-hexyloxy]-cyclohexyl}-3,N-dimethyl-benzamide, trans-N-{4-[6-(Allyl-methyl-amino)-hexyloxy]-cyclohexyl}-3,4-dimethoxy-N-methyl-benzamide, trans-N-{4-[6-(Allyl-methyl-amino)-hexyloxy]-cyclohexyl}-4-methoxy-N-methyl-benzamide, trans-N-{4-[6-(Allyl-methyl-amino)-hexyloxy]-cyclohexyl}-4-fluoro-N-methyl-3-nitro-benzamide, trans-4-Acetyl-N-{4-[6-(allyl-methyl-amino)-hexyloxy]-cyclohexyl}-N-methyl-benzamide, trans-N-{4-[7-(Allyl-methyl-amino)-heptyloxy]-cyclohexyl}-N-methyl-4-trifluoromethyl-benzamide, trans-N-{4-[5-(Allyl-methyl-amino)-pentyloxy]-cyclohexyl}-N-methyl-4-trifluoromethyl-benzamide, trans-N-{4-[4-(Allyl-methyl-amino)-butoxy]-cyclohexyl}-3-cyano-N-methyl-benzamide, trans-N-{4-[5-(Allyl-methyl-amino)-pentyloxy]-cyclohexyl}-4-bromo-N-methyl-benzamide, trans-N-{4-[4-(Allyl-methyl-amino)-butoxy]-cyclohexyl}-4-bromo-N-methyl-benzamide, trans-5-Bromo-thiophene-2-carboxylic acid {4-[4-(allyl-methyl-amino)-butoxy]-cyclohexyl}-methyl-amide, trans-N-{4-[5-(Allyl-methyl-amino)-pentyloxy]-cyclohexyl}-4-fluoro-N-methyl-benzamide, trans-N-{4-[4-(Allyl-methyl-amino)-butoxy]-cyclohexyl}-4-fluoro-N-methyl-benzamide, trans-1-{4-[6-(Allyl-methyl-amino)-hexyloxy]-cyclohexyl}-3-(2,4-difluoro-phenyl)-1-methyl-urea, trans-1-{4-[6-(Allyl-methyl-amino)-hexyloxy]-cyclohexyl}-3-(2,4-dimethoxy-phenyl)-1-methyl-urea, trans-1-{4-[6-(Allyl-methyl-amino)-hexyloxy]-cyclohexyl}-3-(4-fluoro-phenyl)-1-methyl-urea, trans-1-{4-[6-(Allyl-methyl-amino)-hexyloxy]-cyclohexyl}-3-(4-methoxy-phenyl)-1-methyl-urea, trans-1-{4-[6-(Allyl-methyl-amino)-hexyloxy]-cyclohexyl}-1-methyl-3-p-tolyl-urea, trans-1-{4-[6-(Allyl-methyl-amino)-hexyloxy]-cyclohexyl}-3-(4-methoxy-2-methyl-phenyl)-1-methyl-urea, trans-1-{4-[6-(Allyl-methyl-amino)-hexyloxy]-cyclohexyl}-3-(2,4-dimethyl-phenyl)-1-methyl-urea, trans-1-{4-[6-(Allyl-methyl-amino)-hexyloxy]-cyclohexyl}-1-methyl-3-(3,4,5-trimethoxy-phenyl)-urea, trans-1-{4-[6-(Allyl-methyl-amino)-hexyloxy]-cyclohexyl}-3-(3,4-dimethyl-phenyl)-1-methyl-urea, trans-3-(4-Acetyl-phenyl)-1-{4-[6-(allyl-methyl-amino)-hexyloxy]-cyclohexyl}-1-methyl-urea, trans-1-{4-[6-(Allyl-methyl-amino)-hexyloxy]-cyclohexyl}-3-(4-chloro-phenyl)-1-methyl-urea, trans-1-{4-[6-(Allyl-methyl-amino)-hexyloxy]-cyclohexyl}-1-methyl-3-phenyl-urea, trans-1-{4-[6-(Allyl-methyl-amino)-hexyloxy]-cyclohexyl}-1-methyl-3-(4-trifluoromethyl-phenyl)-urea, trans-1-{4-[6-(Allyl-methyl-amino)-hexyloxy]-cyclohexyl}-3-(3,4-dichloro-phenyl)-1-methyl-urea, trans-1-{4-[6-(Allyl-methyl-amino)-hexyloxy]-cyclohexyl}-3-(4-bromo-phenyl)-1-methyl-urea, trans-1-{4-[6-(Allyl-methyl-amino)-hexyloxy]-cyclohexyl}-1-methyl-3-naphthalen-2-yl-urea, trans-1-{4-[6-(allyl-methyl-amino)-hexyloxy]-cyclohexyl}-1-methyl-3-(4-nitro-phenyl)-urea, trans-1-{4-[6-(Allyl-methyl-amino)-hexyloxy]-cyclohexyl}-3-(4-dimethylamino-phenyl)-1-methyl-urea, trans-1-{4-[7-(Allyl-methyl-amino)-heptyloxy]-cyclohexyl}-1-methyl-3-p-tolyl-urea, trans-1-{4-[7-(Allyl-methyl-amino)-heptyloxy]-cyclohexyl}-3-(4-fluoro-phenyl)-1-methyl-urea, trans-1-{4-[7-(Allyl-methyl-amino)-heptyloxy]-cyclohexyl}-3-(4-bromo-phenyl)-1-methyl-urea, trans-1-{4-[7-(Allyl-methyl-amino)-heptyloxy]-cyclohexyl}-3-(4-butyl-phenyl)-1-methyl-urea, trans-1-{4-[5-(Allyl-methyl-amino)-pentyloxy]-cyclohexyl}-1-methyl-3-p-tolyl-urea, trans-1-{4-[5-(Allyl-methyl-amino)-pentyloxy]-cyclohexyl}-3-(4-fluoro-phenyl)-1-methyl-urea, trans-1-{4-[5-(Allyl-methyl-amino)-pentyloxy]-cyclohexyl}-3-(4-bromo-phenyl)-1-methyl-urea, trans-1-{4-[4-(Allyl-methyl-amino)-butoxy]-cyclohexyl}-1-methyl-3-p-tolyl-urea, trans-1-{4-[4-(Allyl-methyl-amino)-butoxy]-cyclohexyl}-3-(4-fluoro-phenyl)-1-methyl-urea, trans-1-{4-[4-(Allyl-methyl-amino)-butoxy]-cyclohexyl}-3-(4-bromo-phenyl)-1-methyl-urea, trans-1-{4-[4-(Allyl-methyl-amino)-butoxy]-cyclohexyl}-3-(4-butyl-phenyl)-1-methyl-urea, trans-Methyl-{4-[4-(methyl-propyl-amino)-butoxy]-cyclohexyl}-carbamic acid 4-trifluoromethyl-phenyl ester, trans-N-(4-[6-(Allyl-methyl-amino)-hexyloxy]-cyclohexyl)-4-bromo-N-methyl-benzenesulfonamide, trans-4-Bromo-N-[4-(6-dimethylamino-hexyloxy)-cyclohexyl]-N-methyl-benzenesulfonamide, trans-4-Bromo-N-(4-{6-[(2-methoxy-ethyl)-methyl-amino]-hexyloxy}-cyclohexyl)-N-methyl-benzenesulfonamide, trans-N-(4-[6-(Allyl-methyl-amino)-hexyloxy]-cyclohexyl)-N-methyl-4-trifluoromethyl-benzenesulfonamide, trans-N-[4-(6-Dimethylamino-hexyloxy)-cyclohexyl]-N-methyl-4-trifluoromethyl-benzenesulfonamide, trans-N-(4-{6-[(2-Methoxy-ethyl)-methyl-amino]-hexyloxy}-cyclohexyl)-N-methyl-4-trifluoromethyl-benzenesulfonamide, trans-4-Bromo-N-[4-(6-diethylamino-hexyloxy)-cyclohexyl]-N-methyl-benzenesulfonamide, trans-4-Bromo-N-{4-[6-(isopropyl-methyl-amino)-hexyloxy]-cyclohexyl}-N-methyl-benzenesulfonamide, trans-4-Bromo-N-methyl-N-[4-(6-pyrrolidin-1-yl-hexyloxy)-cyclohexyl]-benzenesulfonamide, trans-N-[4-(6-Diethylamino-hexyloxy)-cyclohexyl]-N-methyl-4-trifluoromethyl-benzenesulfonamide, trans-N-{4-[6-(Isopropyl-methyl-amino)-hexyloxy]-cyclohexyl}-N-methyl-4-trifluoromethyl-benzenesulfonamide, trans-N-Methyl-N-[4-(6-pyrrolidin-1-yl-hexyloxy)-cyclohexyl]-4-trifluoromethyl-benzenesulfonamide, trans-4-Chloro-N-(4-{6-[(2-methoxy-ethyl)-methyl-amino]-hexyloxy}-cyclohexyl)-N-methyl-benzenesulfonamide, trans-(4-{6-[(2-Methoxy-ethyl)-methyl-amino]-hexyloxy}-cyclohexyl)-methyl-carbamic acid 4-chloro-phenyl ester, trans-4-Chloro-N-(4-{6-[(2-methoxy-ethyl)-methyl-amino]-hexyloxy}-cyclohexyl)-benzenesulfonamide, trans-4-Bromo-N-(4-{6-[(2-methoxy-ethyl)-methyl-amino]-hexyloxy}-cyclohexyl)-benzenesulfonamide, trans-4-Chloro-N-(4-{6-[(2-methoxy-ethyl)-methyl-amino]-hexyloxy}-cyclohexyl)-N-propyl-benzenesulfonamide, trans-4-Bromo-N-(4-{6-[(2-methoxy-ethyl)-methyl-amino]-hexyloxy}-cyclohexyl)-N-propyl-benzenesulfonamide, trans-4-Chloro-N-(4-{6-[(2-methoxy-ethyl)-methyl-amino]-hexyloxy}-cyclohexyl)-N-(2,4,5-trifluoro-benzyl)-benzenesulfonamide, trans-4-Bromo-N-(4-{6-[(2-methoxy-ethyl)-methyl-amino]-hexyloxy}-cyclohexyl)-N-(2,4,5-trifluoro-benzyl)-benzenesulfonamide, trans-(4-{6-[(2-Methoxy-ethyl)-methyl-amino]-hexyloxy}-cyclohexyl)-carbamic acid 4-chloro-phenyl ester, trans-Ethyl-(4-{6-[(2-methoxy-ethyl)-methyl-amino]-hexyloxy}-cyclohexyl)-carbamic acid 4-chloro-phenyl ester, trans-(4-{6-[(2-Methoxy-ethyl)-methyl-amino]-hexyloxy}-cyclohexyl)-propyl-carbamic acid 4-chloro-phenyl ester, trans-(4-{6-[(2-Methoxy-ethyl)-methyl-amino]-hexyloxy}-cyclohexyl)-(2,4,5-trifluoro-benzyl)-carbamic acid 4-chloro-phenyl ester, trans-Ethyl-(4-{6-[ethyl-(2-hydroxy-ethyl)-amino]-hexyloxy}-cyclohexyl)-carbamic acid benzyl ester, trans-Benzyl-(4-{6-[ethyl-(2-hydroxy-ethyl)-amino]-hexyloxy}-cyclohexyl)-carbamic acid benzyl ester, trans-(4-{6-[Ethyl-(2-hydroxy-ethyl)-amino]-hexyloxy}-cyclohexyl)-methyl-carbamic acid benzyl ester, trans-Allyl-(4-{6-[ethyl-(2-hydroxy-ethyl)-amino]-hexyloxy}-cyclohexyl)-carbamic acid benzyl ester, trans-(4-{6-[Ethyl-(2-hydroxy-ethyl)-amino]-hexyloxy}-cyclohexyl)-(2,4,5-trifluoro-benzyl)-carbamic acid benzyl ester, trans-[4-(6-Azetidin-1-yl-hexyloxy)-cyclohexyl]-ethyl-carbamic acid benzyl ester, trans-[4-(6-Azetidin-1-yl-hexyloxy)-cyclohexyl]-benzyl-carbamic acid benzyl ester, trans-[4-(6-Azetidin-1-yl-hexyloxy)-cyclohexyl]-methyl-carbamic acid benzyl ester, trans-Ethyl-(4-{6-[(2-hydroxy-ethyl)-methyl-amino]-hexyloxy}-cyclohexyl)-carbamic acid benzyl ester, trans-Benzyl-(4-{6-[(2-hydroxy-ethyl)-methyl-amino]-hexyloxy}-cyclohexyl)-carbamic acid benzyl ester, trans-(4-{6-[(2-Hydroxy-ethyl)-methyl-amino]-hexyloxy}-cyclohexyl)-methyl-carbamic acid benzyl ester, trans-Allyl-(4-{6-[(2-hydroxy-ethyl)-methyl-amino]-hexyloxy}-cyclohexyl)-carbamic acid benzyl ester, trans-(4-{6-[(2-Hydroxy-ethyl)-methyl-amino]-hexyloxy}-cyclohexyl)-(2,4,5-trifluoro-benzyl)-carbamic acid benzyl ester, trans-Ethyl-(4-{6-[(2-methoxy-ethyl)-methyl-amino]-hexyloxy}-cyclohexyl)-carbamic acid benzyl ester, trans-Benzyl-(4-{6-[(2-methoxy-ethyl)-methyl-amino]-hexyloxy}-cyclohexyl)-carbamic acid benzyl ester, trans-(4-{6-[(2-Methoxy-ethyl)-methyl-amino]-hexyloxy}-cyclohexyl)-methyl-carbamic acid benzyl ester, trans-(4{-6-[(2-Methoxy-ethyl)-methyl-amino]-hexyloxy}-cyclohexyl)-(2,4,5-trifluoro-benzyl)-carbamic acid benzyl ester, trans-Ethyl-[4-(6-morpholin-4-yl-hexyloxy)-cyclohexyl]-carbamic acid benzyl ester, trans-Benzyl-[4-(6-morpholin-4-yl-hexyloxy)-cyclohexyl]-carbamic acid benzyl ester, trans-Methyl-[4-(6-morpholin-4-yl-hexyloxy)-cyclohexyl]-carbamic acid benzyl ester, trans-Allyl-[4-(6-morpholin-4-yl-hexyloxy)-cyclohexyl]-carbamic acid benzyl ester, trans-[4-(6-Morpholin-4-yl-hexyloxy)-cyclohexyl]-(2,4,5-trifluoro-benzyl)-carbamic acid benzyl ester, trans-Ethyl-[4-(6-pyrrolidin-1-yl-hexyloxy)-cyclohexyl]-carbamic acid benzyl ester, trans-Benzyl-[4-(6-pyrrolidin-1-yl-hexyloxy)-cyclohexyl]-carbamic acid benzyl ester, trans-Methyl-[4-(6-pyrrolidin-1-yl-hexyloxy)-cyclohexyl]-carbamic acid benzyl ester, trans-Allyl-[4-(6-pyrrolidin-1-yl-hexyloxy)-cyclohexyl]-carbamic acid benzyl ester, trans-[4-(6-Pyrrolidin-1-yl-hexyloxy)-cyclohexyl]-(2,4,5-trifluoro-benzyl)-carbamic acid benzyl ester, trans-{4-[6-(Allyl-methyl-amino)-hexyloxy]-cyclohexyl}-methyl-carbamic acid benzyl ester, trans-{4-[6-(Allyl-methyl-amino)-hexyloxy]-cyclohexyl}-ethyl-carbamic acid benzyl ester, trans-Allyl-{4-[6-(allyl-methyl-amino)-hexyloxy]-cyclohexyl}-carbamic acid benzyl ester, trans-{4-[6-(Allyl-methyl-amino)-hexyloxy]-cyclohexyl}-benzyl-carbamic acid benzyl ester, trans-{4-[6-(Allyl-methyl-amino)-hexyloxy]-cyclohexyl}-(2,4,5-trifluoro-benzyl)-carbamic acid benzyl ester, trans-[4-(6-Dimethylamino-hexyloxy)-cyclohexyl]-methyl-carbamic acid benzyl ester, trans-[4-(6-Dimethylamino-hexyloxy)-cyclohexyl]-ethyl-carbamic acid benzyl ester, trans-Allyl-[4-(6-dimethylamino-hexyloxy)-cyclohexyl]-carbamic acid benzyl ester, trans-Benzyl-[4-(6-dimethylamino-hexyloxy)-cyclohexyl]-carbamic acid benzyl ester, trans-[4-(6-Dimethylamino-hexyloxy)-cyclohexyl]-(2,4,5-trifluoro-benzyl)-carbamic acid benzyl ester, trans-(4-[5-(Allyl-methyl-amino)-pentyloxy]-cyclohexyl)-methyl-carbamic acid tert-butyl ester, trans-(4-[3-(Allyl-methyl-amino)-propoxy]-cyclohexyl)-methyl-carbamic acid tert-butyl ester, trans-(4-[4-(Allyl-methyl-amino)-butoxy]-cyclohexyl)-methyl-carbamic acid tert-butyl ester, trans-(4-[7-(Allyl-methyl-amino)-heptyloxy]-cyclohexyl)-methyl-carbamic acid tert-butyl ester, trans-4-Chloro-N-ethyl-N-(4-{6-[(2-methoxy-ethyl)-methyl-amino]-hexyloxy}-cyclohexyl)-benzenesulfonamide, trans-4-Bromo-N-ethyl-N-(4-{6-[(2-methoxy-ethyl)-methyl-amino]-hexyloxy}-cyclohexyl)-benzenesulfonamide, trans-{4-[4-(Allyl-methyl-amino)-butoxy]-cyclohexyl}-methyl-carbamic acid 4-chloro-phenyl ester, trans-{4-[5-(Allyl-methyl-amino)-pentyloxy]-cyclohexyl}-methyl-carbamic acid 4-chloro-phenyl ester, trans-(4-{6-[Ethyl-(2-hydroxy-ethyl)-amino]-hexyloxy}-cyclohexyl)-methyl-carbamic acid 4-chloro-phenyl ester, trans-(4-{4-[Ethyl-(2-hydroxy-ethyl)-amino]-butoxy}-cyclohexyl)-methyl-carbamic acid 4-chloro-phenyl ester, trans-(4-{5-[Ethyl-(2-hydroxy-ethyl)-amino]-pentyloxy}-cyclohexyl)-methyl-carbamic acid 4-chloro-phenyl ester, trans-[4-(6-Dimethylamino-hexyloxy)-cyclohexyl]-methyl-carbamic acid 4-chloro-phenyl ester, trans-[4-(4-Dimethylamino-butoxy)-cyclohexyl]-methyl-carbamic acid 4-chloro-phenyl ester, trans-[4-(5-Dimethylamino-pentyloxy)-cyclohexyl]-methyl-carbamic acid 4-chloro-phenyl ester, trans-(4-{6-[Ethyl-(2-methoxy-ethyl)-amino]-hexyloxy}-cyclohexyl)-methyl-carbamic acid 4-chloro-phenyl ester, trans-(4-{4-[Ethyl-(2-methoxy-ethyl)-amino]-butoxy}-cyclohexyl)-methyl-carbamic acid 4-chloro-phenyl ester, trans-{4-[3-(Allyl-methyl-amino)-propoxy]-cyclohexyl}-methyl-carbamic acid 4-chloro-phenyl ester, trans-(4-{3-[Ethyl-(2-methoxy-ethyl)-amino]-propoxy}-cyclohexyl)-methyl-carbamic acid 4-chloro-phenyl ester, trans-(4-{5-[Ethyl-(2-methoxy-ethyl)-amino]-pentyloxy}-cyclohexyl)-methyl-carbamic acid 4-chloro-phenyl ester, trans-[4-(3-Dimethylamino-propoxy)-cyclohexyl]-methyl-carbamic acid 4-chloro-phenyl ester, trans-(4-{3-[Ethyl-(2-hydroxy-ethyl)-amino]-propoxy}-cyclohexyl)-methyl-carbamic acid 4-chloro-phenyl ester, trans-Methyl-[4-(3-piperidin-1-yl-propoxy)-cyclohexyl]-carbamic acid 4-chloro-phenyl ester, trans-Methyl-[4-(4-piperidin-1-yl-butoxy)-cyclohexyl]-carbamic acid 4-chloro-phenyl ester, trans-Methyl-[4-(6-piperidin-1-yl-hexyloxy)-cyclohexyl]-carbamic acid 4-chloro-phenyl ester, trans-Methyl-[4-(5-piperidin-1-yl-pentyloxy)-cyclohexyl]-carbamic acid 4-chloro-phenyl ester, trans-[4-(3-Diethylamino-propoxy)-cyclohexyl]-methyl-carbamic acid 4-chloro-phenyl ester, trans-[4-(6-Diethylamino-hexyloxy)-cyclohexyl]-methyl-carbamic acid 4-chloro-phenyl ester, trans-[4-(4-Diethylamino-butoxy)-cyclohexyl]-methyl-carbamic acid 4-chloro-phenyl ester, trans-[4-(5-Diethylamino-pentyloxy)-cyclohexyl]-methyl-carbamic acid 4-chloro-phenyl ester, trans-Methyl-[4-(3-pyrrolidin-1-yl-propoxy)-cyclohexyl]-carbamic acid 4-chloro-phenyl ester, trans-Methyl-[4-(6-pyrrolidin-1-yl-hexyloxy)-cyclohexyl]-carbamic acid 4-chloro-phenyl ester, trans-(4-{6-[(2-Hydroxy-ethyl)-methyl-amino]-hexyloxy}-cyclohexyl)-methyl-carbamic acid 4-chloro-phenyl ester, trans-(4-{4-[(2-Hydroxy-ethyl)-methyl-amino]-butoxy}-cyclohexyl)-methyl-carbamic acid 4-chloro-phenyl ester, trans-(4-{5-[(2-Hydroxy-ethyl)-methyl-amino]-pentyloxy}-cyclohexyl)-methyl-carbamic acid 4-chloro-phenyl ester, trans-Methyl-[4-(4-pyrrolidin-1-yl-butoxy)-cyclohexyl]-carbamic acid 4-chloro-phenyl ester, trans-Methyl-[4-(5-pyrrolidin-1-yl-pentyloxy)-cyclohexyl]-carbamic acid 4-chloro-phenyl ester, trans-(4-{3-[(2-Hydroxy-ethyl)-methyl-amino]-propoxy}-cyclohexyl)-methyl-carbamic acid 4-chloro-phenyl ester, trans-[4-(5-Dimethylamino-pentyloxy)-cyclohexyl]-methyl-carbamic acid 4-chloro-phenyl ester N-oxide, trans-{4-[5-(Allyl-methyl-amino)-pentyl]-cyclohexyl}-methyl-carbamic acid 4-trifluoromethyl-phenyl ester, trans-(4-{5-[Ethyl-(2-hydroxy-ethyl)-amino]-pentyl}-cyclohexyl)-methyl-carbamic acid 4-trifluoromethyl-phenyl ester, trans-{4-[5-(Allyl-methyl-amino)-pentyl]-cyclohexyl}-methyl-carbamic acid 4-bromo-phenyl ester, trans-(4-{5-[Ethyl-(2-hydroxy-ethyl)-amino]-pentyl}-cyclohexyl)-methyl-carbamic acid 4-bromo-phenyl ester, trans-{4-[5-(Allyl-methyl-amino)-pentyl]-cyclohexyl}-methyl-carbamic acid 3,4-difluoro-phenyl ester, trans-(4-{5-[Ethyl-(2-hydroxy-ethyl)-amino]-pentyl}-cyclohexyl)-methyl-carbamic acid 3,4-difluoro-phenyl ester, trans-{4-[5-(Allyl-methyl-amino)-pentyl]-cyclohexyl}-methyl-carbamic acid 4-chloro-phenyl ester, trans-{4-[3-(Allyl-methyl-amino)-propoxymethyl]-cyclohexyl}-methyl-carbamic acid 4-chloro-phenyl ester, trans-(4-{3-[Ethyl-(2-hydroxy-ethyl)-amino]-propoxymethyl}-cyclohexyl)-methyl-carbamic acid 4-chloro-phenyl ester, trans-[4-(3-Azetidin-1-yl-propoxymethyl)-cyclohexyl]-methyl-carbamic acid 4-chloro-phenyl ester, trans-Methyl-[4-(3-piperidin-1-yl-propoxymethyl)-cyclohexyl]-carbamic acid 4-chloro-phenyl ester, trans-(4-{3-[Ethyl-(2-methoxy-ethyl)-amino]-propoxymethyl}-cyclohexyl)-methyl-carbamic acid 4-chloro-phenyl ester, trans-{4-[4-(Allyl-methyl-amino)-butoxymethyl]-cyclohexyl}-methyl-carbamic acid 4-chloro-phenyl ester, trans-{4-[2-(Allyl-methyl-amino)-ethoxymethyl]-cyclohexyl}-methyl-carbamic acid 4-chloro-phenyl ester, trans-N-{4-[3-(Allyl-methyl-amino)-propoxymethyl]-cyclohexyl}-N-methyl-4-trifluoromethyl-benzenesulfonamide, (trans)-N-(4-{3-[Ethyl-(2-hydroxy-ethyl)-amino]-propoxymethyl}-cyclohexyl)-N-methyl-4-trifluoromethyl-benzenesulfonamide, trans-N-[4-(3-Azetidin-1-yl-propoxymethyl)-cyclohexyl]-N-methyl-4-trifluoromethyl-benzenesulfonamide, trans-N-Methyl-N-[4-(3-piperidin-1-yl-propoxymethyl)-cyclohexyl]-4-trifluoromethyl-benzenesulfonamide, (trans)-N-[4-(2-Dimethylamino-ethylsulfanylmethyl)-cyclohexyl]-N-methyl-4-trifluoromethyl-benzenesulfonamide, trans-N-[4-(2-Diethylamino-ethylsulfanylmethyl)-cyclohexyl]-N-methyl-4-trifluoromethyl-benzenesulfonamide, trans-N-{4-[2-(Allyl-methyl-amino)-ethylsulfanylmethyl]-cyclohexyl}-N-methyl-4-trifluoromethyl-benzenesulfonamide, trans-[4-(2-Diethylamino-ethylsulfanylmethyl)-cyclohexyl]-methyl-carbamic acid 4-chloro-phenyl ester, trans-{4-[2-(Allyl-methyl-amino)-ethylsulfanylmethyl]-cyclohexyl}-methyl-carbamic acid 4-chloro-phenyl ester, trans-{4-[3-(Allyl-methyl-amino)-propylsulfanylmethyl]-cyclohexyl}-methyl-carbamic acid 4-chloro-phenyl ester, trans-[4-(2-Dimethylamino-ethylsulfanylmethyl)-cyclohexyl]-methyl-carbamic acid 4-chloro-phenyl ester, trans-(4-{2-[Ethyl-(2-hydroxy-ethyl)-amino]-ethylsulfanylmethyl}-cyclohexyl)-methyl-carbamic acid 4-chloro-phenyl ester, trans-Methyl-{4-[2-(methyl-propyl-amino)-ethylsulfanylmethyl]-cyclohexyl}-carbamic acid 4-chloro-phenyl ester, trans-{4-[3-(Allyl-methyl-amino)-prop-1-ynyl]-cyclohexyl}-methyl-carbamic acid 4-chloro-phenyl ester, trans-(4-{3-[Ethyl-(2-hydroxy-ethyl)-amino]-prop-1-ynyl}-cyclohexyl)-methyl-carbamic acid 4-chloro-phenyl ester, trans-(4-{3-[Ethyl-(2-hydroxy-ethyl)-amino]-propyl}-cyclohexyl)-methyl-carbamic acid 4-chloro-phenyl ester, trans-Methyl-{4-[4-(methyl-propyl-amino)-butoxy]-cyclohexyl}-carbamic acid 3,4-difluoro-phenyl ester, trans-[4-[6-(Allyl-methyl-amino)-hexyloxy]-cyclohexyl]-methyl-sulfamic acid benzyl amide, trans-{4-[6-(Allyl-methyl-amino)-hexyloxy]-cyclohexyl}-methyl-sulfamic acid phenyl amide, trans-4-[({4-[6-(Allyl-methyl-amino)-hexyloxy]-cyclohexyl}-methyl-sulfamoyloxy)-methyl]-benzoic acid methyl ester, trans-{4-[6-(Allyl-methyl-amino)-hexyloxy]-cyclohexyl}-methyl-sulfamic acid butyl amide, trans-{4-[6-(Allyl-methyl-amino)-hexyloxy]-cyclohexyl}-methyl-sulfamic acid phenethyl amide, trans-{4-[6-(Allyl-methyl-amino)-hexyloxy]-cyclohexyl}-methyl-sulfamic acid furan-2-ylmethyl amide, trans-({4-[6-(Allyl-methyl-amino)-hexyloxy]-cyclohexyl}-methyl-sulfonylamino)-acetic acid ethyl ester, trans-{4-[6-(Allyl-methyl-amino)-hexyloxy]-cyclohexyl}-methyl-sulfamic acid cyclopropyl amide, trans-{4-[6-(Allyl-methyl-amino)-hexyloxy]-cyclohexyl}-methyl-sulfamic acid 2,2,2-trifluoro-ethyl amide, trans-{4-[6-(Allyl-methyl-amino)-hexyloxy]-cyclohexyl}-methyl-sulfamic acid benzo[1,3]dioxol-5-ylmethyl amide, trans-{4-[6-(Allyl-methyl-amino)-hexyloxy]-cyclohexyl}-methyl-sulfamic acid 4-fluorobenzyl amide, trans-{4-[6-(Allyl-methyl-amino)-hexyloxy]-cyclohexyl}-methyl-sulfamic acid (4-chloro-phenyl)-amide, trans-{4-[6-(Allyl-methyl-amino)-hexyloxy]-cyclohexyl}-methyl-sulfamic acid (4-fluoro-phenyl)-amide, trans-{4-[6-(Allyl-methyl-amino)-hexyloxy]-cyclohexyl}-methyl-sulfamic acid (4-bromo-phenyl)-amide, trans-{4-[6-(Allyl-methyl-amino)-hexyloxy]-cyclohexyl}-methyl-sulfamic acid (p-tolyl)-amide, trans-{4-[6-(Allyl-methyl-amino)-hexyloxy]-cyclohexyl}-methyl-sulfamic acid (3,4-difluoro-phenyl)-amide, trans-{4-[6-(Allyl-methyl-amino)-hexyloxy]-cyclohexyl}-methyl-sulfamic acid (4-trifluoromethyl-phenyl)-amide, trans-{4-[6-(Allyl-methyl-amino)-hexyloxy]-cyclohexyl}-methyl-sulfamic acid (3-fluoro-phenyl)-amide, trans-{4-[6-(Allyl-methyl-amino)-hexyloxy]-cyclohexyl}-methyl-sulfamic acid (4-cyano-phenyl)-amide, trans-{4-[6-(Allyl-methyl-amino)-hexyloxy]-cyclohexyl}-methyl-sulfamic acid (2,4-difluoro-phenyl)-amide, trans-{4-[6-(Allyl-methyl-amino)-hexyloxy]-cyclohexyl}-methyl-sulfamic acid (4-methoxy-phenyl)-amide, trans-{4-[6-(Allyl-methyl-amino)-hexyloxy]-cyclohexyl}-methyl-sulfamic acid (2,5-difluoro-phenyl)-amide, trans-{4-[5-(Allyl-methyl-amino)-pentyloxy]-cyclohexyl}-methyl-sulfamic acid benzyl amide, trans-{4-[5-(Allyl-methyl-amino)-pentyloxy]-cyclohexyl}-methyl-sulfamic acid phenyl amide, trans-{4-[5-(Allyl-methyl-amino)-pentyloxy]-cyclohexyl}-methyl-sulfamic acid p-chlorophenyl amide, trans-{4-[5-(Allyl-methyl-amino)-pentyloxy]-cyclohexyl}-methyl-sulfamic acid p-bromophenyl amide, trans-{4-[5-(Allyl-methyl-amino)-pentyloxy]-cyclohexyl}-methyl-sulfamic acid p-methylphenyl amide, trans-{4-[5-(Allyl-methyl-amino)-pentyloxy]-cyclohexyl}-methyl-sulfamic acid p-trifluoromethylphenyl amide, trans-{4-[5-(Allyl-methyl-amino)-pentyloxy]-cyclohexyl}-methyl-sulfamic acid p-cyanophenyl amide, trans-{4-[5-(Allyl-methyl-amino)-pentyloxy]-cyclohexyl}-methyl-sulfamic acid p-methoxyphenyl amide, trans-{4-[5-(Allyl-methyl-amino)-pentyloxy]-cyclohexyl}-methyl-sulfamic acid 3,4-difluorophenyl amide, trans-{4-[5-(Allyl-methyl-amino)-pentyloxy]-cyclohexyl}-methyl-sulfamic acid 3-fluorophenyl amide, trans-{4-[5-(Allyl-methyl-amino)-pentyloxy]-cyclohexyl}-methyl-sulfamic acid 2,4-difluorophenyl amide, trans-{4-[5-(Allyl-methyl-amino)-pentyloxy]-cyclohexyl}-methyl-sulfamic acid 2,5-difluorophenyl amide, trans-{4-[3-(Allyl-methyl-amino)-propoxy]-cyclohexyl}-methyl-sulfamic acid phenyl amide, trans-{4-[3-(Allyl-methyl-amino)-propoxy]-cyclohexyl}-methyl-sulfamic acid 3,4-difluorophenyl amide, trans-{4-[3-(Allyl-methyl-amino)-propoxy]-cyclohexyl}-methyl-sulfamic acid 4-chlorophenyl amide, trans-{4-[3-(Allyl-methyl-amino)-propoxy]-cyclohexyl}-methyl-sulfamic acid benzyl amide, trans-{4-[4-(Allyl-methyl-amino)-butoxy]-cyclohexyl}-methyl-sulfamic acid phenyl amide, trans-{4-[4-(Allyl-methyl-amino)-butoxy]-cyclohexyl}-methyl-sulfamic acid 3-fluoro phenyl amide, trans-{4-[4-(Allyl-methyl-amino)-butoxy]-cyclohexyl}-methyl-sulfamic acid 3,4-difluoro phenyl amide, trans-{4-[4-(Allyl-methyl-amino)-butoxy]-cyclohexyl}-methyl-sulfamic acid 4-chloro phenyl amide, trans-{4-[4-(Allyl-methyl-amino)-butoxy]-cyclohexyl}-methyl-sulfamic acid benzyl amide, trans-({4-[4-(Allyl-methyl-amino)-butoxy]-cyclohexyl}-methyl-sulfamoylamino)-acetic acid ethyl ester, trans-{4-[7-(Allyl-methyl-amino)-heptyloxy]-cyclohexyl}-methyl-sulfamic acid phenyl amide, trans-{4-[7-(Allyl-methyl-amino)-heptyloxy]-cyclohexyl}-methyl-sulfamic acid 3-fluoro-phenyl amide, trans-{4-[7-(Allyl-methyl-amino)-heptyloxy]-cyclohexyl}-methyl-sulfamic acid 3,4-difluoro-phenyl amide, trans-{4-[7-(Allyl-methyl-amino)-heptyloxy]-cyclohexyl}-methyl-sulfamic acid 4-chloro-phenyl amide, trans-{4-[7-(Allyl-methyl-amino)-heptyloxy]-cyclohexyl}-methyl-sulfamic acid furan-2-ylmethyl amide, trans-{4-[7-(Allyl-methyl-amino)-heptyloxy]-cyclohexyl}-methyl-sulfamic acid benzyl amide, trans-({4-[7-(Allyl-methyl-amino)-heptyloxy]-cyclohexyl}-methyl-sulfamoyloxy)-acetic acid ethyl amide, trans-1-{4-[6-(Allyl-methyl-amino)-hexyloxy]-cyclohexyl}-3-(2-bromo-4-fluoro-phenyl)-1-methyl-thiourea, trans-1-{4-[6-(Allyl-methyl-amino)-hexyloxy]-cyclohexyl}-3-(4-bromo-2-methyl-phenyl)-1-methyl-thiourea, trans-1-{4-[6-(Allyl-methyl-amino)-hexyloxy]-cyclohexyl}-1-methyl-3-(4-trifluoromethyl-phenyl)-thiourea, trans-1-{4-[6-(Allyl-methyl-amino)-hexyloxy]-cyclohexyl}-3-(4-chloro-phenyl)-1-methyl-thiourea, trans-1-{4-[6-(Allyl-methyl-amino)-hexyloxy]-cyclohexyl}-3-(4-methoxy-phenyl)-1-methyl-thiourea, trans-1-{4-[6-(Allyl-methyl-amino)-hexyloxy]-cyclohexyl}-3-(4-cyano-phenyl)-1-methyl-thiourea, trans-1-{4-[6-(Allyl-methyl-amino)-hexyloxy]-cyclohexyl}-1-methyl-3-(3-methyl-butyl)-thiourea, trans-1-{4-[6-(Allyl-methyl-amino)-hexyloxy]-cyclohexyl}-3-sec-butyl-1-methyl-thiourea, trans-1-{4-[4-(Allyl-methyl-amino)-butoxy]-cyclohexyl}-1-methyl-3-(4-trifluoromethyl-phenyl)-thiourea, trans-1-{4-[4-(Allyl-methyl-amino)-butoxy]-cyclohexyl}-3-(4-cyano-phenyl)-1-methyl-thiourea, trans-1-{4-[4-(Allyl-methyl-amino)-butoxy]-cyclohexyl}-1-methyl-3-(3-methyl-butyl)-thiourea, trans-1-{4-[7-(Allyl-methyl-amino)-heptyloxy]-cyclohexyl}-1-methyl-3-(4-trifluoromethyl-phenyl)-thiourea, trans-1-{4-[7-(Allyl-methyl-amino)-heptyloxy]-cyclohexyl}-3-(4-cyano-phenyl)-1-methyl-thiourea, trans-1-{4-[7-(Allyl-methyl-amino)-heptyloxy]-cyclohexyl}-1-methyl-3-(3-methyl-butyl)-thiourea, trans-1-{4-[3-(Allyl-methyl-amino)-propoxy]-cyclohexyl}-1-methyl-3-(4-trifluoromethyl-phenyl)-thiourea, trans-[4-(6-Dimethylamino-hexyloxy)-cyclohexyl]-carbamic acid benzyl ester, trans-[4-(5-Dimethylamino-pentyloxy)-cyclohexyl]-carbamic acid benzyl ester, trans-{4-[6-(Allyl-methyl-amino)-hexyloxy]-cyclohexyl}-carbamic acid benzyl ester, trans-N-{4-[5-(Allyl-methyl-amino)-pentyl]-cyclohexyl}-N-methyl-4-trifluoromethyl-benzenesulfonamide, trans-N-(4-{5-[Ethyl-(2-hydroxy-ethyl)-amino]-pentyl}-cyclohexyl)-N-methyl-4-trifluoromethyl-benzenesulfonamide, and trans-{4-[4-(Allyl-methyl-amino)-butyl]-cyclohexyl}-methyl-carbamic acid 4-chloro-phenyl ester, and pharmaceutically acceptable salts thereof.

Other preferred compounds of general formula (I) are those selected from the group consisting of trans-N-[4-(3-Allylamino-propoxy)-cyclohexyl]-N-methyl-4-trifluoromethyl-benzenesulfonamide, trans-N-{4-[4-(Allyl-methyl-amino)-butoxy]-cyclohexyl}-N-ethyl-4-trifluoromethyl-benzenesulfonamide, trans-N-[4-(4-Dimethylamino-butoxy)-cyclohexyl]-N-ethyl-4-trifluoromethyl-benzenesulfonamide, trans-N-Ethyl-N-(4-{4-[(2-hydroxy-ethyl)-methyl-amino]-butoxy}-cyclohexyl)-4-trifluoromethyl-benzenesulfonamide, trans-N-Ethyl-N-(4-{4-[(2-methoxy-ethyl)-methyl-amino]-butoxy}-cyclohexyl)-4-trifluoromethyl-benzenesulfonamide, trans-N-Ethyl-N-(4-{4-[ethyl-(2-hydroxy-ethyl)-amino]-butoxy}-cyclohexyl)-4-trifluoromethyl-benzenesulfonamide, trans-N-Ethyl-N-(4-{4-[ethyl-(2-methoxy-ethyl)-amino]-butoxy}-cyclohexyl)-4-trifluoromethyl-benzenesulfonamide, trans-N-(4-{4-[Bis-(2-hydroxy-ethyl)-amino]-butoxy}-cyclohexyl)-N-ethyl-4-trifluoromethyl-benzenesulfonamide, trans-N-[4-(4-Diethylamino-butoxy)-cyclohexyl]-N-ethyl-4-trifluoromethyl-benzenesulfonamide, trans-N-[4-(4-Allylamino-butoxy)-cyclohexyl]-N-ethyl-4-trifluoromethyl-benzenesulfonamide, trans-N-Ethyl-N-[4-(4-piperidin-1-yl-butoxy)-cyclohexyl]-4-trifluoromethyl-benzenesulfonamide, trans-N-Ethyl-N-{4-[4-(4-methyl-piperazin-1-yl)-butoxy]-cyclohexyl}-4-trifluoromethyl-benzenesulfonamide, trans-[4-(6-Dimethylamino-hexyloxy)-cyclohexyl]-carbamic acid benzyl ester, trans-[4-(5-Dimethylamino-pentyloxy)-cyclohexyl]-carbamic acid benzyl ester, trans-N-{4-[4-(2-Hydroxy-ethylamino)-butyl]-cyclohexyl}-N-methyl-4-trifluoromethyl-benzenesulfonamide, trans-N-[4-(5-Ethylamino-pentyl)-cyclohexyl]-N-methyl-4-trifluoromethyl-benzenesulfonamide, trans-N-(4-{5-[Ethyl-(2-hydroxy-ethyl)-amino]-pentyl}-cyclohexyl)-N-methyl-4-trifluoromethyl-benzenesulfonamide N-oxide, trans-N-(4-{5-[Ethyl-(2-fluoro-ethyl)-amino]-pentyl}-cyclohexyl)-N-methyl-4-trifluoromethyl-benzenesulfonamide, trans-4-Bromo-N-[4-(2-diisopropylamino-ethoxy)-cyclohexyl]-N-methyl-benzenesulfonamide, trans-4-Bromo-N-methyl-N-[4-(2-piperidin-1-yl-ethoxy)-cyclohexyl]-benzenesulfonamide, Trans-4-Bromo-N-[4-(2-diethylamino-ethoxy)-cyclohexyl]-N-methyl-benzenesulfonamide, trans-4-Bromo-N-methyl-N-[4-(2-morpholin-4-yl-ethoxy)-cyclohexyl]-benzenesulfonamide, trans-4-Bromo-N-methyl-N-[4-(2-pyrrolidin-1-yl-ethoxy)-cyclohexyl]-benzenesulfonamide, trans-N-[4-(3-Dimethylamino-3-methyl-butoxy)-cyclohexyl]-N-methyl-4-trifluoromethyl-benzenesulfonamide, trans-N-{4-[2-(1-Dimethylamino-cyclopropyl)-ethoxy]-cyclohexyl}-N-methyl-4-trifluoromethyl-benzenesulfonamide, trans-N-[4-(5-Diethylamino-5-methyl-hexyl)-cyclohexyl]-N-methyl-4-trifluoromethyl-benzenesulfonamide, trans-N-{4-[4-(1-Diethylamino-cyclopropyl)-butyl]-cyclohexyl}-N-methyl-4-trifluoromethyl-benzenesulfonamide, trans-N-[4-(4-Dimethylamino-pentyloxy)-cyclohexyl]-N-methyl-4-trifluoromethyl-benzenesulfonamide, trans-N-[4-(2-Diethylamino-ethoxy)-cyclohexyl]-N-methyl-4-trifluoromethyl-benzenesulfonamide, trans-N-Methyl-N-[4-(2-piperidin-1-yl-ethoxy)-cyclohexyl]-4-trifluoromethyl-benzenesulfonamie, trans-N-[4-(2-Diisopropylamino-ethoxy)-cyclohexyl]-N-methyl-4-trifluoromethyl-benzenesulfonamide, trans-N-Methyl-N-[4-(2-pyrrolidin-1-yl-ethoxy)-cyclohexyl]-4-trifluoromethyl-benzenesulfonamide, trans-N-Methyl-N-[4-(2-morpholin-4-yl-ethoxy)-cyclohexyl]-4-trifluoromethyl-benzenesulfonamide, trans-N-Methyl-N-[4-(4-piperidin-1-yl-pentyloxy)-cyclohexyl]-4-trifluoromethyl-benzenesulfonamide, trans-[4-(3-Dimethylamino-3-methyl-but-1-ynyl)-cyclohexyl]-methyl-carbamic acid tert-butyl ester, cis-N-(4-{5-[Ethyl-(2-hydroxy-ethyl)-amino]-pentyl}-cyclohexyl)-N-methyl-4-trifluoromethyl-benzenesulfonamide, trans-(4-{4-[Ethyl-(2-hydroxy-ethyl)-amino]-butyl}-cyclohexyl)-methyl-carbamic acid 4-chloro-phenyl ester, trans-{4-[4-(Allyl-methyl-amino)-butyl]-cyclohexyl}-methyl-carbamic acid 4-trifluoromethyl-phenyl ester, trans-(4-{4-[Ethyl-(2-hydroxy-ethyl)-amino]-butyl}-cyclohexyl)-methyl-carbamic acid 4-trifluoromethyl-phenyl ester, trans-{4-[4-(Allyl-methyl-amino)-butyl]-cyclohexyl}-methyl-carbamic acid 4-bromo-phenyl ester, trans-(4-{4-[Ethyl-(2-hydroxy-ethyl)-amino]-butyl}-cyclohexyl)-methyl-carbamic acid 4-bromo-phenyl ester, trans-Methyl-{4-[4-(methyl-propyl-amino)-butyl]-cyclohexyl}-carbamic acid 4-bromo-phenyl ester, trans-[4-(4-Diethylamino-butyl)-cyclohexyl]-methyl-carbamic acid 4-bromo-phenyl ester, trans-[4-(4-Dimethylamino-butyl)-cyclohexyl]-methyl-carbamic acid 4-bromo-phenyl ester, trans-Methyl-[4-(4-piperidin-1-yl-butyl)-cyclohexyl]-carbamic acid 4-bromo-phenyl ester, trans-Methyl-{4-[4-(4-methyl-piperazin-1-yl)-butyl]-cyclohexyl}-carbamic acid 4-bromo-phenyl ester, trans-Methyl-[4-(4-morpholin-4-yl-butyl)-cyclohexyl]-carbamic acid 4-bromo-phenyl ester, trans-Methyl-[4-(4-thiomorpholin-4-yl-butyl)-cyclohexyl]-carbamic acid 4-bromo-phenyl ester, trans-Methyl-[4-(4-piperidin-1-yl-butyl)-cyclohexyl]-carbamic acid 4-trifluoromethyl-phenyl ester, trans-[4-(4-Dimethylamino-butyl)-cyclohexyl]-methyl-carbamic acid 4-trifluoromethyl-phenyl ester, trans-Methyl-[4-(4-thiomorpholin-4-yl-butyl)-cyclohexyl]-carbamic acid 4-trifluoromethyl-phenyl ester, trans-Methyl-{4-[4-(methyl-propyl-amino)-butyl]-cyclohexyl}-carbamic acid 4-trifluoromethyl-phenyl ester, trans-N-{4-[4-(Allyl-methyl-amino)-butyl]-cyclohexyl}-N-methyl-4-trifluoromethyl-benzenesulfonamide, trans-N-(4-{4-[Ethyl-(2-hydroxy-ethyl)-amino]-butyl}-cyclohexyl)-N-methyl-4-trifluoromethyl-benzenesulfonamide, trans-N-Methyl-N-[4-(4-piperidin-1-yl-butyl)-cyclohexyl]-4-trifluoromethyl-benzenesulfonamide, trans-N-[4-(4-Dimethylamino-butyl)-cyclohexyl]-N-methyl-4-trifluoromethyl-benzenesulfonamide, trans-N-Methyl-N-{4-[4-(methyl-propyl-amino)-butyl]-cyclohexyl}-4-trifluoromethyl-benzenesulfonamide, trans-N-(4-{4-[Bis-(2-hydroxy-ethyl)-amino]-butyl}-cyclohexyl)-N-methyl-4-trifluoromethyl-benzenesulfonamide, trans-{4-[5-(Allyl-methyl-amino)-pentyl]-cyclohexyl}-methyl-carbamic acid 2,4-difluoro-phenyl ester, trans-(4-{5-[Ethyl-(2-hydroxy-ethyl)-amino]-pentyl}-cyclohexyl)-methyl-carbamic acid 2,4-difluoro-phenyl ester, trans-(4-{5-[Ethyl-(2-hydroxy-ethyl)-amino]-pentyl}-cyclohexyl)-methyl-carbamic acid 4-chloro-phenyl ester, trans-Methyl-{4-[5-(methyl-propyl-amino)-pentyl]-cyclohexyl}-carbamic acid 4-chloro-phenyl ester, trans-[4-(5-Dimethylamino-pentyl)-cyclohexyl]-methyl-carbamic acid 4-chloro-phenyl ester, trans-Methyl-[4-(5-piperidin-1-yl-pentyl)-cyclohexyl]-carbamic acid 4-chloro-phenyl ester, trans-Methyl-{4-[5-(4-methyl-piperazin-1-yl)-pentyl]-cyclohexyl}-carbamic acid 4-chloro-phenyl ester, trans-{4-[5-(Cyclopropyl-methyl-amino)-pentyl]-cyclohexyl}-methyl-carbamic acid 4-chloro-phenyl ester, trans-N-[4-(5-Diethylamino-pentyl)-cyclohexyl]-N-methyl-4-trifluoromethyl-benzenesulfonamide, trans-N-(4-{5-[Bis-(2-hydroxy-ethyl)-amino]-pentyl}-cyclohexyl)-N-methyl-4-trifluoromethyl-benzenesulfonamide, (cis){4-[5-(Allyl-methyl-amino)-pentyl]-cyclohexyl}-methyl-carbamic acid 4-trifluoromethyl-phenyl ester, trans-{4-[5-(Allylamino)-pentyl]-cyclohexyl}-methyl-carbamic acid 4-trifluoromethyl-phenyl ester, trans-Methyl-[4-(5-methylamino-pentyl)-cyclohexyl]-carbamic acid 4-trifluoromethyl-phenyl ester, trans-N-[4-(5-Allylamino-pentyl)-cyclohexyl]-N-methyl-4-trifluoromethyl-benzenesulfonamide, trans-N-{4-[5-(2-Hydroxy-1,1-dimethyl-ethylamino)-pentyl]-cyclohexyl}-N-methyl-4-trifluoromethyl-benzenesulfonamide, trans-N-Methyl-N-[4-(5-methylamino-pentyl)-cyclohexyl]-4-trifluoromethyl-benzenesulfonamide, (trans)-[4-(5-Dimethylamino-pent-1-ynyl)-cyclohexyl]-methyl-carbamic acid 4-chloro-phenyl ester, trans-Methyl-{4-[5-(methyl-propyl-amino)-pent-1-ynyl]-cyclohexyl}-carbamic acid 4-chloro-phenyl ester, trans-(4-{5-[Ethyl-(2-hydroxy-ethyl)-amino]-pent-1-ynyl}-cyclohexyl)-methyl-carbamic acid 4-chloro-phenyl ester, trans-N-(4-{3-[Bis-(2-hydroxy-ethyl)-amino]-prop-1-ynyl}-cyclohexyl)-N-methyl-4-trifluoromethyl-benzenesulfonamide, trans-N-(4-{3-[Ethyl-(2-hydroxy-ethyl)-amino]-prop-1-ynyl}-cyclohexyl)-N-methyl-4-trifluoromethyl-benzenesulfonamide, trans-[4-(4-Dimethylamino-butoxy)-cyclohexyl]-methyl-carbamic acid isobutyl ester, trans-(4-{4-[Ethyl-(2-hydroxy-ethyl)-amino]-butoxy}-cyclohexyl)-methyl-carbamic acid isobutyl ester, trans-[4-(4-Diethylamino-butoxy)-cyclohexyl]-methyl-carbamic acid isobutyl ester, trans-[4-(4-Azetidin-1-yl-butoxy)-cyclohexyl]-methyl-carbamic acid isobutyl ester, trans-Methyl-[4-(4-morpholin-4-yl-butoxy)-cyclohexyl]-carbamic acid isobutyl ester, trans-Methyl-[4-(4-pyrrolidin-1-yl-butoxy)-cyclohexyl]-carbamic acid isobutyl ester, trans-(4-{4-[Ethyl-(2-methoxy-ethyl)-amino]-butoxy}-cyclohexyl)-methyl-carbamic acid isobutyl ester, trans-Methyl-{4-[4-(methyl-propyl-amino)-butoxy]-cyclohexyl}-carbamic acid isobutyl ester, trans-(4-{4-[Bis-(2-hydroxy-ethyl)-amino]-butoxy}-cyclohexyl)-methyl-carbamic acid isobutyl ester, trans-{4-[4-(Cyclopropylmethyl-methyl-amino)-butoxy]-cyclohexyl}-methyl-carbamic acid isobutyl ester, trans-N-(4-{3-[Bis-(2-hydroxy-ethyl)-amino]-propyl}-cyclohexyl)-N-methyl-4-trifluoromethyl-benzenesulfonamide, trans-N-(4-{3-[Ethyl-(2-hydroxy-ethyl)-amino]-propyl}-cyclohexyl)-N-methyl-4-trifluoromethyl-benzenesulfonamide, trans-[4-(3-Dimethylamino-prop-1-ynyl)-cyclohexyl]-methyl-carbamic acid 4-chloro-phenyl ester, trans-(4-{3-[Bis-(2-hydroxy-ethyl)-amino]-prop-1-ynyl}-cyclohexyl)-methyl-carbamic acid 4-trifluoromethyl-phenyl ester, trans-Methyl-[4-(3-piperidin-1-yl-prop-1-ynyl)-cyclohexyl]-carbamic acid 4-chloro-phenyl ester, trans-[4-(3-Dimethylamino-prop-1-ynyl)-cyclohexyl]-methyl-carbamic acid 4-trifluoromethyl-phenyl ester, trans-Methyl-{4-[3-(methyl-propyl-amino)-prop-1-ynyl]-cyclohexyl}-carbamic acid 4-trifluoromethyl-phenyl ester, trans-Methyl-[4-(3-piperidin-1-yl-prop-1-ynyl)-cyclohexyl]-carbamic acid 4-trifluoromethyl-phenyl ester, trans-{4-[4-(Allyl-methyl-amino)-butoxy]-cyclohexyl}-methyl-carbamic acid 2,4-difluoro-phenyl ester, trans-[4-(4-Dimethylamino-butoxy)-cyclohexyl]-methyl-carbamic acid 2,4-difluoro-phenyl ester, trans-(4-{4-[Ethyl-(2-hydroxy-ethyl)-amino]-butoxy}-cyclohexyl)-methyl-carbamic acid 2,4-difluoro-phenyl ester, trans-Methyl-[4-(4-morpholin-4-yl-butoxy)-cyclohexyl]-carbamic acid 2,4-difluoro-phenyl ester, trans-(4-{4-[Ethyl-(2-methoxy-ethyl)-amino]-butoxy}-cyclohexyl)-methyl-carbamic acid 2,4-difluoro-phenyl ester, trans-Methyl-{4-[4-(methyl-propyl-amino)-butoxy]-cyclohexyl}-carbamic acid 2,4-difluoro-phenyl ester, trans-3,4-Difluoro-N-methyl-N-{4-[4-(methyl-propyl-amino)-butoxy]-cyclohexyl}-benzenesulfonamide, trans-N-(4-{4-[Ethyl-(2-hydroxy-ethyl)-amino]-butoxy}-cyclohexyl)-3,4-difluoro-N-methyl-benzenesulfonamide, trans-2,4-Difluoro-N-methyl-N-{4-[4-(methyl-propyl-amino)-butoxy]-cyclohexyl}-benzenesulfonamide, trans-N-(4-{4-[Ethyl-(2-hydroxy-ethyl)-amino]-butoxy}-cyclohexyl)-2,4-difluoro-N-methyl-benzenesulfonamide, trans-4-Dimethylamino-N-[4-(4-dimethylamino-butoxy)-cyclohexyl]-3-fluoro-N-methyl-benzenesulfonamide, trans-4-Dimethylamino-N-[4-(4-dimethylamino-butoxy)-cyclohexyl]-2-fluoro-N-methyl-benzenesulfonamide, trans-Methyl-{4-[3-(methyl-propyl-amino)-prop-1-ynyl]-cyclohexyl}-carbamic acid 4-chloro-phenyl ester, trans-Methyl-{4-[3-(methyl-propyl-amino)-prop-1-ynyl]-cyclohexyl}-carbamic acid 4-chloro-phenyl ester, trans-[4-(3-Dimethylamino-propyl)-cyclohexyl]-methyl-carbamic acid 4-chloro-phenyl ester, trans-(4-{3-[Ethyl-(2-hydroxy-ethyl)-amino]-propyl}-cyclohexyl)-methyl-carbamic acid 4-trifluoromethyl-phenyl ester, trans-(4-{3-[Bis-(2-hydroxy-ethyl)-amino]-propyl}-cyclohexyl)-methyl-carbamic acid 4-trifluoromethyl-phenyl ester, trans-Methyl-{4-[3-(methyl-propyl-amino)-propyl]-cyclohexyl}-carbamic acid 4-chloro-phenyl ester, trans-(4-{4-[Ethyl-(2-hydroxy-ethyl)-amino]-but-1-ynyl}-cyclohexyl)-methyl-carbamic acid 4-chloro-phenyl ester, trans-N-(4-{5-[Ethyl-(2-hydroxy-ethyl)-amino]-pent-1-ynyl}-cyclohexyl)-N-methyl-4-trifluoromethyl-benzenesulfonamide, trans-N-Methyl-N-{4-[5-(methyl-propyl-amino)-pent-1-ynyl]-cyclohexyl}-4-trifluoromethyl-benzenesulfonamide, trans-N-[4-(4-Dimethylamino-but-1-ynyl)-cyclohexyl]-N-methyl-4-trifluoromethyl-benzenesulfonamide, trans-N-Methyl-N-{4-[4-(methyl-propyl-amino)-but-1-ynyl]-cyclohexyl}-4-trifluoromethyl-benzenesulfonamide, trans-N-(4-{4-[Ethyl-(2-hydroxy-ethyl)-amino]-but-1-ynyl}-cyclohexyl)-N-methyl-4-trifluoromethyl-benzenesulfonamide, trans-Methyl-{4-[3-(methyl-propyl-amino)-prop-1-ynyl]-cyclohexyl}-carbamic acid 4-methoxy-phenyl ester, trans-Methyl-{4-[3-(methyl-propyl-amino)-prop-f-ynyl]-cyclohexyl}-carbamic acid p-tolyl ester, trans-(4-{3-[Ethyl-(2-methoxy-ethyl)-amino]-prop-1-ynyl}-cyclohexyl)-methyl-carbamic acid 4-chloro-phenyl ester, trans-{4-[5-(Allyl-methyl-amino)-pentyl]-cyclohexyl}-methyl-carbamic acid 4-trifluoromethyl-phenyl ester N-oxide, trans-N-Methyl-N-{4-[3-(methyl-propyl-amino)-prop-1-ynyl]-cyclohexyl}-4-trifluoromethyl-benzenesulfonamide, trans-N-[4-(3-Dimethylamino-prop-1-ynyl)-cyclohexyl]-N-methyl-4-trifluoromethyl-benzenesulfonamide, trans-N-(4-{3-[Ethyl-(2-methoxy-ethyl)-amino]-prop-1-ynyl}-cyclohexyl)-N-methyl-4-trifluoromethyl-benzenesulfonamide, trans-Methyl-{4-[4-(methyl-propyl-amino)-but-1-ynyl]-cyclohexyl}-carbamic acid 4-trifluoromethyl-phenyl ester, trans-[4-(4-Dimethylamino-but-1-ynyl)-cyclohexyl]-methyl-carbamic acid 4-trifluoromethyl-phenyl ester, trans-{4-[4-(Allyl-methyl-amino)-but-1-ynyl]-cyclohexyl}-methyl-carbamic acid 4-trifluoromethyl-phenyl ester, trans-(4-{4-[Ethyl-(2-hydroxy-ethyl)-amino]-but-1-ynyl}-cyclohexyl)-methyl-carbamic acid 4-trifluoromethyl-phenyl ester, trans-Methyl-{4-[4-(methyl-propyl-amino)-but-1-ynyl]-cyclohexyl}-carbamic acid 4-chloro-phenyl ester, trans-[4-(4-Dimethylamino-but-1-ynyl)-cyclohexyl]-methyl-carbamic acid 4-chloro-phenyl ester, trans-{4-[4-(Allyl-methyl-amino)-but-1-ynyl]-cyclohexyl}-methyl-carbamic acid 4-chloro-phenyl ester, trans-(1E)-N-Methyl-N-{4-[3-(methyl-propyl-amino)-propenyl]-cyclohexyl}-4-trifluoromethyl-benzenesulfonamide, trans-(1E)-N-[4-(3-Dimethylamino-propenyl)-cyclohexyl]-N-methyl-4-trifluoromethyl-benzenesulfonamide, trans-(1E)-N-{4-[3-(Allyl-methyl-amino)-propenyl]-cyclohexyl}-N-methyl-4-trifluoromethyl-benzenesulfonamide, trans-(1E)-N-(4-{3-[Ethyl-(2-hydroxy-ethyl)-amino]-propenyl}-cyclohexyl)-N-methyl-4-trifluoromethyl-benzenesulfonamide, trans-N-Methyl-4-nitro-N-[4-(4-piperidin-1-yl-butoxy)-cyclohexyl]-benzenesulfonamide, trans-N-(4-{4-[Ethyl-(2-methoxy-ethyl)-amino]-butoxy}-cyclohexyl)-N-methyl-4-nitro-benzenesulfonamide, trans-N-[4-(4-Dimethylamino-butoxy)-cyclohexyl]-N-methyl-4-nitro-benzenesulfonamide, trans-N-{4-[4-(Allyl-methyl-amino)-butoxy]-cyclohexyl}-N-methyl-4-nitro-benzenesulfonamide, trans-N-(4-{4-[Ethyl-(2-hydroxy-ethyl)-amino]-butoxy}-cyclohexyl)-N-methyl-4-nitro-benzenesulfonamide, trans-N-{4-[4-(4-Hydroxy-piperidin-1-yl)-butoxy]-cyclohexyl}-N-methyl-4-nitro-benzenesulfonamide, trans-Methyl-{4-[3-(methyl-propyl-amino)-propyl]-cyclohexyl}-carbamic acid p-tolyl ester, trans-4-Amino-N-methyl-N-{4-[3-(methyl-propyl-amino)-prop-1-ynyl]-cyclohexyl}-benzenesulfonamide, trans-Methyl-{4-[3-(methyl-propyl-amino)-propenyl]-cyclohexyl}-carbamic acid 4-trifluoromethyl-phenyl ester, trans-Methyl-{4-[3-(methyl-propyl-amino)-propenyl]-cyclohexyl}-carbamic acid 4-chloro-phenyl ester, trans-(1E)-(4-{3-[Ethyl-(2-methoxy-ethyl)-amino]-propenyl}-cyclohexyl)-methyl-carbamic acid 4-chloro-phenyl ester, trans-(1E)-(4-{3-[Ethyl-(2-hydroxy-ethyl)-amino]-propenyl}-cyclohexyl)-methyl-carbamic acid 4-chloro-phenyl ester, trans-4-Chloro-N-methyl-N-{4-[3-(methyl-propyl-amino)-prop-1-ynyl]-cyclohexyl}-benzamide, trans-3-(4-Chloro-phenyl)-1-methyl-1-{4-[3-(methyl-propyl-amino)-prop-1-ynyl]-cyclohexyl}-urea, trans-4-Chloro-N-(4-{3-[ethyl-(2-hydroxy-ethyl)-amino]-prop-1-ynyl}-cyclohexyl)-N-methyl-benzamide, trans-3-(4-Chloro-phenyl)-1-(4-{3-[ethyl-(2-hydroxy-ethyl)-amino]-prop-1-ynyl}-cyclohexyl)-1-methyl-urea, trans-[4-(3-Dimethylamino-propenyl)-cyclohexyl]-methyl-carbamic acid 4-trifluoromethyl-phenyl ester, trans-[4-(3-Dimethylamino-propenyl)-cyclohexyl]-methyl-carbamic acid 4-chloro-phenyl ester, trans-Methyl-[4-(3-piperidin-1-yl-propenyl)-cyclohexyl]-carbamic acid 4-chloro-phenyl ester, trans-4-Chloro-N-methyl-N-[4-(3-piperidin-1-yl-prop-1-ynyl)-cyclohexyl]-benzenesulfonamide, trans-4-Chloro-N-methyl-N-{4-[3-(methyl-propyl-amino)-prop-1-ynyl]-cyclohexyl}-benzenesulfonamide, trans-4-Chloro-N-[4-(3-dimethylamino-prop-1-ynyl)-cyclohexyl]-N-methyl-benzenesulfonamide, trans-N-(4-{5-[Ethyl-(2-hydroxy-ethyl)-amino]-pentyl}-cyclohexyl)-4-trifluoromethyl-benzenesulfonamide, trans-N-{4-[5-(2-Hydroxy-ethylamino)-pentyl]cyclohexyl}-4-trifluoromethyl-benzenesulfonamide, and trans-N-[4-(5-Ethylamino-pentyl)-cyclohexyl]-4-trifluoromethyl-benzenesulfonamide and pharmaceutically acceptable salts thereof.

Particularly preferred compounds of general formula (I) are those selected from the group consisting of trans-{4-[6-(Allyl-methyl-amino)-hexyloxy]-cyclohexyl}-methyl-carbamic acid 4-chloro-phenyl ester, trans-{4-[4-(Allyl-methyl-amino)-butoxy]-cyclohexyl}-methyl-carbamic acid 4-trifluoromethyl-phenyl ester, trans-N-[4-(6-Diethylamino-hexyloxy)-cyclohexyl]-N-methyl-4-trifluoromethyl-benzenesulfonamide, trans-{4-[4-(Allyl-methyl-amino)-butoxy]-cyclohexyl}-methyl-carbamic acid 4-chloro-phenyl ester, trans-{4-[2-(Allyl-methyl-amino)-ethylsulfanylmethyl]-cyclohexyl}-methyl-carbamic acid 4-chloro-phenyl ester, trans-{4-[5-(Allyl-methyl-amino)-pentyl]-cyclohexyl}-methyl-carbamic acid 4-chloro-phenyl ester, trans-(4-{4-[Ethyl-(2-hydroxy-ethyl)-amino]-butoxy}-cyclohexyl)-methyl-carbamic acid 4-trifluoromethyl-phenyl ester, trans-N-[4-(3-Allylamino-propoxy)-cyclohexyl]-N-methyl-4-trifluoromethyl-benzenesulfonamide, trans-{4-[5-(Allyl-methyl-amino)-pentyl]-cyclohexyl}-methyl-carbamic acid 4-trifluoromethyl-phenyl ester, trans-(4-{5-[Ethyl-(2-hydroxy-ethyl)-amino]-pentyl}-cyclohexyl)-methyl-carbamic acid 4-trifluoromethyl-phenyl ester, trans-(4-{5-[Ethyl-(2-hydroxy-ethyl)-amino]-pentyl}-cyclohexyl)-methyl-carbamic acid 4-bromo-phenyl ester, trans-N-(4-{5-[Ethyl-(2-hydroxy-ethyl)-amino]-pentyl}-cyclohexyl)-N-methyl-4-trifluoromethyl-benzenesulfonamide, trans-[4-(4-Dimethylamino-butoxy)-cyclohexyl]-methyl-carbamic acid 4-trifluoromethyl-phenyl ester, trans-{4-[5-(Allyl-methyl-amino)-pentyl]-cyclohexyl}-methyl-carbamic acid 4-bromo-phenyl ester, trans-{4-[3-(Allyl-methyl-amino)-prop-1-ynyl]-cyclohexyl}-methyl-carbamic acid 4-chloro-phenyl ester, trans-N-{4-[5-(Allyl-methyl-amino)-pentyl]-cyclohexyl}-N-methyl-4-trifluoromethyl-benzenesulfonamide, trans-(4-{3-[Ethyl-(2-hydroxy-ethyl)-amino]-propyl}-cyclohexyl)-methyl-carbamic acid 4-chloro-phenyl ester, and trans-{4-[4-(Allyl-methyl-amino)-butyl]-cyclohexyl}-methyl-carbamic acid 4-chloro-phenyl ester, and pharmaceutically acceptable salts thereof.

Other particularly preferred compounds of general formula (I) are those selected from the group consisting of trans-N-[4-(4-Dimethylamino-but-1-ynyl)-cyclohexyl]-N-methyl-4-trifluoromethyl-benzenesulfonamide, trans-Methyl-[4-(5-piperidin-1-yl-pentyl)-cyclohexyl]-carbamic acid 4-chloro-phenyl ester, trans-Methyl-[4-(5-methylamino-pentyl)-cyclohexyl]-carbamic acid 4-trifluoromethyl-phenyl ester, trans-(4-{5-[Ethyl-(2-hydroxy-ethyl)-amino]-pent-1-ynyl}-cyclohexyl)-methyl-carbamic acid 4-chloro-phenyl ester, trans-N-Ethyl-N-(4-{4-[(2-hydroxy-ethyl)-methyl-amino]-butoxy}-cyclohexyl)-4-trifluoromethyl-benzenesulfonamide, trans-(1E)-N-(4-{3-[Ethyl-(2-hydroxy-ethyl)-amino]-propenyl}-cyclohexyl)-N-methyl-4-trifluoromethyl-benzenesulfonamide, trans-4-Bromo-N-[4-(2-diisopropylamino-ethoxy)-cyclohexyl]-N-methyl-benzenesulfonamide, trans-Methyl-[4-(4-piperidin-1-yl-butyl)-cyclohexyl]-carbamic acid 4-bromo-phenyl ester, trans-N-Methyl-N-[4-(4-piperidin-1-yl-butyl)-cyclohexyl]-4-trifluoromethyl-benzenesulfonamide, trans-N-(4-{4-[Bis-(2-hydroxy-ethyl)-amino]-butoxy}-cyclohexyl)-N-ethyl-4-trifluoromethyl-benzenesulfonamide, trans-4-Bromo-N-methyl-N-[4-(2-piperidin-1-yl-ethoxy)-cyclohexyl]-benzenesulfonamide, trans-N-[4-(4-Dimethylamino-butoxy)-cyclohexyl]-N-ethyl-4-trifluoromethyl-benzenesulfonamide, trans-Methyl-{4-[3-(methyl-propyl-amino)-prop-1-ynyl]-cyclohexyl}-carbamic acid 4-chloro-phenyl ester, trans-(1E)-N-Methyl-N-{4-[3-(methyl-propyl-amino)-propenyl]-cyclohexyl}-4-trifluoromethyl-benzenesulfonamide, trans-N-(4-{4-[Ethyl-(2-hydroxy-ethyl)-amino]-but-1-ynyl}-cyclohexyl)-N-methyl-4-trifluoromethyl-benzenesulfonamide, trans-N-Methyl-N-{4-[4-(methyl-propyl-amino)-but-1-ynyl]-cyclohexyl}-4-trifluoromethyl-benzenesulfonamide, and trans-N-{4-[2-(1-Dimethylamino-cyclopropyl)-ethoxy]-cyclohexyl}-N-methyl-4-trifluoromethyl-benzenesulfonamide, and pharmaceutically acceptable salts thereof.

Compounds of formula (I) can have one or more asymmetric carbon atoms and can exist in the form of optically pure enantiomers or as racemates. The invention embraces all of these forms.

It will be appreciated, that the compounds of general formula (I) in this invention may be derivatised at functional groups to provide derivatives which are capable of conversion back to the parent compound in vivo.

The present invention also relates to a process for the manufacture of compounds as described above, which process comprises reacting a compound of formula (II)

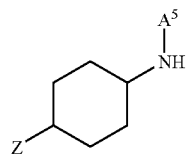

wherein $A^5$ has the significance given above,

Z is a group $(A^1,A^2,)N-C(A^3,A^4)-(CH_2)_m-V-(CH_2)_n$ or $HO-(CH_2)_n$, wherein $A^1, A^2, A^3, A^4$, V, m and n have the significances given above, with $ClSO_2-A^6$, $ClCOO-A^6$, $ClCSO-A^6$, $OCN-A^6$, $SCN-A^6$, $HOOC-A^6$, or $ClSO_2NR^1-A^6$, wherein $A^6$ has the significance given above.

The invention further relates to compounds of formula (I) as defined above, when manufactured according to a process as defined above.

As described above, the compounds of formula (I) of the present invention can be used for the treatment and/or prophylaxis of diseases which are associated with OSC such as hypercholesterolemia, hyperlipemia, arteriosclerosis, vascular diseases, mycoses, parasite infections and gallstones, and/or treatment and/or prophylaxis of impaired glucose tolerance, diabetes, tumors and/or hyperproliferative disorders, preferably for the treatment and/or prophylaxis of hypercholesterolemia and/or hyperlipemia.

Hyperproliferative skin and vascular disorders particularly come into consideration as hyperproliferative disorders.

The invention therefore also relates to pharmaceutical compositions comprising a compound as defined above and a pharmaceutically acceptable carrier and/or adjuvant.

Further, the invention relates to compounds as defined above for use as therapeutic active substances, particularly as therapeutic active substances for the treatment and/or prophylaxis of of diseases which are associated with OSC such as hypercholesterolemia, hyperlipemia, arteriosclerosis, vascular diseases, mycoses, parasite infections, gallstones, tumors and/or hyperproliferative disorders, and/or treatment and/or prophylaxis of impaired glucose tolerance and diabetes, preferably for the treatment and/or prophylaxis of hypercholesterolemia and/or hyperlipemia.

In another embodiment, the invention relates to a method for the treatment and/or prophylaxis of diseases which are associated with OSC such as hypercholesterolemia, hyperlipemia, arteriosclerosis, vascular diseases, mycoses, parasite infections, gallstones, tumors and/or hyperproliferative disorders, and/or treatment and/or prophylaxis of impaired glucose tolerance and diabetes, preferably for the treatment and/or prophylaxis of hypercholesterolemia and/or hyperlipemia, which method comprises administering a compound as defined above to a human being or animal.

The invention further relates to the use of compounds as defined above for the treatment and/or prophylaxis of diseases which are associated with OSC such as hypercholesterolemia, hyperlipemia, arteriosclerosis, vascular diseases, mycoses, parasite infections, gallstones, tumors and/or hyperproliferative disorders, and/or treatment and/or prophylaxis of impaired glucose tolerance and diabetes, preferably for the treatment and/or prophylaxis of hypercholesterolemia and/or hyperlipemia.

In addition, the invention relates to the use of compounds as defined above for the preparation of medicaments for the treatment and/or prophylaxis of diseases which are associated with OSC such as hypercholesterolemia, hyperlipemia, arteriosclerosis, vascular diseases, mycoses, parasite infections, gallstones, tumors and/or hyperproliferative disorders, and/or treatment and/or prophylaxis of impaired glucose tolerance and diabetes, preferably for the treatment and/or prophylaxis of hypercholesterolemia and/or hyperlipemia. Such medicaments comprise a compound as defined above.

The compounds of formula (I) can be manufactured by the methods given below, by the methods given in the examples or by analogous methods. Appropriate reaction conditions for the individual reaction steps are known to the person skilled in the art. Starting materials are either commercially available or can be prepared by methods analogous to the methods given in the examples or by methods known in the art.

Scheme 1a

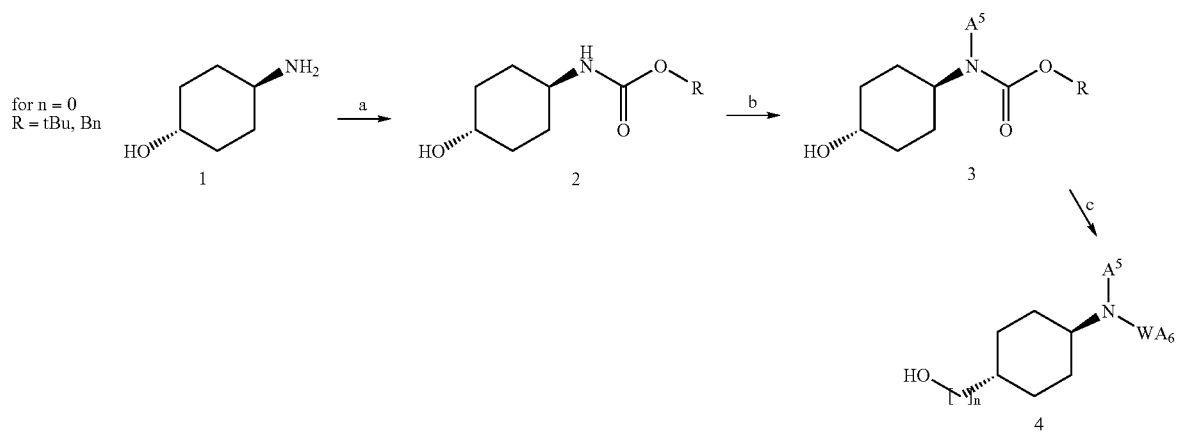

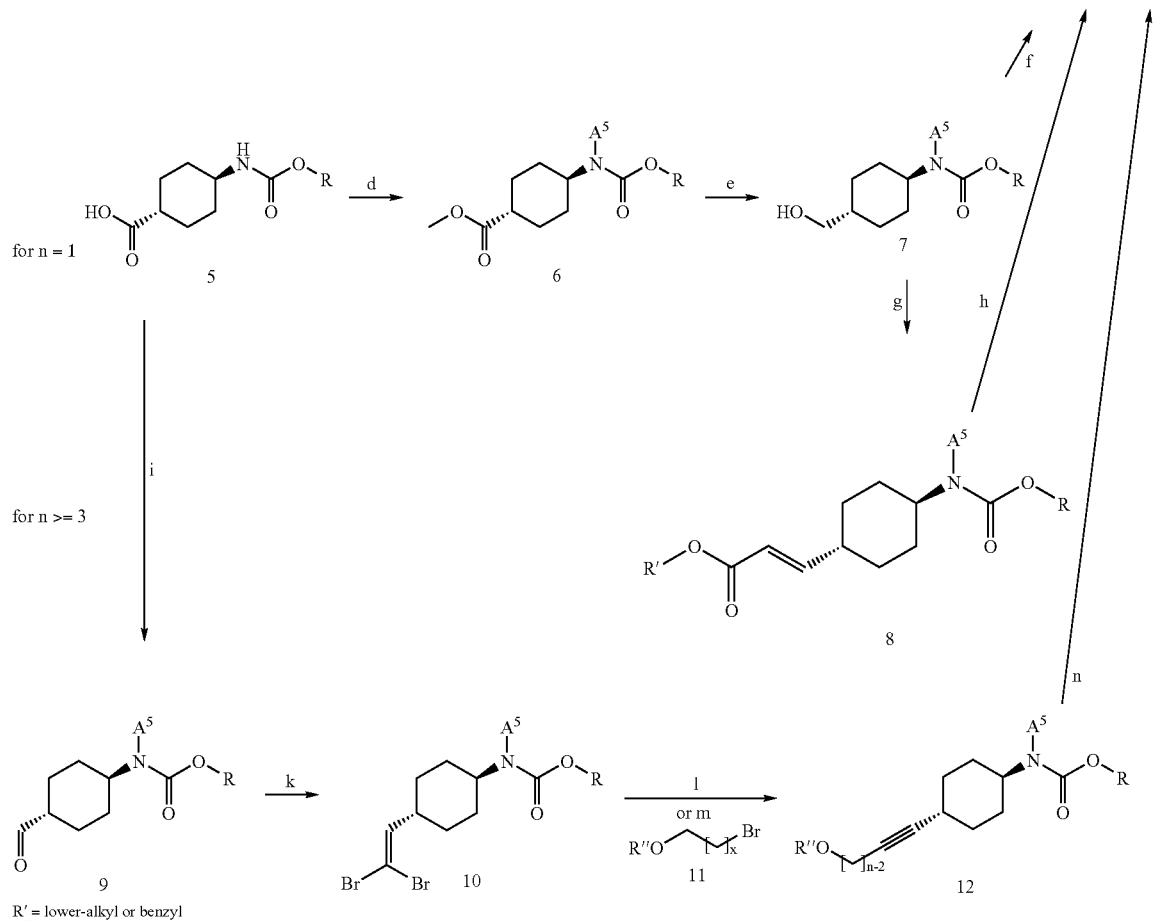
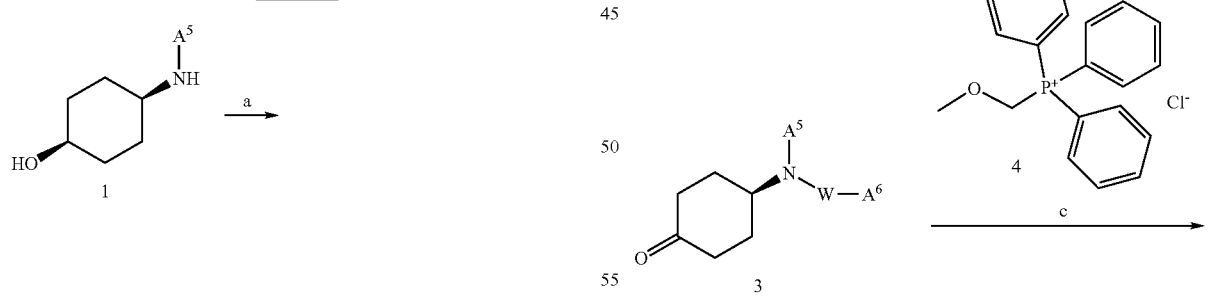
Scheme 1b
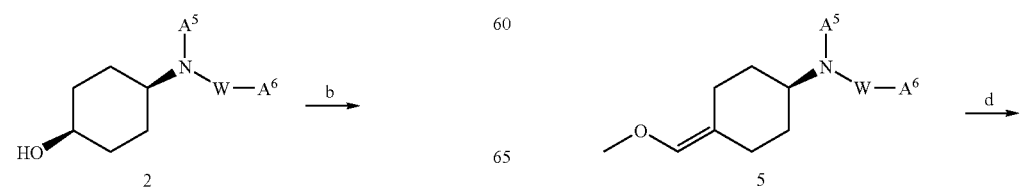

-continued
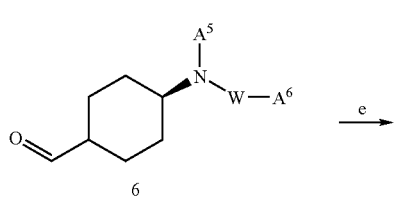
6
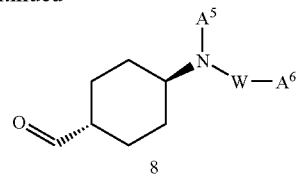
8
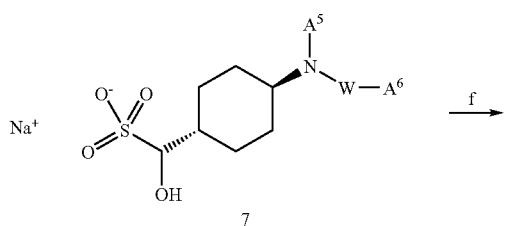
7
Scheme 2
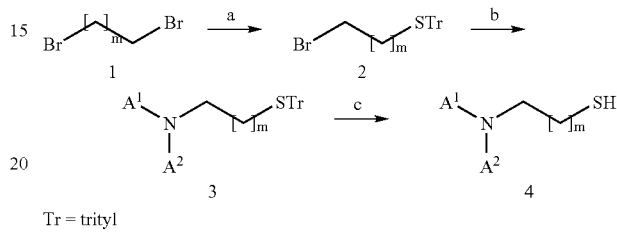
Tr = trityl
Scheme 3
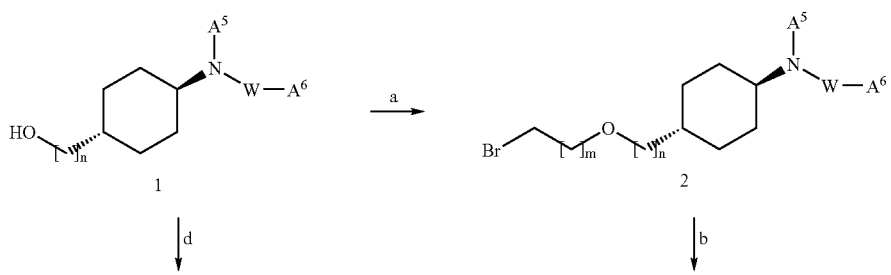
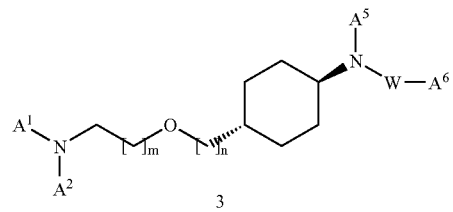
3
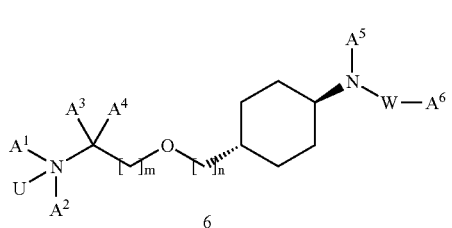
5
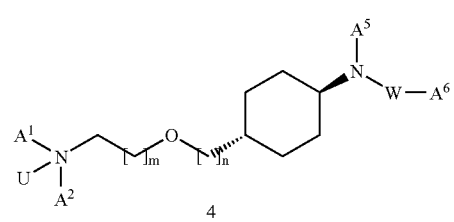
4
6

Scheme 4
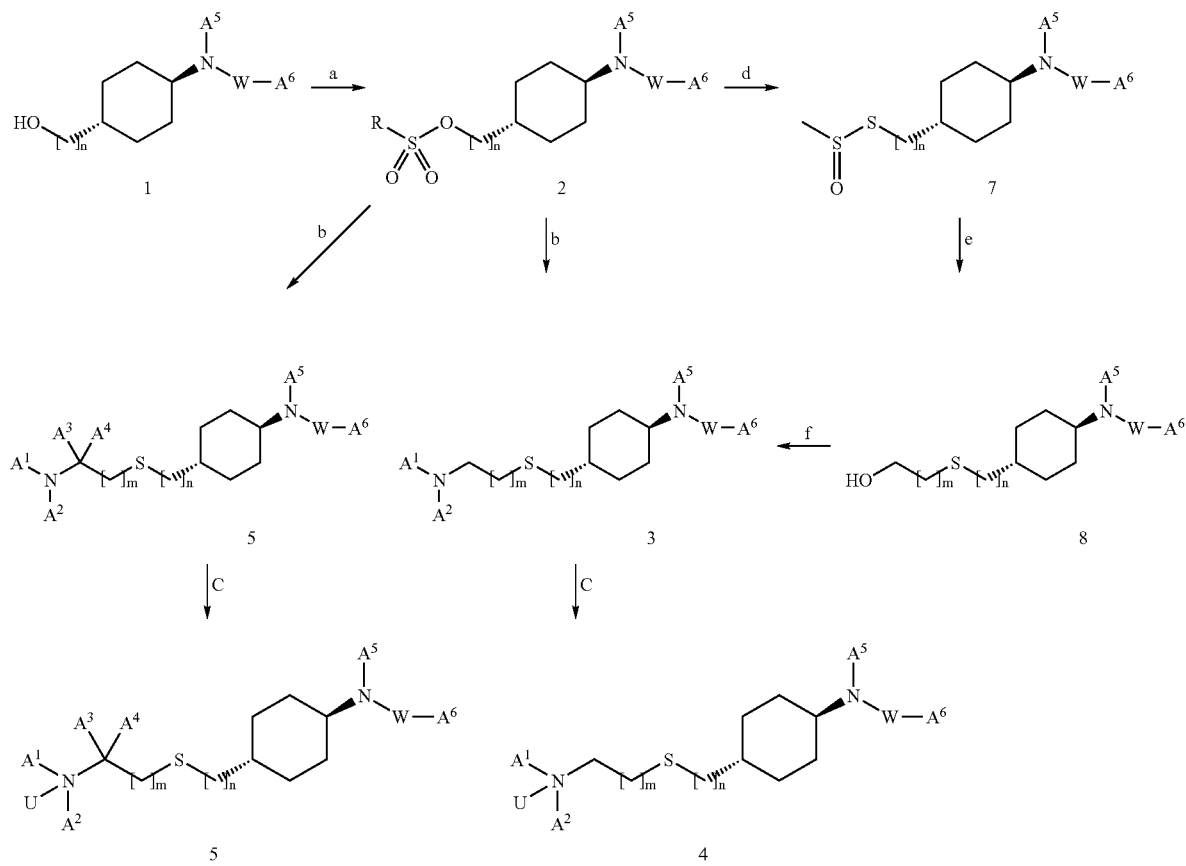
Scheme 5
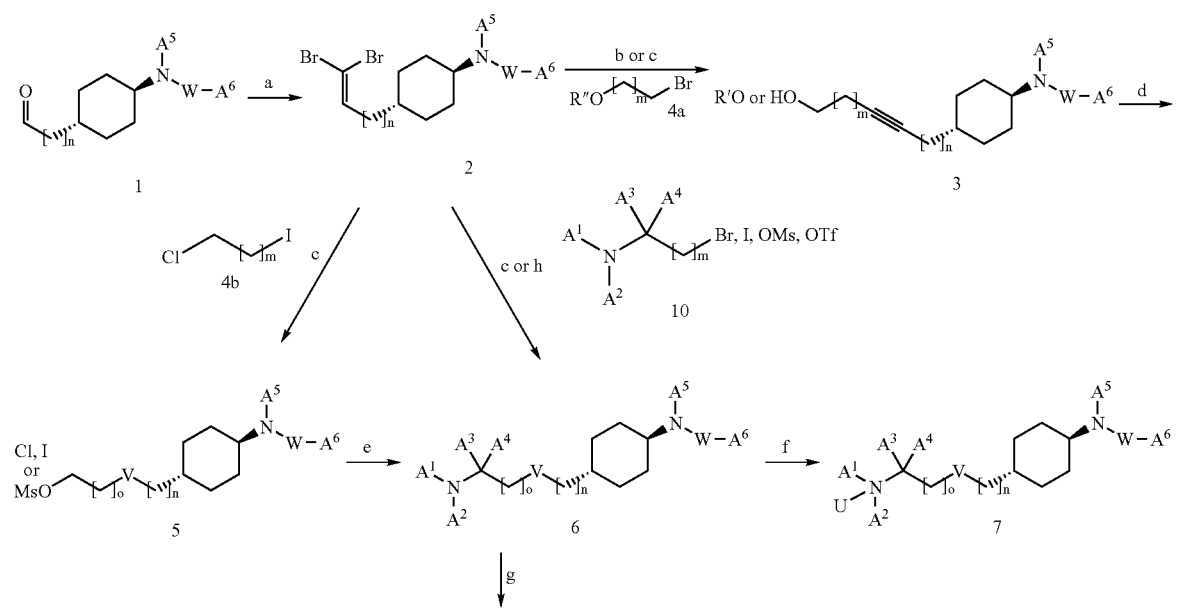

-continued
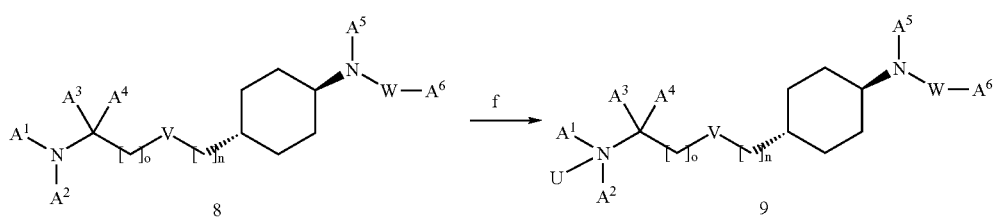
R' = protecting group
for V = CH₂, o = m or m+1 (if e.g. CH=CH or alkyne is hydrogenated to CH₂CH₂)
for V = CH=CH or acetylene, o = m
Scheme 6
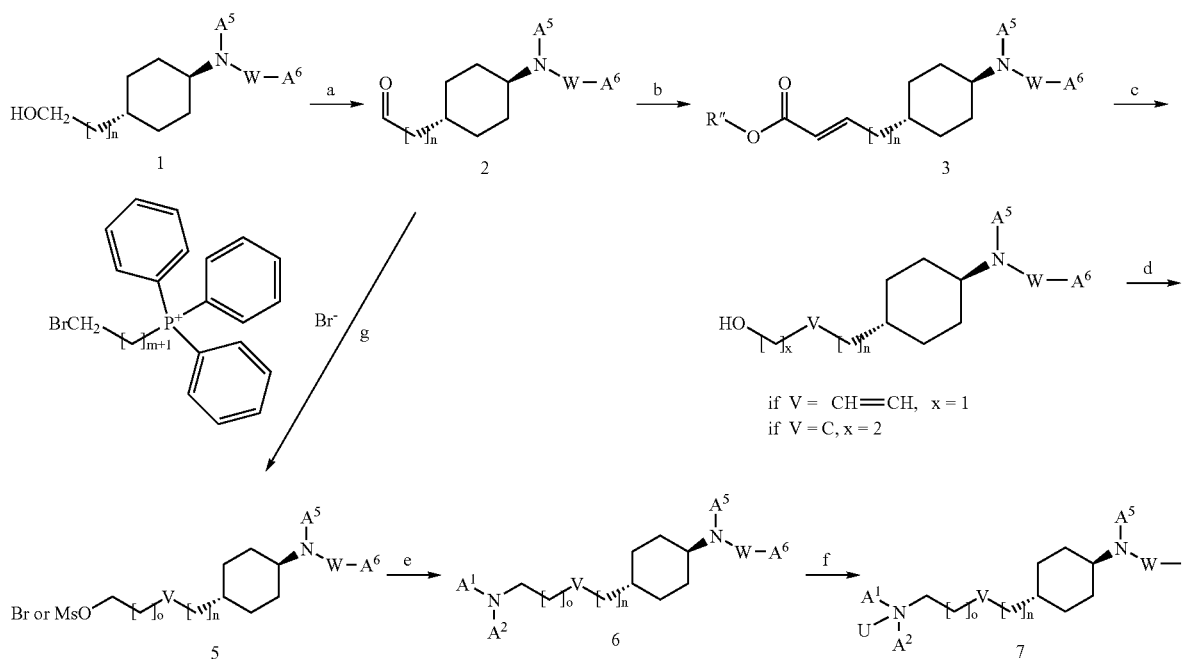
if V = CH=CH, x = 1
if V = C, x = 2
R'' = lower-alkyl or benzyl
fo V = CH₂, o = m or m+1 (if e.g. CH=CH is hydrogenated to CH₂CH₂)
for V = CH=CH, o = m
Scheme 7
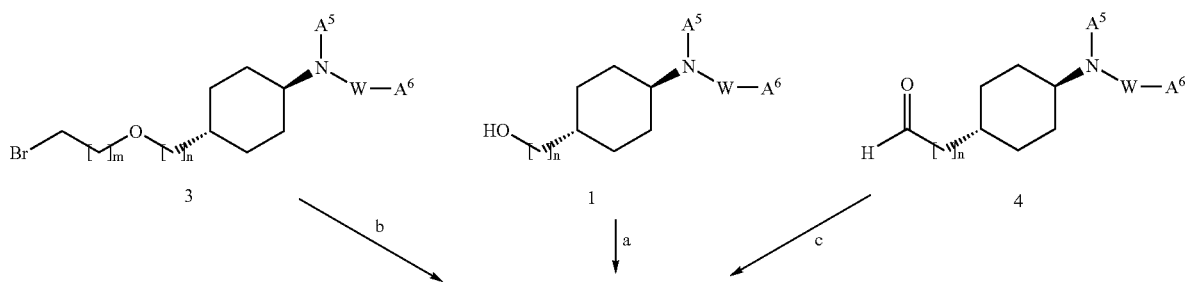

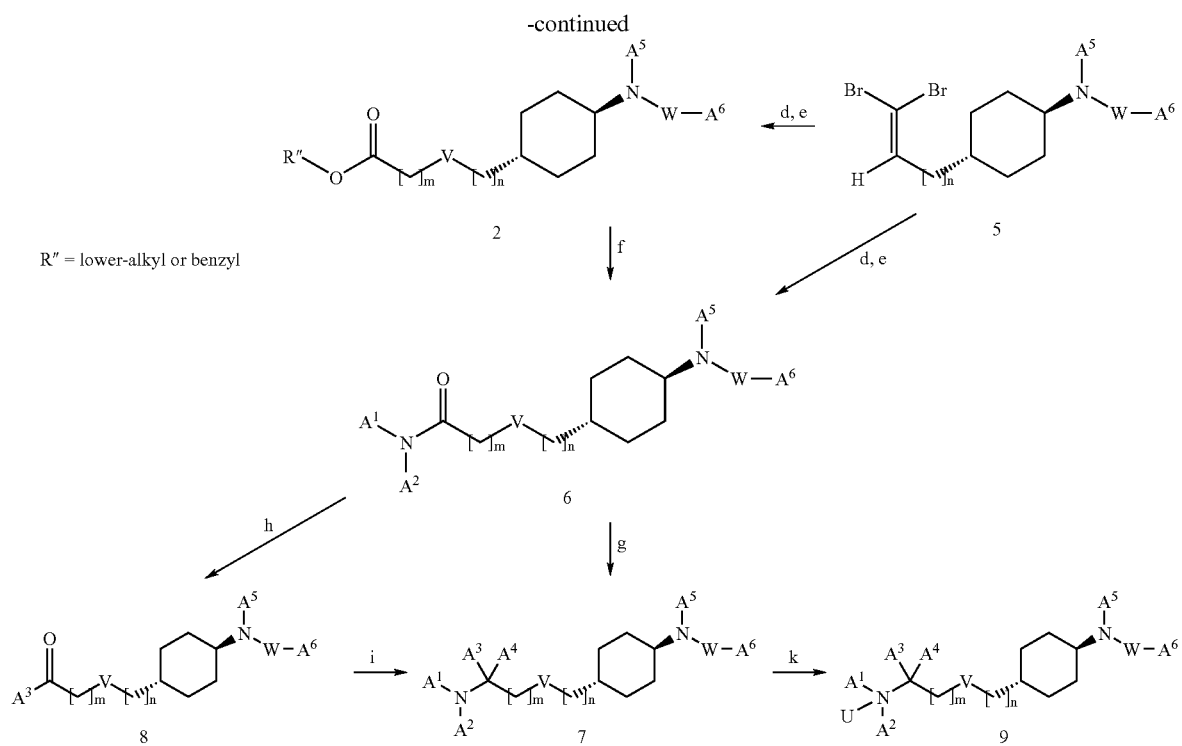

R" = lower-alkyl or benzyl

Scheme 1a:

The preparation of the starting materials for aminocyclohexyl derivatives of formula (I) in which V is O or S is depicted in scheme 1a.

For compounds with n=0, the synthesis starts from trans-4-aminocyclohexanol 1 which is converted to the Z-derivative or the BOC derivative 2 e.g. ZCl, Na$_2$CO$_3$, THF, H$_2$O or (BOC)$_2$O, iPrOH, CH$_2$Cl$_2$, respectively (step a). Lithium aluminum hydride reduction yields trans-4-methylaminocyclohexanol which is either BOC-protected to yield compound 3 or is directly transferred into the desired A$^6$W-derivative 4 using one of the methods described later for compound 3 or 5 in scheme 3. If needed, the aminocyclohexanol derivative can be treated with hexamethyldisilazane at reflux, prior to the introduction of the A$^6$W-moiety. Alternatively, the residue A$^5$ can be introduced via alkylation using sodium hydride and a reactive alkyl or arylalkyl derivative (step b). BOC-deprotection (TFA, CH$_2$Cl$_2$) or Z-deprotection (hydrogenation) followed by treatment with A$^6$W-derivatives gives compounds of the formula 4.

For n=1, the starting material is (trans)-4-tert-butoxycarbonyl amino-cyclohexane-carboxylic acid 5. This is converted to the derivative 6 by ester formation (e.g. carbonyl-di-imidazole, methanol in THF) and direct alkylation using sodium hydride and a reactive alkyl or arylalky derivative (step d). Reduction with lithium aluminum hydride yields the protected alcohol 7.

For n=2, the starting material is trans-4-aminocyclohexyl acetic acid (can be derived from 4-nitrophenylacetic acid according to Karpavichyus, K. I.; Palaima, A. I.; Knunyants, I. L.; BACCAT; Bull. Acad. Sci. USSR Div. Chem. Sci. (Engl. transl.); EN; 29; 1980; 1689-1694; IASKA6; Izv. Akad. Nauk SSSR Ser. Khim.; RU; 10; 1980; 2374-2379 or T. P. Johnston et al. Journal of Medicinal Chemistry, 1977, Vol, No. 2, 279-290.) which can be converted to the corresponding alcohol following the protocol for the compounds 5 to 7.

For n>=3, the starting material is (trans)-4-tert-butoxycarbonyl amino-cyclohexane-carboxylic acid 5. Chain elongation can be achieved using methods known in the art or as described below:

For C$_2$-elongation: Swern oxidation of the alcohol 7 to the corresponding aldehyde followed by Horner-Emmons reaction with triethyl phosphono acetate, sodium methanolate in ethanol gave the unsaturated ester 8. This was subjected to hydrogenation with 10% palladium on carbon in methanol and reduction with lithium aluminum hydride in THF to yield the chain-elongated alcohol 4. This sequence can be repeated to get the C$_4$-elongated alcohol 4.

For C$_2$ up to C$_{(n-1)}$-elongation Corey-Fuchs methodology may be used: Therefore, acid 5 is converted to the Weinreb derivative by treatment with N,O-dimethyl-hydroxyl-amine hydrochloride with EDCI and HOBT in CH$_2$Cl$_2$ at room temperature which is reduced by lithium aluminum hydride to the corresponding aldehyde 9 (step i). This aldehyde 9 can be treated with triphenylphosphine, tetrabromomethane and triethylamine in CH$_2$Cl$_2$ at 0° C. to RT to yield 2,2-Dibromo-vinyl derivative 10. Rearrangement with n-BuLi (ca 1.6 M in hexane) in THF at −78° C., followed by reaction with formaldehyde (−78° C. to RT) gives the propargyl alcohol [step 1, following conditions described in: Marshall, James A.; Bartley, Gary S.; Wallace, Eli M. Total Synthesis of the Pseudopterane (−)-Kallolide B, the Enantiomer of Natural (+)-Kallolide B. J. Org. Chem. (1996), 61(17), 5729-5735; and Baker, Raymond; Boyes, Alastair L.; Swain, Christopher J. Synthesis of talaromycins A, B, C, and E. J. Chem. Soc., Perkin trans. 1 (1990), (5), 1415-21.], from which the propanol derivative 4 can be obtained by hydrogenation with 10% Pd/C.

For longer side chains, the rearrangement is performed with n-BuLi (ca 1.6 M in hexane) in THF at −78° C. as above, followed by addition of a cosolvens such as DMPU and reaction with O-protected 1-bromo-alcohols 11 (step m; e.g. 1-bromo-n-tetrahydropyaranyloxyalkane) to give the O-protected compounds 12. 12 can be converted to the alkanol derivatives by hydrogenation with 10% Pd/C followed by deprotection to yield the derivatives 4.

If $WA^6$ is a protective group, this may be cleaved as described for derivative 3 and the final moieties $WA^6$ may be introduced as described for the compounds in scheme 3.

Scheme 1b:

Scheme 1b describes the synthesis of pure trans-aldehyde building block 8. $A^5$ substituted 4-aminocyclohexanol 1 is converted to the Z-derivative or to the $W-A^6$ derivative 2 (e.g. ZCl, $Na_2CO_3$, THF, $H_2O$ or $W-A^6$-introduction see scheme 3) (step a). Oxidation with TEMPO (2,2,6,6-Tetramethylpiperidine 1-oxyl, radical) and sodium hypochlorite gives ketone 3 (step b). Wittig reaction with (methoxymethyl)triphenylphosphonium chloride 4 in THF and potassium t-butoxide as base gives enolether 5 (step c), which is hydrolysed with 1 N HCl ind THF at reflux (step d). The crude aldehyde 6 (as a cis/trans mixture) can be isomerised via bisulfite-adduct 7 (with disodium pyrosulfite in water/TBME, step e). Bisulfite adduct 7 can then be converted to the pure trans-aldehyde 8 with aqueous $Na_2CO_3$ in water/TBME (step f).

Scheme 2:

Scheme 2 shows the synthesis of aminothiols 4 that are used for the synthesis of compounds with thioether spacers. Triphenylmethanethiol is deprotonated with NaH in DMA and reacted with α,ω-dihaloalkane in DMA (step a). Treatment with the amine $A^1A^2NH$ yields the S-protected amine 3 (step b). Deprotection of the thiol moiety may be achieved by treatment with TFA/triisopropylsilane in $CH_2Cl_2$ at 0° C. to RT to give the aminothiol 4 (step c).

Scheme 3:

The synthesis of ether derivatives of formula (I) is depicted in scheme 3. For the preparation of derivatives with n=0, the aminocyclohexanol derivative 1 can be treated under phase transfer conditions e.g. α,ω-dihaloalkanes, NaOH, $nBu_4NHSO_4$ to yield bromide 2. For n>0, alcohol derivative 1 may be treated with α,ω-dihaloalkane (for $C_4$ or longer alkanes) in the presence of NaH in DMF 0° C. to RT to yield bromide 2. For shorter alkanes the method of choice is the in situ generation of the haloalkane-triflate (from the corresponding haloalkanol with trifluoromethansulfonic anhydride/2,6-di-tert-butylpyridine in $CH_2Cl_2$ at 0° C.). This haloalkane-triflate is then reacted with alcohol 1 with 2,6-di-tert-butylpyridine as base in nitromethane at 60° C. to yield bromide 2 [following a procedure of Befostotskii, Anatoly M.; Hassner, Alfred. Synthetic methods. 41. Etherification of hydroxysteroids via triflates. Tetrahedron Lett. (1994), 35(28), 5075-6].

Amination of bromide 2 with amine $A^1A^2NH$ in DMA or DMF, at RT or in MeOH at RT to reflux yields the final amine 3, optionally DBU may be added. Amine 3 may be converted to a salt or to the N-oxide 4 using a mixture of hydrogen peroxide urea adduct and phthalic anhydride in $CH_2Cl_2$ at RT.

If $A^6W$ in 2 is a protecting moiety this can be cleaved using TFA in $CH_2Cl_2$ for BOC-groups or by hydrogenation in methanol/HCl with Pd/C for Z-groups. The resulting ammonium salt (not shown) may be treated according to one of the procedures described later to derive the appropriate $A^6W$ derivative which is then reacted with an excess of the amine $A^1A^2NH$ in DMA or DMF, at RT optionally with DBU or in MeOH at RT to reflux to yield the final amine 3.

Alternatively, the alcohol 1 can be converted to the amine 5 by attaching the pre-assembled fragment $A^1A^2NC(A^3A^4)(CH_2)_m$—OH, which can be synthesized by known methods, to the mesylate/halogenide of derivative 1 using alkylating conditions (step d). The amine 5 can be converted to its salt or the N-oxide 6 as described above (step c).

Finally, the substitution pattern for $A^6$ in product 5 can be manipulated: e.g. hydrolysis of an acetyl group to an $NH_2$. Furthermore the substitution pattern of $A^1$ or $A^2$ may be modified, e.g. treatment of hydroxyethylamine with DAST.

If $A^6W$ in 3 or 5 is a protecting moiety this can be cleaved prior to salt or N-oxide formation using TFA in $CH_2Cl_2$ for BOC-groups or by hydrogenation in methanol with Pd/C for Z-groups. The resulting amine (not shown) may be treated according to one of the following procedures to derive the appropriate $A^6W$ derivative 3 or 5.

Sulfonamides: Sulfonylation of the amines is done in dioxane or $CH_2Cl_2$ with Huenig's base and a sulfonyl chloride over night at RT to yield the sulfonamide 3 or 5.

Carbamates: The amines may be reacted with $A^6OCOCl$/Huenig's base in dioxane or $CH_2Cl_2$. Alternatively, the chloroformates may be prepared in situ by treatment of $A^6OH$ with $Cl_3COCl$ in the presence of quinoline followed by reaction with the amines in the presence of Huenig's base.

Thiocarbamates: The amines may be reacted with $A^6OCSCl$ in dioxane.

Ureas: The amines may be reacted with isocyanate in dioxane at room temperature.

Thioureas: The amines may be reacted with isothiocyanate in dioxane at room temperature.

Amides: The amines may be reacted with $A^5COCl$/Huenigs base in $CH_2Cl_2$, $A^6COOH$/EDCI/DMAP (via formation of the symmetrical anhydride, and subsequent addition of the starting amine at −10° C. to room temperature) or alternatively with $A^6COOH$/EDCI/DMAP or $A^6COOH$/Huenig's base or NMM/EDCI/HOBT in DMF, dioxane or $CH_2Cl_2$ at room temperature.

Sulfamides: The amines may be reacted with sulfamoyl chlorides in dioxane in the presence of an excess of triethylamine to yield sulfamide 3 or 5. The sulfamoyl chlorides can be prepared from $A^6NH_2$ and chlorosulfonic acid in $CH_2Cl_2$ at 0° C. to room temperature followed by reaction with $PCl_5$ in toluene at 75° C. Alternatively, the sulfamoyl chlorides can be synthesized in acetonitrile with $A^6NH_2$ and sulfuryl chloride at 0° C. to 65° C.

Scheme 4:

Scheme 4 shows the synthesis of thio ether derivatives of formula I in which V is S. For compounds in which n is 0, mesylation is performed under inversion (Mitsunobu conditions, step a). For compounds with n>0, the alcohol 1 can be mesylated with methanesulfonyl chloride in pyridine in the presence of DMAP at 0° C. to RT to yield sulfonate 2 (step a). Sulfonate 2 is then thiolated with the corresponding $A^1A^2$aminoalkanethiol (in analogy to the methods described in context with scheme 2) with NaH as base in DMF at 0° C. to RT to give the final compound 3 or 5, respectively (step b).

Another approach for the synthesis of thioether 3, which opens up the possibility to vary the $A^1A^2$amine terminus at the end, is depicted in steps d-f. Sulfonate 2 is treated with potassium thioacetate in DMF at 100° C. to yield thioacetate 7. Deprotection with 1N LiOH in ethanol and alkylation with haloalkanol gives alcohol 8. The alcohol 8 is treated with methanesulfonyl chloride in pyridine in the presence of DMAP at 0° C. to RT to yield the mesylate/chloride which can be aminated with the corresponding $A^1A^2$amine in the presence of NaI in DMA to yield the final amine 3. If $WA^6$ is a protecting group this can be cleaved and the resulting amine can be converted to the desired $WA^6$ derivative by employing one of the methods described for compounds 3 and 5 in scheme 3.

Finally, the substitution pattern for $A^6$ can be manipulated: e.g. hydrolysis of an acetyl group to an $NH_2$. Furthermore the substitution pattern of $A^1$ or $A^2$ may be modified, e.g. treatment of hydroxyethylamine with DAST.

The amines 3 or 5 can optionally be converted to a salt or to the N-oxide 4 or 6 (step c, with e.g. hydrogen peroxide urea adduct and phthalic anhydride in $CH_2Cl_2$ at RT).

Scheme 5:

In scheme 5 the synthesis of C-analogues aminocyclohexanes of the general structure I in which V is —$CH_2$—, —CH=CH— or —C≡C— is described. The synthesis starts from aldehyde 1 which can be derived from (trans)-4-tert-butoxycarbonyl amino-cyclohexane-carboxylic acid (see scheme 1a, compound 9) or from the corresponding alcohol (compound 4, scheme 1a) by Swern oxidation. Side chain extension is effected through application of the Corey-Fuchs method. The aldehyde 1 is treated with triphenylphosphine, tetra-bromo-methane and triethylamine in $CH_2Cl_2$ at 0° C. to RT to yield 2,2-Dibromo-vinyl derivative 2. Rearrangement with n-BuLi (ca 1.6 M in hexane) in THF at −78° C., followed by reaction with formaldehyde (−78° C. to RT; step b) leads to the propargyl alcohol 3 [following conditions described in: Marshall, James A.; Bartley, Gary S.; Wallace, Eli M. Total Synthesis of the Pseudopterane (−)-Kallolide B, the Enantiomer of Natural (+)-Kallolide B. J. Org. Chem. (1996), 61(17), 5729-5735; and Baker, Raymond; Boyes, Alastair L.; Swain, Christopher J. Synthesis of talaromycins A, B, C, and E. J. Chem. Soc., Perkin trans. 1 (1990), (5), 1415-21.].

For longer side chains, the rearrangement of dibromoalkene 2 is performed with n-BuLi (ca 1.6 M in hexane) in THF at −78° C. as above, followed by addition of a cosolvens such as DMPU and reaction with O-protected 1-bromo-alcohols 4a (e.g. 1-bromo-n-tetrahydro-pyaranyloxyalkane) to yield the O-protected compounds 3 which can be deprotected to the corresponding alkinol 3 derivative in MeOH at 50-60° C. in the presence of catalytic amount of pyridinium toluene-4-sulfonate (step c). Alternatively, the side chain elongation of dibromoalkene 2 can also be performed with chloroalkaneiodide 4b (m>1) under the same conditions as described above to give directly chloride 5. Chloride 5 is then converted via iodide 5 (Finkelstein reaction) to the amine 6 as described later.

Mesylation of alcohol 3 with methanesulfonylchloride, pyridine and DMAP in $CH_2Cl_2$ at 0° C. to RT yields mesylate 5 which can be converted to the amine 6 in DMA or MeOH at RT or at 50-70° C. with an excess of the corresponding amine $NHA^1A^2$ (step e).

If $A^6W$ is a protecting moiety this can be cleaved prior to salt or n-oxide formation using TFA in $CH_2Cl_2$ for BOC-groups or by hydrogenation in methanol with Pd/C for Z-groups. The resulting amine (not shown) may be treated according to one of the procedures described for scheme 3 to yield the appropriate $A^6W$ derivative 6.

Optionally the introduction of the desired $A^6W$ moiety can be performed at an earlier stage, e.g. derivative 2 or O-protected derivative 3 or mesylate, chloride or iodide 5 to enable an optimization of the $NA^1A^2$ terminus at the final step e.

To obtain compounds 6 in which $A^3$ and/or $A^4$ is not H and m>0, compounds 2 can be reacted with compounds 10 under the same condition as described for step c. The building blocks 10 can be prepared by known methods. For the introduction of the group $(A^1,A^2)N$—$C(A^3,A^4)$- wherein $A^3$ and/or $A^4$ is not H and m=0, a two step procedure has to be followed: first the rearrangement with n-BuLi (ca 1.6 M in hexane) in THF at −78° C., followed by reaction with the corresponding aldehyde ($A^3$ or $A^4$-COH) or ketone ($A^3COA^4$, at −78° C. to RT) leading to the $A^3,A^4$ substituted propargyl alcohol which can be transformed to a phosphorester or a chloride (not shown) and reacted with the desired $(A^1,A^2)$-amine in the presence of Tetrakis(triphenylphosphine)palladium (for the phosphorsester) or Cu(I)Cl/Cu bronze and Huenig's base for the chloride to yield the desired $A^3,A^4$-substituted compound 6 (step h). (see: Bartlett, Paul A.; McQuaid, Loretta A. Total synthesis of (□)-methyl shikimate and (□)-3-phosphoshikimic acid. J. Am. Chem. Soc. (1984), 106(25), 7854-60 and Cooper, Matthew A.; Lucas, Mathew A.; Taylor, Joanne M.; Ward, A. David; Williamson, Natalie M. A convenient method for the aromatic amino-Claisen rearrangement of N-(1,1-disubstituted-allyl)anilines. Synthesis (2001), (4), 621-625.)

Compounds in which V is —$CH_2$— or —CH=CH— can be obtained by hydrogenation of compound 6 with Pt/C (yields the saturated analogue 8) or by hydrogenation with other known methods (yields the double bond analogue 8). Alternatively, the alkyne group can already be reduced at an earlier stage e.g. alcohol 3 (e.g. LAH-reduction for m=0, gives V=trans-CH=CH— or hydrogenation with Pt/C or $PtO_2.H_2O$ yields V=$CH_2CH_2$—), and the resulting compound can be transformed further to the final compounds 8 and/or 9.

Finally, the substitution pattern for $A^6$ can be manipulated on amine 6 or 8: e.g., hydrolysis of an acetyl group to an $NH_2$. Furthermore the substitution pattern of $A^1$ or $A^2$ may be modified, e.g. treatment of hydroxyethylamine with DAST.

The amines 6 and 8 can be converted to a salt or as described in step f to the N-oxide 7 and 9, respectively, using a mixture of hydrogen peroxide urea adduct and phthalic anhydride in $CH_2Cl_2$ at RT.

Scheme 6:

The synthesis of C-analogues in which V is —$CH_2$— or —CH=CH— is depicted in scheme 6. Alcohol 1 (see synthesis of alcohol 4 in Scheme 1a) can be transformed to the aldehyde 2 via Swern-oxidation. Alternatively, alcohol 1 can be tosylated (tosylchloride in pyridine) followed by treatment with NaCN (in DMF at 100° C.) and reduction with DIBALH (−78° C. to RT in THF) to give the C1-elongated aldyhyde 2. Horner-Emmons reaction with triethyl phosphono acetate, sodium methanolate in ethanol yields the unsaturated ester 3 (step b). Ester 3 can either be reduced directly to the unsaturated alcohol 4 (V is —CH=CH—, x=1) or can be hydrogenated with 10% Pd/C in methanol and reduced with lithium aluminum hydride in THF to the saturated alcohol 4 (V is —$CH_2$—, x=2). The alcohol is mesylated with methane sulfonyl chloride, triethylamine in $CH_2Cl_2$ to yield mesylate 5 (step d) which is treated with the desired amine $A^1A^2NH$ to yield the derivative 6 (step e). As described for the previous schemes, for the cases $A^6W$ is a protecting group (BOC or Z), this can be cleaved and the appropriate $A^6W$ moiety introduced using the methods shown in scheme 3.

Finally, the substitution pattern for $A^6$ can be manipulated on amine 6: e.g. hydrolysis of an acetyl group to an $NH_2$. Furthermore the substitution pattern of $A^1$ or $A^2$ may be modified, e.g. treatment of hydroxyethylamine with DAST.

The amines 6 can be converted to a salt or, as described in step f, to the N-oxide 7 using a mixture of hydrogen peroxide urea adduct and phthalic anhydride in $CH_2Cl_2$ at RT.

Alternatively the side chain can be directly introduced by treatment of aldehyde 2 via Wittig-reaction to give bromide 5 (step g; aldehyde 2 and Wittigsalt 8 was refluxed in the presence of $K_2CO_3$ or $Cs_2CO_3$ in 2-methyl-2-butanol). Bromide 5 can be transformed directly to amine 6 or N-oxide 7 as described above. For the cases $A^6W$ is a protecting group (BOC or Z), this can be cleaved (i.e. first selective hydrogenation of the double bond with Pt/C, $H_2$ in toluene followed by cleavage of the Z-protection with HBr (33%) in acetic acid) on the stage of 5 or 6 and the appropriate $A^6W$ moiety can be introduced using the methods shown in scheme 3.

Scheme 7:

Another approach for the introduction of the substituted side chain is depicted in scheme 7. It starts by attaching an ω-hydroxycarbonic acid ester via the in situ generated triflate in analogy to Belostotskii, Anatoly M.; Hassner, Alfred. Synthetic methods. 41. Etherification of hydroxysteroids via triflates. Tetrahedron Lett. (1994), 35(28), 5075-6(step a). Alternatively, the ester 2 can be prepared from the bromide 3 (synthesis according to scheme 3) by treatment with e.g. acetocyanhydrine in acetonitrile, followed by a Pinner reaction and hydrolysis of the imidate to the corresponding ester (step b).

For V=CH=CH, the ester 2 or its corresponding acid may be prepared from aldehyde 4 (synthesis described in scheme 6) by treatment with the corresponding Wittig reagent $Ph_3P(CH_2)_{m+1}CO_2R/H$. For V=C, hydrogenation of the Wittig product under standard conditions yields the saturated product 2.

For V=CC, ester 2 or amide 6 may be derived from the dibromoderivative 5 (synthesis according to scheme 5) by rearrangement with n-BuLi (ca 1.6 M in hexane) in THF at −78° C., followed by reaction with chloroformate or dimethylcarbamoyl chloride (−78° C. to RT; step d). For longer side chains, the rearrangement of dibromoalkene 5 may be performed with n-BuLi (ca 1.6 M in hexane) in THF at −78° C. as above, followed by addition of a cosolvens such as DMPU and reaction with a suitable protected 1-bromoalkylalcohol Br—$(CH_2)_mCH_2OH$, followed by oxidation to yield the compound 2 as acid (step e).

Saponification of the ester 2 using standard conditions e.g. LiOH in EtOH, MeOH or THF, followed by treatment with $NHA^1A^2$, EDCI, HOBT and a base such as Huenig's base, $NEt_3$, NMM in $CH_2Cl_2$, DMF, DMA or dioxane gives amide 6. Amide 6 can be transferred to amine 7 ($A^3,A^4$=Me) by reaction with methylmagnesium bromide, $ZrCl_4$ in THF at low temperature (see Stephen M. Denton, Anthony Wood, A Modified Bouveault Reaction for the Preparation of α,α-dimethylamines from Amides, Synlett 1999, 1, 55-56.) or by treatment with other grignard reagents in the presence of $ZrCl_4$ or $Ti(OiPr)_4$ (see V. Chalinski, A. de Meijere, A versatile New Preparation of Cyclopropylamines from acid dialkylamides, Angew. Chem. Int. Ed. Engl. 1996, 35, No 4, 413-4.).

For $A^1$=Me, $A^{2'}$=OMe, the amide 3 can be treated with a grignard reagent $A^3MgX$ to give the corresponding ketone 8. Reductive alkylation of the ketone 8 by treatment with $NHA^1A^2$ in the presence of tetraisopropyl orthotitanate, followed by reduction with $NaCNBH_3$ in ethanol yields the amine 7 (see: R. J. Mattson, K. M. Pham, D. J. Leuck, K. A. Cowen, J. O. C. 1990, 55, 2552-4.).

Amine 7 may be converted to a salt or to the N-oxide 9 using a mixture of hydrogen peroxide urea adduct and phthalic anhydride in $CH_2Cl_2$ at RT.

If $A^6W$ is a protecting moiety this can be cleaved prior to salt or N-oxide formation using TFA in $CH_2Cl_2$ for BOC-groups or by hydrogenation in methanol with Pd/C for Z-groups. The resulting amine (not shown) may be treated according to one of the procedures described before (scheme 3) to derive the appropriate $A^6W$ derivative.

Pure cis- or trans-aminocyclohexane derivative scan be obtained either by separation of the mixtures using HPLC or by using stereochemically defined starting materials.

The following tests were carried out in order to determine the activity of the compounds of formula I and their salts.

Inhibition of Human Liver Microsomal 2,3-oxidosqualene-lanosterol Cyclase (OSC)

Liver microsomes from a healthy volunteer were prepared in sodium phosphate buffer (pH 7.4). The OSC activity was measured in the same buffer, which also contained 1 mM EDTA and 1 mM dithiothreitol. The microsomes were diluted to 0.8 mg/ml protein in cold phosphate buffer. Dry [$^{14}$C]R,S-monooxidosqualene (MOS, 12.8 mCi/mmol) was diluted to 20 nCi/μl with ethanol and mixed with phosphate buffer-1% BSA (bovine serum albumin). A stock solution of 1 mM test substance in DMSO was diluted to the desired concentration with phosphate buffer-1% BSA. 40 μl of microsomes were mixed with 20 μl of the solution of the test substance and the reaction was subsequently started with 20 μl of the [$^{14}$C]R,S-MOS solution. The final conditions were: 0.4 mg/ml of microsomal proteins and 30 μl of [$^{14}$C]R,S-MOS in phosphate buffer, pH 7.4, containing 0.5% albumin, DMSO <0.1% and ethanol <2%, in a total volume of 80 μl.

After 1 hour at 37° C. the reaction was stopped by the addition of 0.6 ml of 10% KOH-methanol, 0.7 ml of water and 0.1 ml of hexane:ether (1:1, v/v) which contained 25 μg of non-radioactive MOS and 25 μg of lanosterol as carriers. After shaking, 1 ml of hexane:ether (1:1, v/v) was added to each test tube, these were again shaken and then centrifuged. The upper phase was transferred into a glass test tube, the lower phase was again extracted with hexane:ether and combined with the first extract. The entire extract was evaporated to dryness with nitrogen, the residue was suspended in 50 μl of hexane:ether and applied to a silica gel plate. Chromatographic separation was effected in hexane:ether (1:1, v/v) as the eluent. The Rf values for the MOS substrate and the lanosterol product were 0.91 and, respectively, 0.54. After drying, radioactive MOS and lanosterol were observed on the silica gel plate. The ratio of MOS to lanosterol was determined from the radioactive bands in order to determine the yield of the reaction and OSC inhibition.

The test was carried out on the one hand with a constant test substance concentration of 100 nM and the percentage OSC inhibition against controls was calculated. The more preferred compounds of the present invention exhibit inhibitions larger than 50%. In addition, the test was carried out with different test substance concentrations and subsequently the $IC_{50}$ value was calculated, i.e. the concentration required to reduce the conversion of MOS into lanosterol to 50% of the control value. The preferred compounds of the present invention exhibit $IC_{50}$ values of 1 nM to 10 μM, preferably of 1-100 nM.

The compounds of formula I and their pharmaceutically acceptable acid addition salts can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils.

The production of the pharmaceutical preparations can be effected in a manner which will be familiar to any person skilled in the art by bringing the described compounds of formula I and their pharmaceutically acceptable acid addition salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers are, however, required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 mg to about 1000 mg, especially about 50 mg to about 500 mg, comes into consideration for the prevention and control of topical and systemic infections by pathogenic fungi. For cholesterol lowering and treatment of impaired glucose tolerance and diabetes the daily dosage conveniently amounts to between 1 and 1000 mg, preferably 10 to 100 mg, for adult patients. Depending on the dosage it is convenient to administer the daily dosage in several dosage units.

The pharmaceutical preparations conveniently contain about 1-500 mg, preferably 10-100 mg, of a compound of formula I.

The following Examples serve to illustrate the present invention in more detail. They are, however, not intended to limit its scope in any manner.

EXAMPLES

Abbreviations:
AcOH=Acetic acid, BOC=t-Butyloxycarbonyl, BuLi=Butyllithium, $CH_2Cl_2$=dichloromethane, DAST=Diethylamino-sulfurtrifluoride, DEAD=Diethyl azodicarboxylate, DBU=1,8-Diazabicyclo[5.4.0]undec-7-ene(1,5-5), DIBALH=Di-i-butylaluminium hydride, DMAP=4-Dimethylaminopyridine, DMPU=1,3-Dimethyl-3,4,5,6-tetrahydro-2(1H)-pyrimidinone, EDCI=N-(3-Dimethylaminopropyl)-N'-ethylcarbodiimide hydrochloride, EtOAc=Ethylacetate, EtOH=Ethanol, $Et_2O$=Diethylether, $Et_3N$=Triethylamine, eq=Equivalents, HOBT=1-Hydroxybenzo-triazole, Huenig's base=$iPr_2NEt$=N-Ethyl diisopropylamine, LAH=Lithium aluminium hydride, LDA=Lithium diisopropylamide, $LiBH_4$=Lithium borohydride, MeOH=Methanol, NaI=Sodium iodide, $PdCl_2(dppf)$=(1,1'-Bis(diphenylphosphino)ferrocene)dichloro-palladium(II).$CH_2Cl_2$ (1:1), $Pd(Ph_3P)_4$=Tetrakis(triphenylphosphine)palladium, Red-Al=Sodium bis(2-methoxyethoxy) aluminium hydride, TEMPO=2,2,6,6-Tetramethylpiperidine 1-oxyl, radical, TBDMSCl=t-Butyldimethylsilyl chloride, TBME=t-Butyl methyl ether, TFA=Trifluoroacetic acid, THF=Tetrahydrofurane, quant=quantitative.

General Remarks

All reactions were performed under argon.

The purification of the final amines by preparative HPLC [e.g. RP-118, acetonitrile (0.1% HCOOH)/water (0.1% HCOOH), 10% to 95% acetonitrile] yielded mixtures of the corresponding amino formate and the corresponding halogenide which was used in the reaction. The ratio was not always determined, the purity the final amino salts was >80% after LC-MS.

Example 1

Example 1.1

To a suspension of 50 g (0.33 mol) trans-4-aminocyclohexanol-hydrochloride and 77 g (0.726 mol, 2.2 eq) $Na_2CO_3$ in 650 ml THF and 150 ml water, 51.2 ml (0.363 mol, 1.1 eq) benzyl chloroformate were added at 5° C. over a period of 20 min. The reaction mixture was stirred at RT for 2 h, diluted with EtOAc and the phases were separated. The organic layer was washed with brine, dried over $Na_2SO_4$, filtered and evaporated. Trituration from hexane yielded 162.4 g (98%) trans-4-Hydroxy-cyclohexylcarbamic acid benzyl ester as white crystals, MS: 249 (M) (in analogy to: Venuti, Michael C.; Jones, Gordon H.; Alvarez, Robert; Bruno, John J.; J. Med. Chem.; 30; 2; 1987; 303-318).

Example 1.2

To a suspension of 37.9 g (0.94 mol, 2.0 eq) LAH in 1.3 l THF was added a suspension of 117 g (0.47 mol) trans-4-Hydroxy-cyclohexylcarbamic acid benzyl ester in 1 l THF over a period of 6 h via a cannula keeping the temperature between 5-10° C. The reaction was refluxed over night and a mixture of $Na_2SO_4$, silica gel and water (160 g, 50 g, 80 ml) was added, stirred for additional 30 min, filtered and concentrated. The crude material was titurated with hexane to yield 27.9 g (46%) trans-4-Methylamino-cyclohexanol. Column chromatography of the mother liquor on silica gel yielded additional 17.1 g (28%) trans-4-Methylamino-cyclohexanol as white solid, MS: 129 (MH$^+$) (in analogy to Venuti, Michael C.; Jones, Gordon H.; Alvarez, Robert; Bruno, John J.; J. Med. Chem.; 30; 2; 1987; 303-318).

Example 1.3

13.32 g (103 mmol) trans-4-Methylamino-cyclohexanol were dissolved in isopropanol and treated with 24.75 g (113.4 mmol) di-tert-butyl-dicarbonate in CH$_2$Cl$_2$. The reaction mixture was stirred at RT over night, concentrated to yield 23.3 g (98%) trans-(4-Hydroxy-cyclohexyl)-methyl-carbamic acid tert-butyl ester as white solid, MS: 229 (M$^+$).

Example 1.4

To a suspension of 2.0 g (8.7 mmol) trans-(4-Hydroxy-cyclohexyl)-methyl-carbamic acid tert-butyl ester in 56.5 ml (261 mmol, 30 eq) 1,4-Dibromobutane, 0.89 g (2.6 mmol, 0.3 eq) tetrabutylammoniumhydrogensulfate and 56 ml 50% aqueous NaOH were added. The mixture was stirred at RT for 4 days, CH$_2$Cl$_2$ was added and the layers were separated. The inorganic layer was extracted with CH$_2$Cl$_2$, the combined organic layers washed with brine and dried over Na$_2$SO$_4$. The excess of dibromide was removed in vacuo and the residue was purified by column chromatography on silica gel with hexane:EtOAc 4:1 as eluent yielding 2.4 g (76%) trans-[4-(4-Bromo-butoxy)-cyclohexyl]-methyl-carbamic acid tert-butyl ester as light yellow oil, MS: 364 (MH$^+$, 1Br).

Example 1.5

To 1.7 g (4.7 mmol) trans-[4-(4-Bromo-butoxy)-cyclohexyl]-methyl-carbamic acid tert-butyl ester in 22 ml DMA, 1.34 ml (14 mmol, 3 eq) N-allylmethylamine were added over a period of 10 min. The reaction was stirred at RT over night, concentrated and the residue was dissolved in CH$_2$Cl$_2$/5% aqueous NaHCO$_3$. The phases were separated and the inorganic phase was extracted with CH$_2$Cl$_2$, the combined organic phases were washed with brine, dried over Na$_2$SO$_4$ and concentrated to yield 1.5 g (92%) trans-(4-[4-(Allyl-methyl-amino)-butoxy]-cyclohexyl)-methyl-carbamic acid tert-butyl ester as colorless oil, MS: 355 (MH$^+$).

Example 1.6

In analogy to examples 1.4 and 1.5, trans-(4-Hydroxy-cyclohexyl)-methyl-carbamic acid tert-butyl ester was reacted with 1,3-dibromopropane to yield trans-[4-(3-Bromo-propoxy)-cyclohexyl]-methyl-carbamic acid tert-butyl ester which was reacted with N-allylmethylamine to yield trans-(4-[3-(Allyl-methyl-amino)-propoxy]-cyclohexyl)-methyl-carbamic acid tert-butyl ester as colorless oil, MS: 341 (MH$^+$).

Example 1.7

In analogy to examples 1.4 and 1.5, trans-(4-Hydroxy-cyclohexyl)-methyl-carbamic acid tert-butyl ester was reacted with 1,5-dibromopentane to yield trans-[4-(5-Bromo-pentyloxy)-cyclohexyl]-methyl-carbamic acid tert-butyl ester which was reacted with N-allylmethylamine to yield trans-(4-[5-(Allyl-methyl-amino)-pentyloxy]-cyclohexyl)-methyl-carbamic acid tert-butyl ester as white oil, MS: 369 (MH$^+$).

Example 1.8

In analogy to examples 1.4 and 1.5, trans-(4-Hydroxy-cyclohexyl)-methyl-carbamic acid tert-butyl ester was reacted with 1,6-dibromohexane to yield trans-[4-(6-Bromo-hexyloxy)-cyclohexyl]-methyl-carbamic acid tert-butyl ester which was reacted with N-allylmethylamine to yield trans-(4-[6-(Allyl-methyl-amino)-hexyloxy]-cyclohexyl)-methyl-carbamic acid tert-butyl ester as light brown oil, MS: 382 (M).

Example 1.9

In analogy to examples 1.4 and 1.5, trans-(4-Hydroxy-cyclohexyl)-methyl-carbamic acid tert-butyl ester was reacted with 1,7-dibromoheptane to yield trans-[4-(7-Bromo-heptyloxy)-cyclohexyl]-methyl-carbamic acid tert-butyl ester which was reacted with N-allylmethylamine to yield trans-(4-[7-(Allyl-methyl-amino)-heptyloxy]-cyclohexyl)-methyl-carbamic acid tert-butyl ester as colorless oil, MS: 397 (MH$^+$).

Example 1.10

2.1 g (5.9 mmol) trans-(4-[4-(Allyl-methyl-amino)-butoxy]-cyclohexyl)-methyl-carbamic acid tert-butyl ester in 28 ml CH$_2$Cl$_2$ were treated with 6 ml TFA at 0° C. for 1 h, the mixture was concentrated in vacuo and dissolved in EtOAc and saturated aqueous NaHCO$_3$ solution. The phases were separated and the inorganic phase was extracted with EtOAc, the combined organic phases were washed with brine, dried over Na$_2$SO$_4$ and evaporated to yield 1.38 g (91%) trans-(4-[4-(Allyl-methyl-amino)-butoxy]-cyclohexyl)-methyl-amine as yellow oil, MS: 255 (MH$^+$).

Example 1.11

In analogy to example 1.10, trans-(4-[3-(Allyl-methyl-amino)-propoxy]-cyclohexyl)-methyl-carbamic acid tert-butyl ester was converted to yield trans-(4-[3-(Allyl-methyl-amino)-propoxy]-cyclohexyl)-methyl-amine as yellow oil, MS: 241 (MH$^+$).

Example 1.12

In analogy to example 1.10, trans-(4-[5-(Allyl-methyl-amino)-pentyloxy]-cyclohexyl)-methyl-carbamic acid tert-butyl ester was converted to yield trans-(4-[5-(Allyl-methyl-amino)-pentyloxy]-cyclohexyl)-methyl-amine as yellow oil, MS: 269 (MH$^+$).

Example 1.13

In analogy to example 1.10, trans-(4-[6-(Allyl-methyl-amino)-hexyloxy]-cyclohexyl)-methyl-carbamic acid tert-butyl ester was converted to yield trans-[4-[6-(Allyl-methyl-amino)-hexyloxy]-cyclohexyl]-methyl-amine as yellow oil, MS: 283 (MH$^+$).

Example 1.14

In analogy to example 1.10, trans-(4-[7-(Allyl-methyl-amino)-heptyloxy]-cyclohexyl)-methyl-carbamic acid tert-butyl ester was converted to yield trans-(4-[7-(Allyl-methyl-amino)-heptyloxy]-cyclohexyl)-methyl-amine as colorless oil, MS: 297 (MH+).

Example 2

A solution of 0.153 mmol of free amine in 0.35 ml dry dioxane was treated with 0.23 mmol isocyanate in 0.54 ml dry dioxane. The solution was allowed to stand over night at room temperature. The resulting reaction mixture was treated with 0.15 ml formic acid and purified by preparative HPLC [RP-18, acetonitrile (0.1% HCOOH)/water (0.1% HCOOH), 10% to 95% acetonitrile]. After evaporation the urea was obtained as amino formate. The following compounds were prepared from the corresponding amines and isocyanates:

| Example | Compound | MS MH+ | Amine | Isocyanate |
|---|---|---|---|---|
| 2.1 | trans-1-{4-[6-(Allyl-methyl-amino)-hexyloxy]-cyclohexyl}-3-(2,4-difluoro-phenyl)-1-methyl-urea | 438 | trans-[4-[6-(Allyl-methyl-amino)-hexyloxy]-cyclohexyl]-methyl-amine | 2,4-Difluoro-phenylisocyanate |
| 2.2 | trans-1-{4-[6-(Allyl-methyl-amino)-hexyloxy]-cyclohexyl}-3-(2,4-dimethoxy-phenyl)-1-methyl-urea | 462 | trans-[4-[6-(Allyl-methyl-amino)-hexyloxy]-cyclohexyl]-methyl-amine | 2,4 Dimethoxy-phenylisocyanate |
| 2.3 | trans-1-{4-[6-(Allyl-methyl-amino)-hexyloxy]-cyclohexyl}-3-(4-fluoro-phenyl)-1-methyl-urea | 420 | trans-[4-[6-(Allyl-methyl-amino)-hexyloxy]-cyclohexyl]-methyl-amine | 4-Fluorophenyl-isocyanate |
| 2.4 | trans-1-{4-[6-(Allyl-methyl-amino)-hexyloxy]-cyclohexyl}-3-(4-methoxy-phenyl)-1-methyl-urea | 432 | trans-[4-[6-(Allyl-methyl-amino)-hexyloxy]-cyclohexyl]-methyl-amine | 4-Methoxy-phenylisocyanate |
| 2.5 | trans-1-{4-[6-(Allyl-methyl-amino)-hexyloxy]-cyclohexyl}-1-methyl-3-p-tolyl-urea | 416 | trans-[4-[6-(Allyl-methyl-amino)-hexyloxy]-cyclohexyl]-methyl-amine | 4-Methylphenyl-isocyanate |
| 2.6 | trans-1-{4-[6-(Allyl-methyl-amino)-hexyloxy-cyclohexyl}-3-(4-methoxy-2-methyl-phenyl)-1-methyl-urea | 446 | trans-[4-[6-(Allyl-methyl-amino)-hexyloxy]-cyclohexyl]-methyl-amine | 4-Methoxy-2-Methylphenyl-isocyanate |
| 2.7 | trans-1-{4-[6-(Allyl-methyl-amino)-hexyloxy]-cyclohexyl}-3-(2,4-dimethyl-phenyl)-1-methyl-urea | 430 | trans-[4-[6-(Allyl-methyl-amino)-hexyloxy]-cyclohexyl]-methyl-amine | 2,4 Dimethyl-phenylisocyanate |
| 2.8 | trans-1-{4-[6-(Allyl-methyl-amino)-hexyloxy]-cyclohexyl}-1-methyl-3-(3,4,5-trimethoxy-phenyl)-urea | 492 | trans-[4-[6-(Allyl-methyl-amino)-hexyloxy]-cyclohexyl]-methyl-amine | 3,4,5 Trimethoxy-phenylisocyanate |
| 2.9 | trans-1-{4-[6-(Allyl-methyl-amino)-hexyloxy]-cyclohexyl}-3-(3,4-dimethyl-phenyl)-1-methyl-urea | 430 | trans-[4-[6-(Allyl-methyl-amino)-hexyloxy]-cyclohexyl]-methyl-amine | 3,4 Dimethyl-phenylisocyanate |
| 2.10 | trans-3-(4-Acetyl-phenyl)-1-{4-[6-(allyl-methyl-amino)-hexyloxy]-cyclohexyl}-1-methyl-urea | 444 | trans-[4-[6-(Allyl-methyl-amino)-hexyloxy]-cyclohexyl]-methyl-amine | 4-Acetylphenyl-isocyanate |
| 2.11 | trans-1-{4-[6-(Allyl-methyl-amino)-hexyloxy]-cyclohexyl}-3-(4-chloro-phenyl)-1-methyl-urea | 436 (1 Cl) | trans-[4-[6-(Allyl-methyl-amino)-hexyloxy]-cyclohexyl]-methyl-amine | 4-Chlorphenyl-isocyanate |
| 2.12 | trans-1-{4-[6-(Allyl-methyl-amino)-hexyloxy]-cyclohexyl}-1-methyl-3-phenyl-urea | 402 | trans-[4-[6-(Allyl-methyl-amino)-hexyloxy]-cyclohexyl]-methyl-amine | Phenylisocyanate |
| 2.13 | trans-1-{4-[6-(Allyl-methyl-amino)-hexyloxy]-cyclohexyl}-1-methyl-3-(4-trifluoromethyl-phenyl)-urea | 470 | trans-[4-[6-(Allyl-methyl-amino)-hexyloxy]-cyclohexyl]-methyl-amine | 4-Trifluoro-methylisocyanate |
| 2.14 | trans-1-{4-[6-(Allyl-methyl-amino)-hexyloxy]-cyclohexyl}-3-(3,4-dichloro-phenyl)-1-methyl-urea | 470 (2 Cl) | trans-[4-[6-(Allyl-methyl-amino)-hexyloxy]-cyclohexyl]-methyl-amine | 3,4 Dichloro-phenylisocyanate |
| 2.15 | trans-1-{4-[6-(Allyl-methyl-amino)-hexyloxy]-cyclohexyl}-3-(4-bromo-phenyl)-1-methyl-urea | 480 (1 Br) | trans-[4-[6-(Allyl-methyl-amino)-hexyloxy]-cyclohexyl]-methyl-amine | 4-Bromphenyl-isocyanate |
| 2.16 | trans-1-{4-[6-(Allyl-methyl-amino)-hexyloxy]- | 452 | trans-[4-[6-(Allyl-methyl-amino)- | 2-Naphthyl-isocyanate |

-continued

| Example | Compound | MS MH+ | Amine | Isocyanate |
|---|---|---|---|---|
| | cyclohexyl}-1-methyl-3-naphthalen-2-yl-urea | | hexyloxy]-cyclohexyl]-methyl-amine | |
| 2.17 | trans-1-{4-[6-(allyl-methyl-amino)-hexyloxy]-cyclohexyl}-1-methyl-3-(4-nitro-phenyl)-urea | 447 | trans-[4-[6-(Allyl-methyl-amino)-hexyloxy]-cyclohexyl]-methyl-amine | 4-Nitrophenyl-isocyanate |
| 2.18 | trans-1-{4-[6-(Allyl-methyl-amino)-hexyloxy]-cyclohexyl}-3-(4-dimethylamino-phenyl)-1-methyl-urea | 445 | trans-[4-[6-(Allyl-methyl-amino)-hexyloxy]-cyclohexyl]-methyl-amine | 4-Dimethyl-aminophenyl-isocyanate |
| 2.19 | trans-1-{4-[7-(Allyl-methyl-amino)-heptyloxy]-cyclohexyl}-1-methyl-3-p-tolyl-urea | 430 | trans-(4-[7-(Allyl-methyl-amino)-heptyloxy]-cyclohexyl)-methyl-amine | 4-Toloyl-isocanate |
| 2.20 | trans-1-{4-[7-(Allyl-methyl-amino)-heptyloxy]-cyclohexyl}-3-(4-fluoro-phenyl)-1-methylurea | 434 | trans-(4-[7-(Allyl-methyl-amino)-heptyloxy]-cyclohexyl)-methyl-amine | 4-Fluorophenyl-isocyanate |
| 2.21 | trans-1-{4-[7-(Allyl-methyl-amino)-heptyloxy]-cyclohexyl}-3-(4-bromo-phenyl)-1-methylurea | 494 (1 Br) | trans-(4-[7-(Allyl-methyl-amino)-heptyloxy]-cyclohexyl)-methyl-amine | 4-Bromophenyl-isocyanate |
| 2.22 | trans-1-{4-[7-(Allyl-methyl-amino)-heptyloxy]-cyclohexyl}-3-(4-butyl-phenyl)-1-methylurea | 472 | trans-(4-[7-(Allyl-methyl-amino)-heptyloxy]-cyclohexyl)-methyl-amine | 4-Butylphenyl-isocyanate |
| 2.23 | trans-1-{4-[5-(Allyl-methyl-amino)-pentyloxy]-cyclohexyl}-1-methyl-3-p-tolyl-urea | 402 | trans-(4-[5-(Allyl-methyl-amino)-pentyloxy]-cyclohexyl)-methyl-amine | 4-Toloyl-isocanate |
| 2.24 | trans-1-{4-[5-(Allyl-methyl-amino)-pentyloxy]-cyclohexyl}-3-(4-fluoro-phenyl)-1-methylurea | 406 | trans-(4-[5-(Allyl-methyl-amino)-pentyloxy]-cyclohexyl)-methyl-amine | 4-Fluorophenyl-isocyanate |
| 2.25 | trans-1-{4-[5-(Allyl-methyl-amino)-pentyloxy]-cyclohexyl}-3-(4-bromo-phenyl)-1-methylurea | 466 (1 Br) | trans-(4-[5-(Allyl-methyl-amino)-pentyloxy]-cyclohexyl)-methyl-amine | 4-Bromophenyl-isocyanate |
| 2.26 | trans-1-{4-[4-(Allyl-methyl-amino)-butoxy]-cyclohexyl}-1-methyl-3-p-tolyl-urea | 388 | trans-(4-[4-(Allyl-methyl-amino)-butoxy]-cyclohexyl)-methyl-amine | 4-Toloyl-isocanate |
| 2.27 | trans-1-{4-[4-(Allyl-methyl-amino)-butoxy]-cyclohexyl}-3-(4-fluoro-phenyl)-1-methylurea | 392 | trans-(4-[4-(Allyl-methyl-amino)-butoxy]-cyclohexyl)-methyl-amine | 4-Fluorophenyl-isocyanate |
| 2.28 | trans-1-{4-[4-(Allyl-methyl-amino)-butoxy]-cyclohexyl}-3-(4-bromo-phenyl)-1-methylurea | 452 (1 Br) | trans-(4-[4-(Allyl-methyl-amino)-butoxy]-cyclohexyl)-methyl-amine | 4-Bromophenyl-isocyanate |
| 2.29 | trans-1-{4-[4-(Allyl-methyl-amino)-butoxy]-cyclohexyl}-3-(4-butyl-phenyl)-1-methylurea | 430 | trans-(4-[4-(Allyl-methyl-amino)-butoxy]-cyclohexyl)-methyl-amine | 4-Butylphenyl-isocyanate |

Example 3

A solution of 0.153 mmol of amine in 0.35 ml dry dioxane was treated with (2 equivalents or 4 equivalents if the amine.dihydrochloride was used) Huenig's base and 0.2 mmol chloroformate in 0.54 ml dry dioxane. The solution was allowed to stand over night at room temperature and the resulting reaction mixture was treated with 0.15 ml formic acid and purified by preparative HPLC [RP-18, acetonitrile (0.1% HCOOH)/water (0.1% HCOOH), 10% to 95% acetonitrile]. After evaporation the carbamate was obtained as a mixture of amino hydrochloride and formate. The following compounds were prepared from the corresponding amines and chloroformates:

| Example | Compound | MS MH+ | Amine | Chloroformate |
|---|---|---|---|---|
| 3.1 | trans-{4-[6-(Allyl-methyl-amino)-hexyloxy]- | 448 | trans-[4-[6-(Allyl-methyl-amino)- | 4-Nitrophenyl-chloroformate |

-continued

| Example | Compound | MS MH+ | Amine | Chloroformate |
|---|---|---|---|---|
| | cyclohexyl}-methyl-carbamic acid 4-nitro-phenyl ester | | hexyloxy]-cyclohexyl]-methyl-amine | |
| 3.2 | trans-{4-[6-(Allyl-methyl-amino)-hexyloxy]-cyclohexyl}-methyl-carbamic acid naphthalen-2-yl ester | 453 | trans-[4-[6-(Allyl-methyl-amino)-hexyloxy]-cyclohexyl]-methyl-amine | 2-Napthyl-chloroformate |
| 3.3 | trans-{4-[6-(Allyl-methyl-amino)-hexyloxy]-cyclohexyl}-methyl-carbamic acid pentafluorophenylmethyl ester | 507 | trans-[4-[6-(Allyl-methyl-amino)-hexyloxy]-cyclohexyl]-methyl-amine | Pentafluorobenzyl chloroformate |
| 3.4 | trans-{4-[6-(Allyl-methyl-amino)-hexyloxy]-cyclohexyl}-methyl-carbamic acid benzyl ester | 417 | trans-[4-[6-(Allyl-methyl-amino)-hexyloxy]-cyclohexyl]-methyl-amine | Benzyl-chloroformate |
| 3.5 | trans-{4-[6-(Allyl-methyl-amino)-hexyloxy]-cyclohexyl}-methyl-carbamic acid phenyl ester | 403 | trans-[4-[6-(Allyl-methyl-amino)-hexyloxy]-cyclohexyl]-methyl-amine | Phenyl-chloroformate |
| 3.6 | trans-{4-[6-(Allyl-methyl-amino)-hexyloxy]-cyclohexyl}-methyl-carbamic acid p-tolyl ester | 417 | trans-[4-[6-(Allyl-methyl-amino)-hexyloxy]-cyclohexyl]-methyl-amine | p-Tolyl-chloroformate |
| 3.7 | trans-{4-[6-(Allyl-methyl-amino)-hexyloxy]-cyclohexyl}-methyl-carbamic acid 4-bromo-phenyl ester | 481 (1 Br) | trans-[4-[6-(Allyl-methyl-amino)-hexyloxy]-cyclohexyl]-methyl-amine | 4-Bromophenyl-chloroformate |
| 3.8 | trans-{4-[6-(Allyl-methyl-amino)-hexyloxy]-cyclohexyl}-methyl-carbamic acid 4-fluoro-phenyl ester | 421 | trans-[4-[6-(Allyl-methyl-amino)-hexyloxy]-cyclohexyl]-methyl-amine | 4-Fluorophenyl-chloroformate |
| 3.9 | trans-{4-[6-(Allyl-methyl-amino)-hexyloxy]-cyclohexyl}-methyl-carbamic acid 4-chloro-phenyl ester | 437 (1 Cl) | trans-[4-[6-(Allyl-methyl-amino)-hexyloxy]-cyclohexyl]-methyl-amine | 4-Chlorophenyl-chloroformate |
| 3.10 | trans-{4-[6-(Allyl-methyl-amino)-hexyloxy]-cyclohexyl}-methyl-carbamic acid hexyl ester | 411 | trans-[4-[6-(Allyl-methyl-amino)-hexyloxy]-cyclohexyl]-methyl-amine | 4-Hexyl-chloroformate |
| 3.11 | trans-{4-[6-(Allyl-methyl-amino)-hexyloxy]-cyclohexyl}-methyl-carbamic acid 4-methoxy-phenyl ester | 433 | trans-[4-[6-(Allyl-methyl-amino)-hexyloxy]-cyclohexyl]-methyl-amine | 4-Methoxy-phenyl-chloroformate |
| 3.12 | trans-{4-[6-(Allyl-methyl-amino)-hexyloxy]-cyclohexyl}-methyl-carbamic acid isobutyl ester | 383 | trans-[4-[6-(Allyl-methyl-amino)-hexyloxy]-cyclohexyl]-methyl-amine | Isobutyl-chloroformate |
| 3.13 | trans-{4-[7-(Allyl-methyl-amino)-heptyloxy]-cyclohexyl}-methyl-carbamic acid 4-bromo-phenyl ester | 495 (1 Br) | trans-(4-[7-(Allyl-methyl-amino)-heptyloxy]-cyclohexyl)-methyl-amine | 4-Bromophenyl-chloroformate |
| 3.14 | trans-{4-[5-(Allyl-methyl-amino)-pentyloxy]-cyclohexyl}-methyl-carbamic acid 4-bromo-phenyl ester | 467 (1 Br) | trans-(4-[5-(Allyl-methyl-amino)-pentyloxy]-cyclohexyl)-methyl-amine | 4-Bromophenyl-chloroformate |
| 3.15 | trans-{4-[4-(Allyl-methyl-amino)-butoxy]-cyclohexyl}-methyl-carbamic acid 4-bromo-phenyl ester | 453 (1 Br) | trans-(4-[4-(Allyl-methyl-amino)-butoxy]-cyclohexyl)-methyl-amine | 4-Bromophenyl-chloroformate |
| 3.16 | trans-{4-[7-(Allyl-methyl-amino)-heptyloxy]-cyclohexyl}-methyl-carbamic acid 4-fluoro-phenyl ester | 435 | trans-(4-[7-(Allyl-methyl-amino)-heptyloxy]-cyclohexyl)-methyl-amine | 4-Fluorophenyl-chloroformate |
| 3.17 | trans-{4-[5-(Allyl-methyl-amino)-pentyloxy]-cyclohexyl}-methyl-carbamic acid 4-fluoro-phenyl ester | 407 | trans-(4-[5-(Allyl-methyl-amino)-pentyloxy]-cyclohexyl)-methyl-amine | 4-Fluorophenyl-chloroformate |
| 3.18 | {4-trans-[4-(Allyl-methyl-amino)-butoxy]-cyclohexyl}-methyl-carbamic acid 4-chloro-phenyl ester | 409 (1 Cl) | trans-(4-[4-(Allyl-methyl-amino)-butoxy]-cyclohexyl)-methyl-amine | 4-chloro-phenyl chloroformate |

| Example | Compound | MS MH+ | Amine | Chloroformate |
|---|---|---|---|---|
| 3.19 | {4-trans-[4-(Allyl-methyl-amino)-butoxy-cyclohexyl]}-methyl-carbamic acid isobutyl ester | 355 | trans-(4-[4-(Allyl-methyl-amino)-butoxy]-cyclohexyl)-methyl-amine | isobutyl chloroformate |
| 3.20 | {4-trans-[4-(Allyl-methyl-amino)-butoxy-cyclohexyl]}-methyl-carbamic acid phenyl ester | 375 | trans-(4-[4-(Allyl-methyl-amino)-butoxy]-cyclohexyl)-methyl-amine | phenyl chloroformate |
| 3.21 | 4-({4-trans-[4-(Allyl-methyl-amino)-butoxy-cyclohexyl]}-methyl-carbamoyloxy)-benzoic acid methyl ester | 433 | trans-(4-[4-(Allyl-methyl-amino)-butoxy]-cyclohexyl)-methyl-amine | 4-methoxy-carbonyl-phenyl chloroformate |
| 3.22 | {4-trans-[4-(Allyl-methyl-amino)-butoxy-cyclohexyl]}-methyl-carbamic acid 4-methoxy-phenyl ester | 405 | trans-(4-[4-(Allyl-methyl-amino)-butoxy]-cyclohexyl)-methyl-amine | 4-methoxy-phenyl chloroformate |
| 3.23 | {4-trans-[4-(Allyl-methyl-amino)-butoxy-cyclohexyl]}-methyl-carbamic acid p-tolyl ester | 389 | trans-(4-[4-(Allyl-methyl-amino)-butoxy]-cyclohexyl)-methyl-amine | p-tolyl chloroformate |
| 3.24 | {4-trans-[3-(Allyl-methyl-amino)-propoxy]-cyclohexyl}-methyl-carbamic acid 4-fluoro-phenyl ester | 379 | trans-(4-[3-(Allyl-methyl-amino)-propoxy]-cyclohexyl)-methyl-amine | 4-fluoro-phenyl chloroformate |
| 3.25 | {4-trans-[3-(Allyl-methyl-amino)-propoxy]-cyclohexyl}-methyl-carbamic acid 4-bromo-phenyl ester | 439 (1 Br) | trans-(4-[3-(Allyl-methyl-amino)-propoxy]-cyclohexyl)-methyl-amine | 4-bromo-phenyl chloroformate |

Example 4

A solution of 1.5 mmol trichloromethyl-chloroformate (diphosgene) in 20 ml $CH_2Cl_2$ was treated at 0° C. with 3 mmol of a suitable substituted phenol and 3 mmol quinoline and then stirred for 3 h at room temperature. The reaction was then cooled (0° C.) and a solution of 1 mmol amine and 2.5 mmol pyridine in 3 ml $CH_2Cl_2$ was added, followed by 1 mmol DMAP. The mixture was stirred over night at room temperature, treated with 0.15 ml formic acid and purified by preparative HPLC [RP-18, acetonitrile (0.1% HCOOH)/water (0.1% HCOOH), 10% to 95% acetonitrile]. After evaporation the carbamate was obtained as a mixture of amino hydrochloride and formate. The following compounds were prepared from the corresponding amines and chloroformates:

Example 5

A solution of 0.143 mmol amine in 0.35 ml dry dioxane was treated with (0.46 mmol; 3 equivalents) Huenig's base and 0.18 mmol sulfonylchloride in 0.5 ml dry dioxane. The solution was allowed to stand over night at room temperature. The resulting reaction mixture was treated with 0.15 ml formic acid and purified by preparative HPLC [RP-18, acetonitrile (0.1% HCOOH)/water (0.1% HCOOH), 10% to 95% acetonitrile]. After evaporation, the sulfonamide was obtained as a mixture of amino hydrochloride and formate. The following compounds were prepared from the corresponding amines and sulfonylchlorides:

| Example | Product | MS MH+ | Amine | In situ generated Chloroformate |
|---|---|---|---|---|
| 4.1 | trans-{4-[6-(Allyl-methyl-amino)-hexyloxy]-cyclohexyl}-methyl-carbamic acid 4-trifluoromethyl-phenyl ester | 471 | trans-[4-[6-(Allyl-methyl-amino)-hexyloxy]-cyclohexyl]-methyl-amine | 4-Trifluoro-methyl-phenyl-chloroformate |
| 4.2 | trans-{4-[5-(Allyl-methyl-amino)-pentyloxy]-cyclohexyl}-methyl-carbamic acid 4-trifluoromethyl-phenyl ester | 457 | trans-(4-[5-(Allyl-methyl-amino)-pentyloxy]-cyclohexyl)-methyl-amine | 4-Trifluoro-phenyl-chloroformate |
| 4.3 | trans-{4-[4-(Allyl-methyl-amino)-butoxy]-cyclohexyl}-methyl-carbamic acid 4-trifluoromethyl-phenyl ester | 443 | trans-(4-[4-(Allyl-methyl-amino)-butoxy]-cyclohexyl)-methyl-amine | 4-trifluoro-methyl-phenyl chloroformate |
| 4.4 | trans{4-[6-(Allyl-methyl-amino)-hexyloxy]-cyclohexyl}-methyl-carbamic acid 2,4-difluoro-phenyl ester | 439 | trans-[4-[6-(Allyl-methyl-amino)-hexyloxy]-cyclohexyl]-methyl-amine | 2,4-difluoro-phenyl chloroformate |

| Example | Compound | MS MH+ | Amine | Sulfonylchloride |
|---|---|---|---|---|
| 5.1 | trans-5-Chloro-thiophene-2-sulfonic acid {4-[6-(allyl-methyl-amino)-hexyloxy]-cyclohexyl}-methyl-amide | 463 (1 Cl) | trans-[4-[6-(Allyl-methyl-amino)-hexyloxy]-cyclohexyl]-methyl-amine | 5-Chloro-thiophene-2-sulphonylchloride |
| 5.2 | trans-N-{4-[6-(Allyl-methyl-amino)-hexyloxy]-cyclohexyl}-4,N-dimethyl-benzenesulfonamide | 437 | trans-[4-[6-(Allyl-methyl-amino)-hexyloxy]-cyclohexyl]-methyl-amine | 4-Tosylsulphonyl-chloride |
| 5.3 | trans-Naphthalene-2-sulfonic acid {4-[6-(allyl-methyl-amino)-hexyloxy]-cyclohexyl}-methyl-amide | 473 | trans-[4-[6-(Allyl-methyl-amino)-hexyloxy]-cyclohexyl]-methyl-amine | 2-Naphthyl-sulphonylchloride |
| 5.4 | trans-N-{4-[6-(Allyl-methyl-amino)-hexyloxy]-cyclohexyl}-N-methyl-methanesulfonamide | 361 | trans-[4-[6-(Allyl-methyl-amino)-hexyloxy]-cyclohexyl]-methyl-amine | Methanesulfonyl-chloride |
| 5.5 | trans-Quinoline-8-sulfonic acid {4-[6-(allyl-methyl-amino)-hexyloxy]-cyclohexyl}-methyl-amide | 474 | trans-[4-[6-(Allyl-methyl-amino)-hexyloxy]-cyclohexyl]-methyl-amine | 8-Quinoline-sulphonylchloride |
| 5.6 | trans-N-{4-[6-(Allyl-methyl-amino)-hexyloxy]-cyclohexyl}-N-methyl-C-phenyl-methanesulfonamide | 437 | trans-[4-[6-(Allyl-methyl-amino)-hexyloxy]-cyclohexyl]-methyl-amine | alpha-Toluene-sulphonylchloride |
| 5.7 | trans-3,5-Dimethyl-isoxazole-4-sulfonic acid {4-[6-(allyl-methyl-amino)-hexyloxy]-cyclohexyl}-methyl-amide | 442 | trans-[4-[6-(Allyl-methyl-amino)-hexyloxy]-cyclohexyl]-methyl-amine | 3,5 Dimethyl-isoxazol-sulphonylchloride |
| 5.8 | trans-Naphthalene-1-sulfonic acid {4-[6-(allyl-methyl-amino)-hexyloxy]-cyclohexyl}-methyl-amide | 473 | trans-[4-[6-(Allyl-methyl-amino)-hexyloxy]-cyclohexyl]-methyl-amine | 1-Naphthyl-sulphonylchloride |
| 5.9 | trans-N-{4-[6-(Allyl-methyl-amino)-hexyloxy]-cyclohexyl}-4-methoxy-N-methyl-benzenesulfonamide | 453 | trans-[4-[6-(Allyl-methyl-amino)-hexyloxy]-cyclohexyl]-methyl-amine | 4-Methoxy-benzene-sulphonylchloride |
| 5.10 | trans-N-{4-[6-(Allyl-methyl-amino)-hexyloxy]-cyclohexyl}-N-methyl-benzenesulfonamide | 423 | trans-[4-[6-(Allyl-methyl-amino)-hexyloxy]-cyclohexyl]-methyl-amine | Benzene-sulphonylchloride |
| 5.11 | trans-N-{4-[6-(Allyl-methyl-amino)-hexyloxy]-cyclohexyl}-4-fluoro-N-methyl-benzenesulfonamide | 441 | trans-[4-[6-(Allyl-methyl-amino)-hexyloxy]-cyclohexyl]-methyl-amine | 4-Fluorobenzene-sulphonylchloride |
| 5.12 | trans-Thiophene-2-sulfonic acid {4-[6-(allyl-methyl-amino)-hexyloxy]-cyclohexyl}-methyl-amide | 429 | trans-[4-[6-(Allyl-methyl-amino)-hexyloxy]-cyclohexyl]-methyl-amine | 2-Thiophene-sulphonylchloride |
| 5.13 | trans-N-{4-[6-(Allyl-methyl-amino)-hexyloxy]-cyclohexyl}-2-fluoro-N-methyl-benzenesulfonamide | 441 | trans-[4-[6-(Allyl-methyl-amino)-hexyloxy]-cyclohexyl]-methyl-amine | 2-Fluorobenzene-sulphonylchloride |
| 5.14 | trans-1-Methyl-1H-imidazole-4-sulfonic acid {4-[6-(allyl-methyl-amino)-hexyloxy]-cyclohexyl}-methyl-amide | 427 | trans-[4-[6-(Allyl-methyl-amino)-hexyloxy]-cyclohexyl]-methyl-amine | 1-Methyl-imidazole-4-sulphonylchloride |
| 5.15 | trans-N-{4-[6-(Allyl-methyl-amino)-hexyloxy]-cyclohexyl}-4-tert-butyl-N-methyl-benzenesulfonamide | 479 | trans-[4-[6-(Allyl-methyl-amino)-hexyloxy]-cyclohexyl]-methyl-amine | 4-tert.-Butyl-benzene-sulphonylchloride |
| 5.16 | trans-N-{4-[6-(Allyl-methyl-amino)-hexyloxy]-cyclohexyl}-4-butoxy-N-methyl-benzenesulfonamide | 495 | trans-[4-[6-(Allyl-methyl-amino)-hexyloxy]-cyclohexyl]-methyl-amine | 4-Butoxybenzene-sulphonylchloride |
| 5.17 | trans-N-{4-[6-(Allyl-methyl-amino)-hexyloxy]-cyclohexyl}-4-chloro-N-methyl-benzenesulfonamide | 457 (1 Cl) | trans-[4-[6-(Allyl-methyl-amino)-hexyloxy]-cyclohexyl]-methyl-amine | 4-Chlorobenzene-sulphonylchloride |
| 5.18 | trans-N-{4-[6-(Allyl-methyl-amino)-hexyloxy]-cyclohexyl}-N-methyl-4-trifluoromethyl-benzenesulfonamide | 491 | trans-[4-[6-(Allyl-methyl-amino)-hexyloxy]-cyclohexyl]-methyl-amine | 4-Trifluoro-methylbenzene-sulphonylchloride |
| 5.19 | trans-N-{4-[6-(Allyl-methyl-amino)-hexyloxy]- | 501 (1 Br) | trans-[4-[6-(Allyl-methyl-amino)- | 4-Brombenzene-sulphonylchloride |

| Example | Compound | MS MH+ | Amine | Sulfonylchloride |
|---|---|---|---|---|
| | cyclohexyl}-4-bromo-N-methyl-benzenesulfonamide | | hexyloxy]-cyclohexyl]-methyl-amine | |
| 5.20 | trans-N-{4-[6-(Allyl-methyl-amino)-hexyloxy]-cyclohexyl}-N-methyl-4-nitro-benzenesulfonamide | 468 | trans-[4-[6-(Allyl-methyl-amino)-hexyloxy]-cyclohexyl]-methyl-amine | 4-Nitrobenzene-sulphonylchloride |
| 5.21 | N-{4-trans-[6-(Allyl-methyl-amino)-hexyloxy]-cyclohexyl}-3-chloro-N-methyl-benzenesulfonamide | 457 (1 Cl) | trans-[4-[6-(Allyl-methyl-amino)-hexyloxy]-cyclohexyl]-methyl-amine | 3-chloro-phenyl sulfonylchloride |
| 5.22 | N-{4-trans-[6-(Allyl-methyl-amino)-hexyloxy]-cyclohexyl}-2,4-difluoro-N-methyl-benzenesulfonamide | 459 | trans-[4-[6-(Allyl-methyl-amino)-hexyloxy]-cyclohexyl]-methyl-amine | 2,4-difluoro-phenyl-sulfonylchloride |
| 5.23 | N-{4-trans-[6-(Allyl-methyl-amino)-hexyloxy]-cyclohexyl}-2-bromo-N-methyl-benzenesulfonamide | 501 (1 Br) | trans-[4-[6-(Allyl-methyl-amino)-hexyloxy]-cyclohexyl]-methyl-amine | 2-bromo-phenyl sulfonylchloride |
| 5.24 | N-{4-trans-[6-(Allyl-methyl-amino)-hexyloxy]-cyclohexyl}-3-bromo-N-methyl-benzenesulfonamide | 501 (1 Br) | trans-[4-[6-(Allyl-methyl-amino)-hexyloxy]-cyclohexyl]-methyl-amine | 3-bromo-phenyl sulfonylchloride |
| 5.25 | N-{4-trans-[6-(Allyl-methyl-amino)-hexyloxy]-cyclohexyl}-2,4-dichloro-N-methyl-benzenesulfonamide | 491 (2 Cl) | trans-[4-[6-(Allyl-methyl-amino)-hexyloxy]-cyclohexyl]-methyl-amine | 2,4-dichloro-phenyl-sulfonylchloride |
| 5.26 | N-{4-trans-[6-(Allyl-methyl-amino)-hexyloxy]-cyclohexyl}-3-fluoro-N-methyl-benzenesulfonamide | 441 | trans-[4-[6-(Allyl-methyl-amino)-hexyloxy]-cyclohexyl]-methyl-amine | 3-fluoro-phenyl sulfonylchloride |
| 5.27 | N-{4-trans-[6-(Allyl-methyl-amino)-hexyloxy]-cyclohexyl}-3,4-dichloro-N-methyl-benzenesulfonamide | 491 (2 Cl) | trans-[4-[6-(Allyl-methyl-amino)-hexyloxy]-cyclohexyl]-methyl-amine | 3,4-dichloro-phenyl-sulfonylchloride |
| 5.28 | N-{4-trans-[6-(Allyl-methyl-amino)-hexyloxy]-cyclohexyl}-2-chloro-N-methyl-benzenesulfonamide | 457 (1 Cl) | trans-[4-[6-(Allyl-methyl-amino)-hexyloxy]-cyclohexyl]-methyl-amine | 2-chloro-phenyl sulfonylchloride |
| 5.29 | N-{4-trans-[6-(Allyl-methyl-amino)-hexyloxy]-cyclohexyl}-3,4-difluoro-N-methyl-benzenesulfonamide | 459 | trans-[4-[6-(Allyl-methyl-amino)-hexyloxy]-cyclohexyl]-methyl-amine | 3,4-difluoro-phenyl-sulfonylchloride |
| 5.30 | N-{4-trans-[4-(Allyl-methyl-amino)-butoxy]-cyclohexyl}-N-methyl-4-trifluoromethyl-benzenesulfonamide | 463 | trans-(4-[4-(Allyl-methyl-amino)-butoxy]-cyclohexyl)-methyl-amine | 4-trifluoromethyl-phenyl-sulfonylchloride |
| 5.31 | N-{4-trans-[3-(Allyl-methyl-amino)-propoxy]-cyclohexyl}-4-chloro-N-methyl-benzenesulfonamide | 415 (1 Cl) | trans-(4-[3-(Allyl-methyl-amino)-propoxy]-cyclohexyl)-methyl-amine | 4-chloro-phenyl-sulfonylchloride |
| 5.32 | N-{4-trans-[4-(Allyl-methyl-amino)-butoxy]-cyclohexyl}-4-chloro-N-methyl-benzenesulfonamide | 429 (1 Cl) | trans-(4-[4-(Allyl-methyl-amino)-butoxy]-cyclohexyl)-methyl-amine | 4-chloro-phenyl-sulfonylchloride |
| 5.33 | N-{4-trans-[4-(Allyl-methyl-amino)-butoxy]-cyclohexyl}-4-bromo-N-methyl-benzenesulfonamide | 473 (1 Br) | trans-(4-[4-(Allyl-methyl-amino)-butoxy]-cyclohexyl)-methyl-amine | 4-bromo-phenyl-sulfonylchloride |
| 5.34 | N-{4-trans-[4-(Allyl-methyl-amino)-butoxy]-cyclohexyl}-N-methyl-C-phenyl-methanesulfonamide | 409 | trans-(4-[4-(Allyl-methyl-amino)-butoxy]-cyclohexyl)-methyl-amine | benzyl-sulfonylchloride |
| 5.35 | N-{4-trans-[4-(Allyl-methyl-amino)-butoxy]-cyclohexyl}-4-fluoro-N-methyl-benzenesulfonamide | 413 | trans-(4-[4-(Allyl-methyl-amino)-butoxy]-cyclohexyl)-methyl-amine | 4-fluoro-phenyl-sulfonylchloride |
| 5.36 | N-{4-trans-[4-(Allyl-methyl-amino)-butoxy]-cyclohexyl}-2-fluoro-N-methyl-benzenesulfonamide | 413 | trans-(4-[4-(Allyl-methyl-amino)-butoxy]-cyclohexyl)-methyl-amine | 2-fluoro-phenyl-sulfonylchloride |
| 5.37 | N-{4-trans-[4-(Allyl-methyl-amino)-butoxy]-cyclohexyl}-N-methyl-benzenesulfonamide | 395 | trans-(4-[4-(Allyl-methyl-amino)-butoxy]-cyclohexyl)-methyl-amine | phenyl-sulfonylchloride |
| 5.38 | 5-Chloro-thiophene-2-sulfonic acid {4-trans-[4- | 436 (1 Cl) | trans-(4-[4-(Allyl-methyl-amino)- | 5-Chloro-thiophene-2- |

-continued

| Example | Compound | MS MH+ | Amine | Sulfonylchloride |
|---|---|---|---|---|
| | (allyl-methyl-amino)-butoxy]-cyclohexyl}-methyl-amide | | butoxy]-cyclohexyl)-methyl-amine | sulfonylchloride |

Example 6

A solution of 0.133 mmol amine in 0.5 ml dry DMF was treated subsequently with 0.17 mmol (1.3 equivalents) acid, 0.266 mmol (2 equvivalents) Huenig's base, 0.266 mmol (2 equivalents) N-(3-Dimethylaminopropyl)-N'-ethylcarbodiimide hydrochloride (EDCI) as well as catalytic amount of Hydroxybenzotriazole (HOBT) (approximately 0.02 mmol). The solution was allowed to stand over night at room temperature. The resulting reaction mixture was treated with 0.15 ml formic acid and purified by preparative HPLC [RP-18, acetonitrile (0.1% HCOOH)/water (0.1% HCOOH), 10% to 95% acetonitrile]. After evaporation, the amide was obtained as a mixture of amino hydrochloride and formate. The following compounds were prepared from the corresponding amines and acids:

| Example | Compound | MS MH+ | Amine | Acid |
|---|---|---|---|---|
| 6.1 | trans-Pyridine-2-carboxylic acid {4-[6-(allyl-methyl-amino)-hexyloxy]-cyclohexyl}-methyl-amide | 388 | trans-[4-[6-(Allyl-methyl-amino)-hexyloxy]-cyclohexyl]-methyl-amine | Picolinic acid |
| 6.2 | trans-1H-Indole-2-carboxylic acid {4-[6-(allyl-methyl-amino)-hexyloxy]-cyclohexyl}-methyl-amide | 426 | trans-[4-[6-(Allyl-methyl-amino)-hexyloxy]-cyclohexyl]-methyl-amine | 1H-Indole-2-carboxylic acid |
| 6.3 | trans-N-{4-[6-(Allyl-methyl-amino)-hexyloxy]-cyclohexyl}-N-methyl-benzamide | 387 | trans-[4-[6-(Allyl-methyl-amino)-hexyloxy]-cyclohexyl]-methyl-amine | Benzoic acid |
| 6.4 | trans-N-{4-[6-(Allyl-methyl-amino)-hexyloxy]-cyclohexyl}-4-chloro-N-methyl-benzamide | 421 (1 Cl) | trans-[4-[6-(Allyl-methyl-amino)-hexyloxy]-cyclohexyl]-methyl-amine | 4-Chloro-benzoic acid |
| 6.5 | trans-N-{4-[6-(Allyl-methyl-amino)-hexyloxy]-cyclohexyl}-4-fluoro-N-methyl-benzamide | 405 | trans-[4-[6-(Allyl-methyl-amino)-hexyloxy]-cyclohexyl]-methyl-amine | 4-Fluoro-benzoic acid |
| 6.6 | trans-N-{4-[6-(Allyl-methyl-amino)-hexyloxy]-cyclohexyl}-4-bromo-N-methyl-benzamide | 465 (1 Br) | trans-[4-[6-(Allyl-methyl-amino)-hexyloxy]-cyclohexyl]-methyl-amine | 4-Bromo-benzoic acid |
| 6.7 | trans-N-{4-[6-(Allyl-methyl-amino)-hexyloxy]-cyclohexyl}-N-methyl-4-trifluoromethyl-benzamide | 455 | trans-[4-[6-(Allyl-methyl-amino)-hexyloxy]-cyclohexyl]-methyl-amine | 4-Trifluoro-methyl-benzoic acid |
| 6.8 | trans-Thiophene-3-carboxylic acid {4-[6-(allyl-methyl-amino)-hexyloxy]-cyclohexyl}-methyl-amide | 393 | trans-[4-[6-(Allyl-methyl-amino)-hexyloxy]-cyclohexyl]-methyl-amine | Thiophene-3-carboxylic acid |
| 6.9 | trans-5-Bromo-thiophene-2-carboxylic acid {4-[6-(allyl-methyl-amino)-hexyloxy]-cyclohexyl}-methyl-amide | 471 (1 Br) | trans-[4-[6-(Allyl-methyl-amino)-hexyloxy]-cyclohexyl]-methyl-amine | 5-Bromo-thiophene-2 carboxylic acid |
| 6.10 | trans-N-{4-[6-(Allyl-methyl-amino)-hexyloxy]-cyclohexyl}-N-methyl-2-thiophen-3-yl-acetamide | 407 | trans-[4-[6-(Allyl-methyl-amino)-hexyloxy]-cyclohexyl]-methyl-amine | 2-Thiophene-3-yl-carboxylic acid |
| 6.11 | trans-N-{4-[6-(Allyl-methyl-amino)-hexyloxy]-cyclohexyl}-2-(2,4-difluoro-phenyl)-N-methyl-acetamide | 437 | trans-[4-[6-(Allyl-methyl-amino)-hexyloxy]-cyclohexyl]-methyl-amine | 2,4-Difluoro-acetic acid |
| 6.12 | trans-5-Fluoro-1H-indole-2-carboxylic acid {4-[6-(allyl-methyl-amino)-hexyloxy]-cyclohexyl}-methyl-amide | 444 | trans-[4-[6-(Allyl-methyl-amino)-hexyloxy]-cyclohexyl]-methyl-amine | 1H-Indole-5-Fluoro-2-carboxylic acid |
| 6.13 | trans-N-{4-[6-(Allyl-methyl-amino)-hexyloxy]-cyclohexyl}-2-(4-fluoro-phenyl)-N-methyl-acetamide | 419 | trans-[4-[6-(Allyl-methyl-amino)-hexyloxy]-cyclohexyl]-methyl-amine | 4-Fluoro-phenylacetic acid |

-continued

| Example | Compound | MS MH+ | Amine | Acid |
|---|---|---|---|---|
| 6.14 | trans-1H-Indole-5-carboxylic acid {4-[6-(allyl-methyl-amino)-hexyloxy]-cyclohexyl}-methyl-amide | 426 | trans-[4-[6-(Allyl-methyl-amino)-hexyloxy]-cyclohexyl]-methyl-amine | 1H-Indole-5-carboxylic acid |
| 6.15 | trans-N-{4-[6-(Allyl-methyl-amino)-hexyloxy]-cyclohexyl}-3-chloro-N-methyl-benzamide | 421 (1 Cl) | trans-[4-[6-(Allyl-methyl-amino)-hexyloxy]-cyclohexyl]-methyl-amine | 3-Chlorobenzoic acid |
| 6.16 | trans-N-{4-[6-(Allyl-methyl-amino)-hexyloxy]-cyclohexyl}-4-fluoro-3,N-dimethyl-benzamide | 419 | trans-[4-[6-(Allyl-methyl-amino)-hexyloxy]-cyclohexyl]-methyl-amine | 4-Fluor-3-Methyl-benzoic acid |
| 6.17 | trans-N-{4-[6-(Allyl-methyl-amino)-hexyloxy]-cyclohexyl}-N-methyl-4-nitro-benzamide | 432 | trans-[4-[6-(Allyl-methyl-amino)-hexyloxy]-cyclohexyl]-methyl-amine | 4-Nitro-benzoic acid |
| 6.18 | trans-N-{4-[6-(Allyl-methyl-amino)-hexyloxy]-cyclohexyl}-4,N-dimethyl-benzamide | 401 | trans-[4-[6-(Allyl-methyl-amino)-hexyloxy]-cyclohexyl]-methyl-amine | p-Toluic acid |
| 6.19 | trans-N-{4-[6-(Allyl-methyl-amino)-hexyloxy]-cyclohexyl}-3-cyano-N-methyl-benzamide | 412 | trans-[4-[6-(Allyl-methyl-amino)-hexyloxy]-cyclohexyl]-methyl-amine | 3-Cyano-benzoic acid |
| 6.20 | trans-N-{4-[6-(Allyl-methyl-amino)-hexyloxy]-cyclohexyl}-3,N-dimethyl-benzamide | 401 | trans-[4-[6-(Allyl-methyl-amino)-hexyloxy]-cyclohexyl]-methyl-amine | m-Toluoic acid |
| 6.21 | trans-N-{4-[6-(Allyl-methyl-amino)-hexyloxy]-cyclohexyl}-3,4-dimethoxy-N-methyl-benzamide | 447 | trans-[4-[6-(Allyl-methyl-amino)-hexyloxy]-cyclohexyl]-methyl-amine | 3,4 Dimethoxy-benzoic acid |
| 6.22 | trans-N-{4-[6-(Allyl-methyl-amino)-hexyloxy]-cyclohexyl}-4-methoxy-N-methyl-benzamide | 417 | trans-[4-[6-(Allyl-methyl-amino)-hexyloxy]-cyclohexyl]-methyl-amine | 4-Methoxy-benzoic acid |
| 6.23 | trans-N-{4-[6-(Allyl-methyl-amino)-hexyloxy]-cyclohexyl}-4-fluoro-N-methyl-3-nitro-benzamide | 450 | trans-[4-[6-(Allyl-methyl-amino)-hexyloxy]-cyclohexyl]-methyl-amine | 4-Fluoro-3-nitro-benzoic acid |
| 6.24 | trans-4-Acetyl-N-{4-[6-(allyl-methyl-amino)-hexyloxy]-cyclohexyl}-N-methyl-benzamide | 429 | trans-[4-[6-(Allyl-methyl-amino)-hexyloxy]-cyclohexyl]-methyl-amine | 4-Acetyl-benzoic acid |
| 6.25 | trans-N-{4-[7-(Allyl-methyl-amino)-heptyloxy]-cyclohexyl}-N-methyl-4-trifluoromethyl-benzamide | 469 | trans-(4-[7-(Allyl-methyl-amino)-heptyloxy]-cyclohexyl)-methyl-amine | 4-Trifluoro-methyl-benzoic acid |
| 6.26 | trans-N-{4-[5-(Allyl-methyl-amino)-pentyloxy]-cyclohexyl}-N-methyl-4-trifluoromethyl-benzamide | 441 | trans-(4-[5-(Allyl-methyl-amino)-pentyloxy]-cyclohexyl)-methyl-amine | 4-Trifluoro-methyl-benzoic acid |
| 6.27 | trans-N-{4-[4-(Allyl-methyl-amino)-butoxy]-cyclohexyl}-3-cyano-N-methyl-benzamide | 384 | trans-(4-[4-(Allyl-methyl-amino)-butoxy]-cyclohexyl)-methyl-amine | 3-Cyano-phenyl-benoic acid |
| 6.28 | trans-N-{4-[5-(Allyl-methyl-amino)-pentyloxy]-cyclohexyl}-4-bromo-N-methyl-benzamide | 451 (1 Br) | trans-(4-[5-(Allyl-methyl-amino)-pentyloxy]-cyclohexyl)-methyl-amine | 4-Bromo-phenyl-benzoic acid |
| 6.29 | trans-N-{4-[4-(Allyl-methyl-amino)-butoxy]-cyclohexyl}-4-bromo-N-methyl-benzamide | 337 (1 Br) | trans-(4-[4-(Allyl-methyl-amino)-butoxy]-cyclohexyl)-methyl-amine | 4-Bromo-phenyl-benzoic acid |
| 6.30 | trans-5-Bromo-thiophene-2-carboxylic acid {4-[4-(allyl-methyl-amino)-butoxy]-cyclohexyl}-methyl-amide | 443 (1 Br) | trans-(4-[4-(Allyl-methyl-amino)-butoxy]-cyclohexyl)-methyl-amine | 2-Bromo-thiophene5-carboxylic acid |
| 6.31 | trans-N-{4-[5-(Allyl-methyl-amino)-pentyloxy]-cyclohexyl}-4-fluoro-N-methyl-benzamide | 391 | trans-(4-[5-(Allyl-methyl-amino)-pentyloxy]-cyclohexyl)-methyl-amine | 4-Fluoro-phenyl-benzoic acid |
| 6.32 | trans-N-{4-[4-(Allyl-methyl-amino)-butoxy]-cyclohexyl}-4-fluoro-N-methyl-benzamide | 377 | trans-(4-[4-(Allyl-methyl-amino)-butoxy]-cyclohexyl)-methyl-amine | 4-Fluoro-phenyl-benzoic acid |

Example 7

A solution of 0.133 mmol amine was treated with 0.17 mmol (1.3 equivalents) isothiocyanate in 0.35 ml dry dioxane. The solution was allowed to stand over night at room temperature, treated with 0.15 ml formic acid and purified by preparative HPLC [RP-18, acetonitrile (0.1% HCOOH)/water (0.1% HCOOH), 10% to 95% acetonitrile]. After evaporation of the corresponding fraction, the thiourea was obtained as amino formate. The following compounds were prepared from the corresponding amines and isothiocyanates:

| Example | Compound | MS MH$^+$ | Amine | Isothiocyanate |
|---|---|---|---|---|
| 7.1 | trans-1-{4-[6-(Allyl-methyl-amino)-hexyloxy]-cyclohexyl}-3-(2-bromo-4-fluoro-phenyl)-1-methyl-thiourea | 514 (1 Br) | trans-[4-[6-(Allyl-methyl-amino)-hexyloxy]-cyclohexyl]-methyl-amine | 2-Bromo-4-fluoro-phenyl-isothiocyanate |
| 7.2 | trans-1-{4-[6-(Allyl-methyl-amino)-hexyloxy]-cyclohexyl}-3-(4-bromo-2-methyl-phenyl)-1-methyl-thiourea | 510 (1 Br) | trans-[4-[6-(Allyl-methyl-amino)-hexyloxy]-cyclohexyl]-methyl-amine | 4-Bromo-2-methyl-phenyl-isothiocyanate |
| 7.3 | trans-1-{4-[6-(Allyl-methyl-amino)-hexyloxy]-cyclohexyl}-1-methyl-3-(4-trifluoromethyl-phenyl)-thiourea | 486 | trans-[4-[6-(Allyl-methyl-amino)-hexyloxy]-cyclohexyl]-methyl-amine | 4-Trifluoro-methyl-phenyl-isothiocyanate |
| 7.4 | trans1-{4-[6-(Allyl-methyl-amino)-hexyloxy]-cyclohexyl}-3-(4-chloro-phenyl)-1-methyl-thiourea | 452 (1 Cl) | trans-[4-[6-(Allyl-methyl-amino)-hexyloxy]-cyclohexyl]-methyl-amine | 4-Chloro-phenyl-isothiocyanate |
| 7.5 | trans1-{4-[6-(Allyl-methyl-amino)-hexyloxy]-cyclohexyl}-3-(4-methoxy-phenyl)-1-methyl-thiourea | 448 | trans-[4-[6-(Allyl-methyl-amino)-hexyloxy]-cyclohexyl]-methyl-amine | 4-Methoxy-phenyl-isothiocyanate |
| 7.6 | trans-1-{4-[6-(Allyl-methyl-amino)-hexyloxy]-cyclohexyl}-3-(4-cyano-phenyl)-1-methyl-thiourea | 443 | trans-[4-[6-(Allyl-methyl-amino)-hexyloxy]-cyclohexyl]-methyl-amine | 4-Cyanophenyl-isothiocyanate |
| 7.7 | trans-1-{4-[6-(Allyl-methyl-amino)-hexyloxy]-cyclohexyl}-1-methyl-3-(3-methyl-butyl)-thiourea | 412 | trans-[4-[6-(Allyl-methyl-amino)-hexyloxy]-cyclohexyl]-methyl-amine | 3-Methylbutyl-isothiocyanate |
| 7.8 | trans-1-{4-[6-(Allyl-methyl-amino)-hexyloxy]-cyclohexyl}-3-sec-butyl-1-methyl-thiourea | 398 | trans-[4-[6-(Allyl-methyl-amino)-hexyloxy]-cyclohexyl]-methyl-amine | sec-Butyl-isothiocyanate |
| 7.9 | trans-1-{4-[4-(Allyl-methyl-amino)-butoxy]-cyclohexyl}-1-methyl-3-(4-trifluoromethyl-phenyl)-thiourea | 458 | trans-{4-[3-(Allyl-methyl-amino)-propoxy]-cyclohexyl}-methyl-amine | 1-Isothiocyanato-4-trifluoro-methyl-benzene |
| 7.10 | trans-1-{4-[4-(Allyl-methyl-amino)-butoxy]-cyclohexyl}-3-(4-cyano-phenyl)-1-methyl-thiourea | 415 | trans-{4-[3-(Allyl-methyl-amino)-propoxy]-cyclohexyl}-methyl-amine | 1-Isothiocyanato-4-cyano-benzene |
| 7.11 | trans-1-{4-[4-(Allyl-methyl-amino)-butoxy]-cyclohexyl}-1-methyl-3-(3-methyl-butyl)-thiourea | 384 | trans-{4-[3-(Allyl-methyl-amino)-propoxy]-cyclohexyl}-methyl-amine | 1-Isothiocyanato-3-methyl-butane |
| 7.12 | trans-1-{4-[7-(Allyl-methyl-amino)-heptyloxy]-cyclohexyl}-1-methyl-3-(4-trifluoromethyl-phenyl)-thiourea | 500 | trans-(4-[7-(Allyl-methyl-amino)-heptyloxy]-cyclohexyl)-methyl-amine | 1-Isothiocyanato-4-trifluoro-methyl-benzene |
| 7.13 | trans-1-{4-[7-(Allyl-methyl-amino)-heptyloxy]-cyclohexyl}-3-(4-cyano-phenyl)-1-methyl-thiourea | 457 | trans-(4-[7-(Allyl-methyl-amino)-heptyloxy]-cyclohexyl)-methyl-amine | 1-Isothiocyanato-4-cyano-benzene |
| 7.14 | trans-1-{4-[7-(Allyl-methyl-amino)-heptyloxy]-cyclohexyl}-1-methyl-3-(3-methyl-butyl)-thiourea | 426 | trans-(4-[7-(Allyl-methyl-amino)-heptyloxy]-cyclohexyl)-methyl-amine | 1-Isothiocyanato-3-methyl-butane |
| 7.15 | trans-1-{4-[3-(Allyl-methyl-amino)-propoxy]-cyclohexyl}-1-methyl-3-(4-trifluoromethyl-phenyl)-thiourea | 444 | trans-{4-[3-(Allyl-methyl-amino)-propoxy]-cyclohexyl}-methyl-amine | 4-Trifluoro-methyl-phenyl-isothiocyanate |

Example 8

The amine (3 eq.) was dissolved in $CH_2Cl_2$ (1 ml/mmol) and placed in an ice bath. A solution of chlorosulfonic acid (1 eq.) in $CH_2Cl_2$ (0.5 ml/mmol) was added slowly (30 min). The reaction mixture was stirred at 0° C. for a further 30 min. Afterward, the ice bath was removed and the stirring was continued for 1 h at room temperature. The precipitate was collected by filtration and dried under high vacuum. This salt was suspended in toluene (1 ml/mmol amine) and PCl$_5$ (1 eq) was added. The mixture was stirred at 75° C. for 2 h, cooled to room temperature and filtered. The solid residue was washed with toluene. The filtrate was evaporated and dried under high vacuum. The crude sulfamoyl chloride was used in the next step without further purification. The following sulfamoyl chlorides were prepared according to the above procedure from the corresponding amine:

Benzylsulfamoyl chloride, Phenylsulfamoyl chloride, 2,4-Difluoro-phenylsulfamoyl chloride, 2,5-Difluoro-phenylsulfamoyl chloride, 3,4-Difluoro-phenylsulfamoyl chloride, 3-Fluoro phenyl-sulfamoyl chloride, 4-Fluoro-phenylsulfamoyl chloride, 4-Chloro-phenylsulfamoyl chloride, 4-Bromo-phenylsulfamoyl chloride, 4-Methyl-phenylsulfamoyl chloride, 4-trifluoromethyl-phenylsulfamoyl chloride, 4-Cyano-phenylsulfamoyl chloride, 4-Methoxy-phenylsulfamoyl chloride, Butylsulfamoyl chloride, Phenethylsulfamoyl chloride, Cyclopropylsulfamoyl chloride, 2,2,2-Trifluoroethylsulfamoyl chloride, 4-Fluoro-benzylsulfamoyl chloride, Furan-2-ylmethylsulfamoyl chloride, Benzo[1,3]dioxol-5-ylmethylsulfamoyl chloride.

Example 9

The amine.hydrochloride (1 eq.) was dissolved in CH$_3$CN and placed in an ice bath. Sulfuryl chloride (3 eq.) was added slowly (20 min). The reaction mixture was stirred at room temperature for 15 min and at 65° C. for 20 h. The solvent was evaporated and the residue was dried under high vacuum. The crude sulfamoyl chloride was used in the next step without further purification. The following sulfamoyl chlorides were prepared according to the above procedure from the corresponding amine:

Chlorosulfonylamino-acetic acid ethyl ester, 4-(Chlorosulfonylamino-methyl)-benzoic acid methyl ester.

Example 10

A solution of 0.135 mmol amine in 0.75 ml dry dioxane was treated with 5 equivalents of triethylamine followed by a solution of 0.175 mmol (1.3 equivalents) sulfamoylchloride in 0.25 ml dry dioxane. The suspension was allowed to stand over night at room temperature, treated with 0.15 ml formic acid and purified by preparative HPLC [RP-18, acetonitrile (0.1% HCOOH)/water (0.1% HCOOH), 10% to 95% acetonitrile]. After evaporation of the corresponding fraction, the sulfamide was obtained as a mixture of amino hydrochloride and formate. The following compounds were prepared from the corresponding amines and sulfamoylchlorides:

| Example | Compound | MS MH$^+$ | Amine | Sulfamoyl-chloride |
| --- | --- | --- | --- | --- |
| 10.1 | trans-[4-[6-(Allyl-methyl-amino)-hexyloxy]-cyclohexyl]-methyl-sulfamic acid benzyl amide | 452 | trans-[4-[6-(Allyl-methyl-amino)-hexyloxy]-cyclohexyl]-methyl-amine | Benzyl-sulfamoylchloride |
| 10.2 | trans-{4-[6-(Allyl-methyl-amino)-hexyloxy]-cyclohexyl}-methyl-sulfamic acid phenyl amide | 438 | trans-[4-[6-(Allyl-methyl-amino)-hexyloxy]-cyclohexyl]-methyl-amine | Phenyl-sulfamoylchloride |
| 10.3 | trans-4-[({4-[6-(Allyl-methyl-amino)-hexyloxy]-cyclohexyl}-methyl-carbamoyloxy)-methyl]-benzoic acid methyl ester | 510 | trans-[4-[6-(Allyl-methyl-amino)-hexyloxy]-cyclohexyl]-methyl-amine | 4-(Chloro-sulfonylamino-methyl)-benzoic acid methyl ester |
| 10.4 | trans-{4-[6-(Allyl-methyl-amino)-hexyloxy]-cyclohexyl}-methyl-sulfamic acid butyl amide | 418 | trans-[4-[6-(Allyl-methyl-amino)-hexyloxy]-cyclohexyl]-methyl-amine | Butyl-sulfamoylchloride |
| 10.5 | trans-{4-[6-(Allyl-methyl-amino)-hexyloxy]-cyclohexyl}-methyl-sulfamic acid phenethyl amide | 466 | trans-[4-[6-(Allyl-methyl-amino)-hexyloxy]-cyclohexyl]-methyl-amine | Phenethyl-sulfamoylchloride |
| 10.6 | trans-{4-[6-(Allyl-methyl-amino)-hexyloxy]-cyclohexyl}-methyl-sulfamic acid furan-2-ylmethyl amide | 442 | trans-[4-[6-(Allyl-methyl-amino)-hexyloxy]-cyclohexyl]-methyl-amine | Furan-2-yl-methyl-sulfamoylchloride |
| 10.7 | trans-({4-[6-(Allyl-methyl-amino)-hexyloxy]-cyclohexyl}-methyl-sulfonylamino)-acetic acid ethyl ester | 448 | trans-[4-[6-(Allyl-methyl-amino)-hexyloxy]-cyclohexyl]-methyl-amine | Chloro-sulfonylamino-acetic acid ethyl ester |
| 10.8 | trans-{4-[6-(Allyl-methyl-amino)-hexyloxy]-cyclohexyl}-methyl-sulfamic acid cyclopropyl amide | 402 | trans-[4-[6-(Allyl-methyl-amino)-hexyloxy]-cyclohexyl]-methyl-amine | Cyclopropyl-sulfamoylchloride |
| 10.9 | trans-{4-[6-(Allyl-methyl-amino)-hexyloxy]-cyclohexyl}-methyl-sulfamic | 444 | trans-[4-[6-(Allyl-methyl-amino)-hexyloxy]- | 2,2,2-Trifluoro-ethyl-sulfamoylchloride |

-continued

| Example | Compound | MS MH+ | Amine | Sulfamoyl-chloride |
|---|---|---|---|---|
| | acid 2,2,2-trifluoro-ethyl amide | | cyclohexyl]-methyl-amine | |
| 10.10 | trans-{4-[6-(Allyl-methyl-amino)-hexyloxy]-cyclohexyl}-methyl-sulfamic acid benzo[1,3]dioxol-5-ylmethyl amide | 496 | trans-[4-[6-(Allyl-methyl-amino)-hexyloxy]-cyclohexyl]-methyl-amine | Benzo[1,3]dioxol-5-yl-methyl-sulfamoylchloride |
| 10.11 | trans-{4-[6-(Allyl-methyl-amino)-hexyloxy]-cyclohexyl}-methyl-sulfamic acid 4-fluorobenzyl amide | 470 | trans-[4-[6-(Allyl-methyl-amino)-hexyloxy]-cyclohexyl]-methyl-amine | 4-Fluoro-benzyl-sulfamoylchloride |
| 10.12 | trans-{4-[6-(Allyl-methyl-amino)-hexyloxy]-cyclohexyl}-methyl-sulfamic acid(4-chloro-phenyl)-amide | 472 (1 Cl) | trans-[4-[6-(Allyl-methyl-amino)-hexyloxy]-cyclohexyl]-methyl-amine | 4-Chloro-phenyl-sulfamoylchloride |
| 10.13 | trans-{4-[6-(Allyl-methyl-amino)-hexyloxy]-cyclohexyl}-methyl-sulfamic acid(4-fluoro-phenyl)-amide | 456 | trans-[4-[6-(Allyl-methyl-amino)-hexyloxy]-cyclohexyl]-methyl-amine | 4-Fluoro-phenyl-sulfamoylchloride |
| 10.14 | trans-{4-[6-(Allyl-methyl-amino)-hexyloxy]-cyclohexyl}-methyl-sulfamic acid(4-bromo-phenyl)-amide | 516 (1 Br) | trans-[4-[6-(Allyl-methyl-amino)-hexyloxy]-cyclohexyl]-methyl-amine | 4-Bromo-phenyl-sulfamoylchloride |
| 10.15 | trans-{4-[6-(Allyl-methyl-amino)-hexyloxy]-cyclohexyl}-methyl-sulfamic acid(p-tolyl)-amide | 452 | trans-[4-[6-(Allyl-methyl-amino)-hexyloxy]-cyclohexyl]-methyl-amine | p-tolyl-sulfamoylchloride |
| 10.16 | trans-{4-[6-(Allyl-methyl-amino)-hexyloxy]-cyclohexyl}-methyl-sulfamic acid(3,4-difluoro-phenyl)-amide | 474 | trans-[4-[6-(Allyl-methyl-amino)-hexyloxy]-cyclohexyl]-methyl-amine | 3,4-Difluoro-phenyl-sulfamoylchloride |
| 10.17 | trans-{4-[6-(Allyl-methyl-amino)-hexyloxy]-cyclohexyl}-methyl-sulfamic acid(4-trifluoromethyl-phenyl)-amide | 506 | trans-[4-[6-(Allyl-methyl-amino)-hexyloxy]-cyclohexyl]-methyl-amine | 4-Trifluoro-methylphenyl-sulfamoylchloride |
| 10.18 | trans-{4-[6-(Allyl-methyl-amino)-hexyloxy]-cyclohexyl}-methyl-sulfamic acid(3-fluoro-phenyl)-amide | 456 | trans-[4-[6-(Allyl-methyl-amino)-hexyloxy]-cyclohexyl]-methyl-amine | 3-Fluoro-phenyl-sulfamoylchloride |
| 10.19 | trans-{4-[6-(Allyl-methyl-amino)-hexyloxy]-cyclohexyl}-methyl-sulfamic acid(4-cyano-phenyl)-amide | 463 | trans-[4-[6-(Allyl-methyl-amino)-hexyloxy]-cyclohexyl]-methyl-amine | 4-Cyano-phenyl-sulfamoylchloride |
| 10.20 | trans-{4-[6-(Allyl-methyl-amino)-hexyloxy]-cyclohexyl}-methyl-sulfamic acid(2,4-difluoro-phenyl)-amide | 474 | trans-[4-[6-(Allyl-methyl-amino)-hexyloxy]-cyclohexyl]-methyl-amine | 2,4-Difluoro-phenyl-sulfamoylchloride |
| 10.21 | trans-{4-[6-(Allyl-methyl-amino)-hexyloxy]-cyclohexyl}-methyl-sulfamic acid(4-methoxy-phenyl)-amide | 468 | trans-[4-[6-(Allyl-methyl-amino)-hexyloxy]-cyclohexyl]-methyl-amine | 4-Methoxy-phenyl-sulfamoylchloride |
| 10.22 | trans-{4-[6-(Allyl-methyl-amino)-hexyloxy]-cyclohexyl}-methyl-sulfamic acid(2,5-difluoro-phenyl)-amide | 474 | trans-[4-[6-(Allyl-methyl-amino)-hexyloxy]-cyclohexyl]-methyl-amine | 2,5-Difluoro-phenyl-sulfamoylchloride |
| 10.23 | trans-{4-[5-(Allyl-methyl-amino)-pentyloxy]-cyclohexyl}-methyl-sulfamic acid benzyl amide | 436 M-H− | trans-(4-[5-(Allyl-methyl-amino)-pentyloxy]-cyclohexyl)-methyl-amine | Benzyl-sulfamoylchloride |
| 10.24 | trans-{4-[5-(Allyl-methyl-amino)-pentyloxy]-cyclohexyl}-methyl-sulfamic | 422 M-H− | trans-(4-[5-(Allyl-methyl-amino)-pentyloxy]- | Phenyl-sulfamoylchloride |

| Example | Compound | MS MH+ | Amine | Sulfamoyl-chloride |
|---|---|---|---|---|
| | acid phenyl amide | | cyclohexyl)-methyl-amine | |
| 10.25 | trans-{4-[5-(Allyl-methyl-amino)-pentyloxy]-cyclohexyl}-methyl-sulfamic acid p-chlorophenyl amide | 456 (1 Cl) M-H⁻ | trans-(4-[5-(Allyl-methyl-amino)-pentyloxy]-cyclohexyl)-methyl-amine | 4-Chloro-phenyl-sulfamoylchloride |
| 10.26 | trans-{4-[5-(Allyl-methyl-amino)-pentyloxy]-cyclohexyl}-methyl-sulfamic acid p-bromophenyl amide | 500 (1 Br) M-H⁻ | trans-(4-[5-(Allyl-methyl-amino)-pentyloxy}-cyclohexyl)-methyl-amine | 4-Bromo-phenyl-sulfamoylchloride |
| 10.27 | trans-{4-[5-(Allyl-methyl-amino)-pentyloxy]-cyclohexyl}-methyl-sulfamic acid p-methylphenyl amide | 436 M-H⁻ | trans-(4-[5-(Allyl-methyl-amino)-pentyloxy]-cyclohexyl)-methyl-amine | 4-Methyl-phenyl-sulfamoylchloride |
| 10.28 | trans-{4-[5-(Allyl-methyl-amino)-pentyloxy]-cyclohexyl}-methyl-sulfamic acid p-trifluoromethylphenyl amide | 490 M-H⁻ | trans-(4-[5-(Allyl-methyl-amino)-pentyloxy]-cyclohexyl)-methyl-amine | 4-Trifluoro-methyl-phenyl-sulfamoylchloride |
| 10.29 | trans-{4-[5-(Allyl-methyl-amino)-pentyloxy]-cyclohexyl}-methyl-sulfamic acid p-cyanophenyl amide | 447 M-H⁻ | trans-(4-[5-(Allyl-methyl-amino)-pentyloxy]-cyclohexyl)-methyl-amine | 4-Cyano-phenyl-sulfamoylchloride |
| 10.30 | trans-{4-[5-(Allyl-methyl-amino)-pentyloxy]-cyclohexyl}-methyl-sulfamic acid p-methoxyphenyl amide | 452 M-H⁻ | trans-(4-[5-(Allyl-methyl-amino)-pentyloxy]-cyclohexyl)-methyl-amine | 4-Methoxy-phenyl-sulfamoylchloride |
| 10.31 | trans-{4-[5-(Allyl-methyl-amino)-pentyloxy]-cyclohexyl}-methyl-sulfamic acid 3,4-difluorophenyl amide | 458 M-H⁻ | trans-(4-[5-(Allyl-methyl-amino)-pentyloxy]-cyclohexyl)-methyl-amine | 3,4-Difluoro-phenyl-sulfamoylchloride |
| 10.32 | trans-{4-[5-(Allyl-methyl-amino)-pentyloxy]-cyclohexyl}-methyl-sulfamic acid 3-fluorophenyl amide | 440 M-H⁻ | trans-(4-[5-(Allyl-methyl-amino)-pentyloxy]-cyclohexyl)-methyl-amine | 3-Fluoro-phenyl-sulfamoylchloride |
| 10.33 | trans-{4-[5-(Allyl-methyl-amino)-pentyloxy]-cyclohexyl}-methyl-sulfamic acid 2,4-difluorophenyl amide | 458 M-H⁻ | trans-(4-[5-(Allyl-methyl-amino)-pentyloxy]-cyclohexyl)-methyl-amine | 2,4-Difluoro-phenyl-sulfamoylchloride |
| 10.34 | trans-{4-[5-(Allyl-methyl-amino)-pentyloxy]-cyclohexyl}-methyl-sulfamic acid 2,5-difluorophenyl amide | 458 M-H⁻ | trans-(4-[5-(Allyl-methyl-amino)-pentyloxy]-cyclohexyl)-methyl-amine | 2,5-Difluoro-phenyl-sulfamoylchloride |
| 10.35 | trans-{4-[3-(Allyl-methyl-amino)-propoxy]-cyclohexyl}-methyl-sulfamic acid phenyl amide | 396 | trans-{4-[3-(Allyl-methyl-amino)-propoxy]-cyclohexyl}-methyl-amine | Phenyl-sulfamoylchloride |
| 10.36 | trans-{4-[3-(Allyl-methyl-amino)-propoxy]-cyclohexyl}-methyl-sulfamic acid 3,4-difluorophenyl amide | 432 | trans-{4-[3-(Allyl-methyl-amino)-propoxy]-cyclohexyl}-methyl-amine | 3,4-Difluoro-phenyl-sulfamoylchloride |
| 10.37 | trans-{4-[3-(Allyl-methyl-amino)-propoxy]-cyclohexyl}-methyl-sulfamic acid 4-chlorophenyl amide | 430 (1 Cl) | trans-{4-[3-(Allyl-methyl-amino)-propoxy]-cyclohexyl}-methyl-amine | 4-Chloro-phenyl-sulfamoylchloride |
| 10.38 | trans-{4-[3-(Allyl-methyl-amino)-propoxy]-cyclohexyl}-methyl-sulfamic acid benzyl amide | 410 | trans-{4-[3-(Allyl-methyl-amino)-propoxy]-cyclohexyl}-methyl-amine | Benzyl-sulfamoylchloride |
| 10.39 | trans-{4-[4-(Allyl-methyl-amino)-butoxy]-cyclohexyl}-methyl-sulfamic acid phenyl amide | 410 | trans-{4-[3-(Allyl-methyl-amino)-propoxy]-cyclohexyl}-methyl-amine | Phenyl-sulfamoylchloride |
| 10.40 | trans-{4-[4-(Allyl-methyl-amino)-butoxy]-cyclohexyl}-methyl-sulfamic acid 3-fluoro phenyl amide | 428 | trans-{4-[3-(Allyl-methyl-amino)-propoxy]-cyclohexyl}-methyl-amine | 3-Fluoro-phenyl-sulfamoylchloride |

-continued

| Example | Compound | MS MH+ | Amine | Sulfamoyl-chloride |
|---|---|---|---|---|
| 10.41 | trans-{4-[4-(Allyl-methyl-amino)-butoxy]-cyclohexyl}-methyl-sulfamic acid 3,4-difluoro phenyl amide | 446 | trans-{4-[3-(Allyl-methyl-amino)-propoxy]-cyclohexyl}-methyl-amine | 3,4-Difluoro-phenyl-sulfamoylchloride |
| 10.42 | trans-{4-[4-(Allyl-methyl-amino)-butoxy]-cyclohexyl}-methyl-sulfamic acid 4-chloro phenyl amide | 444 (1 Cl) | trans-{4-[3-(Allyl-methyl-amino)-propoxy]-cyclohexyl}-methyl-amine | 4-Chloro-phenyl-sulfamoylchloride |
| 10.43 | trans-{4-[4-(Allyl-methyl-amino)-butoxy]-cyclohexyl}-methyl-sulfamic acid benzyl amide | 424 | trans-{4-[3-(Allyl-methyl-amino)-propoxy]-cyclohexyl}-methyl-amine | Benzyl-sulfamoylchloride |
| 10.44 | trans-({4-[4-(Allyl-methyl-amino)-butoxy]-cyclohexyl}-methyl-sulfamoylamino)-acetic acid ethyl ester | 420 | trans-{4-[3-(Allyl-methyl-amino)-propoxy]-cyclohexyl}-methyl-amine | Chloro-sulfonylamino-acetic acid ethyl ester |
| 10.45 | trans-{4-[7-(Allyl-methyl-amino)-heptyloxy]-cyclohexyl}-methyl-sulfamic acid phenyl amide | 452 | trans-(4-[7-(Allyl-methyl-amino)-heptyloxy]-cyclohexyl)-methyl-amine | Phenyl-sulfamoylchloride |
| 10.46 | trans-{4-[7-(Allyl-methyl-amino)-heptyloxy]-cyclohexyl}-methyl-sulfamic acid 3-fluoro-phenyl amide | 470 | trans-(4-[7-(Allyl-methyl-amino)-heptyloxy]-cyclohexyl)-methyl-amine | 3-Fluoro-phenyl-sulfamoylchloride |
| 10.47 | trans-{4-[7-(Allyl-methyl-amino)-heptyloxy]-cyclohexyl}-methyl-sulfamic acid 3,4-difluoro-phenyl amide | 488 | trans-(4-[7-(Allyl-methyl-amino)-heptyloxy]-cyclohexyl)-methyl-amine | 3,4-Difluoro-phenyl-sulfamoylchloride |
| 10.48 | trans-{4-[7-(Allyl-methyl-amino)-heptyloxy]-cyclohexyl}-methyl-sulfamic acid 4-chloro-phenyl amide | 486 (1 Cl) | trans-(4-[7-(Allyl-methyl-amino)-heptyloxy]-cyclohexyl)-methyl-amine | 4-Chloro-phenyl-sulfamoylchloride |
| 10.49 | trans-{4-[7-(Allyl-methyl-amino)-heptyloxy]-cyclohexyl}-methyl-sulfamic acid furan-2-ylmethyl amide | 456 | trans-(4-[7-(Allyl-methyl-amino)-heptyloxy]-cyclohexyl)-methyl-amine | Furan-2-yl-methyl-sulfamoylchloride |
| 10.50 | trans-{4-[7-(Allyl-methyl-amino)-heptyloxy]-cyclohexyl}-methyl-sulfamic acid benzyl amide | 466 | trans-(4-[7-(Allyl-methyl-amino)-heptyloxy]-cyclohexyl)-methyl-amine | Benzylsulfamoyl-chloride |
| 10.51 | trans-({4-[7-(Allyl-methyl-amino)-heptyloxy]-cyclohexyl}-methyl-sulfamoyloxy)-acetic acid ethyl amide | 462 | trans-(4-[7-(Allyl-methyl-amino)-heptyloxy]-cyclohexyl)-methyl-amine | Chlorosulfonyl-amino-acetic acid ethyl ester |

Example 11

Example 11.1

4.01 g (31 mmol) of trans-4-methylamino-cyclohexanol (twice suspended in toluene and evaporated under reduced pressure to remove water) were suspended in 60 ml hexamethyldisilazane and refluxed for 2.5 h. The solution was evaporated under reduced pressure, dissolved in 80 ml $CH_2Cl_2$ and added to a cooled solution (0° C.) of 2.06 ml (17.05 mmol) trichloromethylchloroformate (diphosgene) and 4.40 ml (34.10 mmol) quinoline. The reaction was stirred for 3 h at 0° C. and evaporated. The residue and 8.47 g (65.1 mmol) 3,4-difluorophenol were dissolved in 220 ml THF, treated at 0° C. in small portions with 3.25 g (74.4 mmol) of NaH (ca 55% in oil) and 0.26 g (1.6 mmol) of KI. The reaction was stirred at room temperature over night, cooled (0° C.) and after the addition of 0.68 g (15.5 mmol) of NaH (ca 55% in oil) stirred at RT for 24 h. After the addition of 60 ml water, the pH was adjusted to pH 2 (1 N HCl) and the reaction mixture was stirred for 1 h. The reaction was partitioned between aqueous 1 N NaOH/$Et_2O$ (3×300 ml), the organic phases were dried over $Na_2SO_4$ and evaporated. The residue was dissolved in 200 ml THF/dioxane (1:1). 34 ml 1 N NaOH were added at 0° C. and the mixture was stirred for 3 h. The reaction was partitioned between water/$Et_2O$ (3×300), the organic phase was dried over $Na_2SO_4$ and evaporated to yield 11.6 g crude trans-(4-Hydroxy-cyclohexyl)-methyl-carbamic acid 3,4-difluoro-phenyl ester.

Example 11.2

A solution of 11.6 g (containing 31 mmol) of crude trans-(4-Hydroxy-cyclohexyl)-methyl-carbamic acid 3,4-difluoro-phenyl ester in 110 ml of 1,4-dibromobutane was treated with 3.16 g (9.3 mmol) tetrabutylammonium hydrogen sulfate and 200 ml of aqueous 50% NaOH and stirred for 2.5 days at RT. The reaction was extracted ($CH_2Cl_2$ 2×). The organic phase was dried over $Na_2SO_4$, evaporated and purified by flash silica gel column (first with hexane to remove the dibromobutane and then hexane/EtOAc 1:1) to yield 4.06 g (31%) of trans-[4-(4-bromo-butoxy)-cyclohexyl]-methyl-carbamic acid 3,4-difluoro-phenyl ester, MS: 420 (M, 1Br).

Example 11.3

In analogy to example 11.1 and 11.2, reaction of trans-4-Methylamino-cyclohexanol with alpha, alpha, alpha-trifluoro-p-cresol followed by reaction with 1,4-dibromobutane yielded trans-[4-(4-Bromo-butoxy)-cyclohexyl]-methyl-carbamic acid 4-trifluoromethyl-phenyl ester, MS: 452 ($MH^+$, 1Br).

Example 11.4

To a solution of 16.1 g (124.7 mmol) trans-4-methylamino-cyclohexanol in 40 ml $CH_2Cl_2$, 18.3 ml (130.9 mmol, 1.05 eq) 4-chlorophenylchloroformate and 22.4 ml (130.9 mmol, 1.05 eq) Huenigs base were added at 0° C. The solution was stirred at RT over night, diluted, and washed with 1M HCl, sat. aqueous $NaHCO_3$ solution. The organic phase was dried over $MgSO_4$. Column chromatography on silica gel with EtOAc:hexane 1:1 yielded 32.2 g (91%) trans-(4-Hydroxy-cyclohexyl)-methyl-carbamic acid 4-chloro-phenyl ester as white solid, MS: 283 (M, 1Cl).

Example 11.5

To 1.46 g (5.1 mmol) trans-(4-Hydroxy-cyclohexyl)-methyl-carbamic acid 4-chloro-phenyl ester suspended in 30 ml (190.4 mmol, 37 eq) 1,6-Dibomhexane, 0.53 g (1.5 mmol, 0.3 eq) tetrabutylammoniumhydrogensulfate and 30 ml 50% aqueous NaOH were added. The mixture was stirred at 50° C. for 1 day, $CH_2Cl_2$ was added and the layers were separated. The inorganic layer was extracted with $CH_2Cl_2$, the combined organic layers were washed with brine and dried over $MgSO_4$. The excess of dibromide was removed in vacuo and the residue purified by column chromatography on silica gel with hexane:EtOAc 4:1 as eluent yielding 2.04 g (89%) trans-[4-(6-Bromo-hexyloxy)-cyclohexyl]-methyl-carbamic acid 4-chloro-phenyl ester as light yellow oil, MS: 446 (M, 1Br, 1Cl).

Example 11.6

In analogy to example 11.5, trans-(4-Hydroxy-cyclohexyl)-methyl-carbamic acid 4-chloro-phenyl ester and 1,4-dibrombutane were reacted to yield trans-[4-(4-Bromo-butoxy)-cyclohexyl]-methyl-carbamic acid 4-chloro-phenyl ester as yellowish oil, MS: 418 (M, 1Br, 1Cl).

Example 11.7

In analogy to example 11.5, trans-(4-Hydroxy-cyclohexyl)-methyl-carbamic acid 4-chloro-phenyl ester and 1,5-dibromopentane were reacted to yield trans-[4-(5-Bromo-pentyloxy)-cyclohexyl]-methyl-carbamic acid 4-chloro-phenyl ester as yellow oil, MS: 433 ($MH^+$, 1Br, 1Cl).

Example 11.8

At 0° C., to a solution of 1.26 ml (14.1 mmol) 3-bromo-1-propanol and 3.5 ml (15.3 mmol) 2,6-di-tert-butylpyridine in 7 ml $CH_2Cl_2$, a solution of 2.49 ml (14.8 mmol) trifluoromethansulfonic anhydride in 3.6 ml $CH_2Cl_2$ was added. After 2.5 h stirring at 0° C., the solution was evaporated, dissolved in 7 ml nitromethane and treated with a solution of 2.0 g (7 mmol) trans-(4-Hydroxy-cyclohexyl)-methyl-carbamic acid 4-chloro-phenyl ester and 3.23 ml (14.1 mmol) 2,6-di-tert-butylpyridine in 27 ml nitromethane. The reaction mixture was heated to 60° C. for 3.5 h and then diluted with EtOAc, washed with 1M HCl, sat. aqueous $NaHCO_3$, and water, dried over $MgSO_4$ and evaporated. Purification by flash-chromatography on silica gel with hexane/EtOAc 9:1 yielded trans-[4-(3-Bromo-propoxy)-cyclohexyl]-methyl-carbamic acid 4-chloro-phenyl ester as yellow oil, MS: 405 ($MH^+$, 1Br, 1Cl).

Example 11.9

To 3 g (23.2 mmol) trans-4-Methylamino-cyclohexanol in 120 ml $CH_2Cl_2$ were added 4.2 ml (24.4 mmol, 1.05 eq) N,N-diisopropylethylamine followed by 5.96 g (24.4 mmol, 1.05 eq) 4-(trifluoromethyl)-benzenesulfonyl chloride in 50 ml $CH_2Cl_2$. The mixture was stirred at RT over night and the organic phase extracted with 1M $KHSO_4$, followed by 5% $NaHCO_3$ and brine. The combined organic phases were washed with brine, dried over $Na_2SO_4$ and evaporated. Column chromatography on silica gel with hexane:EtOAc 1:1 yielded 6.0 g (77%) trans-N-(4-Hydroxy-cyclohexyl)-N-methyl-4-trifluoromethyl-benzenesulfonamide as off-white solid, MS: 338 ($MH^+$).

Example 11.10

In analogy to example 11.9D. trans-4-Methylamino-cyclohexanol and 4-bromobenzenesulfonylchloride were reacted to yield trans-4-Bromo-N-(4-hydroxy-cyclohexyl)-N-methyl-benzenesulfonamide as off-white solid, MS: 348 ($MH^+$, 1Br).

Example 11.11

6 g (17.8 mmol) trans-N-(4-Hydroxy-cyclohexyl)-N-methyl-4-trifluoromethyl-benzenesulfonamide were suspended in 100 ml (658 mmol, 37 eq) 1,6-dibromohexane and 1.8 g (5.3 mmol, 0.3 eq) tetra-butylammonium hydrogensulfate and 100 ml 50% aqueous NaOH were added. The reaction mixture was stirred at 50° C. for 2 days, $CH_2Cl_2$ was added and the layers were separated. The inorganic phase was extracted with $CH_2Cl_2$, the combined inorganic phases were washed with brine and dried over $Na_2SO_4$ and evaporated. The excess of the dibromide was removed in vacuo and the residue purified by column chromatography on silica gel with hexane: EtOAc 4:1 yielding 8.3 g (93%) trans-N-[4-(6-Bromo-hexyloxy)-cyclohexyl]-N-methyl-4-trifluoromethyl-benzenesulfonamide as yellow oil, MS: 500 ($MH^+$, 1Br).

Example 11.12

In analogy to example 11.11, trans-4-Bromo-N-(4-hydroxy-cyclohexyl)-N-methyl-benzenesulfonamide and 1,6-dibromohexane were reacted to yield trans-4-Bromo-N-[4-(6-bromo-hexyloxy)-cyclohexyl]-N-methyl-benzenesulfonamide as off-white solid, MS: 510 ($MH^+$, 1Br).

Example 11.13

In analogy to example 11.11, trans-N-(4-Hydroxy-cyclohexyl)-N-methyl-4-trifluoromethyl-benzenesulfonamide and 1,3-dibrompropane were converted to yield trans-N-[4-(3-Bromo-propoxy)-cyclohexyl]-N-methyl-4-trifluoromethyl-benzenesulfonamide as off-white semisolid, MS: 320 [M–$C_3H_6BrO$].

Example 11.14

In analogy to example 11.11, trans-N-(4-Hydroxy-cyclohexyl)-N-methyl-4-trifluoromethyl-benzenesulfonamide and 1,4-Dibrombutane were converted to yield trans-N-[4-(4-Bromo-butoxy)-cyclohexyl]-N-methyl-4-trifluoromethyl-benzenesulfonamide as light yellow semisolid, MS: 320 [M–$C_4H_8BrO$].

Example 11.15

In analogy to example 11.5, trans-(4-Hydroxy-cyclohexyl)-methyl-carbamic acid tert-butyl ester and 1,4-dibrombutane were reacted to yield trans-[4-(4-Bromo-butoxy)-cyclohexyl]-methyl-carbamic acid tert-butyl ester as yellowish oil, MS: 364 ($MH^+$, 1Br).

Example 11.16

5.7 g (15.65 mmol) of trans-[4-(4-Bromo-butoxy)-cyclohexyl]-methyl-carbamic acid tert-butyl ester was treated at RT with 20 ml 4N HCl in dioxane. After 18 h at this temperature, t-butyl methylether was added to give after filtration 4.34 g (92%) of trans-[4-(4-Bromo-butoxy)-cyclohexyl]-methyl-amine hydrochloride, MS: 264 ($MH^+$, 1Br).

Example 11.17

A solution of 1.5 mmol trichloromethyl-chloroformate (diphosgene) in 20 ml $CH_2Cl_2$ was treated at 0° C. with 3 mmol of 2,4-difluoro-phenol and 3 mmol quinoline and then stirred for 3 h at room temperature. The reaction was then cooled (0° C.) and a solution of 1 mmol [4-(4-Bromo-butoxy)-cyclohexyl]-methyl-amine (privously prepared from trans-[4-(4-Bromo-butoxy)-cyclohexyl]-methyl-amine hydrochloride by extraction with aqueous $NaHCO_3$/EtOAc) and 2.5 mmol pyridine in 3 ml $CH_2Cl_2$ was added. The reaction was stirred over night at room temperature, evaporated to give crude trans-[4-(4-Bromo-butoxy)-cyclohexyl]-methyl-carbamic acid 2,4-difluoro-phenyl ester which was used directly in the next step, see Example 12.39-12.44.

Example 11.18

In analogy to example 11.4, trans-[4-(4-Bromo-butoxy)-cyclohexyl]-methyl-amine hydrochloride and isobutyl chloroformate (with 2.1 eq N,N-diisopropylethylamine) were reacted to yield trans-[4-(4-Bromo-butoxy)-cyclohexyl]-methyl-carbamic acid isobutyl ester which was used directly in the next steps see Example 12.45-12.54.

Example 11.19

In analogy to example 11.9, trans-[4-(4-Bromo-butoxy)-cyclohexyl]-methyl-amine hydrochloride and 3,4-difluoro-benzenesulfonyl chloride (with 2.1 eq N,N-diisopropylethylamine) were reacted to yield trans-N-[4-(4-Bromo-butoxy)-cyclohexyl]-3,4-difluoro-N-methyl-benzenesulfonamide which was used directly in the next steps see Example 12.55-12.56 and 12.65 and 12.66.

Example 11.20

In analogy to example 11.9, trans-[4-(4-Bromo-butoxy)-cyclohexyl]-methyl-amine hydrochloride and 2,4-difluoro-benzenesulfonyl chloride (with 2.1 eq N,N-diisopropylethylamine) were reacted to yield trans-N-[4-(4-Bromo-butoxy)-cyclohexyl]-2,4-difluoro-N-methyl-benzenesulfonamide which was used directly in the next steps see Example 12.57-12.58 and 12.65 and 12.66.

Example 11.21

In analogy to example 11.9, trans-[4-(4-Bromo-butoxy)-cyclohexyl]-methyl-amine hydrochloride and 4-nitro-benzenesulfonyl chloride (with 2.1 eq N,N-diisopropylethylamine) were reacted to yield trans-N-[4-(4-Bromo-butoxy)-cyclohexyl]-N-methyl-4-nitro-benzenesulfonamide, MS: 451 ($MH^+$).

Example 11.22

In analogy to example 11.9, trans-4-amino-cyclohexanol and 4-(trifluoromethyl)-benzenesulfonyl chloride were converted to yield trans-N-(4-Hydroxy-cyclohexyl)-4-trifluoromethyl-benzenesulfonamide as white solid, 176.2° C., MS 322 (M-H).

Example 11.23

To 4 g (12.4 mmol) trans-N-(4-Hydroxy-cyclohexyl)-4-trifluoromethyl-benzenesulfonamide in 20 ml DMF were added 5.1 g (37.1 mmol, 3.3 eq) $K_2CO_3$ and 2.04 ml (27.2 mmol, 2.2 eq) ethyl bromide. The mixture was stirred at 35° C. over night, concentrated in vacuo and dissolved in $CH_2Cl_2$ and water. The phases were separated and the inorganic one was extracted $CH_2Cl_2$, the combined organic phases were washed with brine and dried over $Na_2SO_4$. The crude product was purified by column chromatography on silica gel with $CH_2Cl_2$/MeOH 95:5 to yield 1.6 g (38%) trans-N-Ethyl-N-(4-hydroxy-cyclohexyl)-4-trifluoromethyl-benzenesulfonamide as brown oil, MS: 351(M).

Example 11.23

In analogy to example 11.11, trans-N-Ethyl-N-(4-hydroxy-cyclohexyl)-4-trifluoromethyl-benzenesulfonamide and 1,4-Dibromobutane were converted to yield trans-N-[4-(4-Bromo-butoxy)-cyclohexyl]-N-ethyl-4-trifluoromethyl-benzenesulfonamide as colorless oil, MS 470 (M—$CH_3$, 1Br).

Example 12

A solution of 0.25 mmol (1 equivalent) bromide in 0.7 ml dry DMA was treated with a solution of 0.5 mmol (2 equivalents) secondary amine in 0.15 ml dry DMA at room temperature. After 16 h, 2 equivalents of secondary amine were added again to the solution. The reaction mixture was allowed to stand over night at room temperature, treated with 0.2 ml formic acid and purified by preparative HPLC [RP-18, acetonitrile (0.1% HCOOH)/water (0.1% HCOOH), 10% to 95% acetonitrile]. After evaporation, the tertiary amine was obtained as a mixture of amine hydrobromide and formate. The following compounds were prepared from the corresponding bromides and secondary amines:

| Example | Compound | MS MH+ | Bromide | Secondary amine |
|---|---|---|---|---|
| 12.1 | trans-(4-{4-[Ethyl-(2-hydroxy-ethyl)-amino]-butoxy}-cyclohexyl)-methyl-carbamic acid 4-trifluoromethyl-phenyl ester | 461 | trans-[4-(4-Bromo-butoxy)-cyclohexyl]-methyl-carbamic acid 4-trifluoromethyl-phenyl ester | 2-(Ethylamino)-ethanol |
| 12.2 | trans-[4-(4-Diethylamino-butoxy)-cyclohexyl]-methyl-carbamic acid 4-trifluoromethyl-phenyl ester | 445 | trans-[4-(4-Bromo-butoxy)-cyclohexyl]-methyl-carbamic acid 4-trifluoromethyl-phenyl ester | Diethylamine |
| 12.3 | trans-[4-(4-Dimethylamino-butoxy)-cyclohexyl]-methyl-carbamic acid 4-trifluoromethyl-phenyl ester | 417 | trans-[4-(4-Bromo-butoxy)-cyclohexyl]-methyl-carbamic acid 4-trifluoromethyl-phenyl ester | Dimethylamin |
| 12.4 | trans-(4-{4-[Bis-(2-hydroxy-ethyl)-amino]-butoxy}-cyclohexyl)-methyl-carbamic acid 4-trifluoromethyl-phenyl ester | 477 | trans-[4-(4-Bromo-butoxy)-cyclohexyl]-methyl-carbamic acid 4-trifluoromethyl-phenyl ester | Diethanolamine |
| 12.5 | trans-Methyl-{4-[4-(methyl-propyl-amino)-butoxy]-cyclohexyl}-carbamic acid 4-trifluoromethyl-phenyl ester | 445 | trans-[4-(4-Bromo-butoxy)-cyclohexyl]-methyl-carbamic acid 4-trifluoromethyl-phenyl ester | N-Methylpropyl-amine |
| 12.6 | {4-[Trans-4-(Allyl-methyl-amino)-butoxy]-cyclohexyl}-methyl-carbamic acid 3,4-difluoro-phenyl ester | 411 | trans-[4-(4-Bromo-butoxy)-cyclohexyl]-methyl-carbamic acid 3,4-difluoro-phenyl ester; | Allylmethylamine |
| 12.7 | [trans-4-(4-Dimethylamino-butoxy)-cyclohexyl]-methyl-carbamic acid 3,4-difluoro-phenyl ester | 385 | trans-[4-(4-Bromo-butoxy)-cyclohexyl]-methyl-carbamic acid 3,4-difluoro-phenyl ester | Dimethylamine 33% in EtOH 5.6 M |
| 12.8 | (trans-4-{4-[Ethyl-(2-hydroxy-ethyl)-amino]-butoxy}-cyclohexyl)-methyl-carbamic acid 3,4-difluoro-phenyl ester | 429 | trans-[4-(4-Bromo-butoxy)-cyclohexyl]-methyl-carbamic acid 3,4-difluoro-phenyl ester | Ethyl-(2-hydroxy-ethyl)-amine |
| 12.9 | [trans-4-(4-Diethylamino-butoxy)-cyclohexyl]-methyl-carbamic acid 3,4-difluoro-phenyl ester | 413 | trans-[4-(4-Bromo-butoxy)-cyclohexyl]-methyl-carbamic acid 3,4-difluoro-phenyl ester | Diethylamine |
| 12.10 | Methyl-[trans-4-(4-piperidin-1-yl-butoxy)-cyclohexyl]-carbamic acid 3,4-difluoro-phenyl ester | 425 | trans-[4-(4-Bromo-butoxy)-cyclohexyl]-methyl-carbamic acid 3,4-difluoro-phenyl ester | Piperidine |
| 12.11 | [trans-4-(4-Azetidin-1-yl-butoxy)-cyclohexyl]-methyl-carbamic acid 3,4-difluoro-phenyl ester | 397 | trans-[4-(4-Bromo-butoxy)-cyclohexyl]-methyl-carbamic acid 3,4-difluoro-phenyl ester | Azetidine |
| 12.12 | Methyl-[trans-4-(4-morpholin-4-yl-butoxy)-cyclohexyl]-carbamic acid 3,4-difluoro-phenyl ester | 427 | trans-[4-(4-Bromo-butoxy)-cyclohexyl]-methyl-carbamic acid 3,4-difluoro-phenyl ester | Morpholine |
| 12.13 | Methyl-[trans-4-(4-pyrrolidin-1-yl-butoxy)-cyclohexyl]-carbamic acid 3,4-difluoro-phenyl ester | 411 | trans-[4-(4-Bromo-butoxy)-cyclohexyl]-methyl-carbamic acid 3,4-difluoro-phenyl ester | Pyrrolidine |
| 12.14 | (4-{trans-4-[Ethyl-(2-methoxy-ethyl)-amino]-butoxy}-cyclohexyl)-methyl-carbamic acid 3,4-difluoro-phenyl ester | 443 | trans-[4-(4-Bromo-butoxy)-cyclohexyl]-methyl-carbamic acid 3,4-difluoro-phenyl ester | Ethyl-(2-methoxy-ethyl)-amine |
| 12.15 | trans-Methyl-{4-[4-(methyl-propyl-amino)-butoxy]-cyclohexyl}-carbamic acid 3,4-difluoro-phenyl ester | 413 | trans-[4-(4-Bromo-butoxy)-cyclohexyl]-methyl-carbamic acid 3,4-difluoro-phenyl ester | N-Methylpropyl-amine |

The following compounds were further prepared from the corresponding bromides and secondary amines:

| Example | Compound | MS MH+ | Bromide | Secondary amine |
|---|---|---|---|---|
| 12.16 | trans-N-(4-{3-[Ethyl-(2-methoxy-ethyl)-amino]-propoxy}-cyclohexyl)-N-methyl-4-trifluoromethyl-benzenesulfonamide | 481 | trans-N-[4-(3-Bromo-propoxy)-cyclohexyl]-N-methyl-4-trifluoromethyl-benzenesulfonamide | N-(2-methoxy-ethyl)-ethylamine |
| 12.17 | trans-N-{4-[3-(3,6-Dihydro-2H-pyridin-1-yl)-propoxy]-cyclohexyl}-N-methyl-4-trifluoromethyl-benzenesulfonamide | 461 | trans-N-[4-(3-Bromo-propoxy)-cyclohexyl]-N-methyl-4-trifluoromethyl-benzenesulfonamide | 1,2,3,6-Tetra-hydro-pyridine |
| 12.18 | trans-N-Methyl-N-{4-[3-(methyl-propyl-amino)-propoxy]-cyclohexyl}-4-trifluoromethyl-benzenesulfonamide | 451 | trans-N-[4-(3-Bromo-propoxy)-cyclohexyl]-N-methyl-4-trifluoromethyl-benzenesulfonamide | N-Methylpropyl-amine |
| 12.19 | trans-N-(4-{4-[Ethyl-(2-hydroxy-ethyl)-amino]-butoxy}-cyclohexyl)-N-methyl-4-trifluoromethyl-benzenesulfonamide | 481 | trans-N-[4-(4-Bromo-butoxy)-cyclohexyl]-N-methyl-4-trifluoromethyl-benzenesulfonamide | 2-(Ethylamino)-ethanol |
| 12.20 | trans-N-[4-(4-Diethylamino-butoxy)-cyclohexyl]-N-methyl-4-trifluoromethyl-benzenesulfonamide | 465 | trans-N-[4-(4-Bromo-butoxy)-cyclohexyl]-N methyl-4-trifluoromethyl-benzenesulfonamide | N-Diethylamine |
| 12.21 | trans-N-[4-(4-Dimethylamino-butoxy)-cyclohexyl]-N-methyl-4-trifluoromethyl-benzenesulfonamide | 437 | trans-N-[4-(4-Bromo-butoxy)-cyclohexyl]-N-methyl-4-trifluoromethyl-benzenesulfonamide | Dimethylamine 33% in EtOH 5.6 M |
| 12.22 | trans-N-(4-{4-[(2-Methoxy-ethyl)-methyl-amino]-butoxy}-cyclohexyl)-N-methyl-4-trifluoromethyl-benzenesulfonamide | 481 | trans-N-[4-(4-Bromo-butoxy)-cyclohexyl]-N-methyl-4-trifluoromethyl-benzenesulfonamide | N-(2-Methoxy-ethyl)-methyl-amine |
| 12.23 | trans-N-(4-{4-[(2-Hydroxy-ethyl)-methyl-amino]-butoxy}-cyclohexyl)-N-methyl-4-trifluoromethyl-benzenesulfonamide | 467 | trans-N-[4-(4-Bromo-butoxy)-cyclohexyl]-N-methyl-4-trifluoromethyl-benzenesulfonamide | 2-(Methylamino)-ethanol |
| 12.24 | trans-N-(4-{4-[Bis-(2-hydroxy-ethyl)-amino]-butoxy}-cyclohexyl)-N-methyl-4-trifluoromethyl-benzenesulfonamide | 497 | trans-N-[4-(4-Bromo-butoxy)-cyclohexyl]-N-methyl-4-trifluoromethyl-benzenesulfonamide | Diethanolamine |
| 12.25 | trans-N-{4-[4-(Cyclopropylmethyl-methyl-amino)-butoxy]-cyclohexyl}-N-methyl-4-trifluoromethyl-benzenesulfonamide | 477 | trans-N-[4-(4-Bromo-butoxy)-cyclohexyl]-N-methyl-4-trifluoromethyl-benzenesulfonamide | Cyclopropyl-methyl-methyl-amine |
| 12.26 | trans-N-Methyl-N-[4-(4-morpholin-4-yl-butoxy)-cyclohexyl]-4-trifluoromethyl-benzenesulfonamide | 479 | trans-N-[4-(4-Bromo-butoxy)-cyclohexyl]-N-methyl-4-trifluoromethyl-benzenesulfonamide | Morpholine |
| 12.27 | trans-N-{4-[4-(3,6-Dihydro-2H-pyridin-1-yl)-butoxy]-cyclohexyl}-N-methyl-4-trifluoromethyl-benzenesulfonamide | 475 | trans-N-[4-(4-Bromo-butoxy)-cyclohexyl]-N-methyl-4-trifluoromethyl-benzenesulfonamide | 1,2,3,6-Tetra-hydro-pyridine |
| 12.28 | trans-N-Methyl-N-{4-[4-(methyl-propyl-amino)-butoxy]-cyclohexyl}-4-trifluoromethyl-benzenesulfonamide | 465 | trans-N-[4-(4-Bromo-butoxy)-cyclohexyl]-N-methyl-4-trifluoromethyl-benzenesulfonamide | N-Methylpropyl-amine |
| 12.29 | trans-N-(4-{4-[Ethyl-(2-methoxy-ethyl)-amino]-butoxy}-cyclohexyl)-N-methyl-4-trifluoromethyl-benzenesulfonamide | 495 | trans-N-[4-(4-Bromo-butoxy)-cyclohexyl]-N-methyl-4-trifluoromethyl-benzenesulfonamide | N-(2-methoxy-ethyl)-ethylamine |
| 12.30 | trans-N-(4-{3-[(2-Methoxy-ethyl)-methyl-amino]- | 467 | trans-N-[4-(3-Bromo-propoxy)-cyclohexyl]- | N-(2-Methoxy-ethyl)-methyl- |

-continued

| Example | Compound | MS MH+ | Bromide | Secondary amine |
|---|---|---|---|---|
| | propoxy}-cyclohexyl)-N-methyl-4-trifluoromethyl-benzenesulfonamide | | N-methyl-4-trifluoromethyl-benzenesulfonamide | amine |
| 12.31 | trans-N-{4-[3-(Allyl-methyl-amino)-propoxy]-cyclohexyl}N-methyl4-trifluoromethyl-benzenesulfonamide | 449 | trans-N-[4-(3-Bromo-propoxy)-cyclohexyl]-N-methyl-4-trifluoromethyl-benzenesulfonamide | N-Methylallyl-amine |
| 12.32 | trans-N-(4-{3-[Ethyl-(2-hydroxy-ethyl)-amino]-propoxy}-cyclohexyl)N-methyl-4-trifluoromethyl-benzenesulfonamide | 467 | trans-N-[4-(3-Bromo-propoxy)-cyclohexyl]-N-methyl-4-trifluoromethyl-benzenesulfonamide | 2-(Ethylamino)-ethanol |
| 12.33 | trans-N-[4-(3-Diethylamino-propoxy)-cyclohexyl]-N-methyl-4-trifluoromethyl-benzenesulfonamide | 451 | trans-N-[4-(3-Bromo-propoxy)-cyclohexyl]-N-methyl-4-trifluoromethyl-benzenesulfonamide | N-Diethylamine |
| 12.34 | trans-N-(4-{3-[(2-Hydroxy-ethyl)-methyl-amino]-propoxy}-cyclohexyl)-N-methyl-4-trifluoromethyl-benzenesulfonamide | 453 | trans-N-[4-(3-Bromo-propoxy)-cyclohexyl]-N-methyl-4-trifluoromethyl-benzenesulfonamide | 2-(Methylamino)-ethanol |
| 12.35 | trans-N-(4-{3-[Bis-(2-hydroxy-ethyl)-amino]-propoxy}-cyclohexyl)N-methyl-4-trifluoromethyl-benzenesulfonamide | 483 | trans-N-[4-(3-Bromo-propoxy)-cyclohexyl]-N-methyl-4-trifluoromethyl-benzenesulfonamide | Diethanol-amine |
| 12.36 | trans-N-{4-[3-(Cyclopropylmethyl-methyl-amino)-propoxy]-cyclohexyl}-N-methyl-4-trifluoromethyl-benzenesulfonamide | 463 | trans-N-[4-(3-Bromo-propoxy)-cyclohexyl]-N-methyl-4-trifluoromethyl-benzenesulfonamide | Cyclopropyl-methyl-methyl-amine |
| 12.37 | trans-N-Methyl-N-[4-(3-pyrrolidin-1-yl-propoxy)-cyclohexyl]-4-trifluoromethyl-benzenesulfonamide | 449 | trans-N-[4-(3-Bromo-propoxy)-cyclohexyl]-N-methyl-4-trifluoromethyl-benzenesulfonamide | Pyrrolidine |
| 12.38 | trans-N-Methyl-N-[4-(3-morpholin-4-yl-propoxy)-cyclohexyl]-4-trifluoromethyl-benzenesulfonamide | 465 | trans-N-[4-(3-Bromo-propoxy)-cyclohexyl]-N-methyl-4-trifluoromethyl-benzenesulfonamide | Morpholine |

The following compounds were further prepared from the corresponding bromides and secondary amines:

| Example | Compound | MS MH+ | Bromide | Secondary amine |
|---|---|---|---|---|
| 12.39 | trans-{4-[4-(Allyl-methyl-amino)-butoxy]-cyclohexyl}-methyl-carbamic acid 2,4-difluoro-phenyl ester | 411 | trans-[4-(4-Bromo-butoxy)-cyclohexyl]-methyl-carbamic acid 2,4-difluoro-phenyl ester | Allylmethylamine |
| 12.40 | trans-[4-(4-Dimethylamino-butoxy)-cyclohexyl]-methyl-carbamic acid 2,4-difluoro-phenyl ester | 385 | trans-[4-(4-Bromo-butoxy)-cyclohexyl]-methyl-carbamic acid 2,4-difluoro-phenyl ester | Dimethylamine 33% in EtOH 5.6 M |
| 12.41 | trans-(4-{4-[Ethyl-(2-hydroxy-ethyl)-amino]-butoxy}-cyclohexyl)-methyl-carbamic acid 2,4-difluoro-phenyl ester | 429 | trans-[4-(4-Bromo-butoxy)-cyclohexyl]-methyl-carbamic acid 2,4-difluoro-phenyl ester | Ethyl-(2-hydroxy-ethyl)-amine |
| 12.42 | trans-Methyl-[4-(4-morpholin-4-yl-butoxy)-cyclohexyl]-carbamic acid | 427 | trans-[4-(4-Bromo-butoxy)-cyclohexyl]-methyl-carbamic acid | Morpholine |

-continued

| Example | Compound | MS MH+ | Bromide | Secondary amine |
|---|---|---|---|---|
| | 2,4-difluoro-phenyl ester | | 2,4-difluoro-phenyl ester | |
| 12.43 | trans-(4-{Ethyl-(2-methoxy-ethyl)-amino]-butoxy}-cyclohexyl)-methyl-carbamic acid 2,4-difluoro-phenyl ester | 443 | trans-[4-(4-Bromo-butoxy)-cyclohexyl]-methyl-carbamic acid 2,4-difluoro-phenyl ester | Ethyl-(2-methoxy-ethyl)-amine |
| 12.44 | trans-Methyl-{4-[4-(methyl-propyl-amino)-butoxy]-cyclohexyl}-carbamic acid 2,4-difluoro-phenyl ester | 413 | trans-[4-(4-Bromo-butoxy)-cyclohexyl]-methyl-carbamic acid 2,4-difluoro-phenyl ester | N-Methylpropylamine |
| 12.45 | trans-[4-(4-Dimethylamino-butoxy)-cyclohexyl]-methyl-carbamic acid isobutyl ester | 329 | trans-[4-(4-Bromo-butoxy)-cyclohexyl]-methyl-carbamic acid isobutyl ester | Dimethylamine 33% in EtOH 5.6 M |
| 12.46 | trans-(4-{4-[Ethyl-(2-hydroxy-ethyl)-amino]-butoxy}-cyclohexyl)-methyl-carbamic acid isobutyl ester | 373 | trans-[4-(4-Bromo-butoxy)-cyclohexyl]-methyl-carbamic acid isobutyl ester | Ethyl-(2-hydroxy-ethyl)-amine |
| 12.47 | trans-[4-(4-Diethylamino-butoxy)-cyclohexyl]-methyl-carbamic acid isobutyl ester | 357 | trans-[4-(4-Bromo-butoxy)-cyclohexyl]-methyl-carbamic acid isobutyl ester | Diethylamine |
| 12.48 | trans-[4-(4-Azetidin-1-yl-butoxy)-cyclohexyl]-methyl-carbamic acid isobutyl ester | 341 | trans-[4-(4-Bromo-butoxy)-cyclohexyl]-methyl-carbamic acid isobutyl ester | Azetidine |
| 12.49 | trans-Methyl-[4-(4-morpholin-4-yl-butoxy)-cyclohexyl]-carbamic acid isobutyl ester | 371 | trans-[4-(4-Bromo-butoxy)-cyclohexyl]-methyl-carbamic acid isobutyl ester | Morpholine |
| 12.50 | trans-Methyl-[4-(4-pyrrolidin-1-yl-butoxy)-cyclohexyl]-carbamic acid isobutyl ester | 356 | trans-[4-(4-Bromo-butoxy)-cyclohexyl]-methyl-carbamic acid isobutyl ester | Pyrrolidine |
| 12.51 | trans-(4-{4-[Ethyl-(2-methoxy-ethyl)-amino]-butoxy}-cyclohexyl)-methyl-carbamic acid isobutyl ester | 387 | trans-[4-(4-Bromo-butoxy)-cyclohexyl]-methyl-carbamic acid isobutyl ester | Ethyl-(2-methoxy-ethyl)-amine |
| 12.52 | trans-Methyl-{4-[4-(methyl-propyl-amino)-butoxy]-cyclohexyl}-carbamic acid isobutyl ester | 357 | trans-[4-(4-Bromo-butoxy)-cyclohexyl]-methyl-carbamic acid isobutyl ester | N-Methylpropylamine |
| 12.53 | trans-(4-{4-[Bis-(2-hydroxy-ethyl)-amino]-butoxy}-cyclohexyl)-methyl-carbamic acid isobutyl ester | 389 | trans-[4-(4-Bromo-butoxy)-cyclohexyl]-methyl-carbamic acid isobutyl ester | 2-(Hydroxy-ethyl)-amino-ethanol |
| 12.54 | trans-{4-[4-(Cyclopropylmethyl-methyl-amino)-butoxy]-cyclohexyl}-methyl-carbamic acid isobutyl ester | 369 | trans-[4-(4-Bromo-butoxy)-cyclohexyl]-methyl-carbamic acid isobutyl ester | Cyclopropylmethyl-methyl-amine |
| 12.55 | trans-3,4-Difluoro-N-methyl-N-{4-[4-(methyl-propyl-amino)-butoxy]-cyclohexyl}-benzenesulfonamide | 433 | trans-N-[4-(4-Bromo-butoxy)-cyclohexyl]-3,4-difluoro-N-methyl-benzenesulfonamide | N-Methylpropylamine |
| 12.56 | trans-N-(4-{4-[Ethyl-(2-hydroxy-ethyl)-amino]-butoxy}-cyclohexyl)-3,4-difluoro-N-methyl-benzenesulfonamide | 449 | trans-N-[4-(4-Bromo-butoxy)-cyclohexyl]-3,4-difluoro-N-methyl-benzenesulfonamide | 2-(Hydroxy-ethyl)-amino-ethanol |
| 12.57 | trans-2,4-Difluoro-N-methyl-N-{4-[4-(methyl-propyl-amino)-butoxy]-cyclohexyl}-benzenesulfonamide | 433 | trans-N-[4-(4-Bromo-butoxy)-cyclohexyl]-2,4-difluoro-N-methyl-benzenesulfonamide | N-Methylpropylamine |

-continued

| Example | Compound | MS MH+ | Bromide | Secondary amine |
|---|---|---|---|---|
| 12.58 | trans-N-(4-{4-[Ethyl-(2-hydroxy-ethyl)-amino]-butoxy}-cyclohexyl)-2,4-difluoro-N-methyl-benzenesulfonamide | 449 | trans-N-[4-(4-Bromo-butoxy)-cyclohexyl]-2,4-difluoro-N-methyl-benzenesulfonamide | 2-(Hydroxy-ethyl)-amino-ethanol |
| 12.59 | trans-N-Methyl-4-nitro-N-[4-(4-piperidin-1-yl-butoxy)-cyclohexyl]-benzenesulfonamide | 454 | trans-N-[4-(4-Bromo-butoxy)-cyclohexyl]-N-methyl-4-nitro-benzenesulfonamide | Piperidine |
| 12.60 | trans-N-(4-{4-[Ethyl-(2-methoxy-ethyl)-amino]-butoxy}-cyclohexyl)-N-methyl-4-nitro-benzenesulfonamide | 472 | trans-N-[4-(4-Bromo-butoxy)-cyclohexyl]-N-methyl-4-nitro-benzenesulfonamide | Ethyl-(2-methoxy-ethyl)-amine |
| 12.61 | trans-N-[4-(4-Dimethylamino-butoxy)-cyclohexyl]-N-methyl-4-nitro-benzenesulfonamide | 414 | trans-N-[4-(4-Bromo-butoxy)-cyclohexyl]-N-methyl-4-nitro-benzenesulfonamide | Dimethylamine 33% in EtOH 5.6 M |
| 12.62 | trans-N-{4-[4-(Allyl-methyl-amino)-butoxy]-cyclohexyl}-N-methyl-4-nitro-benzenesulfonamide | 439 | trans-N-[4-(4-Bromo-butoxy)-cyclohexyl]-N-methyl-4-nitro-benzenesulfonamide | Allylmethylamine |
| 12.63 | trans-N-(4-{4-[Ethyl-(2-hydroxy-ethyl)-amino]-butoxy}-cyclohexyl)-N-methyl-4-nitro-benzenesulfonamide | 458 | trans-N-[4-(4-Bromo-butoxy)-cyclohexyl]-N-methyl-4-nitro-benzenesulfonamide | 2-(Hydroxy-ethyl)-amino-ethanol |
| 12.64 | trans-N-{4-[4-(4-Hydroxy-piperidin-1-yl)-butoxy]-cyclohexyl}-N-methyl-4-nitro-benzenesulfonamide | 469 (M) | trans-N-[4-(4-Bromo-butoxy)-cyclohexyl]-N-methyl-4-nitro-benzenesulfonamide | 4-Hydroxypiperidine |

The following compounds, in which 2 equivalents of the corresponding amine reacted with 1 equivalent of the corresponding bromide, were further prepared according to the procedure described above:

| Example | Compound | MS MH+ | Bromide | Secondary amine |
|---|---|---|---|---|
| 12.65 | trans-4-Dimethylamino-N-[4-(4-dimethylamino-butoxy)-cyclohexyl]-3-fluoro-N-methyl-benzenesulfonamide | 430 | trans-N-[4-(4-Bromo-butoxy)-cyclohexyl]-3,4-difluoro-N-methyl-benzenesulfonamide. | Dimethylamine 33% in EtOH 5.6 M |
| 12.66 | trans-4-Dimethylamino-N-[4-(4-dimethylamino-butoxy)-cyclohexyl]-2-fluoro-N-methyl-benzenesulfonamide | 430 | trans-N-[4-(4-Bromo-butoxy)-cyclohexyl]-2,4-difluoro-N-methyl-benzenesulfonamide | Dimethylamine 33% in EtOH 5.6 M |

Example 13

1 eq of the bromide is treated with 3 eq of amine in (4-10 ml/mmol bromide) DMA at RT until no starting material can be detected with TLC. The solution is concentrated and the residue is redissolved in $CH_2Cl_2$/5% aqueous $NaHCO_3$. The phases are separated, and the inorganic phase is extracted with $CH_2Cl_2$, the combined organic phases are washed with brine, dried over $Na_2SO_4$. The crude material is purified by flash chromatography. The following compounds were prepared from the corresponding bromides and amines:

| Example | Compound | MS MH+ | Bromide | Amine |
|---|---|---|---|---|
| 13.1 | trans-{4-[4-(Allyl-methyl-amino)-butoxy]-cyclohexyl}-methyl-carbamic acid 4-chloro-phenyl ester | 409 (1 Cl) | trans-[4-(4-Bromo-butoxy)-cyclohexyl]-methyl-carbamic acid 4-chloro-phenyl ester | Allylmethylamine |
| 13.2 | trans-{4-[5-(Allyl-methyl-amino)-pentyloxy]-cyclohexyl}-methyl-carbamic acid 4-chloro-phenyl ester | 424 (1 Cl) | trans-[4-(5-Bromo-pentyloxy)-cyclohexyl]-methyl-carbamic acid 4-chloro-phenyl ester | Allylmethylamine |
| 13.3 | trans-[4-(6-Dimethylamino-hexyloxy)-cyclohexyl]-methyl-carbamic acid 4-chloro-phenyl ester | 411 (1 Cl) | trans-[4-(6-Bromo-hexyloxy)-cyclohexyl]-methyl-carbamic acid 4-chloro-phenyl ester | Dimethylamine 33% in EtOH 5.6 M |
| 13.4 | trans-[4-(4-Dimethylamino-butoxy)-cyclohexyl]-methyl-carbamic acid 4-chloro-phenyl ester | 383 (1 Cl) | trans-[4-(4-Bromo-butoxy)-cyclohexyl]-methyl-carbamic acid 4-chloro-phenyl ester | Dimethylamine 33% in EtOH 5.6 M |
| 13.5 | trans-[4-(5-Dimethylamino-pentyloxy)-cyclohexyl]-methyl-carbamic acid 4-chloro-phenyl ester | 397 (1 Cl) | trans-[4-(5-Bromo-pentyloxy)-cyclohexyl]-methyl-carbamic acid 4-chloro-phenyl ester | Dimethylamine 33% in EtOH 5.6 M |
| 13.6 | trans-(4-{6-[Ethyl-(2-hydroxy-ethyl)-amino]-hexyloxy}-cyclohexyl)-methyl-carbamic acid 4-chloro-phenyl ester | 456 (1 Cl) | trans-[4-(6-Bromo-hexyloxy)-cyclohexyl]-methyl-carbamic acid 4-chloro-phenyl ester | 2-Ethylamino-ethanol |
| 13.7 | trans-(4-{4-[Ethyl-(2-hydroxy-ethyl)-amino]-butoxy}-cyclohexyl)-methyl-carbamic acid 4-chloro-phenyl ester | 427 (1 Cl) | trans-[4-(4-Bromo-butoxy)-cyclohexyl]-methyl-carbamic acid 4-chloro-phenyl ester | 2-Ethylamino-ethanol |
| 13.8 | trans-(4-{5-[Ethyl-(2-hydroxy-ethyl)-amino]-pentyloxy}-cyclohexyl)-methyl-carbamic acid 4-chloro-phenyl ester | 442 (1 Cl) | trans-[4-(5-Bromo-pentyloxy)-cyclohexyl]-methyl-carbamic acid 4-chloro-phenyl ester | 2-Ethylamino-ethanol |
| 13.9 | trans-(4-{6-[Ethyl-(2-methoxy-ethyl)-amino]-hexyloxy}-cyclohexyl)-methyl-carbamic acid 4-chloro-phenyl ester | 470 (1 Cl) | trans-[4-(6-Bromo-hexyloxy)-cyclohexyl]-methyl-carbamic acid 4-chloro-phenyl ester | N-(2-Methoxyethyl) ethylamine |
| 13.10 | trans-(4-{4-[Ethyl-(2-methoxy-ethyl)-amino]-butoxy}-cyclohexyl)-methyl-carbamic acid 4-chloro-phenyl ester | 442 (1 Cl) | trans-[4-(4-Bromo-butoxy)-cyclohexyl]-methyl-carbamic acid 4-chloro-phenyl ester | N-(2-Methoxyethyl) ethylamine |
| 13.11 | trans-{4-[3-(Allyl-methyl-amino)-propoxy]-cyclohexyl}-methyl-carbamic acid 4-chloro-phenyl ester | 395 (1 Cl) | trans-[4-(3-Bromo-propoxy)-cyclohexyl]-methyl-carbamic acid 4-chloro-phenyl ester | Allylmethylamine |
| 13.12 | trans-(4-{3-[Ethyl-(2-methoxy-ethyl)-amino]-propoxy}-cyclohexyl)-methyl-carbamic acid 4-chloro-phenyl ester | 427 (1 Cl) | trans-[4-(3-Bromo-propoxy)-cyclohexyl]-methyl-carbamic acid 4-chloro-phenyl ester | N-(2-Methoxyethyl) ethylamine |
| 13.13 | trans-(4-{5-[Ethyl-(2-methoxy-ethyl)-amino]-pentyloxy}-cyclohexyl)-methyl-carbamic acid 4-chloro-phenyl ester | 456 (1 Cl) | trans-[4-(5-Bromo-pentyloxy)-cyclohexyl]-methyl-carbamic acid 4-chloro-phenyl ester | N-(2-Methoxyethyl) ethylamine |
| 13.14 | trans-[4-(3-Dimethylamino-propoxy)-cyclohexyl]-methyl-carbamic acid 4-chloro-phenyl ester | 369 (1 Cl) | trans-[4-(3-Bromo-propoxy)-cyclohexyl]-methyl-carbamic acid 4-chloro-phenyl ester | Dimethylamine 33% in EtOH 5.6 M |
| 13.15 | trans-(4-{3-[Ethyl-(2-hydroxy-ethyl)-amino]-propoxy}-cyclohexyl)-methyl-carbamic acid 4-chloro-phenyl ester | 413 (1 Cl) | trans-[4-(3-Bromo-propoxy)-cyclohexyl]-methyl-carbamic acid 4-chloro-phenyl ester | 2-Ethylamino-ethanol |
| 13.16 | trans-Methyl-[4-(3-piperidin-1-yl-propoxy)-cyclohexyl]-carbamic acid 4-chloro-phenyl ester | 409 (1 Cl) | trans-[4-(3-Bromo-propoxy)-cyclohexyl]-methyl-carbamic acid 4-chloro-phenyl ester | Piperidine |

-continued

| Example | Compound | MS MH+ | Bromide | Amine |
|---|---|---|---|---|
| 13.17 | trans-Methyl-[4-(4-piperidin-1-yl-butoxy)-cyclohexyl]-carbamic acid 4-chloro-phenyl ester | 424 (1 Cl) | trans-[4-(4-Bromo-butoxy)-cyclohexyl]-methyl-carbamic acid 4-chloro-phenyl ester | Piperidine |
| 13.18 | trans-Methyl-[4-(6-piperidin-1-yl-hexyloxy)-cyclohexyl]-carbamic acid 4-chloro-phenyl ester | 452 (1 Cl) | trans-[4-(6-Bromo-hexyloxy)-cyclohexyl]-methyl-carbamic acid 4-chloro-phenyl ester | Piperidine |
| 13.19 | trans-Methyl-[4-(5-piperidin-1-yl-pentyloxy)-cyclohexyl]-carbamic acid 4-chloro-phenyl ester | 438 (1 Cl) | trans-[4-(5-Bromo-pentyloxy)-cyclohexyl]-methyl-carbamic acid 4-chloro-phenyl ester | Piperidine |
| 13.20 | trans-[4-(3-Diethylamino-propoxy)-cyclohexyl]-methyl-carbamic acid 4-chloro-phenyl ester | 397 (1 Cl) | trans-[4-(3-Bromo-propoxy)-cyclohexyl]-methyl-carbamic acid 4-chloro-phenyl ester | Diethylamine |
| 13.21 | trans-[4-(6-Diethylamino-hexyloxy)-cyclohexyl]-methyl-carbamic acid 4-chloro-phenyl ester | 440 (1 Cl) | trans-[4-(6-Bromo-hexyloxy)-cyclohexyl]-methyl-carbamic acid 4-chloro-phenyl ester | Diethylamine |
| 13.22 | trans-[4-(4-Diethylamino-butoxy)-cyclohexyl]-methyl-carbamic acid 4-chloro-phenyl ester | 411 (1 Cl) | trans-[4-(4-Bromo-butoxy)-cyclohexyl]-methyl-carbamic acid 4-chloro-phenyl ester | Diethylamine |
| 13.23 | trans-[4-(5-Diethylamino-pentyloxy)-cyclohexyl]-methyl-carbamic acid 4-chloro-phenyl ester | 426 (1 Cl) | trans-[4-(5-Bromo-pentyloxy)-cyclohexyl]-methyl-carbamic acid 4-chloro-phenyl ester | Diethylamine |
| 13.24 | trans-Methyl-[4-(3-pyrrolidin-1-yl-propoxy)-cyclohexyl]-carbamic acid 4-chloro-phenyl ester | 395 (1 Cl) | trans-[4-(3-Bromo-propoxy)-cyclohexyl]-methyl-carbamic acid 4-chloro-phenyl ester | Pyrrolidine |
| 13.25 | trans-Methyl-[4-(6-pyrrolidin-1-yl-hexyloxy)-cyclohexyl]-carbamic acid 4-chloro-phenyl ester | 436 (1 Cl) M-H− | trans-[4-(6-Bromo-hexyloxy)-cyclohexyl]-methyl-carbamic acid 4-chloro-phenyl ester | Pyrrolidine |
| 13.26 | trans-(4-{6-[(2-Hydroxy-ethyl)-methyl-amino]-hexyloxy}-cyclohexyl)-methyl-carbamic acid 4-chloro-phenyl ester | 442 (1 Cl) | trans-[4-(6-Bromo-hexyloxy)-cyclohexyl]-methyl-carbamic acid 4-chloro-phenyl ester | 2-(Methylamino)-ethanol |
| 13.27 | trans-(4-{4-[(2-Hydroxy-ethyl)-methyl-amino]-butoxy}-cyclohexyl)-methyl-carbamic acid 4-chloro-phenyl ester | 413 (1 Cl) | trans-[4-(4-Bromo-butoxy)-cyclohexyl]-methyl-carbamic acid 4-chloro-phenyl ester | 2-(Methylamino)-ethanol |
| 13.28 | trans-(4-{5-[(2-Hydroxy-ethyl)-methyl-amino]-pentyloxy}-cyclohexyl)-methyl-carbamic acid 4-chloro-phenyl ester | 427 (1 Cl) | trans-[4-(5-Bromo-pentyloxy)-cyclohexyl]-methyl-carbamic acid 4-chloro-phenyl ester | 2-(Methylamino)-ethanol |
| 13.29 | trans-Methyl-[4-(4-pyrrolidin-1-yl-butoxy)-cyclohexyl]-carbamic acid 4-chloro-phenyl ester | 409 (1 Cl) | trans-[4-(4-Bromo-butoxy)-cyclohexyl]-methyl-carbamic acid 4-chloro-phenyl ester | Pyrrolidine |
| 13.30 | trans-Methyl-[4-(5-pyrrolidin-1-yl-pentyloxy)-cyclohexyl]-carbamic acid 4-chloro-phenyl ester | 424 (1 Cl) | trans-[4-(5-Bromo-pentyloxy)-cyclohexyl]-methyl-carbamic acid 4-chloro-phenyl ester | Pyrrolidine |
| 13.31 | trans-(4-{3-[(2-Hydroxy-ethyl)-methyl-amino]-propoxy}-cyclohexyl)-methyl-carbamic acid 4-chloro-phenyl ester | 399 (1 Cl) | trans-[4-(3-Bromo-propoxy)-cyclohexyl]-methyl-carbamic acid 4-chloro-phenyl ester | 2-(Methylamino)-ethanol |

The following compounds were further prepared from the corresponding bromides and amines:

| Example | Compound | MS MH+ | Educt 1 | Educt 2 |
|---|---|---|---|---|
| 13.32 | trans-N-(4-[6-(Allyl-methyl-amino)-hexyloxy]-cyclohexyl)-4-bromo-N-methyl-benzenesulfonamide | 501 (1 Br) | trans-4-Bromo-N-[4-(6-bromo-hexyloxy)-cyclohexyl]-N-methyl-benzenesulfonamide | N-Allylmethyl-amine |
| 13.33 | trans-4-Bromo-N-[4-(6-dimethylamino-hexyloxy)-cyclohexyl]-N-methyl-benzenesulfonamide | 475 (1 Br) | trans-4-Bromo-N-[4-(6-bromo-hexyloxy)-cyclohexyl]-N-methyl-benzenesulfonamide | Dimethylamine 33% in EtOH 5.6 M |
| 13.34 | trans-4-Bromo-N-(4-{6-[(2-methoxy-ethyl)-methyl-amino]-hexyloxy}-cyclohexyl)-N-methyl-benzenesulfonamide | 519 (1 Br) | trans-4-Bromo-N-[4-(6-bromo-hexyloxy)-cyclohexyl]-N-methyl-benzenesulfonamide | N-(2-Methoxy-ethyl)methyl-amine |
| 13.35 | trans-N-(4-[6-(Allyl-methyl-amino)-hexyloxy]-cyclohexyl)-N-methyl-4-trifluoromethyl-benzenesulfonamide | 528 | trans-N-[4-(6-Bromo-hexyloxy)-cyclohexyl]-N-methyl-4-trifluoromethyl-benzenesulfonamide | N-Allylmethyl-amine |
| 13.36 | trans-N-[4-(6-Dimethylamino-hexyloxy)-cyclohexyl]-N-methyl-4-trifluoromethyl-benzenesulfonamide | 465 | trans-N-[4-(6-Bromo-hexyloxy)-cyclohexyl]-N-methyl-4-trifluoromethyl-benzenesulfonamide | Dimethylamine 33% in EtOH 5.6 M |
| 13.37 | trans-N-(4-{6-[(2-Methoxy-ethyl)-methyl-amino]-hexyloxy}-cyclohexyl)-N-methyl-4-trifluoromethyl-benzenesulfonamide | 509 | trans-N-[4-(6-Bromo-hexyloxy)-cyclohexyl]-N-methyl-4-trifluoromethyl-benzenesulfonamide | N-(2-Methoxy-ethyl)methyl-amine |
| 13.38 | trans-4-Bromo-N-[4-(6-diethylamino-hexyloxy)-cyclohexyl]-N-methyl-benzenesulfonamide | 503 (1 Br) | trans-4-Bromo-N-[4-(6-bromo-hexyloxy)-cyclohexyl]-N-methyl-benzenesulfonamide | Diethylamine |
| 13.39 | trans-4-Bromo-N-{4-[6-(isopropyl-methyl-amino)-hexyloxy]-cyclohexyl}-N-methyl-benzenesulfonamide | 503 (1 Br) | trans-4-Bromo-N-[4-(6-bromo-hexyloxy)-cyclohexyl]-N-methyl-benzenesulfonamide | Isopropylmethyl-amine |
| 13.40 | trans-4-Bromo-N-methyl-N-[4-(6-pyrrolidin-1-yl-hexyloxy)-cyclohexyl]-benzenesulfonamide | 501 (1 Br) | trans-4-Bromo-N-[4-(6-bromo-hexyloxy)-cyclohexyl]-N-methyl-benzenesulfonamide | Pyrrolidine |
| 13.41 | trans-N-[4-(6-Diethylamino-hexyloxy)-cyclohexyl]-N-methyl-4-trifluoromethyl-benzenesulfonamide | 493 | trans-N-[4-(6-Bromo-hexyloxy)-cyclohexyl]-N-methyl-4-trifluoromethyl-benzenesulfonamide | Diethylamine |
| 13.42 | trans-N-{4-[6-(Isopropyl-methyl-amino)-hexyloxy]-cyclohexyl}-N-methyl-4-trifluoromethyl-benzenesulfonamide | 493 | trans-N-[4-(6-Bromo-hexyloxy)-cyclohexyl]-N-methyl-4-trifluoromethyl-benzenesulfonamide | Isopropylmethyl-amine |
| 13.43 | trans-N-Methyl-N-[4-(6-pyrrolidin-1-yl-hexyloxy)-cyclohexyl]-4-trifluoromethyl-benzenesulfonamide | 491 | trans-N-[4-(6-Bromo-hexyloxy)-cyclohexyl]-N-methyl-4-trifluoromethyl-benzenesulfonamide | Pyrrolidine |
| 13.44 | trans-N-[4-(3-Allylamino-propoxy)-cyclohexyl]-N-methyl-4-trifluoromethyl-benzenesulfonamide | 435 | trans-N-[4-(3-Bromo-propoxy)-cyclohexyl]-N-methyl-4-trifluoromethyl-benzenesulfonamide | N-Allylamine |
| 13.45 | trans-N-{4-[4-(Allyl-methyl-amino)-butoxy]-cyclohexyl}-N-ethyl-4-trifluoromethyl-benzenesulfonamide | 477 | trans-N-[4-(4-Bromo-butoxy)-cyclohexyl]-N-ethyl-4-trifluoromethyl-benzenesulfonamide | N-Allyl-methylamine |
| 13.46 | trans-N-[4-(4-Dimethylamino-butoxy)-cyclohexyl]-N-ethyl-4-trifluoromethyl-benzenesulfonamide | 451 | trans-N-[4-(4-Bromo-butoxy)-cyclohexyl]-N-ethyl-4-trifluoromethyl-benzenesulfonamide | Dimethylamine |
| 13.47 | trans-N-Ethyl-N-(4-{4-[(2-hydroxy-ethyl)-methyl- | 481 | trans-N-[4-(4-Bromo-butoxy)-cyclohexyl]- | Methylaminoethanol |

| Example | Compound | MS MH+ | Educt 1 | Educt 2 |
|---|---|---|---|---|
| | amino]-butoxy}-cyclohexyl)-4-trifluoromethyl-benzenesulfonamide | | N-ethyl-4-trifluoromethyl-benzenesulfonamide | |
| 13.48 | trans-N-Ethyl-N-(4-{4-[(2-methoxy-ethyl)-methyl-amino]-butoxy}-cyclohexyl)-4-trifluoromethyl-benzenesulfonamide | 495 | trans-N-[4-(4-Bromo-butoxy)-cyclohexyl]-N-ethyl-4-trifluoromethyl-benzenesulfonamide | N-(Methoxyethyl) methylamine |
| 13.49 | trans-N-Ethyl-N-(4-{4-[ethyl-(2-hydroxy-ethyl)-amino]-butoxy}-cyclohexyl)-4-trifluoromethyl-benzenesulfonamide | 495 | trans-N-[4-(4-Bromo-butoxy)-cyclohexyl]-N-ethyl-4-trifluoromethyl-benzenesulfonamide | Ethylamino-ethanol |
| 13.50 | trans-N-Ethyl-N-(4-{4-[ethyl-(2-methoxy-ethyl)-amino]-butoxy}-cyclohexyl)-4-trifluoromethyl-benzenesulfonamide | 509 | trans-N-[4-(4-Bromo-butoxy)-cyclohexyl]-N-ethyl-4-trifluoromethyl-benzenesulfonamide | N-(Methoxyethyl)-ethylamine |
| 13.51 | trans-N-(4-{4-[Bis-(2-hydroxy-ethyl)-amino]-butoxy}-cyclohexyl)-N-ethyl-4-trifluoromethyl-benzenesulfonamide | 511 | trans-N-[4-(4-Bromo-butoxy)-cyclohexyl]-N-ethyl-4-trifluoromethyl-benzenesulfonamide | Diethanolamine |
| 13.52 | trans-N-[4-(4-Diethylamino-butoxy)-cyclohexyl]-N-ethyl-4-trifluoromethyl-benzenesulfonamide | 479 | trans-N-[4-(4-Bromo-butoxy)-cyclohexyl]-N-ethyl-4-trifluoromethyl-benzenesulfonamide | Diethylamine |
| 13.53 | trans-N-[4-(4-Allylamino-butoxy)-cyclohexyl]-N-ethyl-4-trifluoromethyl-benzenesulfonamide | 463 | trans-N-[4-(4-Bromo-butoxy)-cyclohexyl]-N-ethyl-4-trifluoromethyl-benzenesulfonamide | Allylamine |
| 13.54 | trans-N-Ethyl-N-[4-(4-piperidin-1-yl-butoxy)-cyclohexyl]-4-trifluoromethyl-benzenesulfonamide | 491 | trans-N-[4-(4-Bromo-butoxy)-cyclohexyl]-N-ethyl-4-trifluoromethyl-benzenesulfonamide | Piperidine |
| 13.55 | trans-N-Ethyl-N-{4-[4-(4-methyl-piperazin-1-yl)-butoxy]-cyclohexyl}-4-trifluoromethyl-benzenesulfonamide | 506 | trans-N-[4-(4-Bromo-butoxy)-cyclohexyl]-N-ethyl-4-trifluoromethyl-benzenesulfonamide | 1-Methylpiperazine |

Example 14

A solution of the secondary amine (0.6 mmol; 3.5 equivalents) in 0.7 ml dry DMF is treated with 0.17 mmol (1 equivalent) of the bromide in 0.25 ml dry DMF, as well as with 0.17 mmol (1 equivalent) 1,8-Diazabicyclo[5.4.0]undec-7-ene(1,5-5) (DBU). The reaction mixture is shaken over night at 50° C., then treated with 0.2 ml formic acid and purified by preparative HPLC [RP-18, acetonitrile (0.1% HCOOH)/water (0.1% HCOOH), 10% to 95% acetonitrile]. After evaporation, the tertiary amine is obtained as a mixture of amine formate and hydrobromide. The following compounds can be prepared from the corresponding bromides and secondary amines:

| Example | Compound | MS MH+ | Bromide | Secondary amine |
|---|---|---|---|---|
| 14.1 | trans-4-Bromo-N-(4-{6-[(2-methoxy-ethyl)-methyl-amino]-hexyloxy}-cyclohexyl)-N-methyl-benzenesulfonamide | 519 (1 Br) | trans-4-Bromo-N-[4-(6-bromo-hexyloxy)-cyclohexyl]-N-methyl-benzenesulfonamide | N-(2-methoxy-ethyl)methyl-amine |
| 14.2 | trans-N-(4-{6-[(2-Methoxy-ethyl)-methyl-amino]-hexyloxy}-cyclohexyl)-N-methyl-4-trifluoromethyl-benzenesulfonamide | 509 | trans-N-[4-(6-Bromo-hexyloxy)-cyclohexyl]-N-methyl-4-trifluoromethyl-benzenesulfonamide | N-(2-methoxy-ethyl)methyl-amine |
| 14.3 | trans-4-Bromo-N-methyl-N-[4-(6-morpholin-4-yl-hexyloxy)-cyclohexyl]-benzenesulfonamide | 517 (1 Br) | trans-4-Bromo-N-[4-(6-bromo-hexyloxy)-cyclohexyl]-N-methyl-benzenesulfonamide | Morpholine |

-continued

| Example | Compound | MS MH+ | Bromide | Secondary amine |
|---|---|---|---|---|
| 14.4 | trans-N-[4-(6-Azetidin-1-yl-hexyloxy)-cyclohexyl]-4-bromo-N-methyl-benzenesulfonamide | 487 (1 Br) | trans-4-Bromo-N-[4-(6-bromo-hexyloxy)-cyclohexyl]-N-methyl-benzenesulfonamide | Trimethylene-amine |
| 14.5 | trans-4-Bromo-N-{4-[6-(butyl-methyl-amino)-hexyloxy]-cyclohexyl}-N-methyl-benzenesulfonamide | 517 (1 Br) | trans-4-Bromo-N-[4-(6-bromo-hexyloxy)-cyclohexyl]-N-methyl-benzenesulfonamide | N-Methylbutyl-amine |
| 14.6 | trans-4-Bromo-N-methyl-N-[4-(6-piperidin-1-yl-hexyloxy)-cyclohexyl]-benzenesulfonamide | 515 (1 Br) | trans-4-Bromo-N-[4-(6-bromo-hexyloxy)-cyclohexyl]-N-methyl-benzenesulfonamide | Piperidine |
| 14.7 | trans-4-Bromo-N-{4-[6-(3,6-dihydro-2H-pyridin-1-yl)-hexyloxy]-cyclohexyl}-N-methyl-benzenesulfonamide | 513 (1 Br) | trans-4-Bromo-N-[4-(6-bromo-hexyloxy)-cyclohexyl]-N-methyl-benzenesulfonamide | 1,2,3,6-Tetra-hydro-pyridine |
| 14.8 | trans-4-Bromo-N-(4-{6-[ethyl-(2-hydroxy-ethyl)-amino]-hexyloxy}-cyclohexyl)-N-methyl-benzenesulfonamide | 519 (1 Br) | trans-4-Bromo-N-[4-(6-bromo-hexyloxy)-cyclohexyl]-N-methyl-benzenesulfonamide | 2-(Ethylamino)-ethanol |
| 14.9 | trans-4-Bromo-N-{4-[6-(3-hydroxy-pyrrolidin-1-yl)-hexyloxy]-cyclohexyl}-N-methyl-benzenesulfonamide | 517 (1 Br) | trans-4-Bromo-N-[4-(6-bromo-hexyloxy)-cyclohexyl]-N-methyl-benzenesulfonamide | (R)-3-Hydroxy-pyrrolidine |
| 14.10 | trans-4-Bromo-N-methyl-N-{4-[6-(methyl-propyl-amino)-hexyloxy]-cyclohexyl}-benzenesulfonamide | 503 (1 Br) | trans-4-Bromo-N-[4-(6-bromo-hexyloxy)-cyclohexyl]-N-methyl-benzenesulfonamide | N-Methylpropylamine |
| 14.11 | trans-4-Bromo-N-[4-(6-diallylamino-hexyloxy)-cyclohexyl]-N-methyl-benzenesulfonamide | 527 (1 Br) | trans-4-Bromo-N-[4-(6-bromo-hexyloxy)-cyclohexyl]-N-methyl-benzenesulfonamide | Diallylamine |
| 14.12 | trans-4-Bromo-N-{4-[6-(4-hydroxymethyl-piperidin-1-yl)-hexyloxy]-cyclohexyl}-N-methyl-benzenesulfonamide | 545 (1 Br) | trans-4-Bromo-N-[4-(6-bromo-hexyloxy)-cyclohexyl]-N-methyl-benzenesulfonamide | 4-Hydroxy-methyl-piperidine |
| 14.13 | trans-4-Bromo-N-(4-{6-[(2-hydroxy-ethyl)-methyl-amino]-hexyloxy}-cyclohexyl)-N-methyl-benzenesulfonamide | 505 (1 Br) | trans-4-Bromo-N-[4-(6-bromo-hexyloxy)-cyclohexyl]-N-methyl-benzenesulfonamide | 2-Hydroxyethyl-methylamine |
| 14.14 | trans-4-Bromo-N-methyl-N-{4-[6-(4-methyl-piperidin-1-yl)-hexyloxy]-cyclohexyl}-benzenesulfonamide | 529 (1 Br) | trans-4-Bromo-N-[4-(6-bromo-hexyloxy)-cyclohexyl]-N-methyl-benzenesulfonamide | 4-Methyl-piperidine |
| 14.15 | trans-4-Bromo-N-{4-[6-(4-hydroxy-piperidin-1-yl)-hexyloxy]-cyclohexyl}-N-methyl-benzenesulfonamide | 531 (1 Br) | trans-4-Bromo-N-[4-(6-bromo-hexyloxy)-cyclohexyl]-N-methyl-benzenesulfonamide | 4-Hydroxy-piperidine |
| 14.16 | trans-4-Bromo-N-{4-[6-(cyclopropylmethyl-methyl-amino)-hexyloxy]-cyclohexyl}-N-methyl-benzenesulfonamide | 515 (1 Br) | trans-4-Bromo-N-[4-(6-bromo-hexyloxy)-cyclohexyl]-N-methyl-benzenesulfonamide | N-Methyl-cyclopropane-methylamine |
| 14.17 | trans-[(6-{4-[(4-Bromo-benzenesulfonyl)-methyl-amino]-cyclohexyloxy}-hexyl)-methyl-amino]-acetic acid ethyl ester | 547 (1 Br) | trans-4-Bromo-N-[4-(6-bromo-hexyloxy)-cyclohexyl]-N-methyl-benzenesulfonamide | Sarcosine ethyl ester hydro-chloride |
| 14.18 | trans-N-Methyl-N-[4-(6-morpholin-4-yl-hexyloxy)-cyclohexyl]-4-trifluoromethyl-benzenesulfonamide | 507 | trans-N-[4-(6-Bromo-hexyloxy)-cyclohexyl]-N-methyl-4-trifluoromethyl-benzenesulfonamide | Morpholine |

-continued

| Example | Compound | MS MH+ | Bromide | Secondary amine |
|---|---|---|---|---|
| 14.19 | trans-N-[4-(6-Azetidin-1-yl-hexyloxy)-cyclohexyl]-N-methyl-4-trifluoromethyl-benzenesulfonamide | 477 | trans-N-[4-(6-Bromo-hexyloxy)-cyclohexyl]-N-methyl-4-trifluoromethyl-benzenesulfonamide | Trimethylene-amine |
| 14.20 | trans-N-{4-[6-(Butyl-methyl-amino)-hexyloxy]-cyclohexyl}-N-methyl-4-trifluoromethyl-benzenesulfonamide | 507 | trans-N-[4-(6-Bromo-hexyloxy)-cyclohexyl]-N-methyl-4-trifluoromethyl-benzenesulfonamide | N-Methylbutyl-amine |
| 14.21 | trans-N-Methyl-N-[4-(6-piperidin-1-yl-hexyloxy)-cyclohexyl]-4-trifluoromethyl-benzenesulfonamide | 505 | trans-N-[4-(6-Bromo-hexyloxy)-cyclohexyl]-N-methyl-4-trifluoromethyl-benzenesulfonamide | Piperidine |
| 14.22 | trans-N-{4-[6-(3,6-Dihydro-2H-pyridin-1-yl)-hexyloxy]-cyclohexyl]-N-methyl-4-trifluoromethyl-benzenesulfonamide | 503 | trans-N-[4-(6-Bromo-hexyloxy)-cyclohexyl]-N-methyl-4-trifluoromethyl-benzenesulfonamide | 1,2,3,6-Tetra-hydro-pyridine |
| 14.23 | trans-N-(4-{6-[Ethyl-(2-hydroxy-ethyl)-amino]-hexyloxy}-cyclohexyl)-N-methyl-4-trifluoromethyl-benzenesulfonamide | 509 | trans-N-[4-(6-Bromo-hexyloxy)-cyclohexyl]-N-methyl-4-trifluoromethyl-benzenesulfonamide | 2-(Ethylamino)-ethanol |
| 14.24 | trans-N-{4-[6-(3-Hydroxy-pyrrolidin-1-yl)-hexyloxy]-cyclohexyl}-N-methyl-4-trifluoromethyl-benzenesulfonamide | 507 | trans-N-[4-(6-Bromo-hexyloxy)-cyclohexyl]-N-methyl-4-trifluoromethyl-benzenesulfonamide | (R)-3-Hydroxy-pyrrolidine |
| 14.25 | trans-N-Methyl-N-{4-[6-(methyl-propyl-amino)-hexyloxy]-cyclohexyl}-4-trifluoromethyl-benzenesulfonamide | 493 | trans-N-[4-(6-Bromo-hexyloxy)-cyclohexyl]-N-methyl-4-trifluoromethyl-benzenesulfonamide | N-Methylpropylamine |
| 14.26 | trans-N-[4-(6-Diallylamino-hexyloxy)-cyclohexyl]-N-methyl-4-trifluoromethyl-benzenesulfonamide | 517 | trans-N-[4-(6-Bromo-hexyloxy)-cyclohexyl]-N-methyl-4-trifluoromethyl-benzenesulfonamide | Diallylamine |
| 14.27 | trans-N-{4-[6-(4-Hydroxymethyl-piperidin-1-yl)-hexyloxy]-cyclohexyl}-N-methyl-4-trifluoromethyl-benzenesulfonamide | 535 | trans-N-[4-(6-Bromo-hexyloxy)-cyclohexyl]-N-methyl-4-trifluoromethyl-benzenesulfonamide | 4-Hydroxy-methylpiperidine |
| 14.28 | trans-N-(4-{6-[(2-Hydroxy-ethyl)-methyl-amino]-hexyloxy}-cyclohexyl)-N-methyl-4-trifluoromethyl-benzenesulfonamide | 495 | trans-N-[4-(6-Bromo-hexyloxy)-cyclohexyl]-N-methyl-4-trifluoromethyl-benzenesulfonamide | 2-Hydroxyethyl-methylamine |
| 14.29 | trans-N-{4-[6-(4-Hydroxy-piperidin-1-yl)-hexyloxy]-cyclohexyl}-N-methyl-4-trifluoromethyl-benzenesulfonamide | 521 | trans-N-[4-(6-Bromo-hexyloxy)-cyclohexyl]-N-methyl-4-trifluoromethyl-benzenesulfonamide | 4-Hydroxy-piperidine |
| 14.30 | trans-N-{4-[6-(Cyclopropylmethyl-methyl-amino)-hexyloxy]-cyclohexyl}-N-methyl-4-trifluoromethyl-benzenesulfonamide | 505 | trans-N-[4-(6-Bromo-hexyloxy)-cyclohexyl]-N-methyl-4-trifluoromethyl-benzenesulfonamide | N-Methyl-cyclopropane-methylamine |
| 14.31 | trans-[Methyl-(6-{4-[methyl-(4-trifluoromethyl-benzenesulfonyl)-amino]-cyclohexyloxy}-hexyl)-amino]-acetic acid ethyl ester | 537 | trans-N-[4-(6-Bromo-hexyloxy)-cyclohexyl]-N-methyl-4-trifluoromethyl-benzenesulfonamide | Sarcosine ethyl ester hydro-chloride |

Example 15

A solution of 1.02 mmol (6 equivalents) primary amine in 0.7 ml dry DMF was treated with 0.17 mmol (1 equivalent) bromide in 0.25 ml dry DMF, as well as with 0.17 mmol (1 equivalent), 1,8-Diazabicyclo[5.4.0]undec-7-ene(1,5-5) (DBU). The reaction mixture was shaken over night at 50° C., treated with 0.2 ml formic acid and purified by preparative HPLC [RP-18, acetonitrile (0.1% HCOOH)/water (0.1% HCOOH), 10% to 95% acetonitrile]. After evaporation, the secondary amine was obtained as a mixture of amine formates and hydrobromides. The following compounds were prepared from the corresponding bromides and amines:

1.5 eq) imidazole and 6.65 g (44.1 mmol, 1.1 eq) TBDMSCl in 20 ml DMF were added at 0° C. The mixture was warmed to 50° C. and stirred at that temperature for 2 h. A saturated solution of NaHCO$_3$ was added, the mixture was concentrated and redissolved in ether/water. The phases were separated and the inorganic phase was extracted with ether. The combined organic phases were washed with brine, dried over Na$_2$SO$_4$ and concentrated. The crude product was purified on silica gel with hexane:EtOAc 5:1 as eluent yielding 11.8 g (81%) trans-[4-(tert-Butyl-dimethyl-silanyloxy)-cyclohexyl]-carbamic acid benzyl ester as colorless gum, MS: 348 (M–CH$_3$).

| Example | Compound | MS MH$^+$ | Bromide | Amine |
|---|---|---|---|---|
| 15.1 | trans-N-[4-(6-Allylamino-hexyloxy)-cyclohexyl]-4-bromo-N-methyl-benzenesulfonamide | 487 (1 Br) | trans-4-Bromo-N-[4-(6-bromo-hexyloxy)-cyclohexyl]-N-methyl-benzenesulfonamide | Allylamine |
| 15.2 | trans-4-Bromo-N-{4-[6-(2-hydroxy-ethylamino)-hexyloxy]-cyclohexyl}-N-methyl-benzenesulfonamide | 491 (1 Br) | trans-4-Bromo-N-[4-(6-bromo-hexyloxy)-cyclohexyl]-N-methyl-benzenesulfonamide | 2-Ethanolamine |
| 15.3 | trans-4-Bromo-N-[4-(6-ethylamino-hexyloxy)-cyclohexyl]-N-methyl-benzenesulfonamide | 475 (1 Br) | trans-4-Bromo-N-[4-(6-bromo-hexyloxy)-cyclohexyl]-N-methyl-benzenesulfonamide | Ethylamine |
| 15.4 | trans-N-{4-[4-(2-Hydroxy-ethylamino)-butoxy]-cyclohexyl}-N-methyl-4-trifluoromethyl-benzenesulfonamide | 453 | trans-N-[4-(4-Bromo-butoxy)-cyclohexyl]-N-methyl-4-trifluoromethyl-benzenesulfonamide | Ethanolamine |
| 15.5 | trans-N-[4-(4-Ethylamino-butoxy)-cyclohexyl]-N-methyl-4-trifluoromethyl-benzenesulfonamide | 437 | trans-N-[4-(4-Bromo-butoxy)-cyclohexyl]-N-methyl-4-trifluoromethyl-benzenesulfonamide | N-Ethylamine |
| 15.6 | trans-N-{4-[3-(2-Hydroxy-ethylamino)-propoxy]-cyclohexyl}-N-methyl-4-trifluoromethyl-benzenesulfonamide | 439 | trans-N-[4-(3-Bromo-propoxy)-cyclohexyl]-N-methyl-4-trifluoromethyl-benzenesulfonamide | Ethanolamine |
| 15.7 | trans-N-[4-(3-Ethylamino-propoxy)-cyclohexyl]-N-methyl-4-trifluoromethyl-benzenesulfonamide | 423 | trans-N-[4-(3-Bromo-propoxy)-cyclohexyl]-N-methyl-4-trifluoromethyl-benzenesulfonamide | N-Ethylamine |
| 15.8 | trans-N-[4-(6-Allylamino-hexyloxy)-cyclohexyl]-N-methyl-4-trifluoromethyl-benzenesulfonamide | 477 | trans-N-[4-(6-Bromo-hexyloxy)-cyclohexyl]-N-methyl-4-trifluoromethyl-benzenesulfonamide | Allylamine |
| 15.9 | trans-N-[4-(3-Allylamino-propoxy)-cyclohexyl]-N-methyl-4-trifluoromethyl-benzenesulfonamide | 435 | trans-N-[4-(3-Bromo-propoxy)-cyclohexyl]-N-methyl-4-trifluoromethyl-benzenesulfonamide | N-Methylallyl-amine |
| 15.10 | trans-N-[4-(4-Allylamino-butoxy)-cyclohexyl]-N-methyl-4-trifluoromethyl-benzenesulfonamide | 449 | trans-N-[4-(4-Bromo-butoxy)-cyclohexyl]-N-methyl-4-trifluoromethyl-benzenesulfonamide | Allylamine |

Example 16

Example 16.1

To 10 g (40.1 mmol) trans-4-Hydroxy-cyclohexylcarbamic acid benzyl ester in 40 ml DMF, 4.09 g (60.1 mmol,

Example 16.2

To a suspension of 0.58 g (55% in mineral oil, 13 mmol, 1.2 eq) sodium hydride in 20 ml DMF, a solution of 4.2 g (11 mmol) trans-[4-(tert-Butyl-dimethyl-silanyloxy)-cyclohexyl]-carbamic acid benzyl ester in 10 ml DMF was added slowly. The temperature was raised slowly to 50° C. and kept at that temperature for 1 h. At RT 0.9 ml (14 mmol; 1.3 eq) iodomethane were added and the mixture stirred over night. Additional 0.58 g (55% in mineral oil, 13 mmol, 1.2 eq) sodium hydride and 0.9 ml (14 mmol; 1.3 eq) iodomethane were added and the reaction mixture was stirred for 1 day. Aqueous NH$_4$Cl solution was added and the inorganic phase was extracted with ether, washed with brine, dried over Na$_2$SO$_4$ and evaporated yielding 3.1 g (72%) trans-[4-(tert-Butyl-dimethyl-silanyloxy)-cyclohexyl]-methyl-carbamic acid benzyl ester.

Example 16.3

To a solution of 3.1 g (8 mmol) trans-[4-(tert-Butyl-dimethyl-silanyloxy)-cyclohexyl]-methyl-carbamic acid benzyl ester in 20 ml THF, 10.3 ml (1M, 10.3 mmol, 1.3 eq) Tetrabutylammonium fluoride in THF were added at 6° C. and the mixture was stirred at RT for 2 days. Water was added and the phases were separated and the inorganic phase was extracted with ether and EtOAc. The combined organic phases were washed with brine, dried over Na$_2$SO$_4$ and evaporated. Column chromatography on silica gel with a gradient EtOAc:hexane 1:4—EtOAc yielded 1.9 g 1.9 g (92%) trans-(4-Hydroxy-cyclohexyl)-methyl-carbamic acid benzyl ester as orange oil, MS: 263 (M).

Example 16.4

In analogy to examples 16.2 and 16.3, from trans-[4-(tert-Butyl-dimethyl-silanyloxy)-cyclohexyl]-carbamic acid benzyl ester and bromoethane, trans-Ethyl-(4-hydroxy-cyclohexyl)-carbamic acid benzyl ester was obtained as orange oil, MS: 277 (M).

Example 16.5

In analogy to examples 16.2 and 16.3, from trans-[4-(tert-Butyl-dimethyl-silanyloxy)-cyclohexyl]-carbamic acid benzyl ester and allyl bromide, trans-Allyl-(4-hydroxy-cyclohexyl)-carbamic acid benzyl ester was obtained as orange oil, MS: 289 (M).

Example 16.6

In analogy to examples 16.2 and 16.3, from trans-[4-(tert-Butyl-dimethyl-silanyloxy)-cyclohexyl]-carbamic acid benzyl ester and benzyl bromide, trans-Benzyl-(4-hydroxy-cyclohexyl)-carbamic acid benzyl ester was obtained as orange oil, MS: 340 (MH$^+$).

Example 16.7

In analogy to examples 16.2 and 16.3, from trans-[4-(tert-Butyl-dimethyl-silanyloxy)-cyclohexyl]-carbamic acid benzyl ester and 2,4,5-trifluorobenzyl bromide, trans-(4-Hydroxy-cyclohexyl)-(2,4,5-trifluoro-benzyl)-carbamic acid benzyl ester was obtained as orange oil, MS: 394 (MH$^+$).

Example 16.8

To 1.9 g (7 mmol) trans-(4-Hydroxy-cyclohexyl)-methyl-carbamic acid benzyl ester suspended in 40.7 ml (267 mmol, 37 eq) 1,6-dibomohexane, 0.74 g (2.0 mmol, 0.3 eq) tetrabutyl ammonium hydrogensulfate and 40 ml 50% aqueous NaOH were added. The mixture was stirred at RT for 3 days, CH$_2$Cl$_2$ was added and the layers were separated. The inorganic layer was extracted with CH$_2$Cl$_2$, the combined organic layers were washed with brine and dried over Na$_2$SO$_4$. The excess of dibromide was removed in vacuo and the residue was purified by column chromatography on silica gel with hexane:EtOAc 4:1 as eluent yielding 2.0 g (64%) trans-[4-(6-Bromo-hexyloxy)-cyclohexyl]-methyl-carbamic acid benzyl ester as light yellow oil, MS: 425 (M, 1Br).

Example 16.9

In analogy to example 16.8, trans-[4-(6-Bromo-hexyloxy)-cyclohexyl]-ethyl-carbamic acid benzyl ester was obtained as light yellow liquid, MS: 439 (M, 1Br), from trans-Ethyl-(4-hydroxy-cyclohexyl)-carbamic acid benzyl ester.

Example 16.10

In analogy to example 16.8, trans-Allyl-[4-(6-bromo-hexyloxy)-cyclohexyl]-carbamic acid benzyl ester was obtained as light yellow liquid, MS: 451 (M, 1Br), from trans-Allyl-(4-hydroxy-cyclohexyl)-carbamic acid benzyl ester.

Example 16.11

In analogy to example 16.8, trans-Benzyl-[4-(6-bromo-hexyloxy)-cyclohexyl]-carbamic acid benzyl ester was obtained as light yellow liquid, MS: 501 (M, 1Br), from trans-Benzyl-(4-hydroxy-cyclohexyl)-carbamic acid benzyl ester.

Example 16.12

In analogy to example 16.8, trans-[4-(6-Bromo-hexyloxy)-cyclohexyl]-(2,4,5-trifluoro-benzyl)-carbamic acid benzyl ester was obtained as light yellow liquid, MS: 555 (M, 1Br), from trans-(4-Hydroxy-cyclohexyl)-(2,4,5-trifluoro-benzyl)-carbamic acid benzyl ester.

Example 16.13

In analogy to example 16.8, from trans-(4-Hydroxy-cyclohexyl)-carbamic acid benzyl ester and 1,6-dibromo-hexane was obtained trans-[4-(6-Bromo-hexyloxy)-cyclohexyl]-carbamic acid benzyl ester as white solid, MS: 412 (MH$^+$, 1Br).

Example 16.14

In analogy to example 16.8, from trans-(4-Hydroxy-cyclohexyl)-carbamic acid benzyl ester and 1,5-dibromopentane was obtained trans-[4-(5-Bromo-pentyloxy)-cyclohexyl]-carbamic acid benzyl ester as white solid, MS: 398 (MH$^+$, 1Br).

Example 17

1 eq of the bromide is treated with 3 eq of each amine in (1 ml/mmol bromide) DMF in the presence of 1 eq diisopropylethylamine and a catalytic amount of NaI at RT until no starting material can be detected with HPLC. Formic acid is added and the crude materials are purified by preparative HPLC [RP-18, acetonitrile (0.1% HCOOH)/water (0.1% HCOOH), 10% to 95% acetonitrile]. After evaporation the amines were obtained as a mixture of amine formates and hydrobromides. The following compounds were prepared from the corresponding bromides and amines:

| Example | Compound | MS MH+ | Bromide | Amine |
|---|---|---|---|---|
| 17.1 | trans-Ethyl-(4-{6-[ethyl-(2-hydroxy-ethyl)-amino]-hexyloxy}-cyclohexyl)-carbamic acid benzyl ester | 449 | trans-[4-(6-Bromo-hexyloxy)-cyclohexyl]-ethyl-carbamic acid benzyl ester | 2-(Ethylamino)-ethanol |
| 17.2 | trans-Benzyl-(4-{6-[ethyl-(2-hydroxy-ethyl)-amino]-hexyloxy}-cyclohexyl)-carbamic acid benzyl ester | 511 | trans-Benzyl-[4-(6-bromo-hexyloxy)-cyclohexyl]-carbamic acid benzyl ester | 2-(Ethylamino)-ethanol |
| 17.3 | trans-(4-{6-[Ethyl-(2-hydroxy-ethyl)-amino]-hexyloxy}-cyclohexyl)-methyl-carbamic acid benzyl ester | 435 | trans-[4-(6-Bromo-hexyloxy)-cyclohexyl]-methyl-carbamic acid benzyl ester | 2-(Ethylamino)-ethanol |
| 17.4 | trans-Allyl-(4-{6-[ethyl-(2-hydroxy-ethyl)-amino]-hexyloxy}-cyclohexyl)-carbamic acid benzyl ester | 461 | trans-Allyl-[4-(6-bromo-hexyloxy)-cyclohexyl]-carbamic acid benzyl ester | 2-(Ethylamino)-ethanol |
| 17.5 | trans-(4-{6-[Ethyl-(2-hydroxy-ethyl)-amino]-hexyloxy}-cyclohexyl)-(2,4,5-trifluoro-benzyl)-carbamic acid benzyl ester | 565 | trans-[4-(6-Bromo-hexyloxy)-cyclohexyl]-(2,4,5-trifluoro-benzyl)-carbamic acid benzyl ester | 2-(Ethylamino)-ethanol |
| 17.6 | trans-[4-(6-Azetidin-1-yl-hexyloxy)-cyclohexyl]-ethyl-carbamic acid benzyl ester | 417 | trans-[4-(6-Bromo-hexyloxy)-cyclohexyl]-ethyl-carbamic acid benzyl ester | Azetidine |
| 17.7 | trans-[4-(6-Azetidin-1-yl-hexyloxy)-cyclohexyl]-benzyl-carbamic acid benzyl ester | 479 | trans-Benzyl-[4-(6-bromo-hexyloxy)-cyclohexyl]-carbamic acid benzyl ester | Azetidine |
| 17.8 | trans-[4-(6-Azetidin-1-yl-hexyloxy)-cyclohexyl]-methyl-carbamic acid benzyl ester | 403 | trans-[4-(6-Bromo-hexyloxy)-cyclohexyl]-methyl-carbamic acid benzyl ester | Azetidine |
| 17.9 | trans-Ethyl-(4-{6-[(2-hydroxy-ethyl)-methyl-amino]-hexyloxy}-cyclohexyl)-carbamic acid benzyl ester | 435 | trans-[4-(6-Bromo-hexyloxy)-cyclohexyl]-ethyl-carbamic acid benzyl ester | 2-(Methylamino)-ethanol |
| 17.10 | trans-Benzyl-(4-{6-[(2-hydroxy-ethyl)-methyl-amino]-hexyloxy}-cyclohexyl)-carbamic acid benzyl ester | 497 | trans-Benzyl-[4-(6-bromo-hexyloxy)-cyclohexyl]-carbamic acid benzyl ester | 2-(Methylamino)-ethanol |
| 17.11 | trans-(4-{6-[(2-Hydroxy-ethyl)-methyl-amino]-hexyloxy}-cyclohexyl)-methyl-carbamic acid benzyl ester | 421 | trans-[4-(6-Bromo-hexyloxy)-cyclohexyl]-methyl-carbamic acid benzyl ester | 2-(Methylamino)-ethanol |
| 17.12 | trans-Allyl-(4-{6-[(2-hydroxy-ethyl)-methyl-amino]-hexyloxy}-cyclohexyl)-carbamic acid benzyl ester | 447 | trans-Allyl-[4-(6-bromo-hexyloxy)-cyclohexyl]-carbamic acid benzyl ester | 2-(Methylamino)-ethanol |
| 17.13 | trans-(4-{6-[(2-Hydroxy-ethyl)-methyl-amino]-hexyloxy}-cyclohexyl)-(2,4,5-trifluoro-benzyl)-carbamic acid benzyl ester | 551 | trans-[4-(6-Bromo-hexyloxy)-cyclohexyl]-(2,4,5-trifluoro-benzyl)-carbamic acid benzyl ester | 2-(Methylamino)-ethanol |
| 17.14 | trans-Ethyl-(4-{6-[(2-methoxy-ethyl)-methyl-amino]-hexyloxy}-cyclohexyl)-carbamic acid benzyl ester | 449 | trans-[4-(6-Bromo-hexyloxy)-cyclohexyl]-ethyl-carbamic acid benzyl ester | N-(2-Methoxy-ethyl)-methyl-amine |
| 17.15 | trans-Benzyl-(4-{6-[(2-methoxy-ethyl)-methyl-amino]-hexyloxy}-cyclohexyl)-carbamic acid benzyl ester | 511 | trans-Benzyl-[4-(6-bromo-hexyloxy)-cyclohexyl]-carbamic acid benzyl ester | N-(2-Methoxy-ethyl)-methyl-amine |
| 17.16 | trans-(4-{6-[(2-Methoxy-ethyl)-methyl-amino]- | 435 | trans-[4-(6-Bromo-hexyloxy)- | N-(2-Methoxy-ethyl)-methyl- |

-continued

| Example | Compound | MS MH+ | Bromide | Amine |
|---|---|---|---|---|
| | hexyloxy}-cyclohexyl)-methyl-carbamic acid benzyl ester | | cyclohexyl]-methyl-carbamic acid benzyl ester | amine |
| 17.17 | trans-(4-{6-[(2-Methoxy-ethyl)-methyl-amino]-hexyloxy}-cyclohexyl)-(2,4,5-trifluoro-benzyl)-carbamic acid benzyl ester | 565 | trans-[4-(6-Bromo-hexyloxy)-cyclohexyl]-(2,4,5-trifluoro-benzyl)-carbamic acid benzyl ester | N-(2-Methoxy-ethyl)-methyl-amine |
| 17.18 | trans-Ethyl-[4-(6-morpholin-4-yl-hexyloxy)-cyclohexyl]-carbamic acid benzyl ester | 447 | trans-[4-(6-Bromo-hexyloxy)-cyclohexyl]-ethyl-carbamic acid benzyl ester | Morpholine |
| 17.19 | trans-Benzyl-[4-(6-morpholin-4-yl-hexyloxy)-cyclohexyl]-carbamic acid benzyl ester | 509 | trans-Benzyl-[4-(6-bromo-hexyloxy)-cyclohexyl]-carbamic acid benzyl ester | Morpholine |
| 17.20 | trans-Methyl-[4-(6-morpholin-4-yl-hexyloxy)-cyclohexyl]-carbamic acid benzyl ester | 433 | trans-[4-(6-Bromo-hexyloxy)-cyclohexyl]-methyl-carbamic acid benzyl ester | Morpholine |
| 17.21 | trans-Allyl-[4-(6-morpholin-4-yl-hexyloxy)-cyclohexyl]-carbamic acid benzyl ester | 459 | trans-Allyl-[4-(6-bromo-hexyloxy)-cyclohexyl]-carbamic acid benzyl ester | Morpholine |
| 17.22 | trans-[4-(6-Morpholin-4-yl-hexyloxy)-cyclohexyl]-(2,4,5-trifluoro-benzyl)-carbamic acid benzyl ester | 563 | trans-[4-(6-Bromo-hexyloxy)-cyclohexyl]-(2,4,5-trifluoro-benzyl)-carbamic acid benzyl ester | Morpholine |
| 17.23 | trans-Ethyl-[4-(6-pyrrolidin-1-yl-hexyloxy)-cyclohexyl]-carbamic acid benzyl ester | 431 | trans-[4-(6-Bromo-hexyloxy)-cyclohexyl]-ethyl-carbamic acid benzyl ester | Pyrrolidine |
| 17.24 | trans-Benzyl-[4-(6-pyrrolidin-1-yl-hexyloxy)-cyclohexyl]-carbamic acid benzyl ester | 493 | trans-Benzyl-[4-(6-bromo-hexyloxy)-cyclohexyl]-carbamic acid benzyl ester | Pyrrolidine |
| 17.25 | trans-Methyl-[4-(6-pyrrolidin-1-yl-hexyloxy)-cyclohexyl]-carbamic acid benzyl ester | 417 | trans-[4-(6-Bromo-hexyloxy)-cyclohexyl]-methyl-carbamic acid benzyl ester | Pyrrolidine |
| 17.26 | trans-Allyl-[4-(6-pyrrolidin-1-yl-hexyloxy)-cyclohexyl]-carbamic acid benzyl ester | 443 | trans-Allyl-[4-(6-bromo-hexyloxy)-cyclohexyl]-carbamic acid benzyl ester | Pyrrolidine |
| 17.27 | [4-(6-Pyrrolidin-1-yl-hexyloxy)-cyclohexyl]-(2,4,5-trifluoro-benzyl)-carbamic acid benzyl ester | 547 | trans-[4-(6-Bromo-hexyloxy)-cyclohexyl]-(2,4,5-trifluoro-benzyl)-carbamic acid benzyl ester | Pyrrolidine |
| 17.28 | [4-(6-Dimethylamino-hexyloxy)-cyclohexyl]-carbamic acid benzyl ester | 377 | trans-[4-(6-Bromo-hexyloxy)-cyclohexyl]-methyl-carbamic acid benzyl ester | dimethylamine |
| 17.29 | trans-[4-(5-Dimethylamino-pentyloxy)-cyclohexyl]-carbamic acid benzyl ester | 363 | trans-[4-(5-Bromo-pentyloxy)-cyclohexyl]-carbamic acid benzyl ester | dimethylamine |

Example 18

1 eq of the bromide (0.13 mmol bromide/1 ml DMF) is treated with 3 eq of amine in the presence of 1 eq diisopropylethylamine and a catalytic amount of NaI at RT until no starting material can be detected with HPLC. Formic acid is added and the crude materials are purified by prep HPLC [RP-18, acetonitrile (0.1% HCOOH)/water (0.1% HCOOH), 10% to 95% acetonitrile]. After purification, the product is extractet with EtOAc and sat. NaHCO$_3$/H$_2$O to isolate the free amine. The following compounds were prepared from the corresponding bromides and amines:

| Example | Compound | MS MH+ | Bromide | Amine |
|---|---|---|---|---|
| 18.1 | trans-{4-[6-(Allyl-methyl-amino)-hexyloxy]-cyclohexyl}-methyl-carbamic acid benzyl ester | 417 | trans-[4-(6-Bromo-hexyloxy)-cyclohexyl]-methyl-carbamic acid benzyl ester | N-Allylmethyl-amine |
| 18.2 | trans-{4-[6-(Allyl-methyl-amino)-hexyloxy]-cyclohexyl}-ethyl-carbamic acid benzyl ester | 431 | trans-[4-(6-Bromo-hexyloxy)-cyclohexyl]-ethyl-carbamic acid benzyl ester | N-Allylmethyl-amine |
| 18.3 | trans-Allyl-{4-[6-(Allyl-methyl-amino)-hexyloxy]-cyclohexyl}-carbamic acid benzyl ester | 443 | trans-Allyl-[4-(6-bromo-hexyloxy)-cyclohexyl]-carbamic acid benzyl ester | N-Allylmethyl-amine |
| 18.4 | trans-{4-[6-(Allyl-methyl-amino)-hexyloxy]-cyclohexyl}-benzyl-carbamic acid benzyl ester | 493 | trans-Benzyl-[4-(6-bromo-hexyloxy)-cyclohexyl]-carbamic acid benzyl ester | N-Allylmethyl-amine |
| 18.5 | trans-{4-[6-(Allyl-methyl-amino)-hexyloxy]-cyclohexyl}-(2,4,5-trifluoro-benzyl)-carbamic acid benzyl ester | 547 | trans-[4-(6-Bromo-hexyloxy)-cyclohexyl]-(2,4,5-trifluoro-benzyl)-carbamic acid benzyl ester | N-Allylmethyl-amine |
| 18.6 | trans-[4-(6-Dimethylamino-hexyloxy)-cyclohexyl]-methyl-carbamic acid benzyl ester | 391 | trans-[4-(6-Bromo-hexyloxy)-cyclohexyl]-methyl-carbamic acid benzyl ester | Dimethylamine 33% in EtOH 5.6 M |
| 18.7 | trans-[4-(6-Dimethylamino-hexyloxy)-cyclohexyl]-ethyl-carbamic acid benzyl ester | 405 | trans-[4-(6-Bromo-hexyloxy)-cyclohexyl]-ethyl-carbamic acid benzyl ester | Dimethylamine 33% in EtOH 5.6 M |
| 18.8 | trans-Allyl-[4-(6-dimethylamino-hexyloxy)-cyclohexyl]-carbamic acid benzyl ester | 417 | trans-Allyl-[4-(6-bromo-hexyloxy)-cyclohexyl]-carbamic acid benzyl ester | Dimethylamine 33% in EtOH 5.6 M |
| 18.9 | trans-Benzyl-[4-(6-dimethylamino-hexyloxy)-cyclohexyl]-carbamic acid benzyl ester | 467 | trans-Benzyl-[4-(6-bromo-hexyloxy)-cyclohexyl]-carbamic acid benzyl ester | Dimethylamine 33% in EtOH 5.6 M |
| 18.10 | trans-[4-(6-Dimethylamino-hexyloxy)-cyclohexyl]-(2,4,5-trifluoro-benzyl)-carbamic acid benzyl ester | 521 | trans-[4-(6-Bromo-hexyloxy)-cyclohexyl]-(2,4,5-trifluoro-benzyl)-carbamic acid benzyl ester | Dimethylamine 33% in EtOH 5.6 M |

Example 19

Example 19.1

In analogy to example 17, trans-(4-{6-[(2-Methoxy-ethyl)-methyl-amino]-hexyloxy}-cyclohexyl)-methyl-carbamic acid benzyl ester, MS: 435 (MH+), was obtained from trans-[4-(6-Bromo-hexyloxy)-cyclohexyl]-methyl-carbamic acid benzyl ester and N-(2-Methoxyethyl)methylamine.

Example 19.2

Hydrogenation of 0.43 g (0.001 mmol) trans-(4-{6-[(2-Methoxy-ethyl)-methyl-amino]-hexyloxy}-cyclohexyl)-methyl-carbamic acid benzyl ester in 4 ml EtOAc in the presence of 0.06 g 10% Pd/C for 1 h yielded after removal of the catalyst and evaporation of the solvent 0.29 g (98%) trans-(4-{6-[(2-Methoxy-ethyl)-methyl-amino]-hexyloxy}-cyclohexyl)-methyl-amine as colorless oil, MS: 301 (MH+).

Example 19.3

In analogy to examples 19.1 and 19.2, trans-Ethyl-(4-{6-[(2-methoxy-ethyl)-methyl-amino]-hexyloxy}-cyclohexyl)-amine, MS: 315 (MH+), was obtained from trans-[4-(6-Bromo-hexyloxy)-cyclohexyl]-ethyl-carbamic acid benzyl ester and N-(2-Methoxyethyl)methylamine.

Example 19.4

In analogy to examples 19.1 and 19.2, trans-Benzyl-(4-{6-[(2-methoxy-ethyl)-methyl-amino]-hexyloxy}-cyclohexyl)-amine, MS: 377 (MH+), was obtained from trans-Benzyl-[4-(6-bromo-hexyloxy)-cyclohexyl]-carbamic acid benzyl ester and N-(2-Methoxyethyl)methylamine.

Example 19.5

In analogy to examples 19.1 and 19.2, trans-4-{6-[(2-Methoxy-ethyl)-methyl-amino]-hexyloxy}-cyclohexylamine, MS: 287 (MH+), was obtained from trans-Benzyl-

[4-(6-bromo-hexyloxy)-cyclohexyl]-carbamic acid benzyl ester and N-(2-Methoxyethyl)methylamine (hydrogenation over night).

Example 19.6

In analogy to examples 19.1 and 19.2, trans-(4-{6-[(2-Methoxy-ethyl)-methyl-amino]-hexyloxy}-cyclohexyl)-(2,4,5-trifluoro-benzyl)-amine, MS: 431 (MH$^+$), was obtained from trans-[4-(6-Bromo-hexyloxy)-cyclohexyl]-(2,4,5-trifluoro-benzyl)-carbamic acid benzyl ester and N-(2-Methoxyethyl)methylamine.

Example 19.7

In analogy to examples 19.1 and 19.2, trans-(4-{6-[(2-Methoxy-ethyl)-methyl-amino]-hexyloxy}-cyclohexyl)-propyl-amine, MS: 329 (MH$^+$), was obtained from trans-Allyl-[4-(6-bromo-hexyloxy)-cyclohexyl]-carbamic acid benzyl ester and N-(2-Methoxyethyl)methylamine.

Example 20

1 eq of the amine is treated with sulfonylchloride (1.1 eq for each NH$_2$) in (2-5 ml/mmol amine) dioxane in the presence of 1.1 eq of diisopropylamine at RT until no starting material can be detected with TLC. The solutions are diluted with EtOAc and washed with saturated aqueous NaHCO$_3$, brine and dried over Na$_2$SO$_4$. Flash chromatography or purification by prep HPLC [RP-18, acetonitrile (0.1% HCOOH)/water (0.1% HCOOH), 10% to 95% acetonitrile] followed by extraction with EtOAc and sat. NaHCO$_3$/H$_2$O yields the free amines. The following compounds were prepared from the corresponding amines and sulfonylchlorides:

| Example | Compound | MS MH$^+$ | Amine | Sulfonylchloride |
|---|---|---|---|---|
| 20.1 | trans-4-Chloro-N-(4-{6-[(2-methoxy-ethyl)-methyl-amino]-hexyloxy}-cyclohexyl)-N-methyl-benzenesulfonamide | 475 (1 Cl) | trans-(4-{6-[(2-Methoxy-ethyl)-methyl-amino]-hexyloxy}-cyclohexyl)-methyl-amine | 4-Chlorobenzene-sulfonylchloride |
| 20.2 | trans-4-Chloro-N-(4-{6-[(2-methoxy-ethyl)-methyl-amino]-hexyloxy}-cyclohexyl)-benzenesulfonamide | 461 (1 Cl) | trans-4-{6-[(2-Methoxy-ethyl)-methyl-amino]-hexyloxy}-cyclohexylamine | 4-Chlorobenzene-sulfonylchloride |
| 20.3 | trans-4-Bromo-N-(4-{6-[(2-methoxy-ethyl)-methyl-amino]-hexyloxy}-cyclohexyl)-benzenesulfonamide | 505 (1 Br) | trans-4-{6-[(2-Methoxy-ethyl)-methyl-amino]-hexyloxy}-cyclohexylamine | 4-Bromobenzene-sulfonylchloride |
| 20.4 | trans-4-Chloro-N-ethyl-N-(4-{6-[(2-methoxy-ethyl)-methyl-amino]-hexyloxy}-cyclohexyl)-benzenesulfonamide | 489 (1 Cl) | trans-Ethyl-(4-{6-[(2-methoxy-ethyl)-methyl-amino]-hexyloxy}-cyclohexyl)-amine | 4-Chlorobenzene-sulfonylchloride |
| 20.5 | trans-4-Bromo-N-ethyl-N-(4-{6-[(2-methoxy-ethyl)-methyl-amino]-hexyloxy}-cyclohexyl)-benzenesulfonamide | 533 (1 Br) | trans-Ethyl-(4-{6-[(2-methoxy-ethyl)-methyl-amino]-hexyloxy}-cyclohexyl)-amine | 4-Bromobenzene-sulfonylchloride |
| 20.6 | trans-4-Chloro-N-(4-{6-[(2-methoxy-ethyl)-methyl-amino]-hexyloxy}-cyclohexyl)-N-propyl-benzenesulfonamide | 503 (1 Cl) | trans-(4-{6-[(2-Methoxy-ethyl)-methyl-amino]-hexyloxy}-cyclohexyl)-propyl-amine | 4-Chlorobenzene-sulfonylchloride |
| 20.7 | trans-4-Bromo-N-(4-{6-[(2-methoxy-ethyl)-methyl-amino]-hexyloxy}-cyclohexyl)-N-propyl-benzenesulfonamide | 547 (1 Br) | trans-(4-{6-[(2-Methoxy-ethyl)-methyl-amino]-hexyloxy}-cyclohexyl)-propyl-amine | 4-Bromobenzene-sulfonylchloride |
| 20.8 | trans-4-Chloro-N-(4-{6-[(2-methoxy-ethyl)-methyl-amino]-hexyloxy}-cyclohexyl)-N-(2,4,5-trifluoro-benzyl)-benzenesulfonamide | 605 (1 Cl) | trans-(4-{6-[(2-Methoxy-ethyl)-methyl-amino]-hexyloxy}-cyclohexyl)-(2,4,5-trifluoro-benzyl)-amine | 4-Chlorobenzene-sulfonylchloride |
| 20.9 | trans-4-Bromo-N-(4-{6-[(2-methoxy-ethyl)-methyl-amino]-hexyloxy}-cyclohexyl)-N-(2,4,5-trifluoro-benzyl)-benzenesulfonamide | 649 (1 Br) | trans-(4-{6-[(2-Methoxy-ethyl)-methyl-amino]-hexyloxy}-cyclohexyl)-(2,4,5-trifluoro-benzyl)-amine | 4-Bromobenzene-sulfonylchloride |

Example 21

1 eq of the amine is treated with chloroformate (1.1 eq for each $NH_2$) in (2-5 ml/mmol amine) dioxane in the presence of 1.1 eq of diisopropylamine at RT until no starting material can be detected with TLC. The solutions are diluted with EtOAc and washed with saturated aqueous $NaHCO_3$, brine and dried over $Na_2SO_4$. Flash chromatography or purification by prep HPLC [RP-18, acetonitrile (0.1% HCOOH)/water (0.1% HCOOH), 10% to 95% acetonitrile] followed by extraction with EtOAc and sat. $NaHCO_3/H_2O$ yields the free amines. The following compounds were prepared from the corresponding amines and chloroformates:

| Example | Compound | MS MH+ | Amine | Chloroformate |
|---|---|---|---|---|
| 21.1 | trans-(4-{6-[(2-Methoxy-ethyl)-methyl-amino]-hexyloxy}-cyclohexyl)-methyl-carbamic acid 4-chloro-phenyl ester | 455 (1 Cl) | trans-(4-{6-[(2-Methoxy-ethyl)-methyl-amino]-hexyl-oxy}-cyclohexyl)-methyl-amine | 4-Chlorophenyl-chloroformate |
| 21.2 | trans-(4-{6-[(2-Methoxy-ethyl)-methyl-amino]-hexyloxy}-cyclohexyl)-carbamic acid 4-chloro-phenyl ester | 441 (1 Cl) | trans-4-{6-[(2-Methoxy-ethyl)-methyl-amino]-hexyloxy}-cyclohexylamine | 4-Chlorophenyl-chlorofbrmate |
| 21.3 | trans-Ethyl-(4-{6-[(2-methoxy-ethyl)-methyl-amino]-hexyloxy}-cyclohexyl)-carbamic acid 4-chloro-phenyl ester | 469 (1 Cl) | trans-Ethyl-(4-{6-[(2-methoxy-ethyl)-methyl-amino]-hexyloxy}-cyclohexyl)-amine | 4-Chlorophenyl-chloroformate |
| 21.4 | trans-(4-{6-[(2-Methoxy-ethyl)-methyl-amino]-hexyloxy}-cyclohexyl)-propyl-carbamic acid 4-chloro-phenyl ester | 483 (1 Cl) | trans-(4-{6-[(2-Methoxy-ethyl)-methyl-amino]-hexyl-oxy}-cyclohexyl)-propyl-amine | 4-Chlorophenyl-chloroformate |
| 21.5 | trans-(4-{6-[(2-Methoxy-ethyl)-methyl-amino]-hexyloxy}-cyclohexyl)-(2,4,5-trifluoro-benzyl)-carbamic acid 4-chloro-phenyl ester | 585 (1 Cl) | trans-(4-{6-[(2-Methoxy-ethyl)-methyl-amino]-hexyl-oxy}-cyclohexyl)-(2,4,5-trifluoro-benzyl)-amine | 4-Chlorophenyl-chloroformate |

Example 22

Example 22.1

To 15.0 g (60 mmol) trans-4-Hydroxy-cyclohexylcarbamic acid benzyl ester suspended in 183 ml (1.2 mol, 20 eq) 1,6-Dibromohexane, 6.1 g (i8 mmol, 0.3 eq) tetrabutyl-ammoniumhydrogensulfate and 183 ml 50% aqueous NaOH were added. The mixture was stirred at RT for 4 days, $CH_2Cl_2$ was added and the layers were separated. The inorganic layer was extracted with $CH_2Cl_2$, the combined organic layers were washed with brine and dried over $Na_2SO_4$. The excess of dibromide was removed in vacuo and the residue was purified by column chromatography on silica gel with hexane:EtOAc 1:1 as eluent yielding 3.4 g (14%) trans-[4-(6-Bromo-hexyloxy)-cyclohexyl]-carbamic acid benzyl ester as white solid, MS: 412 (MH+, 1Br) and 11.2 g (32%) trans-(6-Bromo-hexyl)-[4-(6-bromo-hexyloxy)-cyclohexyl]-carbamic acid benzyl ester as yellow oil, MS: 574 (MH+, 2Br).

Example 22.2

In analogy to example 22.1, trans-[4-(5-Bromo-pentyloxy)-cyclohexyl]-carbamic acid benzyl ester was obtained as white solid, MS: 398 (MH+, 1Br), from trans-4-Hydroxy-cyclohexylcarbamic acid benzyl ester and 1,5-Dibromopentane.

Example 22.3

1.7 g (4.12 mmol) trans-[4-(6-Bromo-hexyloxy)-cyclohexyl]-carbamic acid benzyl ester in DMA were treated with 2.2 ml 5.6M (12.4 mmol, 3 eq) dimethylamine in ethanol. The solution was stirred at RT over night, concentrated and the residue was redissolved in $CH_2Cl_2$/5% aqueous $Na_2CO_3$, the phases were separated and the inorganic phase was extracted with $CH_2Cl_2$, the combined organic phases were washed with brine, dried over $Na_2SO_4$ and concentrated. The crude product was purified over silica gel with $CH_2Cl_2$:MeOH 9:1 yielding 1.3 g (84%) trans-[4-(6-Dimethylamino-hexyloxy)-cyclohexyl]-carbamic acid benzyl ester as light yellow solid, MS: 377 (MH+).

Example 22.4

In analogy to example 22.3, trans-[4-(5-Dimethylamino-pentyloxy)-cyclohexyl]-carbamic acid benzyl ester was obtained as light yellow solid, MS: 363 (MH+), from trans-[4-(5-Bromo-pentyloxy)-cyclohexyl]-carbamic acid benzyl ester and dimethylamine (33% in EtOH 5.6M).

Example 22.5

In analogy to example 22.3, trans-{4-[6-(Allyl-methyl-amino)-hexyloxy]-cyclohexyl}-carbamic acid benzyl ester was obtained as off-white solid, MS 403 (MH+), from trans-[4-(6-Bromo-hexyloxy)-cyclohexyl]-carbamic acid benzyl ester and N— allylmethylamine.

Example 23

Example 23.1

30 g (123.3 mmol) BOC-trans-1,4-amino cyclo-hexane carboxylic acid and 22 g (135.6 mmol) Carbonyl-di-imidazol were dissolved in 300 ml THF and stirred at RT for 30 min. 50 ml (1.23 mol) of methanol were added and the solution was refluxed for 3 h. The solution was evaporated under reduced pressure, dissolved in ether and washed with 1N HCl and water. The ether-phase was concentrated in vacuum to yield 31.7 g trans-4-tert-Butoxy carbonylamino-cyclohexane carboxylic acid methyl ester, MS: 275.4(M+NH$_4^+$).

Example 23.2

A solution of 1.52 g (40 mmol) LAH in 7 ml THF was refluxed and treated for 2.5 h with a solution of 5.15 g (20 mmol) of trans-4-tert-butoxycarbonylamino-cyclohexanecarboxylic acid methyl ester in 35 ml THF. The reaction was heated for 15 h, cooled (0° C.) and hydrolyzed with 10 ml water. The mixture was diluted with THF, dried over Na$_2$SO$_4$, filtered and evaporated. The residue was dissolved in CH$_2$Cl$_2$, dried over Na$_2$SO$_4$, filtered and evaporated to yield 2.89 g (100%) of trans-(4-Methylamino-cyclohexyl)-methanol, mp: 87-88° C.; MS: 143 (M).

Example 23.3

A solution of 1.00 g (7 mmol) of (trans)-(4-Methylamino-cyclohexyl)-methanol in 20 ml pyridine was treated at 0° C. with 1.80 (7.35 mmol) 4-(trifluoromethyl)-benzenesulfonyl chloride. The reaction was stirred 40 min at 0° C. and poured on ice-water. Acidification (25% HCl), extraction (Et$_2$O, 3×) and drying of the organic phase over Na$_2$SO$_4$ yielded after evaporation and flash column chromatography on silica gel with CH$_2$Cl$_2$/MeOH (99:1 to 98:2) 0.71 g (18%) trans-4-Trifluoromethyl-benzenesulfonic acid 4-[methyl-(4-trifluoromethyl-benzenesulfonyl)-amino]-cyclohexylmethyl ester, MS: 560 (MH$^+$), and 0.68 (28%) of trans-N-(4-Hydroxymethyl-cyclohexyl)-N-methyl-4-trifluoromethyl-benzenesulfonamide, MS: 352 (MH$^+$).

Example 23.4

4.60 g (32.14 mmol) of trans-(4-Methylamino-cyclohexyl)-methanol was suspended in 85 ml hexamethyldisilazane and refluxed for 5 h. The solution was evaporated under reduced pressure and dissolved in 50 ml THF. 6.14 g (32.14 mmol) of 4-chlorophenylchloroformate were added slowly at 0° C. and stirred for 16 h at room temperature. 30 ml H$_2$O were added and after 1 h the solvents were evaporated. The residue was extracted with water/Et$_2$O (3×), the organic phases were washed with 10% NaCl, dried over Na$_2$SO$_4$ and evaporated to yield after flash-chromatography on silica gel (hexane/EtOAc 4:1 to 1:1) 5.48 g (57%) of trans-(4-Hydroxymethyl-cyclohexyl)-methyl-carbamic acid 4-chloro-phenyl ester, MS: 298 (MH$^+$, 1Cl).

Example 23.5

A solution of 0.6 g (2.03 mmol) of trans-(4-Hydroxymethyl-cyclohexyl)-methyl-carbamic acid 4-chloro-phenyl ester in 15 ml CH$_2$Cl$_2$ was treated with 0.17 ml (2.24 mmol) methanesulfonylchloride, 0.5 ml (6.1 mmol) pyridine and 0.25 g (2.03 mmol) DMAP at 0° C. The reaction mixture was warmed up over night to room temperature, water (2 ml) was added and the reaction mixture was stirred for 5 min. After extraction with aqueous 10% KHSO$_4$/Et$_2$O (3×), the organic phases were washed with aqueous saturated NaHCO$_3$ (2×), aqueous 10% NaCl, dried over Na$_2$SO$_4$ and evaporated to yield 0.74 g (96%) of trans-Methanesulfonic acid 4-[(4-chloro-phenoxycarbonyl)-methyl-amino]-cyclohexylmethyl ester, mp: 134-135° C.; MS: 376 (MH$^+$, 1 Cl).

Example 23.6

[following a procedure of Belostotskii, Anatoly M.; Hassner, Alfred. Synthetic methods. 41. Etherification of hydroxysteroids via triflates. Tetrahedron Lett. (1994), 35(28), 5075-6.]. A solution of 0.175 ml (2 mmol) 3-bromo-1-propanol and 0.48 ml 2,6-di-tert-butylpyridine in 1 ml CH$_2$Cl$_2$ was treated at 0° C. with a solution of 0.35 ml (2.1 mmol) trifluoromethansulfonic anhydride in 0.5 ml CH$_2$Cl$_2$. After 2.5 h at 0° C., the violet solution was evaporated, dissolved in 1 ml nitromethane and treated with a solution of 0.375 g (1 mmol) trans-N-(4-Hydroxymethyl-cyclohexyl)-N-methyl-4-trifluoromethyl-benzenesulfonamide and 0.45 ml (2 mmol) 2,6-di-tert-butylpyridine in 3 ml nitromethane (during 3 min). The reaction was heated (60° C.) for 3.5 h and then extracted with aqueous 10% KHSO$_4$/EtOAc (3×). The organic phases were washed with aqueous saturated NaHCO$_3$, aqueous 10% NaCl, dried over Na$_2$SO$_4$ and evaporated. Purification by flash-chromatography on silica gel (hexane/EtOAc 9:1) yielded 0.3 g (64%) of trans-N-[4-(3-Bromo-propoxymethyl)-cyclohexyl]-N-methyl-4-trifluoromethyl-benzenesulfonamide, MS: 452 (M–F, 1Br).

Example 23.7

In analogy to example 23.6, trans-[4-(3-Bromo-propoxymethyl)-cyclohexyl]-methyl-carbamic acid 4-chlorophenyl ester, MS: 418 (MH$^+$, 1Br, 1Cl) was obtained from trans-(4-Hydroxymethyl-cyclohexyl)-methyl-carbamic acid 4-chloro-phenyl ester and 3-bromo-1-propanol.

Example 23.8

In analogy to example 23.6, trans-[4-(2-Bromo-ethoxymethyl)-cyclohexyl]-methyl-carbamic acid 4-chloro-phenyl ester, MS: 404 (MH$^+$, 1Br, 1Cl) was obtained from trans-(4-Hydroxymethyl-cyclohexyl)-methyl-carbamic acid 4-chloro-phenyl ester and 2-bromoethanol.

Example 23.9

A solution of 1.5 g (5.04 mmol) of trans-(4-Hydroxymethyl-cyclohexyl)-methyl-carbamic acid 4-chloro-phenyl in 30 ml of DMF was treated with 1.19 ml (15.11 mmol) of 1,4-dibromobutane and at 0° C. with 0.28 g (5.79 mmol) of 55% NaH in small portions. The reaction was stirred for 16 h at RT. The reaction was treated again with 1.19 ml (15.11 mmol) of 1,4-dibromobutane and at 0° C. with 0.28 g (5.79 mmol) of 55% NaH in small portions and stirred for 3 days at RT. The solution was then poured into cooled aqueous saturated NH$_4$Cl and extracted (Et$_2$O 3×). The organic phase was washed with water, dried over Na$_2$SO$_4$, evaporated and purified by flash silica gel column (first with hexane to remove the dibromobutane and then Hexane/EtOAc 4:1 to 1:1) to yield 0.59 g (27%) of trans-[4-(4-Bromo-butoxymethyl)-cyclohexyl]-methyl-carbamic acid 4-chloro-phenyl ester, MS: 432 (MH$^+$, 1Br, 1Cl).

Example 23.10

A solution of 69 mg (0.146 mmol) of trans-N-[4-(3-Bromo-propoxymethyl)-cyclohexyl]-N-methyl-4-trifluoromethyl-benzenesulfonamide in 0.8 ml DMA was treated at 0° C. with 0.028 ml (0.29 mmol) of N-allylmethylamine and stirred at RT for 22 h. The solution was cooled (0° C.) and treated again with 0.028 ml (0.29 mmol) of N-allylmethylamine. After 6 h at RT, the solution was concentrated and dissolved in aqueous saturated $NaHCO_3/Et_2O$ (3×). The organic phase was dried over $Na_2SO_4$ and evaporated. Flash column chromatography on silica gel with $CH_2Cl_2/MeOH$ (95:5) yielded 43 mg (64%) of trans-N-{4-[3-(Allyl-methyl-amino)-propoxymethyl]-cyclohexyl}-N-methyl-4-trifluoromethyl-benzenesulfonamide, MS: 463 ($MH^+$).

Example 23.11

In analogy to example 23.10, trans-N-(4-{3-[Ethyl-(2-hydroxy-ethyl)-amino]-propoxymethyl}-cyclohexyl)-N-methyl-4-trifluoromethyl-benzenesulfonamide, MS: 481 ($MH^+$), was obtained from trans-N-[4-(3-Bromo-propoxymethyl)-cyclohexyl]-N-methyl-4-trifluoromethyl-benzenesulfonamide and 2-ethylaminoethanol.

Example 23.12

In analogy to example 23.10, trans-N-[4-(3-Azetidin-1-yl-propoxymethyl)-cyclohexyl]-N-methyl-4-trifluoromethyl-benzenesulfonamide, MS: 449 ($MH^+$), was obtained from trans-N-[4-(3-Bromo-propoxymethyl)-cyclohexyl]-N-methyl-4-trifluoromethyl-benzenesulfonamide and trimethylenimine.

Example 23.13

In analogy to example 23.10, trans-N-Methyl-N-[4-(3-piperidin-1-yl-propoxymethyl)-cyclohexyl]-4-trifluoromethyl-benzenesulfonamide, MS: 477 ($MH^+$), was obtained from trans-N-[4-(3-Bromo-propoxymethyl)-cyclohexyl]-N-methyl-4-trifluoromethyl-benzenesulfonamide and piperidine.

Example 23.14

In analogy to example 23.10, trans-{4-[3-(Allyl-methyl-amino)-propoxymethyl]-cyclohexyl}-methyl-carbamic acid 4-chloro-phenyl ester, MS: 409 ($MH^+$, 1Cl) was obtained from trans-[4-(3-Bromo-propoxymethyl)-cyclohexyl]-methyl-carbamic acid 4-chloro-phenyl ester and N-allylmethylamine.

Example 23.15

In analogy to example 23.10, trans-(4-{3-[Ethyl-(2-hydroxy-ethyl)-amino]-propoxymethyl}-cyclohexyl)-methyl-carbamic acid 4-chloro-phenyl ester, MS: 427 ($MH^+$, 1Cl) was obtained from trans-[4-(3-Bromo-propoxymethyl)-cyclohexyl]-methyl-carbamic acid 4-chloro-phenyl ester and 2-ethylaminoethanol.

Example 23.16

In analogy to example 23.10, trans-[4-(3-Azetidin-1-yl-propoxymethyl)-cyclohexyl]-methyl-carbamic acid 4-chloro-phenyl ester, MS: 395 ($MH^+$, 1Cl) was obtained from trans-[4-(3-Bromo-propoxymethyl)-cyclohexyl]-methyl-carbamic acid 4-chloro-phenyl ester and trimethylenimine.

Example 23.17

In analogy to example 23.10, trans-Methyl-[4-(3-piperidin-1-yl-propoxymethyl)-cyclohexyl]-carbamic acid 4-chloro-phenyl ester, MS: 423 ($MH^+$, 1Cl) was obtained from trans-[4-(3-Bromo-propoxymethyl)-cyclohexyl]-methyl-carbamic acid 4-chloro-phenyl ester and piperidine.

Example 23.18

In analogy to example 23.10, trans-(4-{3-[Ethyl-(2-methoxy-ethyl)-amino]-propoxymethyl}-cyclohexyl)-methyl-carbamic acid 4-chloro-phenyl ester, MS: 441 ($MH^+$, 1Cl) was obtained from trans-[4-(3-Bromo-propoxymethyl)-cyclohexyl]-methyl-carbamic acid 4-chloro-phenyl ester and N-(2-methoxyethyl)ethylamine.

Example 23.19

In analogy to example 23.10, trans-{4-[4-(Allyl-methyl-amino)-butoxymethyl]-cyclohexyl}-methyl-carbamic acid 4-chloro-phenyl ester, MS: 423 ($MH^+$, 1Cl) was obtained from trans-[4-(4-Bromo-butoxymethyl)-cyclohexyl]-methyl-carbamic acid 4-chloro-phenyl ester and N-allylmethylamine.

Example 23.20

In analogy to example 23.10, trans-{4-[2-(Allyl-methyl-amino)-ethoxymethyl]-cyclohexyl}-methyl-carbamic acid 4-chloro-phenyl ester, MS: 395 ($MH^+$, 1Cl) was obtained from trans-[4-(2-Bromo-ethoxymethyl)-cyclohexyl]-methyl-carbamic acid 4-chloro-phenyl ester and N-allylmethylamine.

Example 24

Example 24.1

5.53 g (20 mmol) triphenylmethanethiol in 50 ml DMA were deprotonated at 0° C. with 0.87 g (20 mmol) of 55% NaH. The reaction was stirred for 30 min at RT, dropped slowly (30 min) to a cooled (0° C.) solution of 1.72 ml (20 mmol) of 1,2-dibromoethane in 50 ml DMA. The reaction mixture was stirred for 6 h at RT, cooled (0° C.) and treated with 3.83 ml (40 mmol) of N-allylmethylamine. After 16 h at RT, the reaction was cooled (0° C.) and treated again with 3.83 ml (40 mmol) of N-allylmethylamine. After 24 h at RT, the solution was concentrated and dissolved in aqueous saturated $NaHCO_3/Et_2O$ (3×). The organic phase was dried over $Na_2SO_4$ and evaporated. Flash column chromatography on silica gel with $CH_2Cl_2/MeOH$ (99.5:0.5 to 95:5) yielded 3.27 (44%) of Allyl-methyl-(2-tritylsulfanyl-ethyl)-amine, MS: 374 ($MH^+$).

Example 24.2

A solution of 1.12 g (3 mmol) of Allyl-methyl-(2-tritylsulfanyl-ethyl)-amine in 30 ml $CH_2Cl_2$ was treated at 0° C. with 8.7 ml TFA followed by 6.15 ml (30 mmol) triisopropylsilane. After 30 min at RT, the reaction mixture was evaporated, dissolved in toluene (3×) and evaporated. The TFA-salt was precipitated from ether/pentane. The oil was dissolved in ether, washed with aqueous saturated NaHCO$_3$, aqueous 10% NaCl, dried over Na$_2$SO$_4$ and evaporated carefully to yield 0.366 g (93%) of 2-(Allyl-methyl-amino)-ethanethiol, MS: 132 (MH$^+$).

Example 24.3

In analogy to examples 24.1 and 24.2, N-Allylmethylamine and 1,3-dibrompropane were converted to 3-(Allyl-methyl-amino)-propane-1-thiol, MS: 145 (MH$^+$).

Example 24.4

A solution of 280 mg (0.5 mmol) of trans-4-Trifluoromethyl-benzenesulfonic acid 4-[methyl-(4-trifluoromethyl-benzenesulfonyl)-amino]-cyclohexylmethyl ester and 78 mg (0.55 mmol) of 2-dimethylaminoethanethiol hydrochloride in 4.5 ml DMF was treated at 0° C. with 48 mg (1.1 mmol) of 55% NaH, stirred for 20 h at RT. After cooling (0° C.) and treatment with a catalytic amount of NaI followed by 78 mg (0.55 mmol) of 2-dimethylaminoethanethiol hydrochloride and 48 mg (1.1 mmol) of 55% NaH the reaction mixture was stirred for 18 h at RT. The reaction was neutralized (aqueous 10% KHSO$_4$, at 0° C.) and poured into aqueous sat. NaHCO$_3$/Et$_2$O (3×). The organic phases were washed with aqueous 10% NaCl solution, dried over Na$_2$SO$_4$ and evaporated. Purification by flash column chromatography on silica gel with CH$_2$Cl$_2$/MeOH (95:5) yielded 138 mg (63%) of trans-N-[4-(2-Dimethylamino-ethylsulfanylmethyl)-cyclohexyl]-N-methyl-4-trifluoromethyl-benzenesulfonamide, MS: 439 (MH$^+$).

Example 24.5

In analogy to example 24.4, trans-4-Trifluoromethyl-benzenesulfonic acid 4-[methyl-(4-trifluoromethyl-benzenesulfonyl)-amino]-cyclohexylmethyl ester and 2-(allyl-methyl-amino)-ethanethiol were converted to trans-N-{4-[2-(Allyl-methyl-amino)-ethylsulfanylmethyl]-cyclohexyl}-N-methyl-4-trifluoromethyl-benzenesulfonamide, MS: 465 (MH$^+$).

Example 24.6

In analogy to example 24.4, trans-4-Trifluoromethyl-benzenesulfonic acid 4-[methyl-(4-trifluoromethyl-benzenesulfonyl)-amino]-cyclohexylmethyl ester and 2-diethylaminoethanethiol hydrochloride with an excess of NaH were converted to trans-N-[4-(2-Diethylamino-ethylsulfanylmethyl)-cyclohexyl]-N-methyl-4-trifluoromethyl-benzenesulfonamide, MS: 467 (MH$^+$).

Example 24.7

In analogy to example 24.4, trans-Methanesulfonic acid 4-[(4-chloro-phenoxycarbonyl)-methyl-amino]-cyclohexylmethyl ester and 2-diethylaminoethanethiol hydrochloride with an excess of NaH were converted to trans-[4-(2-Diethylamino-ethylsulfanylmethyl)-cyclohexyl]-methyl-carbamic acid 4-chloro-phenyl ester, MS: 413 (MH$^+$, 1Cl).

Example 24.8

In analogy to example 24.4, trans-Methanesulfonic acid 4-[(4-chloro-phenoxycarbonyl)-methyl-amino]-cyclohexylmethyl ester and 2-(allyl-methyl-amino)-ethanethiol were converted to trans-{4-[2-(Allyl-methyl-amino)-ethylsulfanylmethyl]-cyclohexyl}-methyl-carbamic acid 4-chloro-phenyl ester, MS: 411 (MH$^+$, 1Cl).

Example 24.9

In analogy to example 24.4, trans-Methanesulfonic acid 4-[(4-chloro-phenoxycarbonyl)-methyl-amino]-cyclohexylmethyl ester and 3-(allyl-methyl-amino)-propane-1-thiol were converted to trans-{4-[3-(Allyl-methyl-amino)-propylsulfanylmethyl]-cyclohexyl}-methyl-carbamic acid 4-chloro-phenyl ester, MS: 425 (MH$^+$, 1Cl).

Example 24.10

In analogy to example 24.4, trans-Methanesulfonic acid 4-[(4-chloro-phenoxycarbonyl)-methyl-amino]-cyclohexylmethyl ester and 2-(dimethylamino)-ethane-1-thiol were converted to trans-[4-(2-Dimethylamino-ethylsulfanylmethyl)-cyclohexyl]-methyl-carbamic acid 4-chloro-phenyl ester, MS: 385 (MH$^+$, 1Cl).

Example 25

Example 25.1

To 1.72 g (4.58 mmol) trans-Methanesulfonic acid 4-[(4-chloro-phenoxycarbonyl)-methyl-amino]-cyclohexylmethyl ester in 17 ml DMF, 0.78 g (6.86 mmol, 1.5 eq) potassium thioacetate were added and the mixture was heated to 100° C. for 10 min. The mixture was concentrated under vacuum and the residue was dissolved in saturated NaHCO$_3$/Et$_2$O (3×). The organic phases were washed with brine, dried over Na$_2$SO$_4$ and evaporated to yield 1.69 g (quantitative) of trans-Thioacetic acid S-{4-[(4-chloro-phenoxycarbonyl)-methyl-amino]-cyclohexylmethyl}ester, MS: 356 (MH$^+$).

Example 25.2

A solution of 0.63 g (corresponds to 1.7 mmol) crude trans-Thioacetic acid S-{4-[(4-chloro-phenoxycarbonyl)-methyl-amino]-cyclohexylmethyl} ester in 20 ml degassed (Ar) ethanol was treated with 5.1 ml 1N LiOH and 10 min later with 0.5 ml (6.8 mmol) 2-bromo-ethanol. The reaction mixture was stirred for 1.25 h, cooled (0° C.) and neutralized with aqueous 10% KHSO$_4$/Et$_2$O (3×). The organic phases were washed with aqueous 10% NaCl and dried over Na$_2$SO$_4$ to yield after evaporation with toluene 0.67 g (quantitative) trans-[4-(2-Hydroxy-ethylsulfanylmethyl)-cyclohexyl]-methyl-carbamic acid 4-chloro-phenyl ester, MS: 358 (MH$^+$, 1Cl).

Example 25.3

A solution of 645 mg (corresponds to 1.65 mmol) of trans-[4-(2-Hydroxy-ethylsulfanylmethyl)-cyclohexyl]-methyl-carbamic acid 4-chloro-phenyl ester in 12 ml CH$_2$Cl$_2$ was treated at 0° C. with 0.14 ml (1.82 mmol) methanesulfonylchloride, 0.20 ml (2.45 mmol) pyridine and 202 mg (1.65 mmol) DMAP. The reaction mixture was warmed up over night to room temperature. Water (2 ml) was added and the reaction was stirred for 5 min. After extraction with aqueous 10% KHSO$_4$/Et$_2$O (3×), the organic phases were washed with aqueous saturated NaHCO$_3$ (2×), aqueous 10% NaCl, dried over Na$_2$SO$_4$ and evaporated to yield 650 mg (quantitative) trans-[4-(2-Chloro-ethylsulfanylmethyl)-cyclohexyl]-methyl-carbamic acid 4-chloro-phenyl ester, MS: 376 (MH$^+$, 2Cl).

Example 25.4

A solution of 94 mg (0.25 mmol) of trans-[4-(2-Chloro-ethylsulfanylmethyl)-cyclohexyl]-methyl-carbamic acid 4-chloro-phenyl ester in 1 ml DMA was treated with a catalytic amount of NaI and with 0.05 ml (0.5 mmol) of 2-ethylaminoethanol and stirred at RT for 16 h. The reaction mixture was stirred for 1 week, adding every day twice 0.05 ml (0.5 mmol) of 2-ethylaminoethanol. The solution was concentrated and the residual oil was extracted with aqueous sat. $NaHCO_3/Et_2O$ (3×). The organic phases were washed with aqueous 10% NaCl solution and dried over $Na_2SO_4$ to yield after flash column chromatography on silica gel ($CH_2Cl_2$MeOH 95:5) 40 mg (39%) of trans-(4-{2-[Ethyl-(2-hydroxy-ethyl)-amino]-ethylsulfanylmethyl}-cyclo-hexyl)-methyl-carbamic acid 4-chloro-phenyl ester, MS: 429 ($MH^+$, 1Cl).

Example 25.5

In analogy to example 25.4, trans-[4-(2-Chloro-ethylsulfanylmethyl)-cyclohexyl]-methyl-carbamic acid 4-chloro-phenyl ester and N-methylpropylamine were converted to trans-Methyl-{4-[2-(methyl-propyl-amino)-ethylsulfanylmethyl]-cyclohexyl}-carbamic acid 4-chloro-phenyl ester, MS: 429 ($MH^+$, 1Cl).

Example 26

Example 26.1

A solution of 20 g (82.2 mmol) trans-4-tert-Butoxycarbonylamino-cyclohexanecarboxylic acid in 1.2 l $CH_2Cl_2$ was treated with 12.83 g (131.5 mmol) N,O-dimethylhydroxylamine hydrochloride, 10.85 ml (98.6 mmol) N-methylmorpholine and at 0° C. with 18.91 g (98.64 mmol) EDCI and 12.62 g (82.2 mmol) HOBT. The reaction mixture was stirred 2 h at room temperature and extracted with aqueous 10% $KHSO_4/Et_2O$ (3×). The organic phases were washed with aqueous saturated $NaHCO_3$, 10% NaCl and dried over $Na_2SO_4$ to yield 24.25 g (quantitative) trans-[4-(Methoxy-methyl-carbamoyl)-cyclohexyl]-carbamic acid tert-butyl ester, mp: 130-140° C., slowly dec.; MS: 287 ($MH^+$).

Example 26.2

A solution of 24.18 g (82 mmol) of trans-[4-(Methoxy-methyl-carbamoyl)-cyclohexyl]-carbamic acid tert-butyl ester in 80 ml of DMF was treated at 0° C. with 5.37 g (123 mmol) of 55% NaH in small portions. The reaction was stirred for 1 h at 0° C., then treated slowly (20 min) with 40.9 ml (656 mmol) iodomethane and warmed up to RT over night. The reaction is cooled and neutralized with aqueous 10% $KHSO_4$ and poured into water/$Et_2O$ (3×). The organic phase was washed with aqueous 10% NaCl, dried over $Na_2SO_4$ evaporated and purified by flash silica gel column ($CH_2Cl_2$/EtOAc 9:1 to 1:1) to yield 20.69 g (84%) of trans-[4-(Methoxy-methyl-carbamoyl)-cyclohexyl]-methyl-carbamic acid tert-butyl ester, MS: 301 ($MH^+$).

Example 26.3

A solution of 2.09 g (55 mmol) LAH in 250 ml THF was cooled (−50° C.) and treated during 25 min with a solution of 15.02 g (50 mmol) of trans-[4-(Methoxy-methyl-carbamoyl)-cyclohexyl]-methyl-carbamic acid tert-butyl ester in 250 ml THF. The reaction was warmed up to +15° C. for 3.5 h, cooled (−78° C.) and hydrolyzed with a suspension of 15 g $MgSO_4.7H_2O$, 15 g silica gel in 50 ml aqueous 10% $KHSO_4$. The cooling bath was removed, THF was added, the mixture was stirred for 30 min and filtered. After evaporation, the residue was dissolved in $CH_2Cl_2$, dried over $Na_2SO_4$ and evaporated to yield 12.83 (quantitative) trans-(4-Formyl-cyclohexyl)-methyl-carbamic acid tert-butyl ester, MS: 241 (M).

Example 26.4

A solution of 52.45 g (200 mmol) triphenylphosphine in 200 ml $CH_2Cl_2$ was treated with 33.16 g (100 mmol) tetrabromomethane (the reaction heated up to reflux) and after 50 min with 32.06 ml (230 mmol) triethylamine (the reaction heated up to reflux and became dark violet). After cooling (0° C.), 12.83 g (50 mmol) of trans-(4-Formyl-cyclohexyl)-methyl-carbamic acid tert-butyl ester in 125 ml $CH_2Cl_2$ were added during 10 min. The solution was stirred for 16 h at RT, evaporated and filtered through silica gel (deactivated with hexane/$Et_3N$) with hexane and then hexane/ether 4:1 to 1:1 as eluent to yield 13.28 g (67%) of trans-[4-(2,2-Dibromo-vinyl)-cyclohexyl]-methyl-carbamic acid tert-butyl ester, mp: 93-99° C., dec.; MS: 396 ($MH^+$, 2Br).

Example 26.5

The following reaction was performed in analogy to the reaction described in: Marshall, James A.; Bartley, Gary S.; Wallace, Eli M. Total Synthesis of the Pseudopterane (−)-Kallolide B, the Enantiomer of Natural (+)-Kallolide B. J. Org. Chem. (1996), 61(17), 5729-5735 and Baker, Raymond; Boyes, Alastair L.; Swain, Christopher J. Synthesis of talaromycins A, B, C, and E. J. Chem. Soc., Perkin trans. 1 (1990), (5), 1415-21.). A solution of 993 mg (2.5 mmol) of trans-[4-(2,2-Dibromo-vinyl)-cyclohexyl]-methyl-carbamic acid tert-butyl ester in 20 ml THF was treated at −78° C. with 3.28 ml (5.25 mmol) of BuLi (ca 1.6 M in hexane). After 2 h at this temperature 790 mg (25 mmol) of paraformaldehyde were added. The reaction mixture was warmed up to RT for 3 h and after 1 h at this temperature extracted with water/ether (3×). The organic phases were washed with aqueous 10% NaCl, dried over $Na_2SO_4$ and evaporated. Purification by flash-chromatography on silica gel (hexane/EtOAc 4:1) yielded 530 g (79%) of trans-[4-(3-Hydroxy-prop-1-ynyl)-cyclohexyl]-methyl-carbamic acid tert-butyl ester, MS: 268 ($MH^+$).

Example 26.6

A solution of 3.97 g (10 mmol) of trans-[4-(2,2-Dibromo-vinyl)-cyclohexyl]-methyl-carbamic acid tert-butyl ester in 160 ml THF was treated at −78° C. with 13.13 ml (21 mmol) of BuLi (ca 1.6 M in hexane) and stirred for 2 h. 11 ml DMPU were added and 10 min later 4.60 g (20 mmol) of 1-bromo-3-tetrahydropyranyloxypropane in 15 ml THF were added over a period of 20 min. The reaction mixture was warmed up to RT for 16 h, cooled, poured into cooled aqueous saturated $NH_4Cl$ and extracted ($Et_2O$ 3×). The organic phase was washed with aqueous 10% NaCl, water, dried over $Na_2SO_4$, evaporated and purified by flash silica gel column (Hexane/EtOAc 98:2 to 90:10) to yield 1.61 g (42%) of trans-Methyl-{4-[5-(tetrahydro-pyran-2-yloxy)-pent-1-ynyl]-cyclohexyl}-carbamic acid tert-butyl ester, MS: 378 (M−H).

Example 26.7

A solution of 520 mg (1.95 mmol) of trans-[4-(3-Hydroxy-prop-1-ynyl)-cyclohexyl]-methyl-carbamic acid tert-butyl ester in 14 ml $CH_2Cl_2$ was treated at 0° C. with 0.17 ml (2.14 mmol) methanesulfonylchloride, 0.235 ml (2.92 mmol) pyridine and 238 mg (1.95 mmol) DMAP. The reaction mixture was warmed up over night to room temperature, water (2 ml) was added and the reaction was stirred for 5 min. After extraction with aqueous 10% $KHSO_4/Et_2O$ (3×) the organic phases were washed with aqueous saturated $NaHCO_3$ (2×), aqueous 10% NaCl, dried over $Na_2SO_4$ and evaporated to yield 435 mg (65%) of trans-Methanesulfonic acid 3-[4-(tert-butoxycarbonyl-methyl-amino)-cyclohexyl]-prop-2-ynyl ester, MS: 345 (M).

Example 26.8

A solution of 420 mg (1.22 mmol) of trans-Methanesulfonic acid 3-[4-(tert-butoxycarbonyl-methyl-amino)-cyclohexyl]-prop-2-ynyl ester in 4 ml DMA was treated at 0° C. with 0.234 ml (2.43 mmol) of N-allylmethylamine and stirred at RT for 16 h. The solution was concentrated and the residual oil was extracted with aqueous sat. $NaHCO_3/Et_2O$ (3×). The organic phases were washed with aqueous 10% NaCl solution and dried over $Na_2SO_4$ to yield after flash column chromatography on silica gel with hexane/EtOAc (2:1) 355 mg (91%) trans-{4-[3-(Allyl-methyl-amino)-prop-1-ynyl]-cyclohexyl}-methyl-carbamic acid tert-butyl ester, MS: 321 ($MH^+$).

Example 26.9

A solution of 200 mg (0.62 mmol) of trans-{4-[3-(Allyl-methyl-amino)-prop-1-ynyl]-cyclohexyl}-methyl-carbamic acid tert-butyl ester in 3.5 ml $CH_2Cl_2$ was treated at 0° C. with 1.7 ml TFA (for 20 min). After 30 min at this temperature, the reaction mixture was evaporated, treated with 1 N $NaOH/CH_2Cl_2$ (3×). The organic phase was dried over $Na_2SO_4$ and evaporated to yield 147 mg (quantitative) of trans-{4-[3-(Allyl-methyl-amino)-prop-1-ynyl]-cyclohexyl}-methyl-amine, MS: 221 ($MH^+$).

Example 26.10

A solution of 66 mg (0.3 mmol) of trans-{4-[3-(Allyl-methyl-amino)-prop-1-ynyl]-cyclohexyl}-methyl-amine in 0.3 ml dioxane was treated with 0.103 ml (0.6 mmol; 2 equivalents) Huenig's base and dropwise with a solution of 0.042 ml (0.27 mmol) 4-chlorophenylchloroformate in 0.16 ml dioxane (during 10 min). After 5 min at RT, the mixture was dissolved in aqueous saturated $NaHCO_3/Et_2O$ (3×). The organic phase was dried over $Na_2SO_4$ and evaporated. Flash column chromatography on silica gel with $CH_2Cl_2/MeOH$ (99:1 to 97:3) yielded 68 mg (61%) of trans-{4-[3-(Allyl-methyl-amino)-prop-1-ynyl]-cyclohexyl}-methyl-carbamic acid 4-chloro-phenyl ester, MS: 375 ($MH^+$, 1Cl).

Example 26.11

In a similar way as described in example 26.5, trans-[4-(2,2-Dibromo-vinyl)-cyclohexyl]-methyl-carbamic acid tert-butyl ester and dimethylcarbamoyl chloride gave trans-(4-Dimethylcarbamoylethynyl-cyclohexyl)-methyl-carbamic acid tert-butyl ester, mp: 115-117° C.; MS: 309 ($MH^+$).

Example 27

Example 27.1

A solution of 975 mg (3.28 mmol) of trans-[4-(2,2-Dibromo-vinyl)-cyclohexyl]-methyl-carbamic acid tert-butyl ester in 20 ml $CH_2Cl_2$ was treated at 0° C. with 10 ml TFA (for 20 min). After 2 h at RT, the reaction was evaporated, treated with aqueous saturated $NaHCO_3$(+$Na_2CO_3$)/$Et_2O$ (3×), dried over $Na_2SO_4$ and evaporated to yield 981 mg (87%) of trans-[4-(2,2-Dibromo-vinyl)-cyclohexyl]-methyl-amine, MS: 295 (M, 2Br).

Example 27.2

In analogy to example 26.10 trans-[4-(2,2-Dibromo-vinyl)-cyclohexyl]-methyl-amine and 4-chlorophenylchloroformate were converted to trans-[4-(2,2-Dibromo-vinyl)-cyclohexyl]-methyl-carbamic acid 4-chloro-phenyl ester, MS: 449 (M, 2Br, 1 Cl).

Example 27.3

In analogy to example 26.5, trans-[4-(2,2-Dibromo-vinyl)-cyclohexyl]-methyl-carbamic acid 4-chloro-phenyl ester and BuLi (ca 1.6 M in hexane) with paraformaldehyde were converted to trans-[4-(3-Hydroxy-prop-1-ynyl)-cyclohexyl]-methyl-carbamic acid 4-chloro-phenyl ester, MS: 321 (M, 1Cl).

Example 27.4

In analogy to example 26.7, trans-[4-(3-Hydroxy-prop-1-ynyl)-cyclohexyl]-methyl-carbamic acid 4-chloro-phenyl ester and methanesulfonylchloride/pyridine were converted to trans-Methanesulfonic acid 3-{4-[(4-chloro-phenoxycarbonyl)-methyl-amino]-cyclohexyl}-prop-2-ynyl ester, MS: 400 ($MH^+$, 1Cl).

Example 27.5

In analogy to example 26.8, trans-Methanesulfonic acid 3-{4-[(4-chloro-phenoxycarbonyl)-methyl-amino]-cyclohexyl}-prop-2-ynyl ester and 2-ethylaminoethanol were converted to trans-(4-{3-[Ethyl-(2-hydroxy-ethyl)-amino]-prop-1-ynyl}-cyclohexyl)-methyl-carbamic acid 4-chloro-phenyl ester, MS: 393 ($MH^+$, 1Cl).

Example 28

Example 28.1

A suspension of 65 mg (0.165 mmol) of trans-(4-{3-[Ethyl-(2-hydroxy-ethyl)-amino]-prop-1-ynyl}-cyclohexyl)-methyl-carbamic acid 4-chloro-phenyl ester in 5 ml MeOH and 7 mg Pt/C 10% was hydrogenated (1 atm) for 16 h. The reaction was filtered (Celite) and evaporated. Flash column chromatography on silica gel with $CH_2Cl_2/MeOH$ (9:1) gave 21 mg (32%) of trans-(4-{3-[Ethyl-(2-hydroxy-ethyl)-amino]-propyl}-cyclohexyl)-methyl-carbamic acid 4-chloro-phenyl ester, MS: 397 ($MH^+$, 1Cl).

Example 28.2

In analogy to example 28.1, trans-N-(4-{3-[Ethyl-(2-hydroxy-ethyl)-amino]-prop-1-ynyl}-cyclohexyl)-N-methyl-4-trifluoromethyl-benzenesulfonamide gave trans-N-(4-{3-

[Ethyl-(2-hydroxy-ethyl)-amino]-propyl}-cyclohexyl)-N-methyl-4-trifluoromethyl-benzenesulfonamide, MS: 451 (MH+).

Example 28.3

In analogy to example 28.1, trans-N-(4-{3-[Bis-(2-hydroxy-ethyl)-amino]-prop-1-ynyl}-cyclohexyl)-N-methyl-4-trifluoromethyl-benzenesulfonamide gave trans-N-(4-{3-[Bis-(2-hydroxy-ethyl)-amino]-propyl}-cyclohexyl)-N-methyl-4-trifluoromethyl-benzenesulfonamide, MS: 467 (MH+).

Example 29

Example 29.1

16.2 g (62.95 mmol) of 4-trans-4-tert-Butoxy carbonylamino-cyclohexanecarboxylic acid methyl ester and 5.87 ml (94.43 mmol) of methyl iodid in 100 ml DMF were treated under stirring and ice-cooling with 3.57 g (81.84 mmol) of NaH (55% in oil). The solution was stirred at RT for 20 h and then treated under ice-cooling with 1N HCl. The reaction-mixture was dissolved in ether and washed 4 times with water. The ether-phases were concentrated in vacuum to yield 17.5 g of clean trans-4-(tert-Butoxycarbonyl-methyl-amino)-cyclohexanecarboxylic acid methyl ester, MS: 201 (M–OC$_4$H$_9$).

Example 29.2

17.1 g (62.95 mmol) of trans-4-(tert-Butoxycarbonyl-methyl-amino)-cyclohexanecarboxylic acid methyl ester, dissolved in 150 ml of THF, were treated with 2.74 g (126 mmol) LiBH$_4$. The reaction-mixture was stirred under reflux for 6 h and then 200 ml of 1N HCl were dropped to the solution under ice-cooling. The mixture was dissolved in ether and washed with water. The solvent was evaporated under reduced pressure yielding 16.2 g trans-(4-Hydroxymethyl-cyclo-hexyl)-methyl-carbamic acid tert-butyl ester.

Example 29.3

To a dry-ice cooled solution of 8.94 ml (125.9 mmol) DMSO in 150 ml CH$_2$Cl$_2$ was added 5.95 ml (69.24 mmol) oxalylchloride. After 5 min at −78° C., a solution of 16.2 g (66.5 mmol) trans-(4-Hydroxymethyl-cyclohexyl)-methyl-carbamic acid tert-butyl ester in 50 ml of CH$_2$Cl$_2$, was added slowly. 10 min later, 43.8 ml (314.75 mmol) of Et$_3$N was added, and the mixture was allowed to attain RT. The mixture was partitioned between Et$_2$O/1N HCl and water. The solvent was evaporated under reduced pressure yielding 16.12 g of clean (4-Formyl-cyclohexyl)-methyl-carbamic acid tert-butyl ester, MS: 241 (M).

Example 29.4

To a solution of 13.71 g (56.8 mmol) trans-(4-Formyl-cyclohexyl)-methyl-carbamic acid tert-butyl ester and 17.8 g (83.46 mmol) triethyl-phosphono-acetat in 150 ml ethanol was added under ice-cooling, 6.0 g (110 mmol) NaOMe. After stirring the reaction mixture for 20 h at RT, it was concentrated under reduced pressure and then extracted with Et$_2$O and water. The organic layer was evaporated to dryness and the crude product purified by chromatography on silica gel with EtOAc/Hexane 1:4 yielding 8.4 g (56%, 4 steps) of clean trans-3-[4-(tert-Butoxy carbonyl methyl-amino)-cyclohexyl]-acrylic acid ethyl-ester, MS: 238 (M–OtBu).

Example 29.5

A solution of 6 g (19.26 mmol) trans-3-[4-(tert-Butoxy carbonyl methyl-amino)-cyclohexyl]-acrylic acid ethyl-ester and 600 mg of Pd/C (10%) was stirred over H$_2$-atmosphere for 20 h. After filtration of the solution, the methanol was evaporated under reduced pressure to yield 5.82 g of clean trans-3-[4-(tert-Butoxycarbonyl methyl-amino)cyclohexyl]-propanoic acid ethyl-ester. To a solution of this ester in 60 ml of THF was added 917 mg (40 mmol) LiBH$_4$. The solution was refluxed for 8 h and then cooled with an ice-bath to 0° C. At this temperature was dropped slowly 1N HCl to the reaction-mixture to destroy excess of LiBH$_4$. The reaction-mixture was diluted with Et$_2$O and then washed with water: The organic layers were evaporated to dryness to yield 3.39 g (73%) of clean trans-[4-(3-Hydroxy-propyl)-cyclohexyl]-methyl-carbamic acid tert-butyl ester, MS: 271 (M).

Example 29.6

1.4 ml (16.24 mmol) oxalylchloride was added to a dry-ice cooled solution (−78° C.) of 1.78 ml (25 mmol) DMSO in 40 ml CH$_2$Cl$_2$. After 10 min. stirring at −78° C., 2.39 g (12.49 mmol) of trans-[4-(3-Hydroxy-propyl)-cyclohexyl]-methyl-carbamic acid tert-butyl ester, dissolved in 5 ml CH$_2$Cl$_2$, was added. 15 min later, 8.7 ml (62.4 mmol) Et$_3$N was added and the reaction-mixture was allowed to attain RT. The mixture was diluted with Et$_2$O and then washed with 1N HCl and water. After evaporation of the solvents, a solution of crude trans-Methyl-[4-(3-oxo-propyl)-cyclohexyl]-carbamic acid tert-butyl ester (3.24 g, 12.02 mmol) and of 2.73 ml (13.3 mmol) triethyl phosphono acetate in 30 ml ethanol, was treated under ice-cooling with 1.37 g (24.05 mmol) NaOMe. The solution was stirred for 20 h at RT, and then concentrated in vacuo. The crude residue was dissolved in Et$_2$O and washed with water. The organic layers were concentrated in vacuo and the crude product purified by chromatography on silica gel with EtOAc/Hexane 1:4 to yield 2.46 g (58%, 2 steps) of clean trans-5-[4-(tert-Butoxycarbonyl-methyl-amino)-cyclohexyl]-pent-2-enoic acid ethyl ester, MS: 339 (M).

Example 29.7

A solution of 2.45 g (7.2 mmol) trans-5-[4-(tert-Butoxycarbonyl-methyl-amino)-cyclohexyl]-pent-2-enoic acid ethyl ester and 200 mg of Pd/C (10%) in 40 ml MeOH was stirred for 20 h under H$_2$-atmosphere. After filtration and evaporation of the methanol under vacuo, 2.39 g 5-[4-(tert-Butoxy carbonyl-methyl-amino)-cyclohexyl]-pentanoic acid ethyl ester could be isolated. 2.05 g (6.0 mmol) of this ester and 470 mg (12 mmol) of LiAlH$_4$ were stirred in 20 ml of THF at RT for 5 h. Exess of LiAlH$_4$ was destroyed by adding 10 ml of EtOAc and by carefully dropping brine to the reaction-mixture. The solution was dissolved in ether and washed with 1N HCl and water. The organic phase was concentrated under reduced pressure yielding 1.75 g (97%) of clean trans-[4-(5-Hydroxy pentyl)-cyclohexyl)-methyl-carbamic acid tert-butyl ester, MS: 300 (MH+).

Example 29.8

To a solution of 1.75 g (5.84 mmol) trans-[4-(5-Hydroxy pentyl)-cyclohexyl)-methyl-carbamic acid tert-butyl ester and 0.5 ml (6.42 mmol) of methanesulfonyl chloride in 20 ml $CH_2Cl_2$ was added, under cooling with an ice bath, 1.56 ml (11.7 mmol) of $Et_3N$. The mixture was stirred for 3 h at RT. The reaction-mixture was then partitioned between ether/1N HCl and water. The ether-solution was concentrated in vacuo to yield 2.12 g (96%) of clean trans-Methansulfonic acid 5[-4-(tert-butoxy carbonyl-methyl-amino)-cyclohexyl)-pentylester.

Example 29.9

200 mg (0.53 mmol) of trans-Methansulfonic acid 5[-4-(tert-butoxy carbonyl-methyl-amino)-cyclohexyl)-pentyl ester, dissolved in 2 ml of $CH_2Cl_2$, was treated with 2 ml of TFA. After stirring for 20 min at RT, the solution was concentrated in vacuo to yield 245 mg of pure trans-Methansulfonic acid 5-(4-methyl amino-cyclohexyl)-pentylester.trifluoroacetic acid salt, MS: 278 ($MH^+$).

Example 29.10

To a solution of 245 mg (0.53 mmol) trans-Methansulfonic acid 5-(4-methyl amino-cyclohexyl)-pentyl ester.trifluoroacetic acid salt and 143.5 mg (0.75 mmol) 4-chlorophenyl chloroformate in 4 ml dioxane, was added at RT 1.54 ml (3.12 mmol) Hünig's base. The mixture was stirred for 1 h, then extracted with EtOAc/1N HCl and water. The organic phases were concentrated under reduced pressure and purified by chromatography on silica gel with EtOAc/hexane 1:3 to yield 167 mg (73%, 2 steps) of pure trans-Methanesulfonic acid 5-{4-[(4-chloro-phenoxycarbonyl)-methyl-amino]-cyclohexyl}-pentyl ester, MS: 432 ($MH^+$, 1Cl).

Example 29.11

A solution of 160 mg (0.37 mmol) trans-Methanesulfonic acid 5-{4-[(4-chloro-phenoxycarbonyl)-methyl-amino]-cyclohexyl}-pentyl ester and of 0.21 ml N-allylmethylamine in 3 ml of methanol was stirred over night at 60° C. The solution was concentrated in vacuo, and the residue then purified by chromatography on silica gel with 1N $NH_3$/methanol 1:10 to yield 110 mg pure trans-{4-[5-(Allyl-methyl-amino)-pentyl]-cyclohexyl}-methyl-carbamic acid 4-chloro-phenyl ester, MS: 407 ($MH^+$, 1Cl).

Example 29.12

In analogy to examples 29.10 and 29.11, trans-Methansulfonic acid 5-(4-methyl amino-cyclohexyl)-pentyl ester.trifluoroacetic acid salt and 4-trifluoromethyl-phenyl chloroformate were reacted, followed by treatment with N-allylmethylamine to yield trans-{4-[5-(Allyl-methyl-amino)-pentyl]-cyclohexyl}-methyl-carbamic acid 4-trifluoromethyl-phenyl ester, MS: 441 ($MH^+$).

Example 29.13

In analogy to examples 29.10 and 29.11, trans-Methansulfonic acid 5-(4-methyl amino-cyclohexyl)-pentyl ester.trifluoroacetic acid salt and 4-trifluoromethyl-phenyl chloroformate were reacted, followed by treatment with 2-ethylamino-ethanol to yield trans-(4-{5-[Ethyl-(2-hydroxy-ethyl)-amino]-pentyl}-cyclohexyl)-methyl-carbamic acid 4-trifluoromethyl-phenyl ester, MS: 459 ($MH^+$).

Example 29.14

In analogy to examples 29.10 and 29.11, trans-Methansulfonic acid 5-(4-methyl amino-cyclohexyl)-pentyl ester.Trifluoroacetic acid salt and 4-bromophenyl chloroformate were reacted, followed by treatment with N-allylmethylamine to yield trans-{4-[5-(Allyl-methyl-amino)-pentyl]-cyclohexyl}-methyl-carbamic acid 4-bromo-phenyl ester, MS: 451 ($MH^+$, 1Br).

Example 29.15

In analogy to examples 29.10 and 29.11, trans-Methansulfonic acid 5-(4-methyl amino-cyclohexyl)-pentyl ester.Trifluoroacetic acid salt and 4-bromophenyl chloroformate were reacted, followed by treatment with by 2-ethylamino-ethanol to yield trans-(4-{5-[Ethyl-(2-hydroxy-ethyl)-amino]-pentyl}-cyclohexyl)-methyl-carbamic acid 4-bromo-phenyl ester, MS: 469 ($MH^+$, 1Br).

Example 29.16

In analogy to examples 29.10 and 29.11, trans-Methansulfonic acid 5-(4-methyl amino-cyclohexyl)-pentyl ester.Trifluoroacetic acid salt and 3,4-difluoro-phenyl chloroformate were reacted, followed by treatment with N-allylmethylamine to yield trans-{4-[5-(Allyl-methyl-amino)-pentyl]-cyclohexyl}-methyl-carbamic acid 3,4-difluoro phenyl ester, MS: 409 ($MH^+$).

Example 29.17

In analogy to examples 29.10 and 29.11, trans-Methansulfonic acid 5-(4-methyl amino-cyclohexyl)-pentyl ester.Trifluoroacetic acid salt and 3,4-difluoro-phenyl chloroformate were reacted, followed by treatment with 2-ethylamino-ethanol to yield trans-(4-{5-[Ethyl-(2-hydroxy-ethyl)-amino]-pentyl}-cyclohexyl)-methyl-carbamic acid 3,4-difluoro-phenyl ester, MS: 427 ($MH^+$).

Example 29.18

In analogy to examples 29.10 and 29.11, trans-Methansulfonic acid 5-(4-methyl amino-cyclohexyl)-pentyl ester.Trifluoroacetic acid salt and 4-(trifluoromethyl)benzenesulphonyl chloride were reacted, followed by treatment with N-allylmethylamine to yield trans-N-{4-[5-(Allyl-methyl-amino)-pentyl]-cyclohexyl}-N-methyl-4-trifluoromethyl-benzenesulfonamide, MS: 461 ($MH^+$).

Example 29.19

In analogy to examples 29.10 and 29.11, trans-Methansulfonic acid 5-(4-methyl amino-cyclohexyl)-pentyl ester.Trifluoroacetic acid salt and 4-(trifluoromethyl)benzenesulphonyl chloride were reacted, followed by treatment with 2-ethylamino-ethanol to yield trans-N-(4-{5-[Ethyl-(2-hydroxy-ethyl)-amino]-pentyl}-cyclohexyl)-N-methyl-4-trifluoromethyl-benzenesulfonamide, MS: 479 ($MH^+$).

Example 29.20

In analogy to examples 29.10 and 29.11, trans-Methansulfonic acid 5-(4-methyl amino-cyclohexyl)-pentyl ester.Trifluoroacetic acid salt and 3,5-difluoro-phenyl chloroformate were reacted, followed by treatment with N-allyl-N-methylamine to give trans-{4-[5-(Allyl-methyl-amino)-pentyl]-cyclohexyl}-methyl-carbamic acid 3,5-difluoro-phenyl ester, MS: 409 (MH$^+$).

Example 29.21

In analogy to examples 29.10 and 29.11, trans-Methansulfonic acid 5-(4-methyl amino-cyclohexyl)-pentyl ester.Trifluoroacetic acid salt and 3,5-difluoro-phenyl chloroformate were reacted, followed by treatment with 2-ethylamino-ethanol to give trans-(4-{5-[Ethyl-(2-hydroxy-ethyl)-amino]-pentyl}-cyclohexyl)-methyl-carbamic acid 3,5-difluoro-phenyl ester, MS: 427 (MH$^+$).

Example 29.22

In analogy to examples 29.10 and 29.11, trans-Methansulfonic acid 5-(4-methyl amino-cyclohexyl)-pentyl ester.Trifluoroacetic acid salt and 4-chlorophenyl chloroformate were reacted, followed by treatment with 2-ethylamino-ethanol to give trans-(4-{5-[Ethyl-(2-hydroxy-ethyl)-amino]-pentyl}-cyclohexyl)-methyl-carbamic acid 4-chloro-phenyl ester, MS: 425 (MH$^+$, 1Cl).

Example 29.23

In analogy to examples 29.10 and 29.11, trans-Methansulfonic acid 5-(4-methyl amino-cyclohexyl)-pentyl ester.Trifluoroacetic acid salt and 4-chlorophenyl chloroformate were reacted, followed by treatment with methyl-propyl-amine to give trans-Methyl-{4-[5-(methyl-propyl-amino)-pentyl]-cyclohexyl}-carbamic acid 4-chloro-phenyl ester, MS: 409 (MH$^+$, 1Cl).

Example 29.24

In analogy to examples 29.10 and 29.11, trans-Methansulfonic acid 5-(4-methyl amino-cyclohexyl)-pentyl ester.Trifluoroacetic acid salt and 4-chlorophenyl chloroformate were reacted, followed by treatment with dimethylamine to give trans-Methyl-{4-[5-(dimethylamino)-pentyl]-cyclohexyl}-carbamic acid 4-chloro-phenyl ester, MS: 381 (MH$^+$, 1Cl).

Example 29.25

In analogy to examples 29.10 and 29.11, trans-Methansulfonic acid 5-(4-methyl amino-cyclohexyl)-pentyl ester.Trifluoroacetic acid salt and 4-chlorophenyl chloroformate were reacted, followed by treatment with piperidine to give trans-Methyl-[4-(5-piperidin-1-yl-pentyl)-cyclohexyl]-carbamic acid 4-chloro-phenyl ester, MS: 421 (MH$^+$, 1Cl).

Example 29.26

In analogy to examples 29.10 and 29.11, trans-Methansulfonic acid 5-(4-methyl amino-cyclohexyl)-pentyl ester.Trifluoroacetic acid salt and 4-chlorophenyl chloroformate were reacted, followed by treatment with N-methyl-piperazine to give trans-Methyl-{4-[5-(4-methyl-piperazin-1-yl)-pentyl]-cyclohexyl}-carbamic acid 4-chloro-phenyl ester, MS: 436 (MH$^+$, 1Cl).

Example 29.27

In analogy to examples 29.10 and 29.11, trans-Methansulfonic acid 5-(4-methyl amino-cyclohexyl)-pentyl ester.Trifluoroacetic acid salt and 4-chlorophenyl chloroformate were reacted, followed by treatment with N-methyl-N-cyclopropyl-amine to give trans {4-[5-(Cyclopropyl-methyl-amino)-pentyl]-cyclohexyl}-methyl-carbamic acid 4-chloro-phenyl ester, MS: 407 (MH$^+$, 1Cl).

Example 29.28

In analogy to examples 29.10 and 29.11, trans-Methansulfonic acid 5-(4-methyl amino-cyclohexyl)-pentyl ester.Trifluoroacetic acid salt and 4-trifluoromethyl-phenyl sulfonylchloride were reacted, followed by treatment with diethylamine to give trans N-[4-(5-Diethylamino-pentyl)-cyclohexyl]-N-methyl-4-trifluoromethyl-benzenesulfonamide. MS: 463 (MH$^+$).

Example 29.29

In analogy to examples 29.10 and 29.11, trans-Methansulfonic acid 5-(4-methyl amino-cyclohexyl)-pentyl ester.Trifluoroacetic acid salt and 4-trifluoromethyl-phenyl sulfonylchloride were reacted, followed by treatment with 2-(2-Hydroxy-ethylamino)-ethanol to give trans-N-(4-{5-[Bis-(2-hydroxy-ethyl)-amino]-pentyl}-cyclohexyl)-N-methyl-4-trifluoromethyl-benzenesulfonamide. MS: 495 (MH$^+$).

Example 29.30

In analogy to examples 29.10 and 29.11, trans-Methansulfonic acid 5-(4-methyl amino-cyclohexyl)-pentyl ester.Trifluoroacetic acid salt and 4-trifluoromethyl-phenyl chloroformate were reacted, followed by treatment allylamine to give trans-{4-[5-(Allylamino)-pentyl]-cyclohexyl}-methyl-carbamic acid 4-trifluoromethyl-phenyl ester, MS: 427 (MH$^+$).

Example 29.31

In analogy to examples 29.10 and 29.11, trans-Methansulfonic acid 5-(4-methyl amino-cyclohexyl)-pentyl ester.Trifluoroacetic acid salt and 4-trifluoromethyl-phenyl chloroformate were reacted, followed by treatment with methylamine to give trans-Methyl-[4-(5-methylamino-pentyl)-cyclohexyl]-carbamic acid 4-trifluoromethyl-phenyl ester, MS: 401 (MH$^+$).

Example 29.32

In analogy to examples 29.11, from trans-N-[4-(5-Bromopentyl)-cyclohexyl]-N-methyl-4-trifluoromethyl-benzenesulfonamide and allylamine was prepared trans-N-[4-(5-Allylamino-pentyl)-cyclohexyl]-N-methyl-4-trifluoromethyl-benzenesulfonamide, MS: 447 (MH$^+$).

Example 29.33

In analogy to examples 29.11, from trans-N-[4-(5-Bromopentyl)-cyclohexyl]-N-methyl-4-trifluoromethyl-benzenesulfonamide and 2.amino-2-methyl-1-propanol was prepared trans-N-{4-[5-(2-Hydroxy-1,1-dimethyl-ethylamino)-pentyl]-cyclohexyl}-N-methyl-4-trifluoromethyl-benzenesulfonamide, MS: 479 (MH$^+$).

Example 29.34

In analogy to examples 29.11, from trans-N-[4-(5-Bromo-pentyl)-cyclohexyl]-N-methyl-4-trifluoromethyl-benzene-sulfonamide and methylamine was prepared trans-N-Methyl-N-[4-(5-methylamino-pentyl)-cyclohexyl]-4-trifluoromethyl-benzenesulfonamide, MS: 421(MH$^+$).

Example 29.35

In analogy to examples 29.11, from trans-N-[4-(5-Bromo-pentyl)-cyclohexyl]-N-methyl-4-trifluoromethyl-benzene-sulfonamide and ethanolamine (6 eq, in DMA) was prepared trans-N-{4-[4-(2-Hydroxy-ethylamino)-butyl]-cyclohexyl}-N-methyl-4-trifluoromethyl-benzenesulfonamide, MS: 451 (MH$^+$).

Example 29.36

In analogy to examples 29.11, from trans-N-[4-(5-Bromo-pentyl)-cyclohexyl]-N-methyl-4-trifluoromethyl-benzene-sulfonamide and ethylamine (6 eq, in DMA) was prepared trans-N-[4-(5-Ethylamino-pentyl)-cyclohexyl]-N-methyl-4-trifluoromethyl-benzenesulfonamide, MS: 435 (MH$^+$).

Example 29.37

In analogy to examples 29.4-29.9 and 29.12, from trans/cis-(4-Formyl-cyclohexyl)-methyl-carbamic acid tert-butyl ester was prepared (trans)-{4-[5-(Allyl-methyl-amino)-pentyl]-cyclohexyl}-methyl-carbamic acid 4-trifluoromethyl-phenyl ester and (cis){4-[5-(Allyl-methyl-amino)-pentyl]-cyclohexyl}-methyl-carbamic acid 4-trifluoromethyl-phenyl ester, MS: 441 (MH$^+$), which could be separated using HPLC (ChiralpakAD, 20 um 5×50 cm von Daicel Chem. Industrie Ltd, eluent: 9.0 l n-heptane/1.0 l isopropanol).

Example 30

Example 30.1

To a suspension of 1.39 g (4.4 mmol, 2.2 eq) Hydrogen peroxide.Urea adduct in CH$_2$Cl$_2$, 338.5 mg (2.2 mmol, 1.1 eq) phthalic anhydride were added and stirred for 15 min at RT. 800 mg (2.01 mmol) trans-[4-(5-Dimethylamino-pentyloxy)-cyclohexyl]-methyl-carbamic acid 4-chloro-phenyl ester in CH$_2$Cl$_2$ was added and the mixture was stirred at RT for 2 h. 5% aqueous K$_2$CO$_3$ solution was added and the inorganic-phase was extracted with CH$_2$Cl$_2$. The organic phases were washed with water and brine and dried over MgSO$_4$. Column chromatography yielded 525 mg (63%) trans-[4-(5-Dimethylamino-pentyloxy)-cyclohexyl]-methyl-carbamic acid 4-chloro-phenyl ester N-oxide as colourless oil, MS: 413 (MH$^+$, 1Cl).

Example 30.2

In analogy to example 30.1, trans-{4-[5-(Allyl-methyl-amino)-pentyl]-cyclohexyl}-methyl-carbamic acid 4-trifluoromethyl-phenyl ester gave after precipitation (CH$_2$Cl$_2$/Et$_2$O) trans-{4-[5-(Allyl-methyl-amino)-pentyl]-cyclohexyl}-methyl-carbamic acid 4-trifluoromethyl-phenyl ester N-oxide, MS: 457 (MH$^+$).

Example 30.3

400 mg (8.4 mmol) trans-N-(4-{5-[Ethyl-(2-hydroxy-ethyl)-amino]-pentyl}-cyclohexyl)-N-methyl-4-trifluoromethyl-benzenesulfonamide were suspended in toluene and evaporated (3×), redissolved in 1 ml DMF and treated with 102.4 mg (1.5 mmol, 1.8 eq) imidazole. At 0° C., 176 mg (11.7 mmol, 1.4 eq) TBDMSCl in 2 ml DMF were added, and the reaction mixture was stirred at 50° C. for 1 h. The solution was added to an aqueous solution of NaHCO$_3$ and extracted with ether. The organic layer was washed with water and brine, and dried over Na$_2$SO$_4$. 509 mg crude trans-N-[4-(5-{[2-(tert-Butyl-dimethyl-silanyloxy)-ethyl]-ethyl-amino}-pentyl)-cyclohexyl]-N-methyl-4-trifluoromethyl-benzenesulfonamide were isolated as light yellow oil.

Example 30.4

175 mg (1.86 mmol) H$_2$O$_2$-Urea adduct suspended in 2 ml CH$_2$Cl$_2$ were treated with 137 mg (0.9 mmol) phthalic anhydride. After stirring at RT for 15 min to this mixture was added 500 mg (8.4 mmol) crude trans-N-[4-(5-{[2-(tert-Butyl-dimethyl-silanyloxy)-ethyl]-ethyl-amino}-pentyl)-cyclohexyl]-N-methyl-4-trifluoromethyl-benzenesulfonamide in 3 ml CH$_2$Cl$_2$ and the solution was stirred at RT. The mixture was washed with an aqueous solution of NaHCO$_3$, the organic phase was washed with brine and dried over Na$_2$SO$_4$. 348 mg crude trans-N-[4-(5-{[2-(tert-Butyl-dimethyl-silanyloxy)-ethyl]-ethyl-amino}-pentyl)-cyclohexyl]-N-methyl-4-trifluoromethyl-benzenesulfonamide N-oxide were isolated as colorless oil.

Example 30.5

To 335 mg (5.5 mmol) trans-N-[4-(5-{[2-(tert-Butyl-dimethyl-silanyloxy)-ethyl]-ethyl-amino}-pentyl)-cyclohexyl]-N-methyl-4-trifluoromethyl-benzenesulfonamide N-oxide in 8 ml THF were added 0.83 ml 1M TBAF at 0° C. The solution was stirred at RT for 1 h, partitioned between EtOAc and an aqueous solution of Na$_2$CO$_3$. The organic phase was washed with brine and dried over Na$_2$SO$_4$. Column chromatography with CH$_2$Cl$_2$/MeOH 9:1 yielded 190 mg (44%, 3 steps) trans-N-(4-{5-[Ethyl-(2-hydroxy-ethyl)-amino]-pentyl}-cyclohexyl)-N-methyl-4-trifluoromethyl-benzenesulfonamide N-oxide as colorless oil, MS: 495 (MH$^+$).

Example 31

Example 31.1

5.85 g (14.71 mmol) of trans-[Toluene-4-sulfonic acid 4-(tert-butoxycarbonyl-methyl-amino)-cyclohexylmethyl ester] (synthesized from trans-(4-Hydroxymethyl-cyclohexyl)-methyl-carbamic acid tert-butyl ester and toluene sulfonyl chloride in pyridine), and 1.45 g (29.43 mmol) of sodium cyanide were stirred in 50 ml DMF for 48 h at 100° C. The reaction-mixture was partitioned between ether and water. After drying (Na$_2$SO$_4$) and concentration of the ether-phase in vacuo, 3.74 g of crude trans-[(4-Cyanomethyl-cyclohexyl)-methyl-carbamic acid tert-butyl ester] could be isolated. This crude product (14.82 mmol), dissolved in 30 ml THF, was treated at −78° C. with 13.5 ml (16.18 mmol) of a 1.2M DIBALH-solution in Toluene. The reaction-mixture was stirred 30 min at −78° C. and 15 min at RT. To the reaction-mixture was then carefully dropped 30 ml of 1N HCl. The reaction-mixture was dissolved in ether and washed with water. The ether-solution was dried (Na$_2$SO$_4$) and concentrated under reduced pressure to yield 3.47 g (92%, 2 steps) of crude trans-[Methyl-[4-(2-oxo-ethyl)-cyclohexyl]-carbamic acid tert-butyl ester].

Example 31.2

3.47 g (13.58 mmol) of the crude trans-[Methyl-[4-(2-oxo-ethyl)-cyclohexyl]-carbamic acid tert-butyl ester] and 5.39 g (14.7 mmol) of (Triphenyl-1 5-phosphanylidene)-acetic acid ethyl ester were stirred in 40 ml of CH$_2$Cl$_2$ over night at RT. The reaction-mixture was concentrated in vacuo and then purified by chromatography on silica gel with EtOAc/hexane 1:3 to give 1.57 g (36%) pure 4-[4-(tert-Butoxycarbonyl-methyl-amino)-cyclohexyl]-but-2-enoic acid ethyl ester.

Example 31.3

A solution of 1.57 g (4.82 mmol) 4-[4-(tert-Butoxycarbonyl-methyl-amino)-cyclohexyl]-but-2-enoic acid ethyl ester and 200 mg of Pd/C (10%) in 20 ml of MeOH was stirred at RT under H$_2$-atmosphere for 3 h. After filtration, the solution was concentrated under reduced pressure to dryness, to give 1.58 g of clean trans-4-[4-(tert-Butoxycarbonyl-methyl-amino)-cyclohexyl]-butyric acid ethyl ester. 1.58 g (4.82 mmol) trans-4-[4-(tert-Butoxycarbonyl-methyl-amino)-cyclohexyl]-butyric acid ethyl ester in 20 ml of THF, was treated at RT with 390 mg of LiAlH$_4$. After stirring the solution for 30 min at RT, the excess of LiAlH$_4$ was destroyed by adding dropwise 10 ml of saturated brine under ice-cooling. The reaction mixture was partitioned between Et$_2$O/1M HCl and H$_2$O. The ether-solution was concentrated in vacuo, to give 1.37 g (99%) of pure trans-[4-(4-Hydroxy-butyl)-cyclohexyl]-methyl-carbamic acid tert-butyl ester.

Example 31.4

To a stirred, ice-cooled solution of 1.37 g (4.8 mmol) of trans-[4-(4-Hydroxy-butyl)-cyclohexyl]-methyl-carbamic acid tert-butyl ester and 0.95 ml NEt$_3$ in 15 ml CH$_2$Cl$_2$ was added 0.5 ml (6.8 mmol) methanesulfonyl chloride. After stirring at RT for 2 h, the reaction mixture was partitioned between Et$_2$O, 1M HCl and water. The ether-layer was concentrated in vacuo to give 1.745 g of clean trans-Methanesulfonic acid 4-[4-(tert-butoxycarbonyl-methyl-amino)-cyclohexyl]-butyl ester, that was treated in 5 ml CH$_2$Cl$_2$ with 5 ml of trifluoro acetic acid. After stirring the solution for 30 min at RT, the solution was evaporated under reduced pressure to dryness to give 2.25 g (quant.) trans-Methanesulfonic acid 4-(4-methylamino-cyclohexyl)-butyl ester.trifluoro-acetic acid.

Example 31.5

To a stirred solution of 590 mg (~1.25 mmol) of trans-Methanesulfonic acid 4-(4-methylamino-cyclohexyl)-butyl ester; compound with trifluoro-acetic acid and 0.644 ml of 4-ethylmorpholine in 6 ml CH$_2$Cl$_2$ was added 365 mg (1.91 mmol) of 4-chlorophenyl-chloroformate at RT. The reaction-mixture was stirred at RT for 1 h and then partitioned between Et$_2$O, 1M HCl and water. After concentration of the ether-layer under reduced pressure, the residue was purified by chromatography over silica gel with EtOAc/hexane 1:2 to, give 421 mg (81%) of pure trans-Methanesulfonic acid 4-{4-[(4-chloro-phenoxycarbonyl)-methyl-amino]-cyclohexyl}-butyl ester.

Example 31.6

A solution of 219 mg (0.524 mmol) of trans-Methanesulfonic acid 4-{4-[(4-chloro-phenoxycarbonyl)-methyl-amino]-cyclohexyl}-butyl ester and 0.48 ml of N-allyl methyl-amine in 1 ml of MeOH was stirred over night at RT, and for 2 h under reflux. After concentration of the reaction-mixture in vacuo, the crude product was purified by chromatography over silica gel with EtOAc/H$_2$O/AcOH/Aceton (6:2:1:1) to give 165 mg (80%) of clean trans-{4-[4-(Allyl-methyl-amino)-butyl]-cyclohexyl}-methyl-carbamic acid 4-chloro-phenyl ester, MS: 393 (MH$^+$, 1Cl).

Example 31.7

In analogy to examples 31.6, trans-Methanesulfonic acid 4-{4-[(4-chloro-phenoxycarbonyl)-methyl-amino]-cyclohexyl}-butyl ester was treated with 2-ethylamino-ethanol to give trans-(4-{4-[Ethyl-(2-hydroxy-ethyl)-amino]-butyl}-cyclohexyl)-methyl-carbamic acid 4-chloro-phenyl ester, MS: 411 (MH$^+$, 1Cl).

Example 31.8

In analogy to examples 31.5 and 31.6, trans-Methanesulfonic acid 4-(4-methylamino-cyclohexyl)-butyl ester.trifluoro-acetic acid and 4-trifluoromethyl-phenyl-chloroformate were reacted, followed by treatment with N-allyl-N-methylamine to give trans-{4-[4-(Allyl-methyl-amino)-butyl]-cyclohexyl}-methyl-carbamic acid 4-trifluoromethyl-phenyl ester, MS: 427 (MH$^+$).

Example 31.9

In analogy to examples 31.5 and 31.6, trans-Methanesulfonic acid 4-(4-methylamino-cyclohexyl)-butyl ester.trifluoro-acetic acid and 4-trifluoromethyl-phenyl-chloroformate were reacted, followed by treatment with 2-ethylamino-ethanol to give trans-(4-{4-[Ethyl-(2-hydroxy-ethyl)-amino]-butyl}-cyclohexyl)-methyl-carbamic acid 4-trifluoromethyl-phenyl ester, MS: 445 (MH$^+$).

Example 31.10

In analogy to examples 31.5 and 31.6, trans-Methanesulfonic acid 4-(4-methylamino-cyclohexyl)-butyl ester.trifluoro-acetic acid and 4-bromophenyl-chloroformate were reacted, followed by treatment with N-allyl-N-methylamine to give trans-{4-[4-(Allyl-methyl-amino)-butyl]-cyclohexyl}-methyl-carbamic acid 4-bromo-phenyl ester, MS: 437 (MH$^+$, 1Br).

Example 31.11

In analogy to examples 31.5 and 31.6, trans-Methanesulfonic acid 4-(4-methylamino-cyclohexyl)-butyl ester.trifluoro-acetic acid and 4-bromo phenyl-chloroformate were reacted, followed by treatment with 2-ethylamino-ethanol to give trans-(4-{4-[Ethyl-(2-hydroxy-ethyl)-amino]-butyl}-cyclohexyl)-methyl-carbamic acid 4-bromo-phenyl ester, MS: 455 (MH$^+$, 1Br).

Example 31.12

In analogy to examples 31.5 and 31.6, trans-Methanesulfonic acid 4-(4-methylamino-cyclohexyl)-butyl ester.trifluoro-acetic acid and 4-bromophenyl-chloroformate were reacted, followed by treatment with N-methyl-propyl-amine to give trans-Methyl-{4-[4-(methyl-propyl-amino)-butyl]-cyclohexyl}-carbamic acid 4-bromo-phenyl ester, MS: 439 (MH$^+$, 1Br).

Example 31.13

In analogy to examples 31.5 and 31.6, trans-Methanesulfonic acid 4-(4-methylamino-cyclohexyl)-butyl ester.trifluoro-acetic acid and 4-bromophenyl-chloroformate were reacted, followed by treatment with diethylamine to give trans-Methyl-{4-[4-(diethylamino)-butyl]-cyclohexyl}-carbamic acid 4-bromo-phenyl ester, MS: 439 (MH$^+$, 1Br).

Example 31.14

In analogy to examples 31.5 and 31.6, trans-Methanesulfonic acid 4-(4-methylamino-cyclohexyl)-butyl ester.trifluoro-acetic acid and 4-bromophenyl-chloroformate were reacted, followed by treatment with dimethylamine to give trans-Methyl-{4-[4-(dimethylamino)-butyl]-cyclohexyl}-carbamic acid 4-bromo-phenyl ester, MS: 411 (MH$^+$, 1Br).

Example 31.15

In analogy to examples 31.5 and 31.6, trans-Methanesulfonic acid 4-(4-methylamino-cyclohexyl)-butyl ester.trifluoro-acetic acid and 4-bromophenyl-chloroformate were reacted, followed by treatment with piperidine to give trans-Methyl-[4-(4-piperidin-1-yl-butyl)-cyclohexyl]-carbamic acid 4-bromo-phenyl ester, MS: 451 (MH$^+$, 1Br).

Example 31.16

In analogy to examples 31.5 and 31.6, trans-Methanesulfonic acid 4-(4-methylamino-cyclohexyl)-butyl ester.trifluoro-acetic acid and 4-bromophenyl-chloroformate were reacted, followed by treatment with N-methyl-piperazine to give trans-Methyl-{4-[4-(4-methyl-piperazin-1-yl)-butyl]-cyclohexyl}-carbamic acid 4-bromo-phenyl ester, MS: 466 (MH$^+$, 1Br).

Example 31.17

In analogy to examples 31.5 and 31.6, trans-Methanesulfonic acid 4-(4-methylamino-cyclohexyl)-butyl ester.trifluoro-acetic acid and 4-bromophenyl-chloroformate were reacted, followed by treatment with morpholine to give trans-Methyl-[4-(4-morpholin-4-yl-butyl)-cyclohexyl]-carbamic acid 4-bromo-phenyl ester, MS: 453 (MH$^+$, 1Br).

Example 31.18

In analogy to examples 31.5 and 31.6, trans-Methanesulfonic acid 4-(4-methylamino-cyclohexyl)-butyl ester.trifluoro-acetic acid and 4-bromophenyl-chloroformate were reacted, followed by treatment with thiomorpholine to give trans-Methyl-[4-(4-thiomorpholin-4-yl-butyl)-cyclohexyl]-carbamic acid 4-bromo-phenyl ester, MS: 469 (MH$^+$, 1Br).

Example 31.19

In analogy to examples 31.5 and 31.6, trans-Methanesulfonic acid 4-(4-methylamino-cyclohexyl)-butyl ester.trifluoro-acetic acid and 4-trifluoromethyl-phenyl-chloroformate were reacted, followed by treatment with piperidine to give trans-Methyl-[4-(4-piperidin-1-yl-butyl)-cyclohexyl]-carbamic acid 4-trifluoromethyl-phenyl ester, MS: 441 (MH$^+$).

Example 31.20

In analogy to examples 31.5 and 31.6, trans-Methanesulfonic acid 4-(4-methylamino-cyclohexyl)-butyl ester.trifluoro-acetic acid and 4-trifluoromethyl-phenyl-chloroformate were reacted, followed by treatment with dimethylamine to give trans-[4-(4-Dimethylamino-butyl)-cyclohexyl]-methyl-carbamic acid 4-trifluoromethyl-phenyl ester, MS: 401 (MH$^+$).

Example 31.21

In analogy to examples 31.5 and 31.6, trans-Methanesulfonic acid 4-(4-methylamino-cyclohexyl)-butyl ester.trifluoro-acetic acid and 4-trifluoromethyl-phenyl-chloroformate were reacted, followed by treatment with thiomorpholine to give trans-Methyl-[4-(4-thiomorpholin-4-yl-butyl)-cyclohexyl]-carbamic acid 4-trifluoromethyl-phenyl ester, MS: 459 (MH$^+$).

Example 31.22

In analogy to examples 31.5 and 31.6, trans-Methanesulfonic acid 4-(4-methylamino-cyclohexyl)-butyl ester.trifluoro-acetic acid and 4-trifluoromethyl-phenyl-chloroformate were reacted, followed by treatment with methyl-propyl-amine to give trans-Methyl-{4-[4-(methyl-propyl-amino)-butyl]-cyclohexyl}-carbamic acid 4-trifluoromethyl-phenyl ester, MS: 429 (MH$^+$).

Example 31.23

In analogy to examples 31.5 and 31.6, trans-Methanesulfonic acid 4-(4-methylamino-cyclohexyl)-butyl ester.trifluoro-acetic acid and and 4-trifluoromethyl-phenyl-sulfonylchloride were reacted, followed by treatment with N-allyl-N-methylamine to give trans-N-{4-[4-(Allyl-methyl-amino)-butyl]-cyclohexyl}-N-methyl-4-trifluoromethyl-benzenesulfonamide, MS: 447 (MH$^+$).

Example 31.24

In analogy to examples 31.5 and 31.6, trans-Methanesulfonic acid 4-(4-methylamino-cyclohexyl)-butyl ester.trifluoro-acetic acid and 4-trifluoromethyl-phenyl-sulfonylchloride were reacted, followed by treatment with 2-ethylamino-ethanol to give trans-N-(4-{4-[Ethyl-(2-hydroxy-ethyl)-amino]-butyl}-cyclohexyl)-N-methyl-4-trifluoromethyl-benzenesulfonamide, MS: 465 (MH$^+$).

Example 31.25

In analogy to examples 31.5 and 31.6, trans-Methanesulfonic acid 4-(4-methylamino-cyclohexyl)-butyl ester.trifluoro-acetic acid and 4-trifluoromethyl-phenyl-sulfonylchloride were reacted, followed by treatment with piperidine to give trans-N-Methyl-N-[4-(4-piperidin-1-yl-butyl)-cyclohexyl]-4-trifluoromethyl-benzenesulfonamide, MS: 461 (MH$^+$).

Example 31.26

In analogy to examples 31.5 and 31.6, trans-Methanesulfonic acid 4-(4-methylamino-cyclohexyl)-butyl ester.trifluoro-acetic acid and 4-trifluoromethyl-phenyl-sulfonylchloride were reacted, followed by treatment with dimethlamine to give trans-N-[4-(4-Dimethylamino-butyl)-cyclohexyl]-N-methyl-4-trifluoromethyl-benzenesulfonamide, MS: 421 (MH$^+$).

Example 31.27

In analogy to examples 31.5 and 31.6, trans-Methanesulfonic acid 4-(4-methylamino-cyclohexyl)-butyl ester.trifluoro-acetic acid and 4-trifluoromethyl-phenyl-sulfonylchloride were reacted, followed by treatment with methylpropyl-amine to give trans-N-Methyl-N-{4-[4-(methylpropyl-amino)-butyl]-cyclohexyl}-4-trifluoromethyl-benzenesulfonamide, MS: 449 (MH$^+$).

Example 31.28

In analogy to examples 31.5 and 31.6, trans-Methanesulfonic acid 4-(4-methylamino-cyclohexyl)-butyl ester.trifluoro-acetic acid and 4-trifluoromethyl-phenyl-sulfonylchloride were reacted, followed by treatment with 2-(2-Hydroxy-ethylamino)-ethanol to give trans N-(4-{4-[Bis-(2-hydroxy-ethyl)-amino]-butyl}-cyclohexyl)-N-methyl-4-trifluoromethyl-benzenesulfonamide, MS: 481 (MH$^+$).

Example 32

Example 32.1

A solution of 6.02 g (17.43 mmol) of trans-Methanesulfonic acid 3-[4-(tert-butoxycarbonyl-methyl-amino)-cyclohexyl]-prop-2-ynyl ester in 95 ml CH$_2$Cl$_2$ was treated at 0° C. with 45 ml TFA (for 20 min). After 30 min at this temperature, the reaction was evaporated and evaporated again with toluene (4 times) to give 8.17 g (quantitative) of crude trans-Methanesulfonic acid 3-(4-methylamino-cyclohexyl)-prop-2-ynyl ester.trifluoroacetate, MS: 245 (M).

Example 32.2

A solution of 1.41 g (corresponds to 3.0 mmol) of trans-Methanesulfonic acid 3-(4-methylamino-cyclohexyl)-prop-2-ynyl ester trifluoroacetate in 20 ml CH$_2$Cl$_2$ was first cooled at 0° C., treated with 0.5 ml (3.6 mmol) 4-chlorophenylchloroformate and then with 2.57 ml (15 mmol; 5 equivalents) of Huenigs base (during 3 min). After 45 min at RT, the mixture was dissolved in aqueous 10% KHSO$_4$/Et$_2$O (3×). The organic phases were washed with aqueous 10% NaCl, dried over Na$_2$SO$_4$ and evaporated to give 1.41 g (quantitative) of crude trans-Methanesulfonic acid 3-{4-[(4-chloro-phenoxycarbonyl)-methyl-amino]-cyclohexyl}-prop-2-ynyl ester, MS: 400 (MH$^+$, 1Cl). The crude product was directly used in the next step.

Example 32.3

In analogy to example 32.2, trans-Methanesulfonic acid 3-(4-methylamino-cyclohexyl)-prop-2-ynyl ester trifluoroacetate and 4-trifluoromethylphenylchloroformate were converted to trans-Methanesulfonic acid 3-{4-[methyl-(4-trifluoromethyl-phenoxycarbonyl)-amino]-cyclohexyl}-prop-2-ynyl ester, MS: 434 (MH$^+$).

Example 32.4

In analogy to example 32.2, trans-Methanesulfonic acid 3-(4-methylamino-cyclohexyl)-prop-2-ynyl ester trifluoroacetate and p-tolyl chloroformate were converted to trans-Methanesulfonic acid 3-[4-(methyl-p-tolyloxycarbonyl-amino)-cyclohexyl]-prop-2-ynyl ester, MS: 380 (MH$^+$).

Example 32.5

In analogy to example 32.2, trans-Methanesulfonic acid 3-(4-methylamino-cyclohexyl)-prop-2-ynyl ester trifluoroacetate and 4-methoxyphenyl chloroformate were converted to trans-Methanesulfonic acid 3-{4-[(4-methoxy-phenoxycarbonyl)-methyl-amino]-cyclohexyl}-prop-2-ynyl ester, MS: 396 (MH$^+$).

Example 32.6

In analogy to example 32.2, trans-Methanesulfonic acid 3-(4-methylamino-cyclohexyl)-prop-2-ynyl ester trifluoroacetate and 4-(trifluoromethyl)benzenesulfonylchloride were converted to trans-Methanesulfonic acid 3-{4-[methyl-(4-trifluoromethyl-benzenesulfonyl)-amino]-cyclohexyl}-prop-2-ynyl ester, MS: 454 (MH$^+$).

Example 32.7

In analogy to example 32.2, trans-Methanesulfonic acid 3-(4-methylamino-cyclohexyl)-prop-2-ynyl ester trifluoroacetate and 4-acedamidophenylsulfonyl chloride were converted to trans-Methanesulfonic acid 3-{4-[(4-acetylamino-benzenesulfonyl)-methyl-amino]-cyclohexyl}-prop-2-ynyl ester, MS: 443 (MH$^+$).

Example 32.8

In analogy to example 32.2, trans-Methanesulfonic acid 3-(4-methylamino-cyclohexyl)-prop-2-ynyl ester trifluoroacetate and 4-chlorobenzoylchloride were converted to trans-Methanesulfonic acid 3-{4-[(4-chloro-benzoyl)-methyl-amino]-cyclohexyl}-prop-2-ynyl ester, MS: 398 (MH$^+$, 1Cl).

Example 32.9

A solution of 1.38 g (corresponds to 3.0 mmol) of trans-Methanesulfonic acid 3-(4-methylamino-cyclohexyl)-prop-2-ynyl ester trifluoroacetate in 7 ml dioxane was first cooled to 8° C., treated with 0.69 g (4.5 mmol) 4-chlorophenyl isocyanate and then with 1.2 ml (15 mmol; 5 equivalents) of pyridine (during 3 min). After 45 min at RT, the mixture was dissolved in aqueous 10% KHSO$_4$/Et$_2$O (3×). The organic phases were washed with aqueous 10% NaCl, dried over Na$_2$SO$_4$ and evaporated to give 1.22 g (quantitative) of crude trans-Methanesulfonic acid 3-{4-[3-(4-chloro-phenyl)-1-methyl-ureido]-cyclohexyl}-prop-2-ynyl ester, MS: 398 (MH$^+$, 1Cl). The crude product was directly used in the next step.

Example 32.10

In analogy to example 32.2, trans-Methanesulfonic acid 3-(4-methylamino-cyclohexyl)-prop-2-ynyl ester trifluoroacetate and 4-chlorobenzenesulfonylchloride were converted to trans-Methanesulfonic acid 3-{4-[(4-chloro-benzenesulfonyl)-methyl-amino]-cyclohexyl}-prop-2-ynyl ester, MS: 420 (MH$^+$, 1Cl).

Example 33

A solution of 235 mg (corresponds to 0.5 mmol) of trans-Methanesulfonic acid 3-{4-[(4-chloro-phenoxycarbonyl)-methyl-amino]-cyclohexyl}-prop-2-ynyl ester in 2.5 ml of DMA as cooled at 0° C., treated with 0.76 ml (1 mmol) of N-methylpropylamine and stirred over night at RT. The solvent was evaporated and the residue extracted with aqueous saturated NaHCO$_3$/Et$_2$O (3×). The organic phase was dried with Na$_2$SO$_4$, filtered and evaporated. Purification by flash column chromatography on silica gel (CH$_2$Cl$_2$/MeOH 98:2) gave 153 mg (81%) of pure trans-Methyl-{4-[3-(methyl-propyl-amino)-prop-1-ynyl]-cyclohexyl}-carbamic acid 4-chloro-phenyl ester, MS: 377 (MH$^+$, 1Cl).

The hydrochloride salt was optionally obtained after dissolving the amine in dioxane and addition of 1 equivalent of 4N HCl (in dioxane). Lyophilisation gave trans-Methyl-{4-[3-(methyl-propyl-amino)-prop-1-ynyl]-cyclohexyl}-carbamic acid 4-chloro-phenyl ester; compound with HCl as white powder, MS: 377 (MH$^+$, 1Cl).

The following compounds were prepared from the corresponding mesylates and secondary amines (In case the reaction was not finished after 16 h, an additional 2 equivalents of the amine was added. For Dimethylamine, 33% in EtOH 5.6M, 10 equivalents were added.):

| Example | Compound | MS MH$^+$ | Mesylate | Secondary amine |
|---|---|---|---|---|
| 33.1 | trans-[4-(3-Dimethylamino-prop-1-ynyl)-cyclohexyl]-methyl-carbamic acid 4-chloro-phenyl ester | 349, 1Cl | trans-Methanesulfonic acid 3-{4-[(4-chloro-phenoxycarbonyl)-methyl-amino]-cyclohexyl}-prop-2-ynyl ester | Dimethylamine, 33% in EtOH 5.6 M |
| 33.2 | trans-Methyl-[4-(3-piperidin-1-yl-prop-1-ynyl)-cyclohexyl]-carbamic acid 4-chloro-phenyl ester | 389, 1Cl | trans-Methanesulfonic acid 3-{4-[(4-chloro-phenoxycarbonyl)-methyl-amino]-cyclohexyl}-prop-2-ynyl ester | Piperidine |
| 33.3 | trans-(4-{3-[Bis-(2-hydroxy-ethyl)-amino]-prop-1-ynyl}-cyclohexyl)-methyl-carbamic acid 4-trifluoromethyl-phenyl ester | 443 | trans-Methanesulfonic acid 3-{4-[methyl-(4-trifluoromethyl-phenoxycarbonyl)-amino]-cyclohexyl}-prop-2-ynyl ester | Diethanolamine |
| 33.4 | trans-[4-(3-Dimethylamino-prop-1-ynyl)-cyclohexyl]-methyl-carbamic acid 4-trifluoromethyl-phenyl ester | 383 | trans-Methanesulfonic acid 3-{4-[methyl-(4-trifluoromethyl-phenoxycarbonyl)-amino]-cyclohexyl}-prop-2-ynyl ester | Dimethylamine, 33% in EtOH 5.6 M |
| 33.5 | trans-Methyl-{4-[3-(methyl-propyl-amino)-prop-1-ynyl]-cyclohexyl}-carbamic acid 4-trifluoromethyl-phenyl ester | 411 | trans-Methanesulfonic acid 3-{4-[methyl-(4-trifluoromethyl-phenoxycarbonyl)-amino]-cyclohexyl}-prop-2-ynyl ester | N-Methylpropyl-amine |
| 33.6 | trans-Methyl-[4-(3-piperidin-1-yl-prop-1-ynyl)-cyclohexyl]-carbamic acid 4-trifluoromethyl-phenyl ester | 423 | trans-Methanesulfonic acid 3-{4-[methyl-(4-trifluoromethyl-phenoxycarbonyl)-amino]-cyclohexyl}-prop-2-ynyl ester | Piperidine |

Example 34

A solution of 200 mg (corresponds to 0.43 mmol) of trans-Methanesulfonic acid 3-{4-[(4-chloro-phenoxycarbonyl)-methyl-amino]-cyclohexyl}-prop-2-ynyl ester in 4.3 ml of methanol was cooled to 0° C., treated with 0.44 ml (1 mmol) of Ethyl-(2-methoxy-ethyl)-amine and stirred over night at RT. The solvent was evaporated and the residue extracted with aqueous saturated NaHCO$_3$/Et$_2$O (3×). The organic phase was dried with Na$_2$SO$_4$, filtered and evaporated. Purification by flash column chromatography on silica gel (CH$_2$Cl$_2$/MeOH 99:1) gave 144 mg (83%) of pure trans-(4-{3-[Ethyl-(2-methoxy-ethyl)-amino]-prop-1-ynyl}-cyclohexyl)-methyl-carbamic acid 4-chloro-phenyl ester, MS: 407 (MH$^+$, 1Cl). The following compounds were prepared from the corresponding mesylates and secondary amines:

| Example | Compound | MS MH+ | Mesylate | Secondary amine |
|---|---|---|---|---|
| 34.1 | trans-Methyl-{4-[3-(methyl-propyl-amino)-prop-1-ynyl]-cyclohexyl}-carbamic acid p-tolyl ester | 357 | trans-Methanesulfonic acid 3-[4-(methyl-p-tolyloxycarbonyl-amino)-cyclohexyl]-prop-2-ynyl ester | N-Methylpropyl-amine |
| 34.2 | trans-Methyl-{4-[3-(methyl-propyl-amino)-prop-1-ynyl]-cyclohexyl}-carbamic acid 4-methoxy-phenyl ester | 373 | trans-Methanesulfonic acid 3-{4-[(4-methoxy-phenoxycarbonyl)-methyl-amino]-cyclohexyl}-prop-2-ynyl ester | N-Methylpropyl-amine |
| 34.3 | trans-N-(4-{3-[Ethyl-(2-hydroxy-ethyl)-amino]-prop-1-ynyl}-cyclohexyl)-N-methyl-4-trifluoromethyl-benzenesulfonamide | 447 | trans-Methanesulfonic acid 3-{4-[methyl-(4-trifluoromethyl-benzenesulfonyl)-amino]-cyclohexyl}-prop-2-ynyl ester | Ethyl-(2-hydroxy-ethyl)-amine |
| 34.4 | trans-N-(4-{3-[Bis-(2-hydroxy-ethyl)-amino]-prop-1-ynyl}-cyclohexyl)-N-methyl-4-trifluoromethyl-benzenesulfonamide | 463 | trans-Methanesulfonic acid 3-{4-[methyl-(4-trifluoromethyl-benzenesulfonyl)-amino]-cyclohexyl}-prop-2-ynyl ester | Diethanolamine |
| 34.5 | trans-N-Methyl-N-{4-[3-(methyl-propyl-amino)-prop-1-ynyl-cyclohexyl]-4-trifluoromethyl-benzenesulfonamide | 431 | trans-Methanesulfonic acid 3-{4-[methyl-(4-trifluoromethyl-benzenesulfonyl)-amino]-cyclohexyl}-prop-2-ynyl ester | N-Methylpropyl-amine |
| 34.6 | trans-N-[4-(3-Dimethylamino-prop-1-ynyl)-cyclohexyl]-N-methyl-4-trifluoromethyl-benzenesulfonamide | 403 | trans-Methanesulfonic acid 3-{4-[methyl-(4-trifluoromethyl-benzenesulfonyl)-amino]-cyclohexyl}-prop-2-ynyl ester | Dimethylamine, 33% in EtOH 5.6 M |
| 34.7 | trans-N-(4-{3-[Ethyl-(2-methoxy-ethyl)-amino]-prop-1-ynyl}-cyclohexyl)-N-methyl-4-trifluoromethyl-benzenesulfonamide | 461 | trans-Methanesulfonic acid 3-{4-[methyl-(4-trifluoromethyl-benzenesulfonyl)-amino]-cyclohexyl}-prop-2-ynyl ester | N-(2-Methoxyethyl) ethylamine |
| 34.8 | trans-N-[4-(Methyl-{4-[3-(methyl-propyl-amino)-prop-1-ynyl]-cyclohexyl}-sulfamoyl)-phenyl]-acetamide | 431 | trans-Methanesulfonic acid 3-{4-[(4-acetylamino-benzenesulfonyl)-methyl-amino]-cyclohexyl}-prop-2-ynyl ester | N-Methylpropyl-amine |
| 34.9 | trans-4-Chloro-N-methyl-N-{4-[3-(methyl-propyl-amino)-prop-1-ynyl]-cyclohexyl}-benzamide | 361, 1Cl | trans-Methanesulfonic acid 3-{4-[(4-chloro-benzoyl)-methyl-amino]-cyclohexyl}-prop-2-ynyl ester | N-Methylpropyl-amine |
| 34.10 | trans-4-Chloro-N-(4-{3-[ethyl-(2-hydroxy-ethyl)-amino]-prop-1-ynyl}-cyclohexyl)-N-methyl-benzamide | 377, 1Cl | trans-Methanesulfonic acid 3-{4-[(4-chloro-benzoyl)-methyl-amino]-cyclohexyl}-prop-2-ynyl ester | Ethyl-(2-hydroxy-ethyl)-amine |
| 34.11 | trans-3-(4-Chloro-phenyl)-1-methyl-1-{4-[3-(methyl-propyl-amino)-prop-1-ynyl]-cyclohexyl}-urea | 376, 1Cl | trans-Methanesulfonic acid 3-{4-[3-(4-chloro-phenyl)-1-methyl-ureido]-cyclohexyl}-prop-2-ynyl ester | N-Methylpropyl-amine |
| 34.12 | trans-3-(4-Chloro-phenyl)-1-(4-{3-[ethyl-(2-hydroxy-ethyl)-amino]-prop-1-ynyl}-cyclohexyl)-1-methyl-urea | 392, 1Cl | trans-Methanesulfonic acid 3-{4-[3-(4-chloro-phenyl)-1-methyl-ureido]-cyclohexyl}-prop-2-ynyl ester | Ethyl-(2-hydroxy-ethyl)-amine |
| 34.13 | trans-4-Chloro-N-methyl-N-[4-(3-piperidin-1-yl-prop-1-ynyl)-cyclohexyl]-benzenesulfonamide | 409, 1Cl | trans-Methanesulfonic acid 3-{4-[(4-chloro-benzenesulfonyl)-methyl-amino]-cyclohexyl}-prop-2-ynyl ester | Piperidine |
| 34.14 | trans-4-Chloro-N-methyl-N-{4-[3-(methyl-propyl- | 397, 1Cl | trans-Methanesulfonic acid 3-{4-[(4-chloro- | N-Methylpropyl-amine |

-continued

| Example | Compound | MS MH+ | Mesylate | Secondary amine |
|---|---|---|---|---|
| | amino)-prop-1-ynyl]-cyclohexyl}-benzenesulfonamide | | benzenesulfonyl)-methyl-amino]-cyclohexyl}-prop-2-ynyl ester | |
| 34.15 | trans-4-Chloro-N-[4-(3-dimethylamino-prop-1-ynyl)-cyclohexyl]-N-methyl-benzenesulfonamide | 369, 1Cl | trans-Methanesulfonic acid 3-{4-[(4-chloro-benzenesulfonyl)-methyl-amino]-cyclohexyl}-prop-2-ynyl ester | Dimethylamine, 33% in EtOH 5.6 M |

Example 35

A solution of 44.3 mg (0.1 mmol) of trans-N-[4-(Methyl-{4-[3-(methyl-propyl-amino)-prop-1-ynyl]-cyclohexyl}-sulfamoyl)-phenyl]-acetamide in 5 ml MeOH was treated with 0.37 ml (2 mmol) of sodium methylate (5.4 M in MeOH) and heated at 70° C. for 30 h. The solvent was evaporated and the residue extracted with aqueous saturated NaHCO$_3$/Et$_2$O (3×). The organic phase was dried with Na$_2$SO$_4$, filtered and evaporated. Purification by flash column chromatography on silica gel (CH$_2$Cl$_2$MeOH 97:3) gave 31 mg (82%) of pure trans-4-Amino-N-methyl-N-{4-[3-(methyl-propyl-amino)-prop-1-ynyl]-cyclohexyl}-benzenesulfonamide, MS: 378 (MH+).

Example 36

Example 36.1

A suspension of 3.4 g (12.72 mmol) of trans-[4-(3-Hydroxy-prop-1-ynyl)-cyclohexyl]-methyl-carbamic acid tert-butyl ester in 125 ml ethanol and 810 mg of PtO$_2$.H$_2$O was hydrogenated (1 atm) for 7 h. The reaction was filtered (Celite) and evaporated to give 3.5 g (quantitative) of trans-[4-(3-Hydroxy-propyl)-cyclohexyl]-methyl-carbamic acid tert-butyl ester, MS: 271 (MH).

Example 36.2

In analogy to example 26.7, 32.1 and 32.2 trans-[4-(3-Hydroxy-propyl)-cyclohexyl]-methyl-carbamic acid tert-butyl ester and 4-chlorophenylchloroformate gave trans-Methanesulfonic acid 3-{4-[(4-chloro-phenoxycarbonyl)-methyl-amino]-cyclohexyl}-propyl ester, MS: 404 (MH+, 1Cl).

Example 36.3

In analogy to example 26.7, 32.1 and 32.2 trans-[4-(3-Hydroxy-propyl)-cyclohexyl]-methyl-carbamic acid tert-butyl ester and 4-trifluoromethylphenylchloroformate gave trans-Methanesulfonic acid 3-{4-[methyl-(4-trifluoromethyl-phenoxycarbonyl)-amino]-cyclohexyl}-propyl ester, MS: 438 (MH+).

Example 36.4

In analogy example 26.7, 32.1 and 32.2 trans-[4-(3-Hydroxy-propyl)-cyclohexyl]-methyl-carbamic acid tert-butyl ester and p-tolyl chloroformate gave trans-Methanesulfonic acid 3-[4-(methyl-p-tolyloxycarbonyl-amino)-cyclohexyl]-propyl ester, MS: 384 (MH+).

Example 37

A solution of 293 mg (corresponds to 0.5 mmol) of trans-Methanesulfonic acid 3-{4-[methyl-(4-trifluoromethyl-phenoxycarbonyl)-aminol-cyclohexyl}-propyl ester in 2.5 ml of DMA was cooled to 0° C., treated with 0.195 ml (2 mmol) of Ethyl-(2-hydroxy-ethyl)-amine and stirred over night at RT. A catalytic amount of NaI and 0.195 ml (2 mmol) of Ethyl-(2-hydroxy-ethyl)-amine and after 9 h, 0.88 ml (1 mmol) of Ethyl-(2-hydroxy-ethyl)-amine were added. After 16 h, the solvent was evaporated and the residue extracted with aqueous saturated NaHCO$_3$/Et$_2$O (3×). The organic phase was dried with Na$_2$SO$_4$, filtered and evaporated. Purification by flash column chromatography on silica gel (CH$_2$Cl$_2$/MeOH 9:1) gave 48 mg (22%) of pure trans-(4-{3-[Ethyl-(2-hydroxy-ethyl)-amino]-propyl}-cyclohexyl)-methyl-carbamic acid 4-trifluoromethyl-phenyl ester, MS: 431 (MH+). The following compounds were prepared in analogy:

| Example | Compound | MS MH+ | Mesylate | Secondary amine |
|---|---|---|---|---|
| 37.1 | trans-(4-{3-[Bis-(2-hydroxy-ethyl)-amino]-propyl}-cyclohexyl)-methyl-carbamic acid 4-trifluoromethyl-phenyl ester | 447 | trans-Methanesulfonic acid 3-{4-[methyl-(4-trifluoromethyl-phenoxycarbonyl)-amino]-cyclohexyl}-propyl ester | Diethanolamine |
| 37.2 | trans-[4-(3-Dimethylamino-propyl)-cyclohexyl]-methyl- | 353, 1Cl | trans-Methanesulfonic acid 3-{4-[(4-chloro- | Dimethylamine, 33% in EtOH |

-continued

| Example | Compound | MS MH+ | Mesylate | Secondary amine |
|---|---|---|---|---|
| | carbamic acid 4-chloro-phenyl ester | | phenoxycarbonyl)-methyl-amino]-cyclohexyl}-propyl ester | 5.6 M |
| 37.3 | trans-Methyl-{4-[3-(methyl-propyl-amino)-propyl]-cyclohexyl}-carbamic acid 4-chloro-phenyl ester | 381, 1Cl | trans-Methanesulfonic acid 3-{4-[(4-chloro-phenoxycarbonyl)-methyl-amino]-cyclohexyl}-propyl ester | N-Methylpropyl-amine |
| 37.4 | trans-Methyl-{4-[3-(methyl-propyl-amino)-propyl]-cyclohexyl}-carbamic acid p-tolyl ester | 361 | trans-Methanesulfonic acid 3-[4-(methyl-p-tolyloxycarbonyl-amino)-cyclohexyl]-propyl ester | N-Methylpropyl-amine |

Example 38

Example 38.1

A suspension of 4.5 g (16.8 mmol) of trans-[4-(3-Hydroxy-prop-1-ynyl)-cyclohexyl]-methyl-carbamic acid tert-butyl ester in 180 ml Et$_2$O was cooled (0° C.) and treated slowly with a solution of 13.46 ml (47.1 mmol) of Red-Al (70% in toluene). The solution was stirred 2 h at RT, cooled (0° C.) and treated again with 1.3 ml (4.7 mmol) of Red-Al (70% in toluene). After 2 h at RT, the reaction was cooled (−50° C.) and hydrolyzed with a suspension of 3 g MgSO$_4$.7H$_2$O, 3 g silica gel in 4 ml aqueous 10% KHSO$_4$. The cooling bath was removed, THF was added, the mixture was filtered. After evaporation, the residue was dissolved in CH$_2$Cl$_2$, dried over Na$_2$SO$_4$ and evaporated to yield 3.59 g (quantitative) of trans-(1E)-[4-(3-Hydroxy-propenyl)-cyclohexyl]-methyl-carbamic acid tert-butyl ester, MS: 270 (MH$^+$).

Example 38.2

A solution of 4.37 g (16.35 mmol) of trans-(1E)-[4-(3-Hydroxy-propenyl)-cyclohexyl]-methyl-carbamic acid tert-butyl ester in 120 ml CH$_2$Cl$_2$ was treated at 0° C. with 1.4 ml (17.98 mmol) of methanesulfonylchloride, 1.97 ml (24.52 mmol) pyridine and 2 g (16.35 mmol) of DMAP. The reaction mixture was stirred at RT for 3 h, water (5 ml) was added and the reaction was stirred for 5 min. After extraction with aqueous 10% KHSO$_4$/Et$_2$O (3×), the organic phases were washed with aqueous saturated NaHCO$_3$ (2×), aqueous 10% NaCl, dried over Na$_2$SO$_4$ and evaporated to yield 3.51 g (75%) of trans-(1E)-[4-(3-Chloro-propenyl)-cyclohexyl]-methyl-carbamic acid tert-butyl ester, mp: 42.5-43.9° C.; MS: 387 (MH$^+$, 1Cl).

Example 38.3

In analogy to example 32.1 and 32.2, trans-(1E)-[4-(3-Chloro-propenyl)-cyclohexyl]-methyl-carbamic acid tert-butyl ester and 4-chlorophenylchloroformate gave trans-(1E)-[4-(3-Chloro-propenyl)-cyclohexyl]-methyl-carbamic acid 4-chloro-phenyl ester, MS: 342 (MH$^+$, 2Cl).

Example 38.4

In analogy to example 32.1 and 32.2, trans-(1E)-[4-(3-Chloro-propenyl)-cyclohexyl]-methyl-carbamic acid tert-butyl ester and 4-trifluoromethylphenylchloroformate gave trans-(1E)-[4-(3-Chloro-propenyl)-cyclohexyl]-methyl-carbamic acid 4-trifluoromethyl-phenyl ester, MS: 376 (MH$^+$, 1Cl).

Example 38.5

In analogy to example 32.1 and 32.2, trans-(1E)-[4-(3-Chloro-propenyl)-cyclohexyl]-methyl-carbamic acid tert-butyl ester and 4-(trifluoromethyl)benzenesulfonylchloride gave trans-(1E)-N-[4-(3-Chloro-propenyl)-cyclohexyl]-N-methyl-4-trifluoromethyl-benzenesulfonamide, MS: 360 (M−Cl).

Example 39

A solution of 80 mg (0.23 mmol) of trans-(1E)-[4-(3-Chloro-propenyl)-cyclohexyl]-methyl-carbamic acid 4-chloro-phenyl ester in 4.3 ml of methanol was treated with 0.24 ml (2.34 mmol) N-methylpropylamine and stirred over night at RT. The solvent was evaporated and the residue extracted with aqueous saturated NaHCO$_3$/Et$_2$O (3×). The organic phase was dried with Na$_2$SO$_4$, filtered and evaporated. Purification by flash column chromatography on silica gel (CH$_2$Cl$_2$/MeOH 95:5) gave 46 mg (52%) of trans-(1E)-Methyl-{4-[3-(methyl-propyl-amino)-propenyl]-cyclohexyl}-carbamic acid 4-chloro-phenyl ester, MS: 379 (MH$^+$, 1Cl).

The following compounds were prepared from the corresponding chlorides and secondary amines (In case the reaction was not finished after 16 h, the reaction was heated for 2 h at reflux.):

| Example | Compound | MS MH+ | Chlorides | Secondary amine |
|---|---|---|---|---|
| 39.1 | trans-(1E)-(4-{3-[Ethyl-(2-methoxy-ethyl)-amino]-propenyl}-cyclohexyl)- | 409, 1Cl | trans-(1E)-[4-(3-Chloro-propenyl)-cyclohexyl]-methyl- | N-(2-Methoxyethyl)ethylamine |

-continued

| Example | Compound | MS MH+ | Chlorides | Secondary amine |
|---|---|---|---|---|
| | methyl-carbamic acid 4-chloro-phenyl ester | | carbamic acid 4-chloro-phenyl ester | |
| 39.2 | trans-(1E)-(4-{3-[Ethyl-(2-hydroxy-ethyl)-amino]-propenyl}-cyclohexyl)-methyl-carbamic acid 4-chloro-phenyl ester | 395, 1Cl | trans-(1E)-[4-(3-Chloro-propenyl)-cyclohexyl]-methyl-carbamic acid 4-chloro-phenyl ester | Ethyl-(2-hydroxy-ethyl)-amine |
| 39.3 | trans-(1E)-Methyl-{4-[3-(methyl-propyl-amino)-propenyl]-cyclohexyl}-carbamic acid 4-trifluoromethyl-phenyl ester | 413 | trans-(1E)-[4-(3-Chloro-propenyl)-cyclohexyl]-methyl-carbamic acid 4-trifluoromethyl-phenyl ester | N-Methylpropylamine |
| 39.4 | trans-(1E)-N-Methyl-N-{4-[3-(methyl-propyl-amino)-propenyl]-cyclohexyl}-4-trifluoromethyl-benzenesulfonamide | 433 | trans-(1E)-N-[4-(3-Chloro-propenyl)-cyclohexyl]-N-methyl-4-trifluoromethyl-benzenesulfon-amide | N-Methylpropyl-amine |
| 39.5 | trans-(1E)-N-[4-(3-Dimethylamino-propenyl)-cyclohexyl]-N-methyl-4-trifluoromethyl-benzenesulfonamide | 405 | trans-(1E)-N-[4-(3-Chloro-propenyl)-cyclohexyl]-N-methyl-4-trifluoromethyl-benzenesulfon-amide | Dimethylamine, 33% in EtOH 5.6 M |
| 39.6 | trans-(1E)-N-{4-[3-(Allyl-methyl-amino)-propenyl]-cyclohexyl}-N-methyl-4-trifluoromethyl-benzenesulfonamide | 431 | trans-(1E)-N-[4-(3-Chloro-propenyl)-cyclohexyl]-N-methyl-4-trifluoromethyl-benzenesulfon-amide | N-Allylmethylamine |
| 39.7 | Trans-(1E)-N-(4-{3-[Ethyl-(2-hydroxy-ethyl)-amino]-propenyl}-cyclohexyl)-N-methyl-4-trifluoromethyl-benzenesulfonamide | 405 | trans-(1E)-N-[4-(3-Chloro-propenyl)-cyclohexyl]-N-methyl-4-trifluoromethyl-benzenesulfon-amide | Ethyl-(2-hydroxy-ethyl)-amine |
| 39.8 | trans-(1E)-[4-(3-Dimethylamino-propenyl)-cyclohexyl]-methyl-carbamic acid 4-trifluoromethyl-phenyl ester | 385 | trans-(1E)-[4-(3-Chloro-propenyl)-cyclohexyl]-methyl-carbamic acid 4-trifluoromethyl-phenyl ester | Dimethylamine, 33% in EtOH 5.6 M |
| 39.9 | trans-(1E)-[4-(3-Dimethylamino-propenyl)-cyclohexyl]-methyl-carbamic acid 4-chloro-phenyl ester | 351, 1Cl | trans-(1E)-[4-(3-Chloro-propenyl)-cyclohexyl]-methyl-carbamic acid 4-chloro-phenyl ester | Dimethylamine, 33% in EtOH 5.6 M |
| 39.10 | trans-(1E)-Methyl-[4-(3-piperidin-1-yl-propenyl)-cyclohexyl]-carbamic acid 4-chloro-phenyl ester | 391, 1Cl | trans-(1E)-[4-(3-Chloro-propenyl)-cyclohexyl]-methyl-carbamic acid 4-chloro-phenyl ester | Piperidine |

Example 40

Example 40.1

A solution of 10.0 g (25.2 mmol) of trans-[4-(2,2-Dibromo-vinyl)-cyclohexyl]-methyl-carbamic acid tert-butyl ester in 400 ml THF was treated at −78° C. with 33.0 ml (68.3 mmol) of BuLi (ca 1.6 M in hexane) and stirred for 2 h, then 27.8 ml (230.4 mmol) of DMPU were added and 10 min later 19.0 ml (125.9 mmol) of 2-(2-bromoethoxy) tetrahydro-2H-pyran dissolved in 20 ml were dropped in during 20 min. The reaction was warmed up to RT and stirred over night (approx. 16 h). An aqueous solution of saturated NH$_4$Cl was added and the mixture was extracted with ether (3×). The organic phase was washed with H$_2$O (2×), aqueous 10% NaCl and dried with Na$_2$SO$_4$, filtered and evaporated to give after flash column chromatography on silica gel (Hexane/EtOAc 19:1 to 3:1) 3.5 g (38%) of trans-Methyl-{4-[4-(tetrahydro-pyran-2-yloxy)-but-1-ynyl]-cyclohexyl}-carbamic acid tert-butyl ester, MS: 366 (MH$^+$).

Example 40.2

A solution of 3.45 g (9.44 mmol) of trans-Methyl-{4-[4-(tetrahydro-pyran-2-yloxy)-but-1-ynyl]-cyclohexyl}-carbamic acid tert-butyl ester and 0.7 g (2.83 mmol) of pyrimidium toluene-4-sulfonate in 25 ml MeOH was stirred at 55° C. for 1.5 h. The reaction was partitioned between aqueous solution of 10% KHSO$_4$/ether (3×). The organic phases were washed with aqueous saturated NaHCO$_3$, 10% NaCl, dried over Na$_2$SO$_4$ and evaporated to give 2.85 g (quantitative) of trans-[4-(4-Hydroxy-but-1-ynyl)-cyclohexyl]-methyl-carbamic acid tert-butyl ester, MS: 281 (M).

Example 40.3

A solution of 2.66 g (9.44 mmol) of trans-[4-(4-Hydroxy-but-1-ynyl)-cyclohexyl]-methyl-carbamic acid tert-butyl ester in 75 ml CH$_2$Cl$_2$ was treated at 0° C. with 0.81 ml (10.38 mmol) methanesulfonylchloride, 1.14 ml (14.16 mmol) pyridine and 1.15 g (9.44 mmol) DMAP. The reaction mixture was stirred at RT for 3 h, water (19 ml) was added and the reaction was stirred for 5 min. After extraction with aqueous 10% KHSO$_4$/Et$_2$O (3×) the organic phases were washed with aqueous saturated NaHCO$_3$ (2×), aqueous 10% NaCl, dried over Na$_2$SO$_4$ and evaporated to yield 3.57 g (quantitative) of trans-Methanesulfonic acid 4-[4-(tert-butoxycarbonyl-methyl-amino)-cyclohexyl]-but-3-ynyl ester, MS: 360 (MH$^+$).

Example 40.4

In analogy to example 32.1, trans-Methanesulfonic acid 4-[4-(tert-butoxycarbonyl-methyl-amino)-cyclohexyl]-but-3-ynyl ester with TFA was converted to trans-Methanesulfonic acid 4-(4-methylamino-cyclohexyl)-but-3-ynyl ester trifluoroacetate, MS: 260 (MH$^+$).

Example 40.5

In analogy to example 32.2, trans-Methanesulfonic acid 4-(4-methylamino-cyclohexyl)-but-3-ynyl ester trifluoroacetate and 4-chlorophenylchloroformate were converted to trans-Methanesulfonic acid 4-{4-[(4-chloro-phenoxycarbonyl)-methyl-amino]-cyclohexyl}-but-3-ynyl ester, MS: 414 (MH$^+$, 1Cl).

Example 40.6

In analogy to example 32.2, trans-Methanesulfonic acid 4-(4-methylamino-cyclohexyl)-but-3-ynyl ester trifluoroacetate and 4-trifluoromethylphenylchloroformate were converted to trans-Methanesulfonic acid 4-{4-[methyl-(4-trifluoromethyl-phenoxycarbonyl)-amino]-cyclohexyl}-but-3-ynyl ester, which was directly used in the next reaction.

Example 40.7

In analogy to example 32.2, trans-Methanesulfonic acid 4-(4-methylamino-cyclohexyl)-but-3-ynyl ester trifluoroacetate and 4-(trifluoromethyl)benzenesulfonylchloride were converted to trans-Methanesulfonic acid 4-{4-[methyl-(4-trifluoromethyl-benzenesulfonyl)-amino]-cyclohexyl}-but-3-ynyl ester, MS: 468 (MH$^+$).

Example 41

A solution of 400 mg (corresponds to 0.69 mmol) of crude trans-Methanesulfonic acid 4-{4-[(4-chloro-phenoxycarbonyl)-methyl-amino]-cyclohexyl}-but-3-ynyl ester in 4 ml of methanol was treated with 1.23 ml (6.88 mmol) Dimethylamine (33% in EtOH, 5.6M) and stirred over night at RT. The reaction was heated at 70° C. for 2 h, cooled, evaporated and the residue extracted with aqueous saturated NaHCO$_3$/Et$_2$O (3×). The organic phase was dried with Na$_2$SO$_4$, filtered and evaporated. Purification by flash column chromatography on silica gel (CH$_2$Cl$_2$/MeOH 99:1 to 9:1) gave 84 mg (34%) of trans-[4-(4-Dimethylamino-but-1-ynyl)-cyclohexyl]-methyl-carbamic acid 4-chloro-phenyl ester, MS: 363 (MH$^+$, 1Cl).

The following compounds were prepared from the corresponding mesylates and secondary amines (In case the reaction was not finished after 16 h, additional amine (10 eq) and catalytic amount of NaI was added. The reaction was heated at reflux until completion of the reaction. In some cases DMA was used as solvent instead of MeOH.):

| Example | Compound | MS MH$^+$ | Mesylate | Secondary amine |
|---------|----------|-----------|----------|-----------------|
| 41.1 | trans-{4-[4-(Allyl-methyl-amino)-but-1-ynyl]-cyclohexyl}-methyl-carbamic acid 4-chloro-phenyl ester | 389, 1Cl | trans-Methanesulfonic acid 4-{4-[(4-chloro-phenoxycarbonyl)-methyl-amino]-cyclohexyl}-but-3-ynyl ester | N-Allylmethylamine |
| 41.2 | trans-Methyl-{4-[4-(methyl-propyl-amino)-but-1-ynyl]-cyclohexyl}-carbamic acid 4-chloro-phenyl ester | 391, 1Cl | trans-Methanesulfonic acid 4-{4-[(4-chloro-phenoxycarbonyl)-methyl-amino]-cyclohexyl}-but-3-ynyl ester | N-Methylpropyl-amine |
| 41.3 | trans-(4-{4-[Ethyl-(2-hydroxy-ethyl)-amino]-but-1-ynyl}-cyclohexyl)-methyl-carbamic acid 4-chloro-phenyl ester | 407, 1Cl | trans-Methanesulfonic acid 4-{4-[(4-chloro-phenoxycarbonyl)-methyl-amino]-cyclohexyl}-but-3-ynyl ester | Ethyl-(2-hydroxy-ethyl)-amine |
| 41.4 | trans-(4-{4-[Ethyl-(2-hydroxy-ethyl)-amino]-but-1-ynyl}-cyclohexyl)-methyl-carbamic acid 4-trifluoromethyl-phenyl ester | 441 | trans-Methanesulfonic acid 4-{4-[methyl-(4-trifluoromethyl-phenoxycarbonyl)-amino]-cyclohexyl}-but-3-ynyl ester | Ethyl-(2-hydroxy-ethyl)-amine |
| 41.5 | trans-{4-[4-(Allyl-methyl-amino)-but-1-ynyl]-cyclohexyl}-methyl-carbamic acid 4-trifluoromethyl-phenyl ester | 423 | trans-Methanesulfonic acid 4-{4-[methyl-(4-trifluoromethyl-phenoxycarbonyl)-amino]-cyclohexyl}-but-3-ynyl ester | N-Allylmethylamine |
| 41.6 | trans-[4-(4-Dimethylamino-but-1-ynyl)-cyclohexyl]-methyl-carbamic acid 4- | 397 | trans-Methanesulfonic acid 4-{4-[methyl-(4-trifluoromethyl- | Dimethylamine, 33% in EtOH 5.6 M |

| Example | Compound | MS MH+ | Mesylate | Secondary amine |
|---------|----------|--------|----------|-----------------|
| | trifluoromethyl-phenyl ester | | phenoxycarbonyl)-amino]-cyclohexyl}-but-3-ynyl ester | |
| 41.7 | trans-Methyl-{4-[4-(methyl-propyl-amino)-but-1-ynyl]-cyclohexyl}-carbamic acid 4-trifluoromethyl-phenyl ester | 425 | trans-Methanesulfonic acid 4-{4-[methyl-(4-trifluoromethyl-phenoxycarbonyl)-amino]-cyclohexyl}-but-3-ynyl ester | N-Methylpropyl-amine |
| 41.8 | trans-N-(4-{4-[Ethyl-(2-hydroxy-ethyl)-amino]-but-1-ynyl}-cyclohexyl)-N-methyl-4-trifluoromethyl-benzenesulfonamide | 461 | trans-Methanesulfonic acid 4-{4-[methyl-(4-trifluoromethyl-benzenesulfonyl)-amino]-cyclohexyl}-but-3-ynyl ester | Ethyl-(2-hydroxy-ethyl)-amine |
| 41.9 | trans-N-Methyl-N-{4-[4-(methyl-propyl-amino)-but-1-ynyl]-cyclohexyl}-4-trifluoromethyl-benzenesulfonamide | 445 | trans-Methanesulfonic acid 4-{4-[methyl-(4-trifluoromethyl-benzenesulfonyl)-amino]-cyclohexyl}-but-3-ynyl ester | N-Methylpropyl-amine |
| 41.10 | trans-N-[4-(4-Dimethylamino-but-1-ynyl)-cyclohexyl]-N-methyl-4-trifluoromethyl-benzenesulfonamide | 417 | trans-Methanesulfonic acid 4-{4-[methyl-(4-trifluoromethyl-benzenesulfonyl)-amino]-cyclohexyl}-but-3-ynyl ester | Dimethylamine, 33% in EtOH 5.6 M |

Example 42

Example 42.1

In analogy to example 40.1, trans-[4-(2,2-Dibromo-vinyl)-cyclohexyl]-methyl-carbamic acid tert-butyl ester and 1-chloro-3-iodopropane were converted to trans-[4-(5-Chloro-pent-1-ynyl)-cyclohexyl]-methyl-carbamic acid tert-butyl ester, which was used with no purification directly for the next step.

Example 42.2

In analogy to example 32.1, trans-[4-(5-Chloro-pent-1-ynyl)-cyclohexyl]-methyl-carbamic acid tert-butyl ester was converted to trans-[4-(5-Chloro-pent-1-ynyl)-cyclohexyl]-methyl-ammonium trifluoroacetate. The compound was purified by dissolving the salt in water, washing it with Et$_2$O (3×). The water phase was adjusted to pH 8 (with aqueous saturated NaHCO$_3$) and extracted with EtOAc (3×) to give trans-[4-(5-Chloro-pent-1-ynyl)-cyclohexyl]-methyl-amine, MS: 314 (MH+, 1Cl).

Example 42.3

In analogy to example 32.2, trans-[4-(5-Chloro-pent-1-ynyl)-cyclohexyl]-methyl-amine and 4-(trifluoromethyl)benzenesulfonylchloride was converted to trans-N-[4-(5-Chloro-pent-1-ynyl)-cyclohexyl]-N-methyl-4-trifluoromethyl-benzenesulfonamide, MS: 356 (M–[SO$_2$+H]).

Example 42.4

A solution of 250 mg (0.59 mmol) of trans-N-[4-(5-Chloro-pent-1-ynyl)-cyclohexyl]-N-methyl-4-trifluoromethyl-benzenesulfonamide in 10 ml butan-2-one was treated with 136 mg of NaI (0.91 mmol) and heated at 80° C. for 48 h. Evaporation gave 330 mg of crude trans-N-[4-(5-Iodo-pent-1-ynyl)-cyclohexyl]-N-methyl-4-trifluoromethyl-benzenesulfonamide which was used directly for the next step, MS: 514 (MH+).

Example 43

Example 43.1

In analogy to example 40.1, trans-[4-(2,2-Dibromo-vinyl)-cyclohexyl]-methyl-carbamic acid tert-butyl ester and 2-(3-bromopropoxy)tetrahydro-2H-pyran gave trans-Methyl-{4-[5-(tetrahydro-pyran-2-yloxy)-pent-1-ynyl]-cyclohexyl}-carbamic acid tert-butyl ester, MS: 378 (M–H).

Example 43.2

In analogy to example 40.2, trans-Methyl-{4-[5-(tetrahydro-pyran-2-yloxy)-pent-1-ynyl]-cyclohexyl}-carbamic acid tert-butyl ester gave trans-[4-(5-Hydroxy-pent-1-ynyl)-cyclohexyl]-methyl-carbamic acid tert-butyl ester, MS: 296 (MH+).

Example 43.3

In analogy to example 40.3, trans-[4-(5-Hydroxy-pent-1-ynyl)-cyclohexyl]-methyl-carbamic acid tert-butyl ester gave trans-Methanesulfonic acid 5-[4-(tert-butoxycarbonyl-methyl-amino)-cyclohexyl]-pent-4-ynyl ester, MS: 373 (M).

Example 43.4

In analogy to example 32.1, trans-Methanesulfonic acid 5-[4-(tert-butoxycarbonyl-methyl-amino)-cyclohexyl]-pent-4-ynyl ester gave trans-Methanesulfonic acid 5-(4-methylamino-cyclohexyl)-pent-4-ynyl ester trifluoroacetate, MS: 274 (MH+).

Example 43.5

In analogy to example 32.2, trans-Methanesulfonic acid 5-(4-methylamino-cyclohexyl)-pent-4-ynyl ester trifluoroacetate and 4-chlorophenylchloroformate gave trans-Methanesulfonic acid 5-{4-[(4-chloro-phenoxycarbonyl)-methyl-amino]-cyclohexyl}-pent-4-ynyl ester, MS: 428 (MH$^+$, 1Cl).

Example 44

320 mg (corresponds to 0.59 mmol) of crude trans-N-[4-(5-Iodo-pent-1-ynyl)-cyclohexyl]-N-methyl-4-trifluoromethyl-benzenesulfonamide in 6 ml MeOH was treated with 0.6 ml (5.93 mmol) of N-methylpropylamine. The reaction was stirred overnight at 65° C. and partitioned between aqueous 1N NaOH/Et$_2$O (3×), the organic phases were dried over Na$_2$SO$_4$ and evaporated. Purification by flash column chromatography on silica gel (CH$_2$Cl$_2$, then CH$_2$Cl$_2$/MeOH 95:5 to 9:1) gave 128 mg (47% over two steps) of trans-N-Methyl-N-{4-[5-(methyl-propyl-amino)-pent-1-ynyl]-cyclohexyl}-4-trifluoromethyl-benzenesulfonamide, MS: 459 (MH$^+$). The following compounds can be obtained in analogy:

column chromatography on silica gel (hexane/EtOAc 9:1) gave 16.1 g (73%) of trans-(1E/Z)-[4-(5-Bromo-pent-1-enyl)-cyclohexyl]-carbamic acid tert-butyl ester, MS: 289 (M-butene, 1Br).

Example 45.3

A solution of 14.0 g (40.4 mmol) of trans-(1E/Z)-[4-(5-Bromo-pent-1-enyl)-cyclohexyl]-carbamic acid tert-butyl ester in 140 ml EtOH was treated with 7 ml AcOH and 1.4 g Pt/C$_5$% and hydrogenated with H$_2$ (1 atm) for 1.5 h. The reaction was filtered and evaporated (1x toluene). The residue was dissolved at RT in MeOH (105 ml) and treated with 15.5 ml water. After cooling (0° C.) and filtration, 7.43 g (53%) of trans-[4-(5-Bromo-pentyl)-cyclohexyl]-carbamic acid tert-butyl ester were received, MS: 291 (M-butene, 1Br).

Example 45.4

At 0° C., a solution of 4.4 g (12.63 mmol) of trans-[4-(5-Bromo-pentyl)-cyclohexyl]-carbamic acid tert-butyl ester were received in 9 m MeOH was added to 40 ml of a

| Example | Compound | MS MH$^+$ | Iodide or Mesylate | Secondary amine |
| --- | --- | --- | --- | --- |
| 44.1 | trans-N-(4-{5-[Ethyl-(2-hydroxy-ethyl)-amino]-pent-1-ynyl}-cyclohexyl)-N-methyl-4-trifluoromethyl-benzenesulfonamide | 475 | trans-N-[4-(5-Iodo-pent-1-ynyl)-cyclohexyl]-N-methyl-4-trifluoromethyl-benzenesulfonamide | Ethyl-(2-hydroxy-ethyl)-amine |
| 44.2 | trans-(4-{5-[Ethyl-(2-hydroxy-ethyl)-amino]-pent-1-ynyl}-cyclohexyl)-methyl-carbamic acid 4-chloro-phenyl ester | 421, 1Cl | trans-Methanesulfonic acid 5-{4-[(4-chloro-phenoxycarbonyl)-methyl-amino]-cyclohexyl}-pent-4-ynyl ester | Ethyl-(2-hydroxy-ethyl)-amine |
| 44.3 | Trans-Methyl-{4-[5-(methyl-propyl-amino)-pent-1-ynyl]-cyclohexyl}-carbamic acid 4-chloro-phenyl ester | 405, 1Cl | trans-Methanesulfonic acid 5-{4-[(4-chloro-phenoxycarbonyl)-methyl-amino]-cyclohexyl}-pent-4-ynyl ester | N-Methylpropylamine |
| 44.4 | Trans-[4-(5-Dimethylamino-pent-1-ynyl)-cyclohexyl]-methyl-carbamic acid 4-chloro-phenyl ester | 377, 1Cl | trans-Methanesulfonic acid 5-{4-[(4-chloro-phenoxycarbonyl)-methyl-amino]-cyclohexyl}-pent-4-ynyl ester | Dimethylamine, 33% in EtOH 5.6 M |

Example 45

Example 45.1

In analogy to example 26.3, trans-[4-(Methoxy-methyl-carbamoyl)-cyclohexyl]-carbamic acid tert-butyl ester gave trans-(4-Formyl-cyclohexyl)-carbamic acid tert-butyl ester, which was directly used in the next reaction.

Example 45.2

A solution of 14.4 g (63.34 mmol) of trans-(4-Formyl-cyclohexyl)-carbamic acid tert-butyl ester in 180 ml 2-methyl-2-butanol was treated with 36.5 g (76.32 mmol) (4-bromobutyl)triphenylphosphonium bromide and 82.8 g (254.2 mmol) of cesium carbonate and was heated at 65° C. for 7 h. The reaction was cooled (RT), diluted with hexane/ETOAc (9:1, 500 ml) and filtered. Purification by flash HBr solution in MeOH (made by dropping at 0° C., 4.7 ml (63.07 mmol) of acetylbromide to 35 ml MeOH). The suspension was stirred for 16 h at RT, diluted with toluene and evaporated (2×). The residue was suspended in EtOAc (40 ml) cooled (−10 to −15° C.) and filtered to give 4.05 g (97%) of trans-4-(5-Bromo-pentyl)-cyclohexylamine as hydrobromide salt, MS: 248 (MH$^+$, 1Br).

Example 45.5

A solution of 1.0 g (3.04 mmol) of trans-4-(5-Bromo-pentyl)-cyclohexylammonium bromide in 12 ml CH$_2$Cl$_2$ was first cooled at 0° C., treated with 0.8 g (3.27 mmol) 4-(trifluoromethyl)benzenesulfonylchloride and then with 1.2 ml (7.01 mmol; 2.3 equivalents) of Hünigsbase (during 30 min). After total 1.5 h at 0° C., the mixture was dissolved in aqueous 10% KHSO$_4$/TBME (3×). The organic phases were washed with aqueous saturated NaHCO$_3$ and aqueous 10% NaCl, dried over Na$_2$SO$_4$ and evaporated to give 1.38 g crude product which was crystallized (CH$_2$Cl$_2$/hexane) to give 1.26 g (91%) of pure trans-N-[4-(5-Bromo-pentyl)-cyclohexyl]-4-trifluoromethyl-benzenesulfonamide, MS: 454 (M−H⁻, 1Br).

Example 46

Example 46.1

A solution of 2.4 mg (5.26 mmol) of trans-N-[4-(5-Bromo-pentyl)-cyclohexyl]-4-trifluoromethyl-benzenesulfonamide in 36 ml of EtOH was treated with 2.1 ml (21.53 mmol) of ethyl-(2-hydroxy-ethyl)-amine, 1.8 g (21.43 mmol) of NaHCO$_3$ and stirred over night at 90° C. The reaction cooled, filtered, evaporated and the residue extracted with aqueous saturated NaHCO$_3$/EtOAc (3×). The organic phases were washed with aqueous 10% NaCl, dried (Na$_2$SO$_4$), filtered and evaporated. Purification by flash column chromatography on silica gel (EtOAc/EtOH/NH$_3$ 25% 98:2:1) gave 1.96 g (80%) of trans-N-(4-{5-[Ethyl-(2-hydroxy-ethyl)-amino]-pentyl}-cyclohexyl)-4-trifluoromethyl-benzenesulfonamide, MS: 463 (M−H⁻).

Example 46.2

In analogy to example 46.1, trans-N-[4-(5-Bromo-pentyl)-cyclohexyl]-4-trifluoromethyl-benzenesulfonamide and ethanolamine gave trans-N-{4-[5-(2-Hydroxy-ethylamino)-pentyl]-cyclohexyl}-4-trifluoromethyl-benzenesulfonamide, MS: 437 (MH⁺).

Example 46.3

In analogy to example 46.1 but without NaHCO$_3$ and at 60° C. for 19 h, trans-N-[4-(5-Bromo-pentyl)-cyclohexyl]-4-trifluoromethyl-benzenesulfonamide and 18 equivalent of ethylamine (70% in water) gave trans-N-[4-(5-Ethylamino-pentyl)-cyclohexyl]-4-trifluoromethyl-benzenesulfonamide, MS: 421 (MH⁺).

Example 47

Example 47.1

A well stirred solution of 100 g (774 mmol) of cis-4-Methylamino-cyclohexanol [Schut, Robert N. Analgesic 3-(methylamino)-1,2,3,4-tetrahydrocarbazole from 4-(methylamino)cyclohexanone. Fr. (1968), 3 pp. FR 1515629 19680301] in 775 ml EtOAc was treated with 1.55 l of aqueous 1M NaHCO$_3$ and with 110 ml (774 mmol) of benzyl chloroformate (30 min, Tmax 30° C.). The phases were separated after 2 h at RT. The aqueous phase was extracted (EtOAc), the organic phases were dried (Na$_2$SO$_4$), filtered and evaporated. Purification by column chromatography on silica gel (hexane/EtOAc 2:1) gave 139 g (68%) of cis-(4-Hydroxy-cyclohexyl)-methyl-carbamic acid benzyl ester, MS: 263 (M).

Example 47.2

A solution of 2.63 g (10 mmol) of cis-(4-Hydroxy-cyclohexyl)-methyl-carbamic acid benzyl ester in 16 ml CH$_2$Cl$_2$ was treated with a solution 0.24 g (2 mmol) of KBr and 0.28 g (3.33 mmol) of NaHCO$_3$ in 5 ml of water. The suspension was cooled (0-5° C.) and 8 mg (0.05 mmol) of TEMPO and then 5.7 ml (12.5 mmol) of NaOCl (13%, 2.18 M in water) were added during 20 min. After 1 h at this temperature, again 8 mg (0.05 mmol) of TEMPO and then 2.85 ml (6.25 mmol) of NaOCl (13%, 2.18 M in water) were added. After 1 h, 5 ml of 1M sodium thiosulfat solution was added. The aqueous phase was extracted with CH$_2$Cl$_2$ (2×), the organic phase was dried (Na$_2$SO$_4$), filtered and evaporated to give 2.57 g (99%) of Methyl-(4-oxo-cyclohexyl)-carbamic acid benzyl ester, MS: 261 (M).

Example 47.3

A suspension of 749.88 g (2187.5 mmol) (methoxymethyl)triphenylphosphonium chloride in 2.5 l THF was cooled to −10° C. and deprotonated with 245.5 g (2187.5 mmol) potassium t-butoxide. The dark red solution was stirred at 0-5° C. for 0.5 h, cooled to −20° C. and 457.32 g (261.33 mmol) of Methyl-(4-oxo-cyclohexyl)-carbamic acid benzyl ester in 1.25 l THF were added over a period of 1.25 h. After 1.3 h at RT, the reaction was treated with 1.75 l aqueous 1M NaHCO$_3$ and stirred for 45 min. The phases were separated, the aqueous phase was extracted with TBME (700 ml), the organic phase was dried (Na$_2$SO$_4$), filtered and evaporated. The residue was suspended in hexane (5 l), cooled (0° C.), filtered and evaporated to give 495.2 g (98%) of (4-Methoxymethylene-cyclohexyl)-methyl-carbamic acid benzyl ester, MS: 289 (M).

Example 47.4

A solution of 495 g (1710.6 mmol) of (4-Methoxymethylene-cyclohexyl)-methyl-carbamic acid benzyl ester in 1.7 l THF was treated with 3.42 l of aqueous 1N HCl at RT and heated at reflux for 2 h. The reaction was cooled to RT and extracted with TBME (1.7 and 0.9 l). The organic phase was washed with aqueous 1M NaHCO$_3$, dried (Na$_2$SO$_4$), filtered and evaporated to give 457.4 (97%) of crude (4-Formyl-cyclohexyl)-methyl-carbamic acid benzyl ester (trans:cis ca 70:30).

A solution of 133.2 g (483.7 mmol) of crude (4-Formyl-cyclohexyl)-methyl-carbamic acid benzyl ester in 330 ml MeOH was treated with 24 ml 1M NaOH and stirred at RT for 0.5 h, then 1.40 ml (24.2 mmol) acetic acid were added and the mixture was evaporated to give 144.2 g crude (4-Formyl-cyclohexyl)-methyl-carbamic acid benzyl ester as an oil (trans:cis ca 92:8). A solution of crude 144.2 g (4-Formyl-cyclohexyl)methyl-carbamic acid benzyl ester in 670 ml TBME was added to a solution of 184.0 g (968 mmol) of disodium pyrosulfite in 670 ml water at RT. The reaction was stirred at RT for 16 h, filtered and washed (200 ml TBME) to give 147.2 g of the sodium salt of [4-(Benzyloxycarbonyl-methyl-amino)-cyclohexyl]-hydroxymethanesulfonic acid. This compound was suspended in 250 ml TBME and 780 ml aqueous 1M Na$_2$CO$_3$ and stirred at RT for 0.25 h. The phases were separated, the aqueous phase was extracted with TBME (250 ml), the organic phase was dried (Na$_2$SO$_4$), filtered and evaporated to give 98.9 g (72% over the two steps) of trans-(4-Formyl-cyclohexyl)-methyl-carbamic acid benzyl ester (trans:cis 99.3:0.7), MS: 275 (M).

Example 47.5

A solution of 126.5 g (459.4 mmol) of trans-(4-Formyl-cyclohexyl)-methyl-carbamic acid benzyl ester in 1.27 l 2-methyl-2-butanol was treated with 263.6 g (551.3 mmol) (4-bromobutyl)triphenylphosphonium bromide and 254 g (1838 mmol) of K$_2$CO$_3$ and was heated at reflux for 3.5 h.

The reaction was cooled (RT), filtered and evaporated. The residue was suspended in hexane (1.8 l, first at RT then at 0° C.) and filtered. Purification by column chromatography on silica gel (hexane/EtOAc 4:1) gave 149.9 g (83%) of trans-(1 E/Z)-[4-(5-Bromo-pent-1-enyl)-cyclohexyl]-methyl-carbamic acid benzyl ester, MS: 293 (M, 1Br).

Example 47.6

A solution of 38.61 g (97.9 mmol) of trans-(1E/Z)-[4-(5-Bromo-pent-1-enyl)-cyclohexyl]-methyl-carbamic acid benzyl ester in 500 ml toluene was treated with 4.5 g Pt/C$_5$% and hydrogenated with H$_2$ (1 atm) for 3 days. The reaction was filtered and evaporated to give 36.06 g (93%) of trans-[4-(5-Bromo-pentyl)-cyclohexyl]-methyl-carbamic acid benzyl ester, MS: 396 (MH$^+$, 1Br).

Example 47.7

22.55 g (56.89 mmol) of trans-[4-(5-Bromo-pentyl)-cyclohexyl]-methyl-carbamic acid benzyl ester were dissolved at RT in 100 ml HBr (33% in acetic acid). After 20 min, the reaction was evaporated, suspended in toluene (2×) and evaporated again. The suspension was taken up in hexane and filtered to give 17.49 g (90%) of trans-[4-(5-Bromo-pentyl)-cyclohexyl]-methyl-amine hydrobromide, MS: 262 (MH$^+$, 1Br).

Example 47.8

In analogy to 32.2, trans-[4-(5-Bromo-pentyl)-cyclohexyl]-methyl-amine hydrobromide and 4-trifluoromethylphenylchloroformate were converted to trans-[4-(5-Bromo-pentyl)-cyclohexyl]-methyl-carbamic acid 4-trifluoromethyl-phenyl ester, MS: 450 (MH$^+$, 1Br).

Example 47.9

In analogy to 32.2, trans-[4-(5-Bromo-pentyl)-cyclohexyl]-methyl-amine hydrobromide and 4-(trifluoromethyl) benzenesulfonylchloride were converted to trans-N-[4-(5-Bromo-pentyl)-cyclohexyl]-N-methyl-4-trifluoromethyl-benzenesulfonamide, MS: 470 (MH$^+$, 1Br).

Example 47.10

In analogy to examples 47.5-7, 47.9 and 46.1, from trans/cis-(4-Formyl-cyclohexyl)-methyl-carbamic acid benzyl ester was prepared trans-N-(4-{5-[Ethyl-(2-hydroxy-ethyl)-amino]-pentyl}-cyclohexyl)-N-methyl-4-trifluoromethyl-benzenesulfonamide and cis-N-(4-{5-[Ethyl-(2-hydroxy-ethyl)-amino]-pentyl}-cyclohexyl)-N-methyl-4-trifluoromethyl-benzenesulfonamide RO-72-5688/000, MS: 479 (MH$^+$), which could be separated using HPLC (ChiralpakAD, 20 um 5×50 cm von Daicel Chem. Industrie Ltd, eluent: 8.0 l n-heptane/2.0 l ethanol und 0.1% CF$_3$COOH).

Example 48

To 500 mg (10.5 mmol) trans-N-(4-{5-[Ethyl-(2-hydroxy-ethyl)-amino]-pentyl}-cyclohexyl)-N-methyl-4-trifluoromethyl-benzenesulfonamide in 6 ml CH$_2$Cl$_2$ were added 0.2 ml (1.6 mmol) DAST at −78° C. After 3.5 h at that temperature additional 0.2 ml (1.6 mmol) DAST were added and the mixture was slowly warmed to RT over night. The solution was added to a cooled aqueous solution of Na$_2$CO$_3$ and extracted with EtOAc. The organic phase was washed with brine and dried over Na$_2$SO$_4$. Column chromatography CH$_2$Cl$_2$/MeOH 98:2 yielded 125.4 mg (25%) trans-N-(4-{5-[Ethyl-(2-fluoro-ethyl)-amino]-pentyl}-cyclohexyl)-N-methyl-4-trifluoromethyl-benzenesulfonamide as brown oil, MS: 481 (MH$^+$).

Example 49

Example 49.1

To 350 mg (1 mmol) trans-4-Bromo-N-(4-hydroxy-cyclohexyl)-N-methyl-benzenesulfonamide in 6 ml toluene was added 344 mg (2.0 mmol) 2-diethylamino-ethylchlorid.hydrochloride and a catalytic amount of Bu$_4$NHSO$_4$ followed by 4 ml 50% NaOH. The mixture was stirred at RT over night, the phases were separated and the organic phase dried over Na$_2$SO$_4$. Column chromatography on silica gel with CH$_2$Cl$_2$/MeOH 15:1 yielded 380 mg (84%) trans-4-Bromo-N-[4-(2-diethylamino-ethoxy)-cyclohexyl]-N-methyl-benzenesulfonamide as light yellow oil, MS: 447 (MH$^+$, 1Br).

Example 49.2

In analogy to example 49.1, from trans-4-Bromo-N-(4-hydroxy-cyclohexyl)-N-methyl-benzenesulfonamide and 1-(2-Chlorethyl)-piperidine HCl was prepared trans-4-Bromo-N-methyl-N-[4-(2-piperidin-1-yl-ethoxy)-cyclohexyl]-benzenesulfonamide as light yellow oil, MS: 459 (MH$^+$, 1Br).

Example 49.3

In analogy to example 49.1, from trans-4-Bromo-N-(4-hydroxy-cyclohexyl)-N-methyl-benzenesulfonamide and 4-(2-Chlorethyl)morpholine hydrochloride was prepared trans-4-Bromo-N-methyl-N-[4-(2-morpholin-4-yl-ethoxy)-cyclohexyl]-benzenesulfonamide as colorless oil, MS: 461 (MH$^+$, 1Br).

Example 49.4

In analogy to the example 49.1, from trans-4-Bromo-N-(4-hydroxy-cyclohexyl)-N-methyl-benzenesulfonamide and Chlorethylpyrroline.hydrochloride was prepared trans-4-Bromo-N-methyl-N-[4-(2-pyrrolidin-1-yl-ethoxy)-cyclohexyl]-benzenesulfonamide as colorless oil, MS: 445 (MH$^+$, 1Br).

Example 49.5

In analogy to the example 49.1, from trans-4-Bromo-N-(4-hydroxy-cyclohexyl)-N-methyl-benzenesulfonamide and diisopropylaminoethylchloride.hydrochloride was prepared trans-4-Bromo-N-[4-(2-diisopropylamino-ethoxy)-cyclohexyl]-N-methyl-benzenesulfonamide as colorless oil, MS: 475 (MH$^+$, 1Br).

Example 49.6

In analogy to example 49.1, from trans-N-(4-Hydroxy-cyclohexyl)-N-methyl-4-trifluoromethyl-benzenesulfonamide and Diethylaminoethylchloride.hydrochloride was prepared trans-N-[4-(2-Diethylamino-ethoxy)-cyclohexyl]-N-methyl-4-trifluoromethyl-benzenesulfonamide as light yellow oil, MS: 437 (MH$^+$).

Example 49.7

In analogy to example 49.1, from trans-N-(4-Hydroxy-cyclohexyl)-N-methyl-4-trifluoromethyl-benzenesulfonamide and 1-(2-Chloroethyl)piperidine.hydrochloride was prepared trans-N-Methyl-N-[4-(2-piperidin-1-yl-ethoxy)-cyclohexyl]-4-trifluoromethyl-benzenesulfonamide as light yellow oil, MS: 449 (MH$^+$).

Example 49.8

In analogy to example 49.1, from trans-N-(4-Hydroxy-cyclohexyl)-N-methyl-4-trifluoromethyl-benzenesulfonamide and diisopropylaminoethylchloride.hydrochloride was prepared trans-N-[4-(2-Diisopropylamino-ethoxy)-cyclohexyl]-N-methyl-4-trifluoromethyl-benzenesulfonamide as light yellow oil, MS: 465 (MH$^+$).

Example 49.9

In analogy to example 49.1, from trans-N-(4-Hydroxy-cyclohexyl)-N-methyl-4-trifluoromethyl-benzenesulfonamide and chloroethylpyrrolidine.hydrochloride was prepared trans-N-Methyl-N-[4-(2-pyrrolidin-1-yl-ethoxy)-cyclohexyl]-4-trifluoromethyl-benzenesulfonamide as light yellow oil, MS: 435 (MH$^+$).

Example 49.10

In analogy to example 49.1, from trans-N-(4-Hydroxy-cyclohexyl)-N-methyl-4-trifluoromethyl-benzenesulfonamide and 4-chloroethylmorpholine.hydrochloride was prepared trans-N-Methyl-N-[4-(2-morpholin-4-yl-ethoxy)-cyclohexyl]-4-trifluoromethyl-benzenesulfonamide as colorless oil, MS: 451 (MH$^+$).

Example 50

Example 50.1

1.71 g (10 mmol) (1,4-dioxa-spiro[4.5]dec-8-yl)-methyl-amine (e.g. Reductive amination: Avenell, Kim Y.; Boyfield, Izzy; Hadley, Michael S.; Johnson, Christopher N.; Nash, David J.; Riley, Graham J.; Stemp, Geoffrey; BMCLE8; Bioorg. Med. Chem. Lett.; EN; 9; 18; 1999; 2715-2720.) were stirred with 20 ml (20 mmol) 1M HCl for 1 h. At RT 2.12 g (20 mmol) Na$_2$CO$_3$ were added, followed by the addition of 2.4 g (11.0 mmol) di-tert.butyldicarbonate in 20 ml EtOAc. The solution was stirred at RT for 4 h, the phases were separated and the inorganic one extracted with EtOAc. The combined organic phases were dried over Na$_2$SO$_4$ and concentrated. Crystallization from methylcyclohexane gave 0.95 g (42%) Methyl-(4-oxo-cyclohexyl)-carbamic acid tert-butyl ester.

Example 50.2

5 g (21.99 mmol) Methyl-(4-oxo-cyclohexyl)-carbamic acid tert-butyl ester and 12.68 g (28.59 mmol) (4-Carboxy-butyl)-triphenyl-phosphonium bromide were dispended in 50 ml DMF. In small portions 2.49 g (57.2 mmol, 55%) NaH were added and the slurry was diluted by adding 50 ml DMF. The mixture was stirred at RT over night, 10 ml AcOH were added and the solvent was evaporated under reduced pressure. The residue was dissolved in ether and water, and the inorganic layer was extracted with ether. The combined organic phases were dried over and the crude materil was purified by column chromatography with ETOAc/hexane to give 5.86 g (83%) 5-[4-(tert-Butoxycarbonyl-methyl-amino)-cyclohexylidene]-pentanoic acid.

Example 50.3

5.0 g (16.1 mmol) 5-[4-(tert-Butoxycarbonyl-methyl-amino)-cyclohexylidene]-pentanoic acid in 50 ml methanol were hydrogenated with 0.5 g 10% Pd/C in the presence of 0.94 ml (16.9 mmol, 1.05 eq) sodium methanolate for 1 h at RT. After filtration and evaporation of the solvent, the residue was dissolved in ether and acidified by adding 1M HCl. The organic phase was extracted with water, dried over MgSO$_4$ and evaporated to give 5.3 g (quant) trans-5-[4-(tert-Butoxycarbonyl-methyl-amino)-cyclohexyl]-pentanoic acid as light yellow oil, MS: (312 MH$^+$).

Example 50.4

To 1 g (3.19 mmol) trans-5-[4-(tert-Butoxycarbonyl-methyl-amino)-cyclohexyl]-pentanoic acid in 37 ml CH$_2$Cl$_2$ was added 0.5 ml (4.8 mmol, 1.5 eq) diethylamine and 0.53 ml (4.79 mmol, 1.5 eq) NMM. The solution was cooled to 0° C. and 795 mg (4.15 mmol, 1.3 eq) EDCI and 98 mg (6.4 mmol) HOBT were added. The mixture was stirred at RT over night, partitioned between CH$_2$Cl$_2$ and a saturated aqueous solution of NaHCO$_3$. The organic phase was washed with KHSO$_4$ and brine, dried over Na$_2$SO$_4$ and evaporated. Column chromatography with EtOAc/hexane 1:1 gave 1.05 g (86%) trans-[4-(4-Diethylcarbamoyl-butyl)-cyclohexyl]-methyl-carbamic acid tert-butyl ester as colorless liquid MS: 369 (MH$^+$).

Example 50.5

To 0.99 g (2.7 mmol) trans-[4-(4-Diethylcarbamoyl-butyl)-cyclohexyl]-methyl-carbamic acid tert-butyl ester in 5 ml dioxane were added 7 ml 4M HCl in dioxane at 0° C. The solution was stirred at RT for 2 h, diluted with ether, and the precipitated solid was isolated. 0.83 g (quant.) trans-5-(4-Methylamino-cyclohexyl)-pentanoic acid diethylamide.hydrochloride were isolated as white solid, mp. 122° C., MS: 269 (MH$^+$).

Example 50.6

0.8 g (2.6 mmol) trans-5-(4-Methylamino-cyclohexyl)-pentanoic acid diethylamide.hydrochloride in 20 ml CH$_2$Cl$_2$ was treated with 1.1 ml (6.3 mmol, 2.4 eq) Huenig's base, 706 mg (2.9 mmol, 1.1 eq) 4-(Trifluoromethyl)benzenesulfonyl chloride in 10 ml CH$_2$Cl$_2$ and 32 mg (0.26 mmol, 0.1 eq) DMAP. The solution was stirred at RT over night. Additonal 1.1 ml (6.3 mmol) Huenig's base, 706 mg (2.9 mmol) 4-(Trifluoromethyl)benzenesulfonyl chloride in 10 ml CH$_2$Cl$_2$ and 32 mg (0.26 mmol) DMAP were added and stirring was continued for 3 h. The mixture was partitioned between CH$_2$Cl$_2$ and a saturated aqueous solution of NaHCO$_3$. The organic phase was washed with water, 1M KHSO$_4$ and brine, dried over Na$_2$SO$_4$ and evaporated. Column chromatography with EtOAc/hexane 1:1 gave 1.06 g (84%) trans-5-{4-[Methyl-(4-trifluoromethyl-benzenesulfonyl)-amino]-cyclohexyl}-pentanoic acid diethylamide as colorless oil, MS: 477 (MH$^+$).

Example 50.7

To a solution of 200 mg (0.4 mmol) trans-5-{4-[Methyl-(4-trifluoromethyl-benzenesulfonyl)-amino]-cyclohexyl}-pentanoic acid diethylamide in THF was added 98 mg (4.2 mmol, 1 eq) zirconium(IV) chloride at −10° C. and the reaction mixture was stirred for additional 30 min. 0.8 ml 3M (25.2 mmol, 6 eq) Methylmagnesium bromide in THF were added at −10° C. and the mixture was slowly warmed to RT. After 2 h the mixture was added to a mixture of 30% NaOH and $CH_2Cl_2$. The inorganic phase was extracted with $CH_2Cl_2$ and the combined organic phases were washed with brine and dried over $Na_2SO_4$ and evaporated. The residue was purified using ion exchange resin (Varian, SCX resin) to yield 133 mg (65%) trans-N-[4-(5-Diethylamino-5-methyl-hexyl)-cyclohexyl]-N-methyl-4-trifluoromethyl-benzenesulfonamide as colorless oil, MS: 491 ($MH^+$).

Example 50.8

Analogously to the example 50.4 from trans-5-{4-[Methyl-(4-trifluoromethyl-benzenesulfonyl)-amino]-cyclohexyl}-pentanoic acid diethylamide and ethylmagnesium bromide is prepared trans-N-{4-[4-(1-Diethylamino-cyclopropyl)-butyl]-cyclohexyl}-N-methyl-4-trifluoromethyl-benzenesulfonamide as yellow oil, MS: 489 ($MH^+$).

Example 50.9

Analogously to the example 50.4 from trans-(4-Dimethylcarbamoylethynyl-cyclohexyl)-methyl-carbamic acid tert-butyl ester and methyl magnesium bromide was prepared trans-[4-(3-Dimethylamino-3-methyl-but-1-ynyl)-cyclohexyl]-methyl-carbamic acid tert-butyl ester as yellow oil, MS: 323 ($MH^+$).

Example 51

Example 51.1

To a solution of 0.62 g (5.9 mmol) Methyl beta-hydroxypropionate in 4.5 ml $CH_2Cl_2$ was added 1.4 ml (6.4 mmol, 2.4 eq) 2,6-Di-tert-butylpyridine, followed by 1.03 ml (6.2 mmol, 2.4 eq) trifluoromethane sulfonic acid anhydride at 0° C. The solution was stirred at that temperature for 2.5 h, was concentrated and the residue dissolved in 5 ml nitromethane. To this solution 1 g (2.96 mmol) trans-N-(4-Hydroxy-cyclohexyl)-N-methyl-4-trifluoromethyl-benzenesulfonamide and 1.3 ml (5.9 mmol, 2.0 eq) 2,6-Di-tert-butylpyridine in 10 ml nitromethane were added. The solution was stirred at 60° C. for 3 h, diluted with EtOAc and 1M $KHSO_4$. The inorganic phase was extracted with EtOAc, the combined organic phases were washed with a saturated aqueous solution of $NaHCO_3$, brine and were dried over $Na_2SO_4$ and evaporated. Column chromatography on silica gel with EtOAc/hexane 1:3 gave 1.2 g (95%) trans-3-{4-[Methyl-(4-trifluoromethyl-benzenesulfonyl)-amino]-cyclohexyloxy}-propionic acid methyl as light yellow oil, MS: 424 ($MH^+$).

Example 51.2

1.14 g (2.7 mmol) trans-3-{4-[Methyl-(4-trifluoromethyl-benzenesulfonyl)-amino]-cyclohexyloxy}-propionic acid methyl ester in 27 ml THF were treated with 27 ml 1M LiOH for 1 h at RT. The was acidified by adding 1M $KHSO_4$, and the mixture was extracted with EtOAc. The organic phase was washed with brine, dried over $Na_2SO_4$ and evaporated to give 1.1 g (quant.) trans-3-{4-[Methyl-(4-trifluoromethyl-benzenesulfonyl)-amino]-cyclohexyloxy}-propionic acid as colorless oil, MS: 408 $(M-H)^-$.

Example 51.3 g (2.7 mmol) trans-3-{4-[Methyl-(4-trifluoromethyl-benzenesulfonyl)-amino]-cyclohexyloxy}-propionic acid in 30 ml $CH_2Cl_2$ were treated with 2 ml (4.0 mmol, 1.5 eq) 2M dimethylamine in THF and 0.44 ml (4.03 mmol, 1.5 eq) NMM. The solution was cooled to 0° C. and 670 mg (3.5 mmol, 1.3 eq) EDCI and 82 mg (5.4 mmol, 0.2 eq) HOBT were added. The mixture was stirred at RT over night, partitioned between $CH_2Cl_2$ and a saturated aqueous solution of $NaHCO_3$. The organic phase was washed with $KHSO_4$ and brine, dried over $Na_2SO_4$ and evaporated. Column chromatography with EtOAc gave 1.06 g (90%) trans-N,N-Dimethyl-3-{4-[methyl-(4-trifluoromethyl-benzenesulfonyl)-amino]-cyclohexyloxy}-propionamide as white solid, mp 88° C., MS: 437 ($MH^+$).

Example 51.4

Analogously to the example 50.4, from trans-N,N-Dimethyl-3-{4-[methyl-(4-trifluoromethyl-benzenesulfonyl)-amino]-cyclohexyloxy}-propionamide and methylmagnesium bromide was prepared trans-N-[4-(3-Dimethylamino-3-methyl-butoxy)-cyclohexyl]-N-methyl-4-trifluoromethyl-benzenesulfonamide as colorless oil, MS: 451 ($MH^+$).

Example 51.5

Analogously to the example 50.4, from trans-N,N-Dimethyl-3-{4-[methyl-(4-trifluoromethyl-benzenesulfonyl)-amino]-cyclohexyloxy}-propionamide and ethylmagnesium bromide was prepared trans-N-{4-[2-(1-Dimethylamino-cyclopropyl)-ethoxy]-cyclohexyl}-N-methyl-4-trifluoromethyl-benzenesulfonamide as light yellow oil, MS: 449 ($MH^+$).

Example 52

Example 52.1

To 1.0 g (2.18 mmol) trans-N-[4-(3-Bromo-propoxy)-cyclohexyl]-N-methyl-4-trifluoromethyl-benzenesulfonamide in 10 ml acetonitrile was added 0.29 ml (3.1 mmol) acetocyanhydrine in 5 ml acetonitrile and 0.37 ml (2.5 mmol) 1,8-Diazabicyclo-(5,4,0)-undec-7-ene in 5 ml acetonitrile. The solution was stirred at RT over night. An additonal amount of acetocyanhydrine and 1,8-Diazabicyclo-(5,4,0)-undec-7-ene were added and the solution stirred at 50° C. for 6 h. The mixture was concentrated and dissolved in water/ether. The organic phase was washed with brine, dried over $Na_2SO_4$ and was evaporated to give 366 mg (41%) trans-N-[4-(3-Cyano-propoxy)-cyclohexyl]-N-methyl-4-trifluoromethyl-benzenesulfonamide as light yellow oil, MS: 404 (M).

Example 52.2

0.35 g (0.87 mmol) trans-N-[4-(3-Cyano-propoxy)-cyclohexyl]-N-methyl-4-trifluoromethyl-benzenesulfonamide in 6 ml ethanol were treated with HCl gas at low temperature for 20 min. The mixture was kept at −20° C. for 48 h, was concentrated under reduced pressure to yield 400 mg (quant.) trans-4-{4-[Methyl-(4-trifluoromethyl-benzenesulfonyl)-amino]-cyclohexyloxy}-butyrimidic acid ethyl ester as light brown oil, MS: 451 (MH+).

Example 52.3

400 mg (0.89 mmol) trans-4-{4-[Methyl-(4-trifluoromethyl-benzenesulfonyl)-amino]-cyclohexyloxy}-butyrimidic acid ethyl ester were suspended in 10 ml water and heated to 100° C. for 2.5 h. EtOAc was added, and the inorganic phase was extracted with EtOAc. The combined organic phases were dried over $Na_2SO_4$ and evaporated to give 355 mg (89%) trans-4-{4-[Methyl-(4-trifluoromethyl-benzenesulfonyl)-amino]-cyclohexyloxy}-butyric acid ethyl ester as yellow oil, MS: 452 ($MH^+$).

Example 52.4

350 mg (0.78 mmol) trans-4-{4-[Methyl-(4-trifluoromethyl-benzenesulfonyl)-amino]-cyclohexyloxy}-butyric acid ethyl ester in 3.5 ml ethanol were treated with 3.5 ml 1M LiOH at 60° C. for 2 h. 2M HCl was added (pH 1-2), and the mixture was extracted with $CH_2Cl_2$, the combined organic phases were washed with brine and dried over $Na_2SO_4$ to yield after evaporation 250 mg (76%) trans-4-{4-[Methyl-(4-trifluoromethyl-benzenesulfonyl)-amino]-cyclohexyloxy}-butyric acid as off-white solid, MS: 422 ($M-H^-$).

Example 52.5

250 mg (0.59 mmol) trans-4-{4-[Methyl-(4-trifluoromethyl-benzenesulfonyl)-amino]-cyclohexyloxy}-butyric acid in 7 ml $CH_2Cl_2$ were treated with 0.33 ml (2.95 mmol) NMM, 18 mg (0.12 mmol, 0.2 eq) HOBT, 147 mg (0.77 mmol, 1.3 eq) EDCI.hydrochloride and 127 mg (1.3 mmol, 2.2 eq) N-Methoxymethylamine.hydro-chloride. The mixture was stirred at RT for 3 h, was acidified by adding 1M $KHSO_4$ and extracted with $CH_2Cl_2$. The combined organic phases were washed with brine, dried over $Na_2SO_4$ and evaporated to yield 260 mg (94%) trans-N-Methoxy-N-methyl-4-{4-[methyl-(4-trifluoromethyl-benzenesulfonyl)-amino]-cyclohexyloxy}-butyramide as light yellow oil, MS: 467 ($MH^+$).

Example 52.6

To 260 mg (0.56 mmol) trans-N-Methoxy-N-methyl-4-{4-[methyl-(4-trifluoromethyl-benzenesulfonyl)-amino]-cyclohexyloxy}-butyramide in 10 ml THF were added 0.56 ml 3M (1.67 mmol, 3 eq) methylmagnesiumbromide in THF at −78° C. The solution was slowly warmed to RT over night, a saturated aqueous solution of $NH_4Cl$ was added and the mixture stirred for 30 min. The phases were separated and the inorganic phase was extracted with EtOAc. The combined organic ones were dried over $Na_2SO_4$ and evaporated. Column chromatography on silica gel with EtOAc/hexane 1:1 yielded 143 mg (61%) trans-N-Methyl-N-[4-(4-oxo-pentyloxy)-cyclohexyl]-4-trifluoromethyl-benzenesulfonamide as white solid, MS: 422 ($MH^+$).

Example 52.7

70 mg (0.17 mmol) trans-N-Methyl-N-[4-(4-oxo-pentyloxy)-cyclohexyl]-4-trifluoromethyl-benzenesulfonamide were treated with 31 μM (30% in ethanol, 0.17 mmol) dimethylamine and 61 μM (0.17 mmol) tetraisopropyl orthotitanate. The solution was stirred at RT for 18 h, additional 31 μM (30% in ethanol, 0.17 mmol) dimethylamine and 61 μM (0.17 mmol) tetraisopropyl orthotitanate were added and stirring was continued for 2 h. The mixture was diluted with 1.7 ml ethanol and 7 mg (0.1 mmol) $NaCNBH_3$ were added, and stirring was continued over night. 0.35 ml water was added and the suspension filtered and evaporated. The residue was purified by column chromatography with $CH_2Cl_2$/MeOH 9:1 to give 13.2 mg (18%) trans-N-[4-(4-Dimethylamino-pentyloxy)-cyclohexyl]-N-methyl-4-trifluoromethyl-benzenesulfonamide as colorless oil, MS: 451 ($MH^+$).

Example 52.8

Analogously to example 52.7, from trans-N-Methyl-N-[4-(4-oxo-pentyloxy)-cyclohexyl]-4-trifluoromethyl-benzenesulfonamide and pyrrolidine was prepared trans-N-Methyl-N-[4-(4-piperidin-1-yl-pentyloxy)-cyclohexyl]-4-trifluoromethyl-benzenesulfonamide as colorless oil, MS: 491 ($MH^+$).

Example A

Tablets containing the following ingredients can be manufactured in a conventional manner:

| Ingredients | Per tablet |
| --- | --- |
| Compound of formula I | 10.0–100.0 mg |
| Lactose | 125.0 mg |
| Maize starch | 75.0 mg |
| Talc | 4.0 mg |
| Magnesium stearate | 1.0 mg |

Example B

Capsules containing the following ingredients can be manufactured in a conventional manner:

| Ingredients | Per capsule |
| --- | --- |
| Compound of formula I | 25.0 mg |
| Lactose | 150.0 mg |
| Maize starch | 20.0 mg |
| Talc | 5.0 mg |

Example C

Injection solutions can have the following composition:

| | |
| --- | --- |
| Compound of formula I | 3.0 mg |
| Gelatine | 150.0 mg |
| Phenol | 4.7 mg |
| Water for injection solutions | ad 1.0 ml |

The invention claimed is:

1. A compound selected from the group consisting of compounds of formula (I)

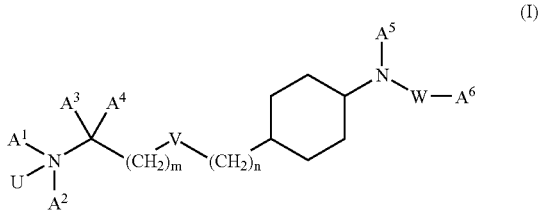

wherein
U is O or a lone pair;
V is O, S;
W is CO, COO, CONR$^1$, CSO, CSNR$^1$, SO$_2$, or SO$_2$NR$^1$;
m and n are each integers from 0 to 7, with the provisos that m+n is 0 to 7 and m is not 0 when V is O or S;
A$^1$ is H, lower-alkyl, hydroxy-lower-alkyl, or lower-alkenyl and
A$^2$ is lower-alkyl, cycloalkyl, cycloalkyl-lower-alkyl, or lower-alkenyl, optionally substituted by R$^2$, or
A$^3$ and A$^4$ are each hydrogen or lower-alkyl, or
A$^5$ is H, lower-alkyl, lower-alkenyl, or aryl-lower-alkyl;
A$^6$ is lower-alkyl, cycloalkyl, aryl, aryl-lower-alkyl, heteroaryl, heteroaryl-lower-alkyl, lower-alkoxy-carbonyl-lower-alkyl;
R$^2$ is hydroxy, hydroxy-lower-alkyl, lower-alkoxy, lower-alkoxycarbonyl, N(R$^4$,R$^5$), or thio-lower-alkoxy;
R$^1$, R$^3$, R$^4$ and R$^5$ independently from each other are hydrogen or lower-alkyl; or
pharmaceutically acceptable salts of the compounds of formula (I), or
pharmaceutically acceptable esters of the compounds of formula (I).

2. The compound according to claim 1, wherein A$^3$ and A$^4$ are not bonded together.

3. The compound according to claim 1, selected from the group consisting of compounds of formula (Ia)

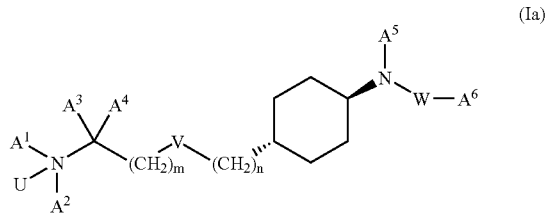

wherein U, V, W, m, n, A$^1$, A$^2$, A$^3$, A$^4$, A$^5$ and A$^6$ are as defined in claim 1;
pharmaceutically acceptable salts of the compounds of formula (Ia); and
pharmaceutically acceptable esters of the compounds of formula (Ia).

4. The compound according to claim 1, wherein U is a lone pair.

5. The compound according to claim 4, wherein V is O.

6. The compound according to claim 4, wherein V is —CH$_2$—.

7. The compound according to claim 4, wherein V is —C=C—.

8. The compound according to claim 4, wherein V is —C≡C—.

9. The compound according to claim 4, wherein W is CO, COO, CONR$^1$, CSNR$^1$, SO$_2$ or SO$_2$NR$^1$ and R$^1$ is hydrogen.

10. The compound according to claim 9, wherein W is COO or SO$_2$.

11. The compound according to claim 10, wherein n is 0.

12. The compound according to claim 10, wherein n is 1.

13. The compound according to claim 10, wherein m is 1 to 6.

14. The compound according to claim 10, wherein m is 0 and V is —C=C— or —C≡C—.

15. The compound according to claim 10, wherein A$^1$ is H, methyl, ethyl, isopropyl, 2-hydroxy-ethyl, or 2-propenyl.

16. The compound according to claim 10, wherein A$^2$ is lower-alkyl, cycloalkyl-lower-alkyl, or lower-alkenyl, optionally substituted with R$^2$, wherein R$^2$ is hydroxy, methoxy, or ethoxycarbonyl.

17. The compound according to claim 16, wherein A$^2$ is methyl, ethyl, 2-hydroxy-ethyl, 2-propenyl, propyl or isopropyl.

18. The compound according to claim 10, wherein A$^1$ and A$^2$ are bonded together.

19. The compound according to claim 18, wherein -A$^1$-A$^2$- is lower-alkylene or lower-alkenylene, optionally substituted by R$^2$, in which one —CH$_2$— group of -A$^1$-A$^2$- can optionally be replaced by O, wherein R$^2$ is hydroxy or 2-hydroxyethyl.

20. The compound according to claim 19, wherein -A$^1$-A$^2$- is —(CH$_2$)$_5$—.

21. The compound according to claim 10, wherein A$^3$ is hydrogen.

22. The compound according to claim 10, wherein A$^4$ is hydrogen.

23. The compound according to claim 10, wherein A$^3$ and A$^4$ are bonded together to form -A$^3$-A$^4$-, and -A$^3$-A$^4$- is —(CH$_2$)$_2$—.

24. The compound according to claim 10, wherein A$^5$ is H, lower-alkyl, lower-alkenyl, or benzyl optionally substituted with halogen.

25. The compounds according to claim 24, wherein A$^5$ is methyl or ethyl.

26. The compound according to claim 25, wherein A$^6$ is lower-alkyl, cycloalkyl, phenyl, naphthyl, phenyl-lower-alkyl, pyridyl, indolyl, indolinyl, thienyl, thienyl-methylene, furyl-methylene, benzodioxyl, chinolyl, isoxazolyl, or imidazolyl, optionally substituted by one or more substituents selected from the group consisting of lower-alkyl, lower-alkoxy, lower-alkylcarbonyl, lower-alkoxycarbonyl, fluorine, chlorine, bromine, CN, CF$_3$, NO$_2$, or N(R$^6$,R$^7$), wherein R$^6$ and R$^7$ independently from each other are hydrogen or lower-alkyl.

27. The compound according to claim 26, wherein A$^6$ is phenyl optionally substituted by one or more substituents selected from the group consisting of fluorine, chlorine, bromine, and CF$_3$.

28. The compound according to claim 27, wherein A$^6$ is 4-chloro-phenyl, 4-bromo-phenyl, or 4-trifluoromethyl-phenyl.

29. The compound according to claim 28, wherein A$^1$ is H, lower alkyl or hydroxy-lower alkyl and A$^2$ is lower alkyl, hydroxy-lower alkyl or lower alkenyl.

30. The compound according to claim 29, wherein A$^3$ and A$^4$ are hydrogen.

31. The compound according to claim 30, wherein V is O.

32. The compound according to claim 30, wherein V is S.

33. The compound according to claim 32, selected from the group consisting of trans-{4-[2-(Allyl-methyl-amino)-ethylsulfanylmethyl]-cyclohexyl}-methyl-carbamic acid 4-chloro-phenyl ester, pharmaceutically acceptable salts thereof and pharmaceutically acceptable esters thereof.

34. The compound according to claim 30, wherein V is —CH$_2$—.

35. The compound according to claim 30, wherein V is —C=C—.

36. The compound according to claim 30, wherein V is —C≡C—.

37. A compound selected from the group consisting of compounds of formula (Ib)

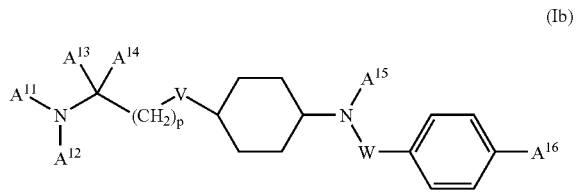

wherein
V is O, S;
W is COO or SO$_2$;
p is an integer from 0 to 7, with the proviso that p is not 0 when V is O or S;
A$^{11}$ is H, lower-alkyl, or hydroxy-lower-alkyl;
A$^{12}$ is lower-alkyl, hydroxy-lower alkyl, or lower-alkenyl
A$^{13}$ and A$^{14}$ are each hydrogen
A$^{15}$ is lower-alkyl; and
A$^{16}$ is halogen or trifluoromethyl;
pharmaceutically acceptable salts of the compounds of formula (Ib), and
pharmaceutically acceptable esters of the compounds of formula (Ib).

38. The compound according to claim 37, wherein A$^{11}$ is H, lower-alkyl, or hydroxy-lower-alkyl and A$^{12}$ is lower-alkyl, hydroxy-lower alkyl, or lower-alkenyl.

39. The compound according to claim 38, selected from the group consisting of trans-N-{4-[2-(1-dimethylamino-cyclopropyl)-ethoxy]-cyclohexyl}-N-methyl-4-trifluoromethyl-benzenesulfonamide, pharmaceutically acceptable salts thereof and pharmaceutically acceptable esters thereof.

40. The compound according to claim 37, whereon A$^{13}$ and A$^{14}$ are hydrogen.

41. The compound according to claim 40, selected from the group consisting of trans-4-bromo-N-methyl-N-[4-(2-piperidin-1-yl-ethoxy)-cyclohexyl]-benzenesulfonamide, pharmaceutically acceptable salts thereof and pharmaceutically acceptable esters thereof.

42. The compound according to claim 40, selected from the group consisting of trans-methyl-[4-(4-piperidin-1-yl-butyl)-cyclohexyl]-carbamic acid 4-bromo-phenyl ester, pharmaceutically acceptable salts thereof and pharmaceutically acceptable esters thereof.

43. The compound according to claim 40, selected from the group consisting of trans-N-methyl-N-[4-(4-piperidin-1-yl-butyl)-cyclohexyl]4-trifluoromethyl-benzenesulfonamide, pharmaceutically acceptable salts thereof and pharmaceutically acceptable esters thereof.

44. The compound according to claim 40, selected from the group consisting of trans-methyl-[4-(5-piperidin-1-yl-pentyl)-cyclohexyl]-carbamic acid 4-cloro-phenyl ester, pharmaceutically acceptable salts thereof and pharmaceutically acceptable esters thereof.

45. The compound according to claim 40, wherein A$^{11}$ is H, lower-alkyl, or hydroxy-lower-alkyl and A$^{12}$ is lower-alkyl, hydroxy-lower alkyl, or lower-alkenyl.

46. The compound according to claim 45, wherein V is O.

47. The compound according to claim 46, wherein W is COO.

48. The compound according to claim 47, selected from the group consisting of trans-{4-[6-(allyl-methyl-amino)-hexyloxy]-cyclohexyl}-methyl-carbamic acid 4-chloro-phenyl ester, pharmaceutically acceptable salts thereof and pharmaceutically acceptable esters thereof.

49. The compound according to claim 47, selected from the group consisting of trans-{4-[4-(allyl-methyl-amino)-butoxy]-cyclohexyl}-methyl-carbamic acid 4-trifluoromethyl-phenyl ester, pharmaceutically acceptable salts thereof and pharmaceutically acceptable esters thereof.

50. The compound according to claim 47, selected from the group consisting of trans-(4-{4-[ethyl-(2-hydroxy-ethyl)-amino]-butoxy}-cyclohexyl)-methyl-carbamic acid 4-trifluoromethyl-phenyl ester, pharmaceutically acceptable salts thereof and pharmaceutically acceptable esters thereof.

51. The compound according to claim 47, selected from the group consisting of trans-[4-(4-dimethylamino-butoxy)-cyclohexyl]-methyl-carbamic acid 4-trifluoromethyl-phenyl ester, pharmaceutically acceptable salts thereof and pharmaceutically acceptable esters thereof.

52. The compound according to claim 47, selected from the group consisting of trans-{4-[4-(allyl-methyl-amino)-butoxy]-cyclohexyl}-methyl-carbamic acid 4-chloro-phenyl ester, pharmaceutically acceptable salts thereof and pharmaceutically acceptable esters thereof.

53. The compound according to claim 46, wherein W is SO$_2$.

54. The compound according to claim 53, selected from the group consisting of trans-N-[4-(3-allylamino-propoxy)-cyclohexyl]-N-methyl-4-trifluoromethyl-benzenesulfonamide, pharmaceutically acceptable salts thereof and pharmaceutically acceptable esters thereof.

55. The compound according to claim 53, selected from the group consisting of trans-N-[4-(6-diethylamino-hexyloxy)-cyclohexyl]-N-methyl-4-trifluoromethyl-benzenesulfonamide, pharmaceutically acceptable salts thereof and pharmaceutically acceptable esters thereof.

56. The compound according to claim 53, selected from the group consisting of trans-N-[4-(4-dimethylamino-butoxy)-cyclohexyl]-N-ethyl-4-trifluoromethyl-benzenesulfonamide, pharmaceutically acceptable salts thereof and pharmaceutically acceptable esters thereof.

57. The compound according to claim 53, selected from the group consisting of trans-N-ethyl-N-(4-{4-[(2-hydroxyethyl)-methyl-amino]-butoxy}-cyclohexyl)-4-trifluoromethyl-benzenesulfonamide, pharmaceutically acceptable salts thereof and pharmaceutically acceptable esters thereof.

58. The compound according to claim 53, selected from the group consisting of trans-N-(4-{4-[bis-(2-hydroxyethyl)-amino]-butoxy}-cyclohexyl)-N-ethyl-4-trifluoromethyl-benzenesulfonamide, pharmaceutically acceptable salts thereof and pharmaceutically acceptable esters thereof.

59. The compound according to claim 53, selected from the group consisting of trans-4-bromo-N-[4-(2-diisopropylamino-ethoxy)-cyclohexyl]-N-methyl-benzenesulfonamide, pharmaceutically acceptable salts thereof and pharmaceutically acceptable esters thereof.

60. The compound according to claim 45, wherein V is S.

61. The compound according to claim 60, wherein W is COO.

62. The compound according to claim 60, wherein W is $SO_2$.

63. The compound according to claim 45, wherein V is —$CH_2$—.

64. The compound according to claim 63, wherein W is COO.

65. The compound according to claim 64, wherein $A^{11}$ is H.

66. The compound according to claim 65, selected from the group consisting of trans-methyl-[4-(5-methylamino-pentyl)-cyclohexyl]-carbamic acid 4-trifluoromethyl-phenyl ester, pharmaceutically acceptable salts thereof and pharmaceutically acceptable esters thereof.

67. The compound according to claim 64, wherein $A^{11}$ is methyl.

68. The compound according to claim 67, selected from the group consisting of trans-{4-[5-(allyl-methyl-amino)-pentyl]-cyclohexyl}-methyl-carbamic acid 4-trifluoromethyl-phenyl ester, pharmaceutically acceptable salts thereof and pharmaceutically acceptable esters thereof.

69. The compound according to claim 67, selected from the group consisting of trans-{4-[5-(allyl-methyl-amino)-pentyl]-cyclohexyl}-methyl-carbamic acid 4-bromo-phenyl ester, pharmaceutically acceptable salts thereof and pharmaceutically acceptable esters thereof.

70. The compound according to claim 67, selected from the group consisting of trans-{4-[5-(allyl-methyl-amino)-pentyl]-cyclohexyl}-methyl-carbamic acid 4-chloro-phenyl ester, pharmaceutically acceptable salts thereof and pharmaceutically acceptable esters thereof.

71. The compound according to claim 67, selected from the group consisting of trans-{4-[4-(allyl-methyl-amino)-butyl]-cyclohexyl}-methyl-carbamic acid 4-chloro-phenyl ester, pharmaceutically acceptable salts thereof and pharmaceutically acceptable esters thereof.

72. The compound according to claim 64, wherein $A^{11}$ is ethyl.

73. The compound according to claim 72, selected from the group consisting of trans-(4-{5-[ethyl-(2-hydroxy-ethyl)-amino]-pentyl}cyclohexyl)-methyl-carbamic acid 4-trifluoromethyl-phenyl ester, pharmaceutically acceptable salts thereof and pharmaceutically acceptable esters thereof.

74. The compound according to claim 72, selected from the group consisting of trans-(4-{5-[ethyl-(2-hydroxy-ethyl)-amino]-pentyl}-cyclohexyl)-methyl-carbamic acid 4-bromo-phenyl ester, pharmaceutically acceptable salts thereof and pharmaceutically acceptable esters thereof.

75. The compound according to claim 72, selected from the group consisting of trans-(4-{3-[ethyl-(2-hydroxy-ethyl)-amino]-propyl}-cyclohexyl)-methyl-carbamic acid 4-chloro-phenyl ester, pharmaceutically acceptable salts thereof and pharmaceutically acceptable esters thereof.

76. The compound according to claim 63, wherein W is $SO_2$.

77. The compound according to claim 76, selected from the group consisting of trans-N-{4-[5-(allyl-methyl-amino)-pentyl]-cyclohexyl}-N-methyl-4-trifluoromethyl-benzenesulfonamide, pharmaceutically acceptable salts thereof and pharmaceutically acceptable esters thereof.

78. The compound according to claim 76, selected from the group consisting of trans-N-(4-{5-[ethyl-(2-hydroxy-ethyl)-amino]-pentyl}-cyclohexyl)-N-methyl-4-trifluoromethyl-benzenesulfonamide, pharmaceutically acceptable salts thereof and pharmaceutically acceptable esters thereof.

79. The compound according to claim 45, wherein V is —C=C—.

80. The compound according to claim 79, wherein W is COO.

81. The compound according to claim 79, wherein W is $SO_2$.

82. The compound according to claim 81, selected from the group consisting of trans-(1E)-N-methyl-N-{4-[3-(methyl-propyl-amino)-propenyl]-cyclohexyl}-4-trifluoromethyl-benzenesulfonamide, pharmaceutically acceptable salts thereof and pharmaceutically acceptable esters thereof.

83. The compound according to claim 81, selected from the group consisting of trans-(1E)-N-(4-{3-[ethyl-(2-hydroxy-ethyl)-amino]-propenyl}-cyclohexyl)-N-methyl-4-trifluoromethyl-benzenesulfonamide, pharmaceutically acceptable salts thereof and pharmaceutically acceptable esters thereof.

84. The compound according to claim 45, wherein V is —C≡C—.

85. The compound according to claim 84, wherein W is COO.

86. The compound according to claim 85, selected from the group consisting of trans-{4-[3-(allyl-methyl-amino)-prop-1-ynyl]-cyclohexyl}-methyl-carbamic acid 4-chloro-phenyl ester, pharmaceutically acceptable salts thereof and pharmaceutically acceptable esters thereof.

87. The compound according to claim 85, selected from the group consisting of trans-(4-{5-[ethyl-(2-hydroxy-ethyl)-amino]-pent-1-ynyl}-cyclohexyl)-methyl-carbamic acid 4-chloro-phenyl ester, pharmaceutically acceptable salts thereof and pharmaceutically acceptable esters thereof.

88. The compound according to claim 85, selected from the group consisting of trans-methyl-{4-[3-(methyl-propyl-amino)-prop-1-ynyl]-cyclohexyl}-carbamic acid 4-chloro-phenyl ester, pharmaceutically acceptable salts thereof and pharmaceutically acceptable esters thereof.

89. The compound according to claim 84, wherein W is $SO_2$.

90. The compound according to claim 89, selected from the group consisting of trans-N-[4-(4-dimethylamino-but-1-ynyl)-cyclohexyl]-N-methyl-4-trifluoromethyl-benzenesulfonamide, pharmaceutically acceptable salts thereof and pharmaceutically acceptable esters thereof.

91. The compound according to claim 89, selected from the group consisting of trans-N-methyl-N-{4-[4-(methyl-propyl-amino)-but-1-ynyl]-cyclohexyl}-4-trifluoromethyl-benzenesulfonamide, pharmaceutically acceptable salts thereof and pharmaceutically acceptable esters thereof.

92. The compound according to claim 89, selected from the group consisting of trans-N-(4-{4-[ethyl-(2-hydroxy-ethyl)-amino]-but-1-ynyl}-cyclohexyl)-N-methyl-4-trifluoromethyl-benzenesulfonamide, pharmaceutically acceptable salts thereof and pharmaceutically acceptable esters thereof.

93. A process for the manufacture of a compound according to claim 1, comprising reacting a compound of formula (II)

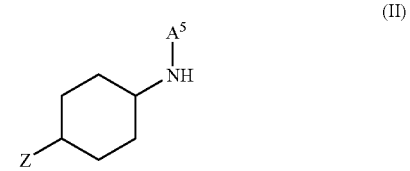

wherein
$A^5$ is as defined in claim 1,

Z is a group $(A^1,A^2,)N-C(A^3,A^4)-(CH_2)_m-V-(CH_2)_n$ or $HO-(CH_2)_n$, wherein $A^1$, $A^2$, $A^3$, $A^4$, V, m and n are defined as in claim 1, with $ClSO_2$-$A^6$, $ClCOO$-$A^6$, $ClCSO$-$A^6$, $OCN$-$A^6$, $SCN$-$A^6$, $HOOC$-$A^6$, or $ClSO_2NR^1$-$A^6$, wherein $A^6$ is as defined in claim 1.

94. A pharmaceutical composition comprising a compound according to claim 1 and at least one of a pharmaceutically acceptable carrier or a pharmaceutically acceptable adjuvant.

* * * * *

UNITED STATES PATENT AND TRADEMARK OFFICE
CERTIFICATE OF CORRECTION

PATENT NO. : 7,335,687 B2  
APPLICATION NO. : 11/014374  
DATED : February 26, 2008  
INVENTOR(S) : Ackermann et al.

Page 1 of 1

It is certified that error appears in the above-identified patent and that said Letters Patent is hereby corrected as shown below:

Title Page, under Abstract (57), the amount of allowed claims delete "94" and insert -- 48 --.  
Col. 171, delete claims 6-8;  
Col. 172, delete claims 14, 18-20 and 23;  
Col. 173, delete claims 34-36, 39 and 41-44;  
Col. 175, delete claims 63-79;  
Col. 176, delete claims 80-92.

Signed and Sealed this

Twenty-fourth Day of June, 2008

JON W. DUDAS  
*Director of the United States Patent and Trademark Office*